US012758751B2

(12) United States Patent
Giasolli

(10) Patent No.: US 12,758,751 B2
(45) Date of Patent: Oct. 13, 2026

(54) BALLOON CATHETER AND METHODS OF USE TO REDUCE RESIDUAL STENOSIS

(71) Applicant: CAGENT VASCULAR, INC., Wayne, PA (US)

(72) Inventor: Robert M. Giasolli, Orange, CA (US)

(73) Assignee: Cagent Vascular, Inc., Wayne, PA (US)

( * ) Notice: Subject to any disclaimer, the term of this patent is extended or adjusted under 35 U.S.C. 154(b) by 0 days.

(21) Appl. No.: 19/053,238

(22) Filed: Feb. 13, 2025

(65) Prior Publication Data

US 2025/0186748 A1 Jun. 12, 2025

Related U.S. Application Data

(63) Continuation of application No. 18/339,049, filed on Jun. 21, 2023.

(60) Provisional application No. 63/355,324, filed on Jun. 24, 2022.

(51) Int. Cl.
*A61M 25/10* (2013.01)

(52) U.S. Cl.
CPC ... *A61M 25/104* (2013.01); *A61M 2025/1031* (2013.01); *A61M 2025/1075* (2013.01); *A61M 2025/1086* (2013.01)

(58) Field of Classification Search
CPC ........ A61M 25/104; A61M 2025/1031; A61M 2025/1075; A61M 2025/1086; A61B 17/22022; A61B 17/2202
See application file for complete search history.

(56) References Cited

U.S. PATENT DOCUMENTS

| | | | |
|---|---|---|---|
| 3,221,746 | A | 12/1965 | Noble |
| 3,635,223 | A | 1/1972 | Klieman |
| 4,287,892 | A | 9/1981 | Schiff |
| 4,446,867 | A | 5/1984 | Leveen et al. |
| 4,465,072 | A | 8/1984 | Taheri |
| 4,665,906 | A | 5/1987 | Jervis |
| 4,699,611 | A | 10/1987 | Bowden |
| 4,795,458 | A | 1/1989 | Regan |
| 4,856,516 | A | 8/1989 | Hillstead |
| 5,009,659 | A | 4/1991 | Hamlin |

(Continued)

FOREIGN PATENT DOCUMENTS

| | | |
|---|---|---|
| AU | 2009226025 | 9/2009 |
| AU | 2015343272 | 7/2020 |

(Continued)

OTHER PUBLICATIONS

International Search Report and Written Opinion for International Application No. PCT/US2009/001786, mailed Sep. 28, 2009 in 8 pages.

(Continued)

*Primary Examiner* — Anh T Dang
(74) *Attorney, Agent, or Firm* — Knobbe, Martens, Olson & Bear, LLP

(57) ABSTRACT

Systems and methods can involve wedge dissectors attached to strips in turn attached to medical balloons, for forming serrations within vascular wall tissue for angioplasty as well reducing vessel recoil, reducing residual stenosis, and increasing volumetric blood flow post angioplasty. The design, methods of use, intended outcomes, and process to build this type of balloon is described herein.

20 Claims, 117 Drawing Sheets

(56) References Cited

U.S. PATENT DOCUMENTS 5,042,707 A 8/1991 Taheri
5,078,736 A 1/1992 Behl
5,152,776 A 10/1992 Pinchuk
5,160,336 A 11/1992 Favre
5,192,291 A 3/1993 Pannek, Jr.
5,196,024 A 3/1993 Barath
5,209,719 A 5/1993 Baruch et al.
5,209,799 A 5/1993 Vigil
5,320,634 A 6/1994 Vigil et al.
5,336,234 A 8/1994 Vigil
5,358,486 A 10/1994 Saab
5,397,355 A 3/1995 Marin et al.
5,411,478 A 5/1995 Stillabower
5,417,707 A 5/1995 Parkola
5,423,851 A 6/1995 Samuels
5,472,406 A 12/1995 de la Torre et al.
5,484,411 A 1/1996 Inderbitzen et al.
5,501,689 A 3/1996 Green
5,514,154 A 5/1996 Lau et al.
5,527,336 A 6/1996 Rosenbluth et al.
5,569,272 A 10/1996 Reed
5,591,197 A 1/1997 Orth et al.
5,593,434 A 1/1997 Williams
5,616,149 A 4/1997 Barath
5,665,098 A 9/1997 Kelly et al.
5,665,116 A 9/1997 Chaisson
5,681,346 A 10/1997 Orth
5,713,860 A 2/1998 Kaplan et al.
5,713,863 A 2/1998 Vigil et al.
5,718,684 A 2/1998 Gupta
5,720,726 A 2/1998 Marcadis et al.
5,797,935 A 8/1998 Barath et al.
5,797,951 A 8/1998 Mueller
5,800,526 A 9/1998 Anderson
5,824,053 A 10/1998 Khosravi et al.
5,868,779 A 2/1999 Ruiz
5,957,949 A 9/1999 Leonhardt et al.
6,007,543 A 12/1999 Ellis
6,036,725 A 3/2000 Avellanet
6,048,332 A 4/2000 Duffy et al.
6,053,943 A 4/2000 Edwin
6,102,904 A 8/2000 Vigil et al.
6,126,685 A 10/2000 Lenker
6,197,013 B1 3/2001 Reed
6,221,102 B1 4/2001 Baker
6,254,608 B1 7/2001 Solar
6,254,642 B1 7/2001 Taylor
6,280,414 B1 8/2001 Shah et al.
6,290,728 B1 9/2001 Phelps
6,371,962 B1 4/2002 Ellis
6,450,989 B2 9/2002 Dubrul et al.
6,475,237 B2 11/2002 Drasler
6,485,496 B1 11/2002 Suyker et al.
6,562,062 B2 5/2003 Jenusaitis et al.
6,607,502 B1 8/2003 Maguire et al.
6,623,452 B2 9/2003 Chien et al.
6,626,861 B1 9/2003 Hart et al.
6,632,231 B2 10/2003 Radisch, Jr.
6,638,246 B1 10/2003 Naimark et al.
6,692,504 B2 2/2004 Kurz
6,719,775 B2 4/2004 Slaker
6,736,784 B1 5/2004 Menne et al.
6,808,518 B2 10/2004 Wellman et al.
6,942,680 B2 9/2005 Grayzel et al.
7,007,698 B2 3/2006 Thornton
7,011,670 B2 3/2006 Radisch, Jr.
7,087,088 B2 8/2006 Berg
7,172,609 B2 2/2007 Radisch, Jr.
7,179,284 B2 2/2007 Khosravi
7,179,345 B2 2/2007 Shkolnik
7,186,237 B2 3/2007 Meyer et al.
7,204,847 B1 4/2007 Gambale
7,211,101 B2 5/2007 Carley
7,252,674 B2 8/2007 Wyzgala et al.
7,270,673 B2 * 9/2007 Yee .................. A61M 25/1002 606/159
7,279,002 B2 10/2007 Shaw et al.
7,291,158 B2 11/2007 Crow
7,303,572 B2 12/2007 Meisheimer
7,326,245 B2 2/2008 Rosenthal et al.
7,331,992 B2 2/2008 Randall
7,344,509 B2 3/2008 Hynynen et al.
7,413,558 B2 8/2008 Kelley et al.
7,500,986 B2 3/2009 Lye et al.
7,611,484 B2 11/2009 Wellman et al.
7,645,245 B2 1/2010 Sekino et al.
7,662,163 B2 2/2010 Grayzel et al.
7,686,824 B2 3/2010 Konstantino
7,691,116 B2 4/2010 Goodin
7,691,119 B2 4/2010 Farnan
7,771,447 B2 8/2010 Kunis
7,878,991 B2 2/2011 Babaev
7,883,537 B2 2/2011 Grayzel et al.
7,931,663 B2 4/2011 Farnan
7,933,660 B2 4/2011 Carr
7,947,015 B2 5/2011 Herweck et al.
7,972,351 B2 7/2011 Trinidad
7,985,234 B2 7/2011 Wang et al.
7,993,358 B2 8/2011 O'Brien
8,002,725 B2 8/2011 Hogendijk
8,038,691 B2 10/2011 Bence et al.
8,052,703 B2 11/2011 St. Martin et al.
8,066,726 B2 11/2011 Kelley
8,092,401 B2 1/2012 Schultheiss
8,114,049 B2 2/2012 Freyman et al.
8,192,675 B2 6/2012 Burton et al.
8,211,354 B2 7/2012 Burton
8,226,601 B2 7/2012 Gunday et al.
8,323,243 B2 12/2012 Schneider et al.
8,361,096 B2 1/2013 Bence et al.
8,364,256 B2 1/2013 Leuer et al.
8,454,637 B2 6/2013 Aggerholm et al.
8,491,615 B2 7/2013 Manderfeld et al.
8,523,887 B2 9/2013 Grayzel et al.
8,557,271 B2 10/2013 Kimble et al.
8,574,248 B2 11/2013 Kassab
8,690,903 B2 4/2014 Bence et al.
8,696,621 B2 4/2014 Gunday et al.
8,728,091 B2 5/2014 Hakala et al.
8,790,299 B2 7/2014 Gunday et al.
9,017,353 B2 4/2015 Bence et al.
9,061,127 B2 6/2015 Weber et al.
9,066,749 B2 6/2015 Burton et al.
9,095,688 B2 8/2015 Burton
9,119,944 B2 9/2015 Chambers et al.
9,173,667 B2 11/2015 Du et al.
9,179,936 B2 11/2015 Feld et al.
9,199,058 B2 12/2015 Lentz
9,199,066 B2 12/2015 Konstantino et al.
9,204,893 B2 12/2015 Rizk et al.
9,216,033 B2 12/2015 Feld et al.
9,226,768 B2 1/2016 Gunderson et al.
9,242,076 B2 1/2016 Burton et al.
9,302,071 B2 4/2016 Manderfeld et al.
9,320,530 B2 4/2016 Grace
9,339,291 B2 5/2016 Aggerholm et al.
9,393,386 B2 7/2016 Schneider et al.
9,415,193 B2 8/2016 Campbell et al.
9,421,025 B2 8/2016 Hawkins et al.
9,480,526 B2 11/2016 Singh
9,480,826 B2 11/2016 Schneider et al.
9,554,965 B2 1/2017 Foehrenbach et al.
9,586,031 B2 3/2017 Konstantino et al.
9,592,119 B2 3/2017 Tilson et al.
9,603,619 B2 3/2017 Bence et al.
9,604,036 B2 3/2017 Burton et al.
9,717,513 B2 8/2017 Golan et al.
9,775,632 B2 10/2017 Pansky et al.
9,801,642 B2 10/2017 Thor et al.
9,987,026 B2 6/2018 Shimizu et al.
10,086,175 B2 10/2018 Torres et al.
10,117,660 B2 11/2018 Cook et al.
10,166,374 B2 1/2019 Giasolli et al.

(56) References Cited

U.S. PATENT DOCUMENTS 10,172,729 B2 1/2019 Fulkerson et al.
10,245,051 B2 4/2019 Spano
10,258,487 B2 4/2019 Fulkerson et al.
10,299,820 B2 5/2019 Kohler et al.
10,300,253 B2 5/2019 Pederson
10,463,842 B2 11/2019 Giasolli et al.
10,471,238 B2 11/2019 Schneider et al.
10,478,214 B2 11/2019 Eaton
10,500,128 B2 12/2019 Engles et al.
10,543,007 B2 1/2020 Donegan
10,555,744 B2 2/2020 Nguyen et al.
10,689,154 B2 6/2020 Giasolli et al.
10,729,892 B2 8/2020 Yamazaki
10,758,256 B2 9/2020 Boyle et al.
10,898,214 B2 1/2021 Schoenle
10,905,863 B2 2/2021 Giasolli et al.
11,000,880 B2 5/2021 Riel et al.
11,040,178 B2 6/2021 Schneider et al.
11,065,645 B2 7/2021 Brouillette et al.
11,123,527 B2 9/2021 Giasolli et al.
11,141,573 B2 10/2021 Schneider et al.
11,166,742 B2 11/2021 Schneider et al.
11,179,169 B2 11/2021 Brouillette et al.
11,219,750 B2 1/2022 Schneider et al.
11,229,777 B2 1/2022 Schneider et al.
11,253,681 B2 2/2022 Williams et al.
11,266,818 B2 3/2022 Giasolli et al.
11,266,819 B2 3/2022 Giasolli et al.
11,278,300 B2 3/2022 Bahmanyar et al.
11,298,513 B2 4/2022 Schneider et al.
11,304,721 B2 4/2022 Netzel
11,369,779 B2 6/2022 Giasolli et al.
11,399,862 B2 8/2022 Massimini et al.
11,419,580 B2 8/2022 Stigall et al.
11,419,619 B2 8/2022 Brouillette et al.
11,426,186 B2 8/2022 Brouillette et al.
11,464,529 B2 10/2022 Singh et al.
11,464,949 B2 10/2022 Chisena et al.
11,491,314 B2 11/2022 Giasolli et al.
11,529,501 B2 12/2022 Schneider et al.
11,583,299 B1 2/2023 Maxwell et al.
11,622,779 B2 4/2023 McGowan et al.
11,672,599 B2 6/2023 Schultheis et al.
11,701,502 B2 7/2023 Schneider et al.
11,717,139 B2 8/2023 Massimini et al.
11,717,654 B2 8/2023 Giasolli et al.
11,738,181 B2 8/2023 Giasolli et al.
11,759,220 B2 9/2023 Baker et al.
11,865,279 B2 1/2024 Gianotti et al.
11,904,119 B2 2/2024 Williams et al.
11,950,799 B2 4/2024 Massimini et al.
11,969,177 B2 4/2024 Baker et al.
12,005,210 B2 6/2024 Chisena et al.
12,011,184 B2 6/2024 Sirhan et al.
12,023,098 B2 7/2024 Nguyen
12,076,082 B2 9/2024 Fanier et al.
12,137,930 B2 11/2024 Müller et al.
12,167,864 B1 12/2024 Maxwell et al.
12,232,760 B2 2/2025 Schneider et al.
12,233,227 B2 2/2025 Giasolli et al.
12,279,782 B2 4/2025 Chisena et al.
12,279,783 B2 4/2025 Brouillette et al.
12,318,100 B2 6/2025 Cioanta
12,329,400 B2 6/2025 Chisena et al.
12,357,798 B2 7/2025 Giasolli et al.
12,364,494 B2 7/2025 Cioanta et al.
12,642,946 B2 6/2026 Giasolli et al.
2001/0016726 A1 8/2001 Dubrul et al.
2001/0020151 A1 9/2001 Reed et al.
2002/0010489 A1* 1/2002 Grayzel .................. A61F 2/958
606/194
2002/0077594 A1 6/2002 Chien et al.
2003/0065303 A1 4/2003 Wellman et al.
2003/0153870 A1 8/2003 Meyer et al.
2003/0158595 A1 8/2003 Randall
2003/0163148 A1 8/2003 Wang et al.
2003/0229370 A1* 12/2003 Miller ............ A61B 17/320725
606/159
2004/0044308 A1 3/2004 Naimark et al.
2004/0098014 A1 5/2004 Flugelman et al.
2004/0106904 A1 6/2004 Gonnelli et al.
2004/0133223 A1 7/2004 Weber
2004/0143287 A1 7/2004 Konstantino et al.
2004/0158270 A1 8/2004 Wyzgala et al.
2004/0176740 A1 9/2004 Chouinard
2004/0186551 A1 9/2004 Kao
2004/0249445 A1 12/2004 Rosenthal et al.
2005/0015048 A1 1/2005 Chiu et al.
2005/0021070 A1 1/2005 Feld et al.
2005/0137618 A1 6/2005 Kunis
2005/0149082 A1 7/2005 Yee et al.
2005/0177130 A1 8/2005 Konstantino et al.
2005/0203388 A1 9/2005 Carr
2005/0209674 A1 9/2005 Kutscher et al.
2005/0228343 A1 10/2005 Kelley
2005/0251164 A1 11/2005 Gifford
2005/0267409 A1 12/2005 Shkolnik
2005/0288629 A1 12/2005 Kunis
2005/0288764 A1 12/2005 Snow
2006/0015134 A1 1/2006 Trinidad
2006/0085023 A1 4/2006 Davies et al.
2006/0122684 A1 6/2006 Lye et al.
2006/0129093 A1 6/2006 Jackson
2006/0149308 A1 7/2006 Melsheimer
2006/0173487 A1 8/2006 Uflacker et al.
2006/0184191 A1 8/2006 O'Brien
2006/0271093 A1 11/2006 Holman
2007/0016232 A1 1/2007 Martin et al.
2007/0021774 A1 1/2007 Hogendijk
2007/0060863 A1 3/2007 Goeken et al.
2007/0093744 A1 4/2007 Elmaleh
2007/0093779 A1 4/2007 Kugler et al.
2007/0191766 A1 8/2007 McMorrow
2007/0191811 A1 8/2007 Berglund
2007/0197963 A1* 8/2007 Griffiths ............ A61M 5/16827
604/97.01
2007/0213761 A1 9/2007 Murphy et al.
2008/0015500 A1 1/2008 Herweck et al.
2008/0097301 A1 4/2008 Alpini et al.
2008/0275483 A1 11/2008 Makower et al.
2009/0157159 A1 6/2009 Schneider et al.
2009/0171278 A1 7/2009 Hirszowicz et al.
2009/0214615 A1 8/2009 Zhao
2009/0227949 A1 9/2009 Knapp et al.
2009/0240270 A1 9/2009 Schneider et al.
2009/0254064 A1 10/2009 Boatman
2009/0270906 A1 10/2009 Hossainy
2009/0281619 A1 11/2009 Le et al.
2009/0292296 A1 11/2009 Pansky et al.
2010/0015196 A1 1/2010 Kimble et al.
2010/0023033 A1 1/2010 Mauch et al.
2010/0042121 A1 2/2010 Schneider et al.
2010/0076539 A1 3/2010 Klocke et al.
2010/0087783 A1 4/2010 Weber et al.
2010/0100029 A1 4/2010 Maskin
2010/0121270 A1 5/2010 Gunday et al.
2010/0274188 A1 10/2010 Chang et al.
2010/0274271 A1 10/2010 Kelly
2011/0015571 A1 1/2011 Voss et al.
2011/0077677 A1 3/2011 Grayzel et al.
2011/0178503 A1 7/2011 Kangas
2011/0213401 A1 9/2011 Grayzel et al.
2011/0264039 A1* 10/2011 Thielen .............. A61B 17/2202
606/192
2012/0041412 A1 2/2012 Roth et al.
2012/0059401 A1 3/2012 Konstantino et al.
2012/0172901 A1 7/2012 Manderfled et al.
2012/0191111 A1 7/2012 Aggerholm et al.
2012/0221013 A1 8/2012 Hawkins et al.
2012/0277783 A1 11/2012 Cummins et al.
2012/0277843 A1 11/2012 Weber et al.
2012/0316495 A1 12/2012 Weber
2013/0018396 A1 1/2013 Gunderson et al.
2013/0066346 A1 3/2013 Pigott

(56) References Cited

U.S. PATENT DOCUMENTS

| | | | |
|---|---|---|---|
| 2013/0110142 A1 | 5/2013 | Bence et al. | |
| 2013/0165958 A1 | 6/2013 | Schneider et al. | |
| 2013/0190725 A1 | 7/2013 | Pacetti et al. | |
| 2013/0211381 A1 | 8/2013 | Feld | |
| 2013/0218181 A1 | 8/2013 | Feld et al. | |
| 2013/0253426 A1 | 9/2013 | Campbell et al. | |
| 2013/0261545 A1 | 10/2013 | Osypka | |
| 2014/0066898 A1 | 3/2014 | Cully et al. | |
| 2014/0066960 A1 | 3/2014 | Feld et al. | |
| 2014/0277002 A1* | 9/2014 | Grace | A61B 17/2202 606/159 |
| 2015/0005695 A1 | 1/2015 | Chambers et al. | |
| 2015/0150586 A1 | 6/2015 | Aggerholm et al. | |
| 2016/0081711 A1 | 3/2016 | Gunderson et al. | |
| 2016/0175568 A1 | 6/2016 | Manderfeld et al. | |
| 2016/0184570 A1 | 6/2016 | Grace et al. | |
| 2016/0206861 A1 | 7/2016 | Do et al. | |
| 2016/0324538 A1 | 11/2016 | Schneider et al. | |
| 2016/0346506 A1 | 12/2016 | Jackson et al. | |
| 2017/0080192 A1 | 3/2017 | Giasolli et al. | |
| 2017/0100570 A1 | 4/2017 | Giasolli et al. | |
| 2017/0112526 A1 | 4/2017 | Burton et al. | |
| 2017/0128703 A1 | 5/2017 | Elgaard Pederson | |
| 2017/0150988 A1 | 6/2017 | Konstantino et al. | |
| 2017/0333686 A1 | 11/2017 | Schneider et al. | |
| 2018/0140804 A1 | 5/2018 | Tsukamoto et al. | |
| 2018/0193612 A1* | 7/2018 | Melsky | A61M 25/10184 |
| 2018/0200491 A1 | 7/2018 | Giasolli et al. | |
| 2018/0304052 A1 | 10/2018 | Schneider et al. | |
| 2018/0304053 A1 | 10/2018 | Eggert et al. | |
| 2019/0262595 A1 | 8/2019 | Ryu et al. | |
| 2019/0282789 A1 | 9/2019 | Mayda | |
| 2020/0060704 A1 | 2/2020 | Ein-Gal | |
| 2020/0140141 A1 | 5/2020 | Giasolli et al. | |
| 2020/0155815 A1 | 5/2020 | Giasolli et al. | |
| 2020/0276364 A1 | 9/2020 | Gandola et al. | |
| 2020/0305926 A1 | 10/2020 | Tarunaga | |
| 2021/0038869 A1 | 2/2021 | Weng et al. | |
| 2021/0100570 A1 | 4/2021 | Schoenle | |
| 2021/0213259 A1 | 7/2021 | Giasolli et al. | |
| 2022/0087709 A1 | 3/2022 | Schneider et al. | |
| 2022/0211983 A1 | 7/2022 | Giasolli et al. | |
| 2022/0226114 A1 | 7/2022 | Hou et al. | |
| 2022/0273324 A1 | 9/2022 | Schultheis | |
| 2022/0287732 A1 | 9/2022 | Anderson et al. | |
| 2022/0401707 A1 | 12/2022 | Giasolli et al. | |
| 2023/0038388 A1 | 2/2023 | Batchelder et al. | |
| 2023/0091201 A1 | 3/2023 | Schneider et al. | |
| 2023/0255635 A1 | 8/2023 | Schultheis et al. | |
| 2023/0255689 A1 | 8/2023 | Schultheis et al. | |
| 2023/0364394 A1 | 11/2023 | Schneider et al. | |
| 2023/0381472 A1 | 11/2023 | Chisena et al. | |
| 2023/0381544 A1 | 11/2023 | Penot et al. | |
| 2023/0398336 A1 | 12/2023 | Giasolli et al. | |
| 2024/0001088 A1 | 1/2024 | Giasolli et al. | |
| 2024/0001092 A1 | 1/2024 | Giasolli | |
| 2024/0041482 A1 | 2/2024 | Wang et al. | |
| 2024/0050112 A1 | 2/2024 | Funder et al. | |
| 2024/0065711 A1 | 2/2024 | Hendrickson | |
| 2024/0081847 A1 | 3/2024 | McGowan et al. | |
| 2024/0122668 A1 | 4/2024 | Krattiger et al. | |
| 2024/0180568 A1 | 6/2024 | Wang et al. | |
| 2024/0197346 A1 | 6/2024 | Chisena et al. | |
| 2024/0277978 A1 | 8/2024 | Chisena et al. | |
| 2024/0285295 A1 | 8/2024 | Cioanta | |
| 2024/0285978 A1 | 8/2024 | Xu et al. | |
| 2024/0293131 A1 | 9/2024 | Sirhan et al. | |
| 2024/0293132 A1 | 9/2024 | Decasper et al. | |
| 2024/0299050 A1 | 9/2024 | Masters | |
| 2024/0366244 A1 | 11/2024 | Schoenle | |
| 2024/0366245 A1 | 11/2024 | Schoenle | |
| 2024/0399121 A1 | 12/2024 | Vacek | |
| 2025/0099724 A1 | 3/2025 | Schoenle | |
| 2025/0127529 A1 | 4/2025 | Sirhan et al. | |
| 2025/0134504 A1 | 5/2025 | Chisena et al. | |
| 2025/0160879 A1 | 5/2025 | Schneider et al. | |
| 2025/0161638 A1 | 5/2025 | Giasolli et al. | |
| 2025/0213828 A1 | 7/2025 | Giasolli et al. | |
| 2025/0241666 A1 | 7/2025 | Chisena et al. | |
| 2025/0241667 A1 | 7/2025 | McGowan et al. | |
| 2025/0261948 A1 | 8/2025 | Schultheis et al. | |
| 2025/0312577 A1 | 10/2025 | Giasolli et al. | |
| 2025/0381372 A1 | 12/2025 | Giasolli et al. | |

FOREIGN PATENT DOCUMENTS

| | | |
|---|---|---|
| CN | 1642593 | 7/2005 |
| CN | 101420913 | 3/2012 |
| CN | 102512747 | 6/2012 |
| CN | 102781508 | 11/2012 |
| CN | 102939125 | 2/2013 |
| CN | 203379465 | 1/2014 |
| CN | 103582508 | 2/2014 |
| CN | 103764218 | 4/2014 |
| CN | 203564643 | 4/2014 |
| CN | 103948972 | 6/2016 |
| CN | 103930158 | 8/2016 |
| CN | 205867283 U | 1/2017 |
| CN | 107405158 | 11/2017 |
| CN | 107405475 | 11/2017 |
| CN | 108348734 | 7/2018 |
| CN | 110114108 | 8/2019 |
| CN | ZL 201080051844.9 | 7/2020 |
| CN | ZL 201580071624.5 | 9/2020 |
| EP | 0083870 A1 | 7/1983 |
| EP | 1604704 | 12/2005 |
| EP | 1809361 | 7/2007 |
| EP | 2254641 | 9/2016 |
| EP | 3215030 | 9/2017 |
| EP | 3215212 | 9/2017 |
| EP | 3349837 | 7/2018 |
| EP | 3541464 | 9/2019 |
| EP | 3826707 | 6/2021 |
| JP | H05-293176 | 11/1993 |
| JP | H09-108358 | 4/1997 |
| JP | H09-192226 | 7/1997 |
| JP | H10-137257 | 5/1998 |
| JP | 2004-504111 | 2/2004 |
| JP | 2005-508709 | 4/2005 |
| JP | 2005-517474 | 6/2005 |
| JP | 2006-501869 | 1/2006 |
| JP | 2007-512873 | 5/2007 |
| JP | 2007-527740 | 10/2007 |
| JP | 2008-519654 | 6/2008 |
| JP | 2008-519655 | 6/2008 |
| JP | 2008-526312 | 7/2008 |
| JP | 2008-529658 | 8/2008 |
| JP | 2011-515147 | 5/2011 |
| JP | 2013-521937 | 6/2013 |
| JP | 2020-156734 | 10/2020 |
| WO | WO 2002/043796 | 6/2002 |
| WO | WO 2002/078511 | 10/2002 |
| WO | WO 2003/051442 | 6/2003 |
| WO | WO 2003/068307 | 8/2003 |
| WO | WO 2003/101310 | 12/2003 |
| WO | WO 2003/013642 | 11/2004 |
| WO | WO 2005/076833 | 8/2005 |
| WO | WO 2006/130194 | 12/2006 |
| WO | WO 2008/020980 | 2/2008 |
| WO | WO 2009/027530 | 3/2009 |
| WO | WO 2009/117158 | 9/2009 |
| WO | WO 2011/035132 | 3/2011 |
| WO | WO 2013/012714 | 1/2013 |
| WO | WO 2015/187872 | 12/2015 |
| WO | WO 2016/073490 | 5/2016 |
| WO | WO 2016/073511 | 5/2016 |
| WO | WO 2016/116821 | 7/2016 |
| WO | WO 2016/163495 | 10/2016 |
| WO | WO 2017/049227 | 3/2017 |
| WO | WO 2018/094077 | 5/2018 |
| WO | WO 2020/023749 | 1/2020 |
| WO | WO 2022/147375 | 7/2022 |
| WO | WO 2023/286056 A1 | 1/2023 |
| WO | WO 2023/039309 A1 | 3/2023 |

(56) References Cited

FOREIGN PATENT DOCUMENTS

| | | | |
|---|---|---|---|
| WO | WO 2023/094348 | A1 | 6/2023 |
| WO | WO 2023/094350 | A1 | 6/2023 |
| WO | WO 2023/154327 | A1 | 8/2023 |
| WO | WO 2023/197367 | A1 | 10/2023 |
| WO | WO 2023/218478 | A1 | 11/2023 |
| WO | WO 2023/229908 | A1 | 11/2023 |
| WO | WO 2023/230232 | A1 | 11/2023 |
| WO | WO 2023/250378 | | 12/2023 |
| WO | WO 2024/044173 | A1 | 2/2024 |
| WO | WO 2024/045386 | A1 | 3/2024 |
| WO | WO 2024/059067 | A1 | 3/2024 |
| WO | WO 2024/072447 | A1 | 4/2024 |
| WO | WO 2024/026398 | A2 | 5/2024 |
| WO | WO 2024/064843 | A2 | 6/2024 |
| WO | WO 2024/127344 | A1 | 6/2024 |
| WO | WO 2024/123796 | A2 | 7/2024 |
| WO | WO 2024/119185 | A2 | 8/2024 |
| WO | WO 2024/167914 | A1 | 8/2024 |
| WO | WO 2024/175335 | A1 | 8/2024 |
| WO | WO 2024/235189 | A1 | 11/2024 |
| WO | WO 2025/069558 | A1 | 4/2025 |
| WO | WO 2025/085835 | A1 | 4/2025 |
| WO | WO 2025/136819 | | 6/2025 |
| WO | WO 2025/144481 | A1 | 7/2025 |
| WO | WO 2025/174771 | A1 | 8/2025 |

OTHER PUBLICATIONS

International Search Report and Written Opinion for International Application No. PCT/US2010/049297, mailed Jun. 21, 2011 in 9 pages.
Supplemental Search Report for European Application No. 09722111.3, mailed Jun. 29, 2011 in 2 pages.
Australian Office Action for Application No. 2009226025 mailed on Oct. 31, 2011 in 4 pages.
Japanese Notice of Rejection in Japanese Patent Application 2011-500815 dated Jun. 26, 2012 in 7 pages.
Japanese Notice of Rejection in Japanese Patent Application 2011-500815 dated Feb. 1, 2013 in 16 pages.
Supplemental European Search Report for European Application No. 10817896.3 dated Jun. 19, 2013 in 8 pages.
European Search Report dated Jun. 7, 2018 in EP application No. 15857951.6 in 7 pages.
Supplemental Search Report for European Application No. 16847495, mailed Apr. 30, 2019 in 9 pages.
International Search Report and Written Opinion for International Application No. PCT/US2019/043443, mailed Oct. 1, 2019 in 14 pages.
International Search Report and Written Opinion for International Application No. PCT/US2015/034060, mailed Nov. 5, 2015 in 23 pages.
International Search Report and Written Opinion for International Application No. PCT/US2015/058847, mailed Feb. 23, 2016 in 12 pages.
International Search Report and Written Opinion for International Application No. PCT/US2015/058874, mailed Mar. 30, 2016 in 22 pages.
International Search Report for Application No. PCT/US2017/062060 dated Mar. 15, 2018 in 11 pages.
European Extended Search Report dated Jun. 13, 2018 in EP application No. 15856760.2 in 9 pages.
Office Action for Chinese Patent Application No. 201580071707.4 dated Jun. 28, 2019 in 8 pages.
Australian Office Action for Application No. 2015343272 mailed on Jul. 24, 2019 in 4 pages.
Australian Office Action for Application No. 2016324292 mailed on Jun. 1, 2020 in 6 pages.
Office Action for Chinese Patent Application No. 201680059509.0 dated Jun. 2, 2020 in 21 pages.
European Extended Search Report dated Jun. 17, 2020 in EP application No. 17872835.8 in 7 pages.
Invitation to Pay Additional Search Fees in PCT Application No. PCT/US2021/071644, mailed on Dec. 2, 2021, in 3 pages.
International Search Report and Written Opinion for PCT/US2021/071644, mailed on Feb. 7, 2022, in 23 pages.
Extended European Search Report for EP 19840947, dated Apr. 2022, in 7 pages.
Office Action with English translation in Japanese Application No. 2019-547248, dated Apr. 5, 2022, in 4 pages.
Office Action with English translation in Japanese Application No. 2020-214640, dated Jul. 6, 2022, in 9 pages.
Office Action in Australian Application No. 2021218145, dated Jul. 29, 2022, in 4 pages.
Office Action in Australian Application No. 2017361422, dated Jul. 28, 2022, in 3 pages.
Examination Report in European Application No. 15856760.2, dated Nov. 22, 2022, in 4 pages.
Examination Report in Australian Application No. 2021218145, dated Dec. 9, 2022, in 2 pages.
Examination Report with English Translation in Japanese Application No. 2019-547248, dated Oct. 19, 2022.
Decision to Grant in Japanese Application No. 2020-214640, dated Dec. 13, 2022.
Examination Report in Australian Application No. 2017361422, dated Dec. 19, 2022.
Examiner's Report in Canadian Application No. 2,998,162, dated Dec. 28, 2022, in 4 pages.
Office Action in Australian Application No. 2021218145, dated Jan. 16, 2023, in 2 pages.
Office Action in Japanese Application No. 2021-503795, dated Apr. 19, 2023, in 19 pages.
Office Action in Australian Application No. 2017361422, dated Jun. 21, 2023, in 3 pages.
International Preliminary Report on Patentability and Written Opinion in application No. PCT/US2021/071644, dated Jul. 4, 2023, in 13 pages.
Office Action in Japanese Application No. 2022-125559, dated Aug. 11, 2023, in 6 pages.
Office Action in Canadian Application No. 2,998,162, dated Oct. 12, 2023, in 10 pages.
Office Action with English translation in Japanese Application No. 2003-002494, dated Nov. 27, 2023, in 9 pages.
Office Action in application No. EP 17872835.8, dated Dec. 15, 2023, in 6 pages.
Office Action with English translation in Chinese application No. 201980062884.4, dated Jan. 9, 2024, in 10 pages.
Office Action in Japanese application No. 2021-503795, dated Jan. 16, 2024, in 11 pages.
International Search Report and Written Opinion in application No. PCT/US2023/68817, mailed on Feb. 16, 2024, in 11 pages.
Office Action in Chinese application No. 202111217588.2, dated Feb. 26, 2024, in 15 pages.
Office Action in Chinese application No. 202111216420.X, dated Feb. 26, 2024, in 15 pages.
Conditional Notice of Allowance in Canadian Application No. 2,998,162, dated Jan. 23, 2025, in 3 pages.
Office Action in Australian application No. 2019310102, dated Mar. 26, 2024, in 2 pages.
Office Action in Japanese Application No. 2022-125559, dated Apr. 23, 2024, in 3 pages.
Examination Report in European Application No. 20194806.4, dated May 23, 2024, in 4 pages.
Notice of Allowance in Japanese Application No. 2021-503795, dated Aug. 13, 2024, in 3 pages.
Notice of Allowance with English translation in Japanese Application No. 2023-002494, dated Sep. 3, 2024, in 5 pages.
Examination Report in Australian application No. 2023216815, dated Sep. 13, 2024, in 2 pages.
Supplementary European Search Report in application No. EP 21916573, dated Oct. 22, 2024, in 10 pages.
Notice of Allowance in Chinese application No. 201980062884.4, dated Oct. 30, 2024, in 7 pages.

(56) References Cited

OTHER PUBLICATIONS

Office Action with English translation in Chinese application No. 202111216420.X, dated Dec. 2, 2024, in 23 pages.
Office Action with English translation in Chinese application No. 202111217588.2, dated Dec. 3, 2024, in 29 pages.
Intent to Grant in European application No. 20194806.4, dated Dec. 13, 2024, in 123 pages.
International Preliminary Report on Patentability and Written Opinion in application No. PCT/US2023/68817, dated Dec. 18, 2024, in 6 pages.
Examination Report issued in Australian application No. 2023237117, dated Jan. 24, 2025, in 4 pages.
Invitation to Pay Additional Search Fees in PCT Application No. PCT/US2024/060076, mailed on Jan. 27, 2025, in 3 pages.
Notice of Allowance received in Australian application No. 2019310102, dated Feb. 20, 2025, in 3 pages.
International Search Report and Written Opinion in application No. PCT/US2024/060076, mailed on Mar. 28, 2025, in 18 pages.
Examination Report in Canadian application No. 3,044,046, dated Apr. 29, 2025, in 4 pages.
Office Action in Chinese application No. 202111216420.X, dated Apr. 17, 2025, in 15 pages.
Office Action in Chinese application No. 202111217588.2, dated Apr. 18, 2025, in 14 pages.
Office Action in European application No. EP 1980947.6, dated Jul. 2, 2025, in 5 pages.
Office Action in Japanese application No. JP 2023-539991, dated Jun. 17, 2025, in 11 pages.
Notice of Allowance in Australian application No. 2023216815, dated Aug. 18, 2025, in 3 pages.
Office Action in Japanese application No. 2024-192474, dated Aug. 26, 2025, in 11 pages.
Office Action in Chinese application No. 202111217588.2, dated Nov. 8, 2025, in 10 pages.
Notice of Allowance in European application No. EP 20194806.4, dated Dec. 18, 2025, in 123 pages.
Examination Report in Canadian application No. 2,969,535, dated Jul. 3, 2026, in 3 pages.
International Preliminary Report on Patentability and Written Opinion in application No. PCT/US2024/060076, dated Jun. 20, 2026, in 13 pages.
Notice of Allowance in Canadian application No. 3,044,046, dated Jun. 30, 2026, in 1 page.

* cited by examiner

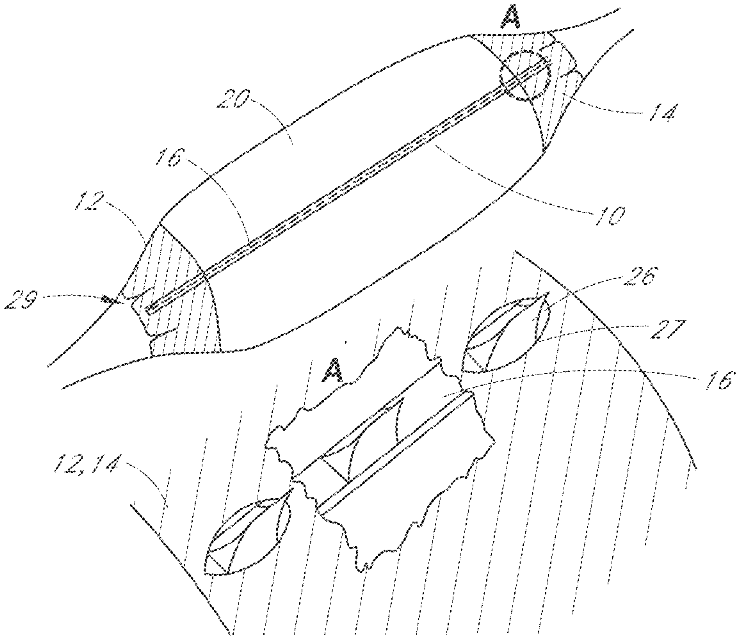
*FIG.* 10

Scanning Electron Microscopy
Porcine tissue at 7-days*

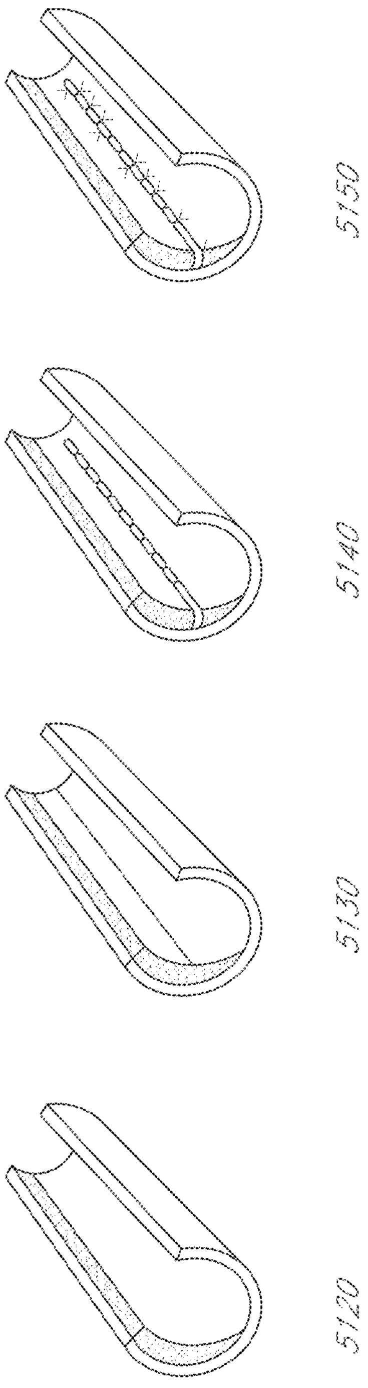
FIG.23F.1

BALLOON CATHETER AND METHODS OF USE TO REDUCE RESIDUAL STENOSIS

CROSS-REFERENCE TO RELATED APPLICATIONS

This application is a continuation application of U.S. patent application Ser. No. 18/339,049 filed on Jun. 21, 2023, which in turn claims priority benefit to U.S. Provisional Patent Application No. U.S. 63/355,324, filed Jun. 24, 2022, each of which is hereby incorporated by reference in its entirety.

BACKGROUND

Field of the Invention

Certain embodiments disclosed herein relate generally to a series of serrated structures integrated with a medical balloon, such as an angioplasty balloon and methods of depositing drug into tissue via serrations. Methods of manufacturing the series of serrated structures and treatment methods involving the series of serrated structures are also disclosed, as well as various wedge dissectors and features of splines that collectively are the serrated structures. Among other things, the wedge dissectors can be used to create perforations in a diseased treatment zone in an effort to control crack propagation, to reduce flow limiting dissections, reduce the need for implants like stents, reduce recoil, increase lumen gain, and increase flow in a diseased treatment zone.

Description of the Related Art

Atherosclerotic occlusive disease is the primary cause of stroke, heart attack, limb loss, and death in the United States and the industrialized world. Atherosclerotic plaque forms a hard layer along the wall of an artery and is comprised of calcium, cholesterol, compacted thrombus and cellular debris. As the atherosclerotic disease progresses, the blood supply intended to pass through a specific blood vessel is diminished or even prevented by the occlusive process. One of the most widely utilized methods of treating clinically significant atherosclerotic plaque is balloon angioplasty.

Balloon angioplasty is a method of opening blocked or narrowed vessels in the body. The balloon angioplasty catheter is placed into the diseased vessel (such as an artery) from a remote access site that is created either percutaneously or through open exposure of the artery. The catheter is passed along the inside of the diseased vessel over a wire that guides the way of the catheter. The portion of the catheter with the balloon attached is placed at the location of the disease (e.g., atherosclerotic plaque) that requires treatment. The balloon is generally inflated to a size that is consistent with the reference vessel diameter of the artery prior to developing occlusive disease.

When the balloon is inflated, the plaque is stretched, compressed, fractured, or broken, depending on its composition, location, and the amount of pressure exerted by the balloon. The plaque is heterogeneous and may be soft in some areas or hard in others causing unpredictable cleavage planes to form under standard balloon angioplasty. Balloon angioplasty can cause plaque disruption and sometimes even arterial injury at the angioplasty site.

Stenotic lesions in peripheral arteries have reduced blood flow to the foot which can limit patient mobility, produce pain, inhibit wound healing and in the most severe instances lead to tissue loss, infection and amputation. One recognized objective of balloon angioplasty in peripheral arteries is to open stenotic lesions and restore blood flow to the foot. Blood flow is related to cross sectional area inside the artery and therefore returning tight stenotic lesion to their neighboring reference vessel diameter with minimal vessel injury is critical. The fundamental mechanism of action for balloon angioplasty is the application of increasing radial expansion forces applied to the stenosis eventually causing the lesion to yield.

SUMMARY

Addressing the desire to increase arterial diameter while minimizing vessel injury requires an innovative approach to the use of angioplasty's mechanism of action. An innovative serration balloon catheter recognizing this objective and has collected evidence of increased lumen gain, reduction in vessel recoil, and increasing volumetric flow while minimizing the degree of dissections (one form of vessel injury) and the need for stents. In addition to increase blood flow, the serration designs inclusive in this patent and related patents, is a serration angioplasty balloon that combines angioplasty with longitudinally oriented serrations through the intima of the artery thereby altering the mechanism of action of angioplasty alone.

The combined features of angioplasty and serration can produce advantages requiring minimal atmospheric pressure to achieve improvements in blood flow. A set of stainless-steel strips are integrated into the angioplasty balloon that when the balloon is inflated produce a series of serrated lines along the intima and typically penetrate the media (as shown in illustration 1). The serrated lines promote the angioplasty energy to follow these lines of weakness which are oriented along the arterial axis. As the lumen expands, the intima and medial tissues separate more gently and predictably enabling more effective blood flow past repaired stenotic lesion. FIG. 1 illustrates a Scanning Electron Microscopy showing the serration effect in porcine tissue after 7 days of healing.

Serration Angioplasty Improving Arterial Volume Flow Rate (Evidence with Calculations Applying Poiseuille's Law)

A mathematical approach to assess improvement in arterial flow allows data between plain angioplasty and serration angioplasty to be compared. With this algorithm, data from a variety of studies can be assessed, independent of each study arterial reference vessel diameter, enabling comparison in flow improvement between studies.

To assess the volume improvement in blood flow, the derived equations utilized established fluid dynamic equations (Poiseuille's Law) stating that flow is directly correlated to the radius of a pipe to the $4^{th}$ power. Additional variables (see Formula 1) including pressure, length, and coefficient of viscosity are inclusive in Poiseuille's Law. Due to the nature of disease morphology and the inaccessibility of the in vivo tissue a simplified fluid dynamic model (Formula 2) is argued to be valid for purpose of comparison.

$$F = \frac{\pi R^4 (P_1 - P_2)}{8nL}$$

Formula 1: Poiseuille's Law

Where, R is the radius of the artery, n is the coefficient of viscosity of blood, L is the length of the vessel (or diseased section), and $P_1 - P_2$ is the difference in pressure.

First, a reflection of the set of assumptions applied to Poiseuille's Law to provide an equation that might provide insight across cardiovascular studies by evaluating the arterial flow improvement across studies.

In the traditional equation, Poiseuille's Law requires laminar flow (e.g., the flow cannot be turbulent) and that the liquid be an incompressible fluid. Although blood could be assumed to be incompressible and generally flowing in a laminar like behavior in the body, turbulent flow has been shown to be present in the arterial system and an increase in turbulent flow has been shown across diseased lesions. Independent of this assumed contradiction to the use of Poiseuille's Law the Law is derived by a second order integral of the circumference of the pipe. Therefore, as the radius R of the artery is increased, flow rate is increased exponentially. In diseased vessels where a stenotic lesion reduces the radius of a vascular segment by one-half, assuming perfused in isolation, the resistance within that narrowed segment increases 16-fold. Note in FIG. 2 (shown as flat horizontal and vertical lines) how low the % Maximum Distal Flow is when the peripheral artery is at 50% its max radius.

The volume flow rate can therefore be highly dependent of the cross section of the artery. For peripheral arteries this simple analogy points to the value of restoring lumen diameter to its unconstrained diameter, thereby increasing the flow rate to more distal tissue (i.e.—the foot). The ability for serration angioplasty to generate a larger lumen consistently has been observed (FIGS. 76, 78A, and 78B) producing a higher volume flow rate over plain balloon angioplasty (FIG. 75). The ability for serration angioplasty to achieve higher volume flow rate can be described as or associated with an optimized outcome such as "vessel remodeling". Vessel remodeling is based on the hypothesis that the internal diameter (D) and wall thickness (w) of each segment in a network are subject to continuous structural adaptation in response to stimuli that the segment experiences. Therefore, when a diseased vessel is effectively treated such that the vessel behavior (compliance, flow dynamics, and internal diameter) are improved, as has been observed with serration angioplasty embodiments, it is appropriate to correlate these outcomes to positive vessel remodeling. From the lumen outward, the layers of the lumen include the intima, the internal elastic lamina, the media, the external elastic lamina, and the adventitia. As described herein, serration angioplasty generated a series of interrupted voids in the vessel wall, typically penetrating through the intima, internal elastic lamina, and into the media. In some methods, only the intima is penetrated. In some methods, only the intima and the internal elastic lamina are penetrated. In some methods, only the intima, the internal elastic lamina, and the media are penetrated. In some methods, the media is penetrated to a depth within the media. In some methods, the media is penetrated to the external elastic lamina. In some methods, the external elastic lamina is not penetrated. In some methods, the media is entirely penetrated. In some methods, the media is partially penetrated. In some methods, only the intima, the internal elastic lamina, the media, and the external elastic lamina are penetrated. In some methods, the adventitia is not penetrated. In some methods, the adventitia is partially penetrated. In some methods, the internal elastic lamina is penetrated but the external elastic lamina is not penetrated. In some methods, at least the internal elastic lamina is penetrated. With the internal elastic lamina being serrated and allowed to relax under the balloon pressure, the treated diseased region becomes less turbulent, less rough, with fewer interruptions or perturbations in the flow stream, reducing wall friction or flow resistance. Observations seen in the vast majority of clinical cases where serration angioplasty is used as either a standalone or a conjunctive therapy the final results show an arterial outline and flow dynamics with minimal to no appearance of vessel or disease discontinuity or disruption to the flow. This phenomena is described herein as stage 1 positive vessel remodeling.

The method for assessing flow improvement for any intervention can be calculated by first starting with the initial arterial flow ($F_i$) which is calculated by taking the half of the product of the Avg. initial RVD and (1−% stenosis) to the $4^{th}$ power. Then taking the final arterial flow ($F_f$) which is calculated by taking half of the product of the Avg. final RVD and (1−% residual stenosis) to the $4^{th}$ power. Taking these two values, the change in flow as the $F_f - F_i$ can be calculated. Therefore the % improvement in flow for the intervention is simply $(F_f - F_i)/F_i$. Finally when comparing data $set_{(1)}$ against data $set_{(2)}$, the % improvement in flow of data $set_{(1)}$ relative to data $set_{(2)}$ can be calculated by taking the % $improvement_{(study\ 1)}$ minus the % $improvement_{(study\ 2)}$ divided by % $improvement_{(study\ 2)}$.

$$F \approx r^4$$

Formula 2: Simplified Version of Poiseuille's Law, where, $F$ is the flow in the artery and $r$ is the radius.

$$F_i = ((RVD/2) \times (1 - \%\ \text{stenosis}))^4$$

Where, $F_i$ is the initial flow across the stenotic lesion.

$$F_f = ((RVD/2) \times (1 - \%\ \text{residual stenosis}))^4$$

And therefore, the % improvement in flow in an artery= $(F_f - F_i)/F_i$

Where, $F_i$ is the initial arterial flow, $F_f$ is final arterial flow.

Finally, a comparative analysis can be performed between multiple studies with different pre-treatment vessel radius by comparing % improvement in flow between studies. The limitation of this technique is that the biggest contributing variable is the degree of initial stenosis. As initial % stenosis increases, the radius for flow decreases which when calculated to the $4^{th}$ power shrinks very quickly for every small increase in initial stenosis.

To reduce the potential of allowing computational misinterpretation in highly occluded vessels, a volume flow rate ratio should be calculated with $(r_{post}/r_{pre})^4$, where $r_{post}$ is the vessel radius post-treatment and $r_{pre}$ is that pre-treatment. Vessel radii (r) were calculated as r=RVD×(1−% stenosis)/2.

Assumptions used to derive the simplified equation, flow=$r^4$.

Flow restrictions or reductions related to turbulence are not considered. Lack of information to assess the potential of turbulence flow is missing from the literature (i.e. stenosis characteristics, accurate three-dimensional arterial structure, etc.).

Interventional data such as balloon sizing and balloon pressure, although offering insight to compliance relative to vessel sizing, does not offer insight into final flow volume.

The assumption is that the cross section is round (like a pipe) but biological growth is seldom if ever truly round.

Two comparative models were identified for assessing post treatment acute improvements in peripheral arteries. One model (FIG. 75) assessed changes in volumetric flow rates and the second (FIG. 76) assessed improvements in residual stenosis versus pre-treatment RVD (pre-treatment). The data reviewed showed serrated balloon angioplasty consistently outperformed plain balloon angioplasty by either method. Serrated balloon angioplasty achieved a 2.4× greater average flow rate ratio over plain balloon angioplasty for stenotic lesions ranging from 62% to 93% and achieved a 62% less residual stenosis for 99-100% stenotic lesions. To simplify the method for calculating the effect of residual stenosis, a simple derivation of Poiseuille's Law is considered. To illustrate the method, the method is used to calculate the effect on the volume of flow when a 5% increase in the vessels radius is achieved.

When blood flows along a blood vessel, the flow F (the volume of blood per unit time that flows past a given point) is proportional to the fourth power of the radius r of the blood vessel:

$$F=kr^4$$

Formula 3: Simplified Version of Poiseuille's Law, where $F$ is the flow in the artery and $r$ is the radius, and k is a constant.

A partially clogged artery can be expanded by an operation called angioplasty, in which a balloon-tipped catheter is inflated inside the artery in order to widen the artery with the goal of restoring the normal blood flow. It is shown that the relative change in flow is highly dependent on the radius, since the flow is proportional to the fourth power of the radius r. Therefore, the relative change in r can dramatically increase flow. The question becomes how will a 5% increase in the radius affect the flow of blood? Applying differential equation to solve, wherein the flow is equal to a constant k times $r^4$ is equation and the differential equations are shown below.

$$F = k(1.00r)^4$$

$$\frac{dF}{dr} = 4k(1.00r)^3$$

Therefore, a 5% increase in radius can be illustrated as a multiple of 1.05.

$$F = k(1.05r)^4$$

$$\frac{dF}{dr} = 4.20k(1.05r)^3$$

Comparing the differential equations, a relative change in radius of 0.05 (5%) results in about a relative increase of blood flow of 0.20 (20%). Since the change in radius is directly proportional to the change in diameter, the effect of the increase in blood flow remains the same. Even very small increases in diameter can have dramatic influence on flow.

In the art of angioplasty, a balloon is used to stretch open an artery. However, the vessel wall often experience stenosis or narrowing after the balloon is removed. The stenosis can be responsible for significant loss of luminal gain.

However, the serration technology described herein, has several advantages over traditional angioplasty. The serration technology significantly can control stenosis by having more permanent lumen gain after the balloon is removed. The serration technology can significantly control stenosis by expanding a balloon using a different modality than angioplasty. While angioplasty relies on high pressures to stretch the artery open, serration technology provides sites of nucleation for one or more permanent cleavage lines. The serration technology can significantly control residual stenosis by altering the surface of the plaque, while leaving the plaque adhered to the vessel wall. The vessel is unable to snap back to a pre-dilation diameter due to the permanent change. The cleavage line or lines are created through low pressure, crack propagation process. By remodeling the vessel through serration technology, As shown by the formulas above, any increase in radius can have significant impacts of flow. Increasing the radius by a mere 5% can increase flow by 20%. In other words, any permanent change in radius can have a four-fold increase in flow. Any permanent change in diameter can have a proportionate impact on flow. In other words, a decrease in residual stenosis by 5% results in an increase in blood flow by 20%. Controlling the inherent ability of the vessel to narrow can lead to dramatic gains in lumen flow.

A simple equation for evaluating the final post treatment flow can be seen as:

$$F = k[(1+L)r]^4$$

$$\frac{dF}{dr} = 4k((1+L)r)^3$$

Formula 4: Simplified Version, where $F$ is the flow in the artery and $r$ is the radius, and $k$ is a constant, and $L$ is the percentage of decrease residual stenosis.

In many cases the need for significant increase in volumetric flow to preserve tissue, save limbs, and organs can be a matter of life and death. The volumetric flow of a vessel is directly correlated with the vessel diameter. Vessel stenosis refers to conditions which narrow the blood vessel, such as the buildup of plaque on the vessel walls. The calculations herein point to the need for designs capable of reducing the interference of the vessel's radii or obstruction to the normalized or healthy radii. There is a need to reduce stenosis by restoring the vessel diameter through positive vessel remodeling. Serration angioplasty has shown effective clinical performance for increasing vessel diameter, while reducing dissections that lead to interrupted flow and pressure drop across the lesion. Serration angioplasty can cause prick points along the internal elastic lamina, which allow the internal elastic lamina to relax, or tear along the serrated line of weakness, under the balloon pressure to restore a normalized or healthy radii of the vessel. Since serration angioplasty does not disturb vast majority of the plaque surface, the plaque remains largely adhered to the enlarged vessel wall. The serrations cause cleavage planes, allowing the plaque to separate only along longitudinal lines. Serration angioplasty can cause the treated region to be less turbulent or less rough with fewer interruptions or perturbations in the flow stream. Serration angioplasty can cause the treated region to have a more uniform arterial diameter across the treated zone. The uniformity of the vessel diameter or the low percentage in variation of vessel diameter across the treatment zone aids in volumetric flow by limiting regional disruption to the flow path way. Serration angioplasty can reduce wall friction or flow resistance. Serration angioplasty can increase the local vessel size in response to relaxing the internal elastic lamina along cleavage planes. The positive remodeling increases the vessel size to increase blood flow. The positive remodeling is an outward compensatory remodeling of the diameter of the vessel. Serration angioplasty has shown clinically an ability to increase lumen gain and reduce recoil both with low residual stenosis. In the second phase of positive remodeling, the lumen recovery can be seen as a relaxing event within the cellular network of the vessel wall including the remodeling of the internal elastic lamina, after serration and expansion under low pressure. The final stage of positive remodeling, lumen enlargement can restore the diseased vessel diameter to the pre-diseased state. The lumen enlargement can restore the diseased vessel diameter to an adjacent non-diseased diameter. The lumen enlargement can restore the vessel diameter to a normalized vessel diameter. The lumen enlargement can restore the vessel diameter to an average diameter of healthy patients.

Designs capable of shifting arterial diameters to nominal without vessel damage or vessel reaction are of great value clinically and are envisioned herein. Serration angioplasty can cause progressive lumen gain. Serration angioplasty can expand the vessel without damage to the underlying tissue or structures. In some methods, the external elastic lamina is not penetrated, and remains intact. In some methods, the adventitia is not penetrated, and remains intact. Serration angioplasty forms longitudinal cleavage planes under low pressure, causing significantly less lifting of the plaque surface and separation of the plaque from the vessel wall.

Technologies available in the market miss the mark with most leaving 30% or greater residual stenosis. These technologies fail to restore the normalized or healthy radii of the vessel. Instead, the resulting vessel is still obstructed by at least 30% of the ideal diameter. Residual stenosis is either an inefficiency of the technology to restore the vessel to its nominal diameter or the subsequent decrease in diameter after treatment, often referred to as recoil. Recoil can be caused by the inherent nature of the diseased vessel, which can be stretched by the angioplasty balloon, but returns toward the pre-treatment diameter once the pressure from the balloon is removed. It is noted that recoil can occur even when the calcium deposits are broken during angioplasty. The vessel itself can include ring-like elastic layers that form boundaries between layers of the vessel. The vessel itself can have elastin fibers. The elastic structures in the vessel are important for rheological function by regulating the internal diameter of the vessel. However, these same elastic structures can contribute to recoil after angioplasty. The vessel is predisposed to returning to its original diameter. Therefore, angioplasty that stretches the vessel wall is trying to counteract the natural tendencies of the vessel. Residual stenosis can be caused by the non-permanent nature of the application of pressure, which may only temporarily remodel the vessel. Recoil is mostly driven by elastin in the artery that is not broken. This elastin is predisposed to return to its original state. Therefore, stretching the vessel during angioplasty is similar to stretching a rubber band. The vessel recoils toward its original diameter after the pressure is removed. To a lesser extent, recoil can also be driven by unaltered plaque which may also recoil to an original diameter. When the balloon pressure is removed, the vessel's elastin can recover alone, or in combination with any remaining plaque, significantly decrease any luminal gain. It is common that post angioplasty the vessel recoils when the balloon pressure is removed, leading to a decrease in diameter of the vessel. The degree of recoil is correlated with many variables, including the lesion location and size, as well as patient specific factors and the treatment device. Elastic recoil of the vessel, leading to residual stenosis, is a significant limitation with current technologies.

To enable greater vessel growth, angioplasty with serration design features offer several unique advantages including low pressure angiography. This enables examination of the blood vessels by radiopaque substances. Serration angioplasty advantageously allows for calcium fracturing also described as lithotripsy. This allows subsequent or concurrent treatment of the plaque surface. In some methods, additional energy such as ultrasonic, electrical or hydraulic shockwaves are applied to the plaque. The value of lithotripsy using Serration, either with ultrasonics or shockwaves or without ultrasonics or shockwaves, is the ability to break the plaque into smaller particles allowing more effective vessel expansion and enabling access for therapeutics through the diseased region and into the deeper tissues. Serration angioplasty advantageously allows for linear disruptive intimal separation. The serrated lines are longitudinally oriented within the vessel. The intima is an inner layer near the lumen of the vessel. In some methods, the plaque remains buried beneath or adhered to the intima. The serrations can extend through the intima and/or the internal elastic lamina to begin the nucleation of the cleavage planes. The cleavage planes can propagate through at least some of the layers of intima, the internal elastic lamina and/or the media. Serration angioplasty advantageously allows for vessel lumen gain without vessel rupture. The cleavage planes do not propagate entirely through the layers of the vessel. The cleavage planes do not propagate through the adventitial layer. The cleavage planes do not propagate through the connective tissue. The cleavage planes do not rupture the vessel wall. Serration angioplasty can have these advantages and more, all while using familiar angioplasty techniques. Here we explore design and methods that aim to limit residual stenosis and increase volumetric flow through the vessel post treatment.

In vessels where poor or no blood flow has occurred for long periods of time it has been noted that myogenic mechanism can occur. The myogenic mechanism is contraction initiated by a muscle fiber instead of outside stimulus. The contraction significantly reduces the blood flow. If the pressure within a vessel is suddenly increased, such as post angioplasty, then the vessel responds by constricting. It is noted that the myogenic mechanism could be the observation described in literature as recoil or more commonly vasospasm. This is part of the autoregulation mechanism of the vessel which maintains constant blood flow at varying pressures. The response is initiated by the vessel itself. Diminishing the pressure within the vessel causes relaxation and vasodilation. When then balloon of angioplasty is removed, the autoregulation mechanism contracts to diminish lumen gain.

The ability of serration angioplasty to penetrate the internal elastic lamina of the vessel can limit the ability of the vessel to undergo myogenic mechanism and the follow-on vasospasm. Serration angioplasty can limit the contraction of the myocyte by penetrating the internal elastic lamina. The circumference of the vessel can be interrupted along cleavage lines, thereby limiting the ability of the muscle fibers to contract. Serration angioplasty can alter the autoregulation mechanism that contracts the vessel to maintain a constant, and thus reduced, blood flow. In addition, serration angioplasty being applied at low pressures allows for the internal elastic lamina to be penetrated and encouraged to separate along the penetrated serrated line. The wedge dissectors described herein can form divots in the plaque surface at low pressure. The wedge dissectors can begin crack propagation through the plaque and the layers of the vessel. Crack propagation can be considered two processes, the act of penetration at the wedge dissectors and the shear-stress effect at the planes oriented to the loading direction. The wedge dissectors can initiate the crack. However, the blunt edge of the wedge dissector is not cutting or scoring the plaque and the underlying tissues. Rather, the low pressure of the balloon facilitates the shearing of the planes, leading to controlled and slow crack propagation through tissue layers. The tension applied by the balloon to the surface of the lumen and the plaque can facilitate steady cleavage plane growth. The low pressure application by the balloon prevents unstable growth or fracture. The depth of the cleavage plane can be controlled in part by the initial depth of penetration of the wedge dissectors and the low pressure balloon angioplasty. The crack growth is controlled to extend through certain layer, while leaving other layers of the vessel wall intact.

Serration technology is the only known method that allows for precise control both the beginning and the end of the cleavage plane. The cleavage planes can propagate through at least some of the layers of intima, the internal elastic lamina and/or the media. In some methods, the crack growth can stop before reaching the external elastic lamina. In some methods, the crack growth can stop before reaching the adventitia. In some methods, the crack growth can stop before extending through the adventitia. The crack propagation can cease due to the limited driving force from the low pressure balloon. The crack propagation can cease due to the small depth of penetration that initiates the crack. The crack propagation can cease due to the changing makeup of the layers. The crack propagation can cease due to the increase resistance from layers. The crack propagation can be slow and steady. The crack propagation can occur over an extended period. The crack propagation can occur over 5 seconds, 10 seconds, 15 seconds, 20 seconds, 25 seconds, 30 seconds, 35 seconds, 40 seconds, 45 seconds, 50 seconds, 55 seconds, 60 seconds, 70 seconds, 80 seconds, 90 seconds, 100 seconds, 120 seconds, 180 seconds, more than 30 seconds, more then 45 seconds, more than 60 seconds or any range of two of the foregoing values. In some cases, the external elastic lamina can also be penetrated and encouraged to separate while minimizing cellular trauma and histological reaction to the cellular separation event. The crack can propagate through the external elastic lamina. The crack can propagate through the adventitia. The adventitia is the outermost layer of the vessel which contains tissue, nerves, and the vasa vasorum. The low pressure crack propagation can extend though the vessel layers in a controlled, slow and steady pace. The crack propagation forms an interruption in the circumference of the vessel, thereby longitudinally segmenting the vessel in the treatment site. The controlled low pressure crack propagation can minimize trauma to the individual cells and tissues. In some cases, the external elastic lamina is not penetrated.

It is envisioned that designs intended to modify the tissue in a more natural and less injurious are of value to tissue healing. While not being bound by a theory, the controlled slow, low pressure expansion and crack propagation is more like a steady pull on the tissue leading to separation at the cellular level. This is in contrast to a cutting action, wherein cutting blade relies on high pressure at the edge to push the material apart. The cutting edge crushes a wider band of cells underneath the edge. Instead of relying on a cutting edge, the serrations can rely on crack propagation which can extend through a single line of cells. The crack can separate adjacent cells, leading to much less cellular trauma. The crack propagation can also occur at lower pressures than needed for cutting. The low pressure is only needed to continue the slow crack propagation, rather than a higher force to cut or score tissue. The separating force can imparted by the tension on the surface of the lumen wall, stretching the tissue to further the crack, rather than the high forces concentrated at a blade tip. Serration technology can thus separate cells better than the sharpest knives. The crack propagates between individual cells, smaller than the thinnest blade edge. The wedge dissector itself does not extend between the individual cells, rather the crack that is initiated by the wedge dissectors extends between the individual cell. The crack propagates at lower pressures. Serration technology can cause longitudinal cleavage planes in a more natural fashion by separating tissue at the cellular level. This separation causes less trauma by impacting a smaller surface area. This separation causes less trauma by impacting few cells. This separation causes less trauma by gently pushing cells along the crack in a slow and controlled manner. In some cases, the gentle tearing is easier for the tissue to repair. During tissue repair, cells migrate to the crack site and eventually form new granulation tissue which matures into scar tissue. In some cases, the scar tissue can restore the tissue structure and function over time. The crack can form a thin, narrow line between cells, which is easier to repair than a thick cut or slice, thereby reducing healing times. The crack can form with limited depth of penetration, which also may be easier to repair than a deeper cut. The crack can form with limited length along the vessel, limited by the length of the lesion, which also may be easier to repair than a cut over a longer length. Further, the reduced trauma to the cells can facilitate healing. These envisioned designs, that include serration, where tissue is minimally torn at the gross anatomical level and encouraged to separate at the cellular level offer advantages that include reduced healing times and increased cellular repair. It is in envisioned that in some of these designs the tearing regions are shallow in depth and shorter in length limiting cellular trauma and encouraging cellular repair.

In angioplasty, in some methods, a balloon is utilized which has an inflated diameter larger than the intended diameter of the vessel. This can be conveyed by a ratio between an expected vessel diameter and a balloon diameter. For instance, a 1:1 ratio would be an equal expected vessel diameter and the balloon diameter. In this example, an expected vessel diameter of 5 mm would utilize a 5 mm balloon. As discussed herein, the autoregulation mechanism of the vessel can cause recoil such that the vessel contracts after the balloon is removed. In some methods, the ratio is different than 1:1, such as 1:1.1, 1:1.2, 1:1.3, 1:1.4, 1:1.5, 1:1.6, 1:1.7, 1:1.8, 1:1.9, or 1:2. For instance, a 1:1.1 ratio would utilize a larger balloon (equal to the vessel diameter times 1.1) compared to the intended diameter of the vessel. In this example, an expected vessel diameter of 5 mm would utilize a 5.5 mm balloon. For instance, a 1:2 ratio would utilize a larger balloon (equal to the vessel diameter times 2) compared to the intended diameter of the vessel. In this example, an expected vessel diameter of 5 mm would utilize a 10 mm balloon.

Serration angioplasty can utilize a balloon with an inflated diameter larger than the intended diameter of the vessel. In some embodiments, the use of designs with serration features of 1:1.1 balloon to reference vessel size have shown to aid in acute vessel radial expansion with minimal vessel reaction or vasospasm. To further increase the vessel's diameter, the use of balloon sizes that are greater than 1:1.1 to the reference vessel diameter is envisioned. The use of serration angioplasty balloon to reference artery ratio of 1:1.1, 1:1.2, 1:1.3, 1:1.4, 1:1.5, 1:1.6, 1:1.7, 1:1.8, 1:1.9, or 1:2 or a fraction between these ratios are envisioned. The serration balloon design enables greater arterial growth which allows for better residual blood flow and low residual stenosis. This includes designs that are able to be used with balloon to artery ratio of greater than 1:1.1.

Using Formula 2: Simplified Version of Poiseuille's Law from above, it can be calculated that percentage of possible total flow volume a vessel can produce is directly correlated with the residual stenosis obstructing the flow and thereby limiting the total flow volume. As the vessel is opened towards the pre-diseased diameter or the native reference vessel diameter, the volumetric flow rate approaches 100 percent (FIG. 2). The 1:1 ratio would be sufficient if other forces were not in play, such as the cellular or systemic mechanisms that can encourage contraction when the outward balloon force is removed. The balloon structure and its outward force against the diseased vessel limits the ability of the vessel to contract during balloon inflation. However, when the balloon is removed, the muscle fibers as well as other cellular structures including but not limited to the elastin rings, such as the internal elastic lamina, can inherently contract on their own accord when the balloon is removed. There are several mechanism that can cause contraction of the vessel after the balloon deflates. The vessel, interstitial tissue, musculature itself can counteract angioplasty through recoil.

The recoil of the vessel after angioplasty is understood to be caused by a combination of factors, including the elastic or inelastic properties of the arterial wall, as opposed to the mechanical forces applied during the procedure.

During angioplasty, as the balloon is inflated inside a narrowed or blocked segment of a diseased artery, an outward pressure is exerted to the artery wall. The pressure from the inflated balloon stretches the vessel wall, causing it to expand and widen the blocked segment. The diameter of the vessel is temporarily enlarged. However, as soon as the balloon is deflated and removed, the vessel wall is known to contract inward, reducing the original gain achieved during the angioplasty, which is understood as recoil.

The degree of recoil can vary depending on the patient's specific anatomy, disease state, and the location of the vessel blockage. If the vessel wall is particularly stiff or fibrotic, then the vessel wall may be more prone to recoil after the balloon is removed. Additionally, if the balloon is not inflated to the appropriate pressure or the size of the balloon is undersized relative to the vessel, the balloon may not fully stretch the arterial wall, leading to incomplete dilation and increased risk of recoil.

In some cases, the use of a stent can help prevent recoil by providing a scaffold to hold the vessel wall open after the angioplasty procedure. However, stents are not always necessary or desirable for every patient or every blockage. Instead, the serration technology described herein addresses recoil by vessel remodeling through a more permanent change in the radius of the vessel. The vessel remodeling can be longer lasting. The vessel remodeling can be non-acute. While other angioplasty techniques may temporarily alter the diameter of the vessel, the serration technology leads to lasting changes, including minutes, hours, days, and months after the procedure. The serration technology has substantially improved recoil, leading to the more permanent change in vessel diameter. The serration technology has the ability to expand the vessel to limit recoil, enabling the greatest lumen and therefore the highest volumetric flow through the vessel is desirable. As described herein, slight increases in radius can lead to a four-fold increase in flow. Similarly, slight decreases in residual stenosis can lead to a four-fold increase in flow. Therefore, clinically significant results can occur if there is a permanent change in radius or stenosis. The use of serration angioplasty capable of minimal vessel trauma with largest volumetric blood flow are described herein. The embodiments herein are non-limiting. The disclosure envisions other embodiments capable of minimal vessel trauma with largest volumetric blood flow. The disclosure envisions other embodiments of vessel remodeling. The disclosure envisions other embodiments of permanent gain in radius and decrease in stenosis.

Serration angioplasty technology, as described herein, induces a series of lines of weakness longitudinally oriented to the vessels axis and is aided by balloon pressure to influence the artery to expand. The expansion occurs with less pressure needed. The low pressure of the balloons gradually expands the artery and gradually propagates the crack. This low pressure expansion is slow and controlled. The series of serrated fissures limit the typical arterial vasoconstriction physiology accompanied by angioplasty alone. There is less recoil with serration technologies due to the manner in which the tissue and plaque are separated. Serration angioplasty technology produces the greatest opportunity for the vessel to reach the reference vessel diameter. Serration angioplasty produces predictable, repeatable lumen gain. Serration angioplasty allows for the controlled depth of crack propagation, leading to defined circumferential segments along the vessel wall. The contraction forces are inherently limited by the cleavage planes, limiting the ability of the muscle fibers to contract. In a study of serration angioplasty technology, physicians were encouraged to increase balloon diameters by 0.5 mm when the residual stenosis did not meet the study end point of 30 percent. For instance, the physicians could increase the ratio from 1:1 to 1:1.1, to utilize a 5.5 mm balloon for a 5 mm intended diameter if the residual stenosis exceeded 30 percent. This increase in balloon diameter led to acute vessel radial expansion with minimal vessel contraction. This increase in balloon diameter can also improve blood flow dynamics by reducing the residual stenosis. Methods where balloon diameters greater than the reference vessel diameter are chosen to improve vascular flow dynamics and improve vascular tone at the system and cellular level are envisioned. Such methods include upsizing the serration balloon technology such that the technology aims to produce sizes greater than 1.1 times the interpreted size of the vessel. The methods can utilize technology with a ratio of 1:1.1, 1:1.2, 1:1.3, 1:1.4, 1:1.5, 1:1.6, 1:1.7, 1:1.8, 1:1.9, or 1:2 to utilize a larger balloon compared to the intended diameter of the vessel.

It is known and reported that vascular measurements from angiography show vascular dimensions smaller than measurements taken from intravascular ultrasound or optical coherence tomography. Angiographic imaging is an examination by x-ray technology of blood vessels using radiopaque substances. Angiographic imaging provides perspective of the flow channel but does not give any perspective image reference for the thickness for the media or adventitia layers. Diseased states for vascular vessels can produce vessel layers with a large variety of thicknesses limiting effective interpretation of the vessels native or healthy diameter. Therefore measurements from commonly used angiography can generate imaging easy to misinterpret the true native vascular diameter. This misinterpretation of imaging can guide the physician to choose treatment modalities that are undersized for the true native vascular diameter and thereby limit the full potential of the lumen volumetric capacity of the transport vessel. Serration angioplasty can be designed to provide effective treatment of vessels with an aim to more fully expand the vessel and reduce vascular recoil using treatment sizing above 1:1.1 to vessel size. It is envisioned that up sizing the treatment option to vessel size 1:1.1, 1:1.2, 1:1.3, 1:1.4, 1:1.5, 1:1.6, 1:1.7, 1:1.8, 1:1.9, or 1:2 or above 1:1, above 1:1.1, above 1:1.2, above 1:1.3, above 1:1.3, above 1:1.4, above 1:1.5, above 1:1.6, above 1:1.7, above 1:1.8, above 1:1.9, above 1:2 or any range of the foregoing, can offer greater advantage and increase volumetric flow rates. In some embodiments, the up sizing of the balloon can prevent the incomplete dilation. In some embodiments, the up sizing of the balloon can reduce the risk of recoil. In some embodiments, the up sizing of the balloon can increase the radius of the vessel leading to four-fold increase of flow relative to the percentage increase of the radius. In some embodiments, the up sizing of the balloon can reduce the stenosis of the vessel leading to four-fold increase of flow relative to the percentage reduction in stenosis. Serration angioplasty can be designed to provide effective treatment of vessels with an aim to more fully expand the vessel to have a stenosis rate less than 30 percent.

There is continuous need to improve the methods for treating occlusive disease, including balloon angioplasty and other related treatment systems. In some embodiments, the ability to inexpensively attached focal intima disrupter is needed. The design of such a balloon requires an innovative approach to fabrication such that the features above the balloon surface are effectively placed with minimal additional cost to the cost of the balloon. Embodiments that enable features to be fused or integrated within the balloon blowing cycle or in series to the balloon blowing offer a significant cost savings and can enable more effective balloon designs. Embodiments with desirable balloon features such as pushability, crossability, profile, robustness, flexibility, and ability to deliver drugs are envisioned and incorporated in balloon designs including diameter, length and cone shape could all be incorporated independent of features protruding above the balloon surface. All embodiments incorporate features and processes that either independently or collectively facilitate strategic cost reduction in catheter based balloon designs.

Balloon Features

Pushability, crossability and flexibility are all desired functions for endovascular technologies. Many of the designs envisioned incorporate longitudinally oriented structures that are incorporated between layers of polymers. In some embodiments, the main shaft comprises longitudinally oriented structures. In some embodiments, the inner member comprises longitudinally oriented structures. In some embodiments, the balloon comprises longitudinally oriented structures. The longitudinally oriented structures can be in the form of strips. The longitudinally oriented structures can be in the form of ridges. The longitudinally oriented structures can comprise the same material as the main shaft, inner member, or balloon to which the longitudinally oriented structures attach. The longitudinally oriented structures can comprise a different material as the main shaft, inner member, or balloon to which the longitudinally oriented structures attach. The longitudinally oriented structures can comprise the same density as the main shaft, inner member, or balloon to which the longitudinally oriented structures attach. The longitudinally oriented structures can comprise a different density as the main shaft, inner member, or balloon to which the longitudinally oriented structures attach. The longitudinally oriented structures can offer structural stability. The longitudinally oriented structures can allow for the translation of the energy across the balloon body. The longitudinally oriented structures can include one or more structures. The longitudinally oriented structures can be disposed circumferentially around the main shaft, inner member, or balloon to which the longitudinally oriented structures attach. The longitudinally oriented structures can be equally spaced. The longitudinally oriented structures can be unequally spaced. The main shaft, inner member, or balloon can include a single longitudinally oriented structure or one or more longitudinally oriented structures.

The longitudinally oriented structures can aid in the transmission of energy from the user to increase pushability of the device. The longitudinally oriented structures can aid in the transmission of energy from the user to increase crossibility of the device. The longitudinally oriented structures can aid in the transmission of energy from the user to increase trackability of the device. The longitudinally oriented structures can enable the device to remain flexible to navigate the vasculature. Therefore, there a needed to increase pushability and crossability, while maintaining flexibility and trackability. The inclusion of longitudinally oriented structures in the main shaft, inner member, or balloon are each areas where ridges of denser material may aid in the translation of energy to aid in increasing pushability while minimizing a decrease in trackability. Two common design criteria for balloon catheters are the features of pushability and navigation ability, or trackability. The catheter must be pushed from a proximal end to advance the catheter through the vessel. The catheter must be able to navigate the non-linear, tortuous vessel. Thus, these two features are opposed since increasing pushability often decreases the navigation or trackability. The serrated balloon balances these criteria in part due to the longitudinally oriented structures. The longitudinally oriented structures can be made from metal, polymer, or other rigid or semirigid materials. The longitudinally oriented structures offer structural stability for translation of the energy across the balloon body. The longitudinally oriented structures offer structural stability while maintaining flexibility during navigation through tortious anatomical features. When metals are used, the material flexibility of the longitudinally oriented structures can be increased through 1, 2, 3, 4, or more tempering steps. The tempering may be performed at much lower temperatures than annealing processes, such as below 300 C, or more commonly between 300 C and 400 C, or at higher temperatures, such as between 400 C and 500 C. The longitudinally oriented structures can be strips with wedge dissectors. The longitudinally oriented structures can deflect along the length, thereby increasing the navigation ability. The two or more longitudinally oriented structures can flex independently of each other. The longitudinally oriented structures can resist compression. The longitudinally oriented structures can allow bending along one direction but resist bending along another direction. In some embodiments, the longitudinally oriented structures can be uncoupled from each other. The longitudinally oriented structures can be spaced apart from each other. The longitudinally oriented structures can curve along vessels. The longitudinally oriented structures can transmit push forces. The longitudinally oriented structures can transmit forces without buckling longitudinally. The longitudinally oriented structures can transmit forces without kinking longitudinally. Due in part to the incorporation of these features and the fact that they lay longitudinally oriented, the balloon is more pushable and capable of crossing highly rigid and diseased lesions. The ability to cross total or highly stenotic occlusions is due in part to the enhanced rigidity that these longitudinally oriented beam like structures of the strips offer to the balloon body. The longitudinal beam elements of the strips are symmetrically oriented around the surface the balloon body which enhance column strength. It is the enhanced column strength provided by the beam array of the strips that increases pushability and crossability. The beam design of the strips with its flat bottom and periodic raised wedge dissectors offers a pliable and flexible beam which offers increase flexibility and torque ability while minimizing the brittleness and maintaining the design's column strength. When the beams of the strips are captured or retained within the balloon layer stack, the beam can be more stable. After pleating the strips under the folds of the balloon wings and crimping the balloon wings down on top of the strips, the layer stack of material that makes up the balloon layers in addition to the strips, increase the stability and enhances the capability of the serration balloon to translating forces from the delivery catheter to the distal end of the balloon and the catheter tip (FIG. 79). The longitudinally oriented structures, such as beams embedded and folded within the balloon, enhance the balloon's column strength allowing greater transfer of energy from the catheter body across the balloon body to the tip of the catheter. The longitudinally oriented structures significantly increase the pushability, while not adversely impacting the ability to navigate to the lesion. The strip can be designed to avoid buckling and kinking along the column, while flexing and deflecting while traversing along the vasculature.

In some embodiments, drug uptake from a drug eluting balloon at a treatment site in a vessel can be improved by a method of pretreating a site in a vessel by expanding a pretreatment balloon at the site to create a plurality of micro fissures into the media layer of the vessel wall. This pretreatment balloon embodiment would have a plurality of strips with each strip containing a plurality of wedge dissectors spaced apart along a surface of each strip. These strips extend longitudinally along an outer surface of the pretreatment balloon. This pretreatment balloon embodiment could then be deflated and rotated by a fraction of an angle, that in some cases is different from the spacing of each strip along the circumference of the balloon. As one non-limiting example, if there are 4 wedge dissectors spaced 90 degrees apart along the circumference of the balloon, the balloon can be rotated, for example, 45 degrees and then reinflated to create new serrations along the vessel wall where there were none previously. The pretreatment balloon would then be re-inflated so that the strips on the pretreatment balloon are at different positions from than the original inflation, and the wedge dissectors are in a position to create serrations in areas of the vessel wall that were previously free of serrations. It is understood that in a clinical setting the effect of rotation a specified or intentional degree can be complicated, due to an individual's tortuosity and degree of disease in their vessel. It is anticipated that the need to predict the angle for rotation is less important and that a physician inflating, deflating, pulling the balloon back at least 1 cm and then rotating the proximal hub and then reinserting the balloon will typically allow the balloon to rotate and be oriented at a different angle from the initial inflation. The pretreatment balloon would then be removed and a drug eluting balloon would be placed at the site. The drug eluting balloon would be expanded to contact with the vessel wall and allow drug to elute from the surface of the drug eluting balloon into the micro fissures, through the intima, and in some cases through the internal elastic lamina, and in some cases into the media or other sub-intimal tissue bed. In some embodiments, the design of the pretreatment balloon can be rotated aiming for, in some cases, between about 1 degree and about 180 degrees or the fraction of the angle separating the wedge dissectors. Typically, the wedge dissectors are placed at circumferential intervals with divisions of 360 degrees. Therefore if 3 wedge dissectors are present then the circumferential spacing is equal to 3 divided by 360 or 120 degrees. In some embodiments, the balloon can be rotated once in a first direction, and then repeated 1, 2, 3, 4, 5, or more times in the same or an opposite direction to increase the number of serrations in the vessel wall.

As one non-limiting example, the balloon can be rotated and then reinflated to create new serrations along the vessel wall where there were none previously. The balloon can be rotated 5 degrees, 10 degrees, 15 degrees, 20 degrees, 25 degrees, 30 degrees, 35 degrees, 40 degrees, 45 degrees, 50 degrees, 55 degrees, 60 degrees, 65 degrees, 70 degrees, 75 degrees, 80 degrees, 85 degrees, 90 degrees, 95 degrees, 100 degrees, 105 degrees, 110 degrees, 115 degrees, 120 degrees, 125 degrees, 130 degrees, 135 degrees, 140 degrees, 145 degrees, 150 degrees, 155 degrees, 160 degrees, 165 degrees, 170 degrees, 175 degrees, 180 degrees, or any range of two of the foregoing values. As one non-limiting example, the balloon can be inflated to create a first set of serrations. The balloon can be deflated, rotated, and then reinflated to create new serrations. The balloon can be rotated in place to create a second set of serrations along the same segment of vessel. The balloon can be rotated to create serrations where there were previously none. As one non-limiting example, if there are four strips wedge dissectors spaced 90 degrees apart, the balloon can be rotated 45 degrees to equally space the serrations along the circumference of the vessel. As one non-limiting example, if there are four strips wedge dissectors spaced 90 degrees apart, the balloon can be rotated less than 45 degrees to unequally space the serrations along the circumference of the vessel. As one non-limiting example, if there are three strips wedge dissectors spaced 120 degrees apart, the balloon can be rotated 60 degrees to equally space the serrations along the circumference of the vessel. As one non-limiting example, if there are three strips wedge dissectors spaced 120 degrees apart, the balloon can be rotated less than 60 degrees to unequally space the serrations along the circumference of the vessel.

In some embodiments, the method of pretreatment of the site is achieved with wedge dissectors that have radially-outward facing surfaces with shapes approximating a rectangular, ellipse, or oval. In some embodiments the shape is more elliptical in general but the arc from the minor axis to the vertex of the major axis does not follow basic elliptical mathematics. In these conditions the final shape is more like a pointed oval in shape.

In some embodiments, the method of depositing drugs through serrations in the tissue uses a pretreatment balloon that has an elongate member having an inner lumen which defines a longitudinal axis, an expandable balloon connected to the elongate member at a distal end of the elongate member, a plurality of strip with each strip of the plurality of strips having a plurality of wedge dissectors spaced apart along a surface of each strip and each strip extends longitudinally along an outer surface of the balloon. The wedge dissectors in this example have strip-facing base surface directly adjacent a surface of each of the strips, an unhoned radially outward facing surface having a length between a proximal edge of the radially outward facing surface and a distal edge of the radially outward facing surface and defining a height of each wedge dissector, and lateral surfaces between the strip-facing base surface and the radially outward facing surface. The radially outward facing surface have a first width at the proximal edge, a second width smaller than the first width between the proximal edge and the distal edge, and a third width at the distal edge larger than the second width. The second width can correspond to a single point along the length of the radially outward facing surface or the second width can correspond to a central segment having a central length in between the proximal edge and the distal edge. The length of each strip can be less than a length of the outer surface of the balloon coaxial to the length of each strip or the length of each strip can be between about 1% and about 50% less than the length of the outer surface of the balloon coaxial to the length of each strip. The total length of the radially outward facing surface of each wedge dissector can be less than a total length of the strip-facing base surface of each wedge dissector. In another example, the radially outward facing surface has a curved surface or has one chamfered surface or a first height at the proximal edge and a second height between the proximal edge and the distal edge where the second height is greater than the first height. In some embodiments, the maximum height of the radially outward facing surface is at a midpoint between the first unbounded edge and the second unbounded edge. The maximal height of the unbounded surface can be offset from a midpoint between the proximal edge and the distal edge. The lateral surface segment of the wedge dissector from the strip-facing base surface to the proximal edge can have one or more a parabolic slope/s as would be generated by chemical etching. The strip tips are typically linked to the carrier tips. The shape of the carrier tips typically has features that are similar in slope and dimension as that of the strips.

In some embodiments, the method of attaching wedge dissectors, with or without serration on to a medical balloon can be achieved by providing a strip inclusive of a plurality of wedge dissectors spaced longitudinally apart along a surface of the strip. Each of the wedge dissectors has a strip tip-facing carrier tip-face directly opposing the strip, due to the fact that the carrier and the strip tips are etched from the same material and remain attached, when separated an unhoned radially outward facing surface is produced when the carrier is separated from the strip tip. Once separated the now free radial outward facing surface has a length between a proximal edge of the radially outward facing surface and a distal edge of the radially outward facing surface and defining a height of each wedge dissector, and lateral surfaces between the strip-facing base surface and the radially outward facing surface.

In some embodiments each unhoned radially outward facing surface of each of the wedge dissectors are attached to an unhoned radially outward facing carrier at attachment zones, where the areas between attachment zones define voids and the strip has a second surface opposing the first surface of the strip. Then, the second surface of the strip is placed into a balloon blowing collet and aligned with the intended final placement of the second surface within, integral, or superficially adjacent to the medical balloon. The strip carrier is detached from the strip after the second surface of the strip is attached to the medical balloon. The second surface of the strip could be bonded to the surface of the medical balloon with an adhesive and/or through other processes such as fusion and/or lamination. The detaching of the strip carrier from the strip could be accomplished using a mechanical force, laser cutting, or other means. The strip carrier could also be integrally formed with the strip. In some cases, the strip carrier and the strip are created using chemical etching.

In some embodiments, a carrier system for attaching wedge dissectors to a medical balloon has a strip including a plurality of wedge dissectors spaced longitudinally apart along a surface of the strip. Each of the wedge dissectors has a strip-facing base surface directly adjacent a first surface of the strip, an unhoned radially outward facing surface having a length between a proximal edge of the radially outward facing surface and a distal edge of the radially outward facing surface and defining a height of each wedge dissector, and lateral surfaces between the strip-facing base surface and the radially outward facing surface. The strip has a second surface opposing the first surface of the strip, and the strip carrier has a free edge. The unhoned radially outward facing surface of each wedge dissectors is attached to the free edge of a strip carrier at attachment zones typically mirroring the wedge dissector shapes and periodicity. There are voids between attachment zones, and the attachment zones configured to be detached upon application of a mechanical force or repeated bidirectional torsional forces. In some cases, the carrier system along with the strips are made from a metal such as stainless steel. Other suitable materials include polymers, co-polymers, and novel materials with composite compositions.

In some methods the attachment of strips to the balloon are completed during the balloon blowing cycle or in a second or third or in any number of steps post balloon blowing. In these methods the carriers are designed to integrate with the balloon blowing molds. One of the blowing methods uses strips that have a compatible material such as a polymer or co-polymer layer on the outer surface of the strip. The coating volume is typically designed to encapsulate the base of the strip and in some cases produce a region neighboring the strip base on the balloon surface that can act as protective bed for the strip to lay down on. The coating of the strip can be accomplished many different ways including but not limited to a dipping, painting, lamination or pre-form attachment methods.

Numerous approaches can be utilized to laminate materials together. In some embodiments, the use of lamination for the purpose of illustrating the bonding of metal strips to the outer surface of a balloon is disclosed.

When a laminate layer stack is used the component strips are typically built integrated along with a long sheet or roll of metal with thousands to millions of strips per roll. The metal rolls might typically be chemically etched to produce the intended design of the carrier and the strips with the desired wedge dissection pattern. The etched rolls are then laminated with polymers, co-polymers, or fiber-reinforced polymers typically into a sandwich like configuration with either both sides laminated, or the like.

In some of the embodiments one or more polymer layers may include fiber-reinforced polymers applied in the laminate and comprise reinforcing fibers embedded in a polymer. The polymer also acts as a bonding means between the various layers. Reinforcing fibers that are suitable for use in the fiber-reinforced polymer include for example glass fibers, carbon fibers and metal fibers, and if required can also include drawn thermoplastic polymer fibers, such as aramid fibers, PBO fibers (Zylon™), M5™ fibers, and ultrahigh molecular weight polyethylene or polypropylene fibers, and/or combinations of the above fibers. It is also possible to use commingled and/or intermingled bundling of fibers like that of rovings. Such rovings comprise a reinforcing fiber and a thermoplastic polymer in fiber form. Examples of suitable matrix materials for the reinforcing fibers are thermoplastic polymers such as polyamides, polyimides, polyethersulphones, polyetheretherketone, polyurethanes, polyethylene, polypropylene, polyphenylene sulphides (PPS), polyamide-imides, acrylonitrile butadiene styrene (ABS), styrene/maleic anhydride (SMA), polycarbonate, polyphenylene oxide blend (PPO), thermoplastic polyesters such as polyethylene terephthalate, polybutylene terephthalate, as well as mixtures and copolymers of one or more of the above polymers.

In embodiments for attaching the strips to the balloon the inclusion of polymers directly onto the base and or sides of the strips is envisioned. In one method of fabrication the strips, the use of chemical etching is envisioned, while other methods like electrochemical machining or other low-cost, high volume, top-down (material removal) or bottom-up (material deposition) processes are envisioned. The strips can be constructed by removing material to create the wedge dissectors. The strips can be constructed by adding material to create the wedge dissectors.

When strips are fabricated from and into a reel of material the use of a secondary process like lamination is envisioned to provide a polymer layer on both sides (top and bottom) on the base of the strip, as shown in FIG. 2 schematically.

The lamination process can lay down a sandwich of materials capturing the stainless steel reel of strip and generating a fused surface of materials capable of flexing with the pliable balloon and effectively affixing to the non-pliable strip of material, as shown schematically in one embodiment in FIG. 3.

In some configurations, the catheter further comprises an expandable member associated with the catheter.

In some configurations, the expandable member comprises a balloon.

In some configurations, the expandable balloon comprises a plurality of strips, each strip comprising a plurality of wedge dissectors thereon.

In some configurations, it is envisioned that the use of additional energy sources in combination with serrations on the outer surface of the balloon can add additional benefit. In some embodiments, the additional energy sources can be separate from the catheter with balloon and wedge dissectors. In some embodiments, the additional energy sources can be integrated with the catheter with balloon and wedge dissectors. The energy sources can provide energy in combination with in combination with serrations on the outer surface of the balloon. The energy sources can provide various functionality such as compressing the plaque, propagating cracks, cracking the medial plaque, cracking the intimal plaque, lesion preparation, and/or breaking up the plaque. One such energy source is ultra-sonic vibrations, ultrasound, or spark derived energy that might be emitted from a transducer within the balloon body. In some embodiments, in the case of vibrational energy, the energy can be transmitted through the guidewire of the catheter. In some embodiments, in the case of vibrational energy, the energy can be transmitted through other separate and independent elements, such as metal elements. The vibrational energy can be translated utilizing longitudinal, radial, or torsional oriented vibrations, or any combination therein. In some embodiments, the sound energy or other energy can be transmitted through the medium (often liquid but sometimes gas) used to fill the balloon and through the balloon wall in addition to the plurality of strips. In such a design, the wedge dissectors may have the same or a slightly different shape to enable the effective transduction of the acoustic or sound wave energy into the tissue. Thereby, the design of the wedge dissectors can enable a more effective transmission modality of the acoustic energy or other energy into the diseased tissues. In some embodiments, the use of pneumatic and/or hydraulic energy delivery is envisioned. It is envisioned that through the use of additional energy sources, such as ultrasound, pneumatic and/or hydraulic, spark, or other energy source, fewer serrated strips might be necessary to produce an effective outcome. Additionally, the periodicity of the wedge dissectors could be made longer with few wedges and longer gaps while producing an effective outcome. The shape of the wedges could be made shallower or shorter while producing an effective outcome. Another benefit of combining multiple modalities of energy (i.e., ultrasonic with pressure) along with serrations is that the complexity of the ultrasonic or other energy emission sources could be reduced. Therefore, in some cases, the use of a series of 0.3, 2, or 1 transducers, arc-generators, or pneumatic and/or hydraulic pumps, may be preferred to produce effective lumen gain or to break-up the disease state for some patients. The energy delivery and the serrations may have a synergistic effect. The energy delivery may be more effective in combination with the nucleation sites provided by the wedge dissectors. The wedge dissectors may increase tissue transduction of energy. The wedge dissectors may concentrate the energy delivery. The wedge dissectors may penetrate plaque easier in combination with energy delivery. The crack may propagate easier or faster with both modalities. The crack may propagate in a more controlled manner with both modalities. This combination of modalities may offer an advantage by reducing the complexity of the integrated system with the balloon and the wedge dissectors, while minimizing the drawbacks of poor tissue transduction of the energy through the disease state and into the tissue by utilizing the wedge dissectors to more effectively transmit the energy through the disease tissue state.

Also disclosed herein are methods of creating serrations in a treatment site in a vessel, providing a balloon catheter comprising a balloon incorporating a plurality of strips, each strip comprising a plurality of wedge dissectors, the balloon catheter further comprising an inner member, a tapered outer sheath, and an elongate tapered coil between the matched tapered outer sheath and the non-tapered inner member, the elongate coil running substantially the entire length of the balloon catheter and through the balloon; expanding the balloon at the site to create a plurality of microfissures into the media layer of the vessel wall without cutting the vessel wall; and removing the balloon from the site.

Also disclosed herein are methods of creating serrations in a treatment site in a vessel, providing a balloon catheter comprising a balloon incorporating a plurality of strips, each strip comprising a plurality of wedge dissectors attached during the balloon blowing process or at any point during manufacturing, the balloon catheter further comprising an inner member, an outer sheath, a hub and a tip; expanding the balloon at the site to create a plurality of microfissures into the intimal layer of the vessel wall without cutting the vessel wall; and removing the balloon from the site. In some embodiments, the balloon is selected that is larger than the intended diameter of the vessel. This can be conveyed by a ratio between an expected vessel diameter and a balloon diameter. In some methods, the ratio is 1:1.1, 1:1.2, 1:1.3, 1:1.4, 1:1.5, 1:1.6, 1:1.7, 1:1.8, 1:1.9, 1:2, or any range of the foregoing. The vessel can be expanded for a variety of clinical purposes. In some embodiments, the use of serration angioplasty can minimize the risk of scar tissue formation, thereby reducing the potential for restenosis over time.

Therefore, the functional use of a larger balloon diameters, which causes larger vessel sizes, can maximize volumetric blood flow. Additionally, there is a clinical need to deliver larger sized devices through the vascular. By using a larger balloon, these larger sized devices can be delivered. The clinical needs for the use of delivering larger sized devices through the enlarged vessel is well known and can be a complicated to achieve without negative clinical outcomes. Often when enlarging a vessel to sizes above the natural diameter, the vessel can dissect, perforate, embolize, or restenosis. The vessel can be expanded for delivering larger sized primary or secondary therapies. In some treatment options or methods, expanding the balloon to a larger diameter can lead to positive vessel remodeling, where the vessel diameter returns to a non-diseased diameter or healthy diameter over time. In some treatment options or methods, the outcome is to generate the highest possible volumetric flow through the vessel. The highest possible volumetric flow can be achieved by an enlarged balloon, such as having a ratio of 1:1.1, 1:1.2, 1:1.3, 1:1.4, 1:1.5, 1:1.6, 1:1.7, 1:1.8, 1:1.9, 1:2, or any range of the foregoing. The highest possible volumetric flow can be used in an effort to heal a wound. The highest possible volumetric flow can be used to maintain tissue life. The highest possible volumetric flow can be used for healing in downstream tissue. There may be additional clinical reasons to provide the highest possible volumetric flow.

In some configurations, the method further comprises performing an index, starting, or initial procedure at the site.

In some configurations the index procedure is selected from the group consisting of: endovascular aortic repair (EVAR), fenestrated endovascular aortic repair (FEVAR), transcatheter aortic valve replacement (TAVR), transcatheter mitral valve repair or replacement, and thoracic endovascular aortic repair (TEVAR).

In some embodiments, an intravascular device is provided. The intravascular device can include a balloon. The intravascular device can include a plurality of strips. In some embodiments, each strip of the plurality of strips includes a plurality of wedge dissectors spaced apart along a surface of each strip. In some embodiments, each strip extends along an outer surface of the balloon. In some embodiments, the wedge dissectors comprise a base surface, an unhoned radially outward facing surface, and sloped side walls extending from the base surface to the unhoned radially outward facing surface. In some embodiments, the balloon is configured to expand and create lobes between the plurality of strips. In some embodiments, the lobes apply a force to the sloped side walls of the wedge dissectors to rotate the wedge dissectors from a generally tangential orientation to a generally perpendicular orientation.

In some embodiments, the lobes apply a force to the sloped side walls of the wedge dissectors to rotate the wedge dissectors from the generally perpendicular orientation to the generally tangential orientation. In some embodiments, the intravascular device is bi-directional to allow the plurality of strips to rotate clockwise or counterclockwise. In some embodiments, the plurality of strips point counterclockwise in the generally tangential orientation before inflation. In some embodiments, the plurality of strips point counterclockwise in the generally tangential orientation after inflation. In some embodiments, the plurality of strips are at least partially covered by a pleat of the balloon in the generally tangential orientation. In some embodiments, each strip is at least partially covered by a pleat of the balloon when the balloon is deflated. In some embodiments, the covered strips are located near the base of the pleated wings of the balloon. In some embodiments the covered strips are oriented with the unhoned radially outward facing surface laying tangential to the circumference of the inner member limiting the unhoned radially outward facing surface from contacting the pleated wings of the balloon. In some embodiments, the sloped side walls in combination with the expansion of the lobes are configured to allow for more effective control of the generally perpendicular orientation of the wedge dissectors. In some embodiments, the unhoned radially outward facing surface is configured to contact a vessel wall while creating little to no separation of plaque from the vessel wall. In some embodiments, the lobes are configured to exert a tensile force on a vessel wall near the regions where the wedge dissectors contact the vessel wall. In some embodiments, the lobes are configured to exert a force on a vessel wall causing the vessel wall to pull away from the wedge dissectors. In some embodiments, the lobes are configured to exert a force on the vessel wall that allows the unhoned radially outward facing surface to create serrations in the vessel wall. In some embodiments, the lobes are configured to exert a force on the vessel wall that allows the unhoned radially outward facing surface to create linear dissected lines. In some embodiments, the sloped side walls in combination with the expansion of the lobes are configured to produce a plurality of longitudinally oriented lines into or through one or more of the layers of the tissue. The unhoned radially outward facing surface of each wedge dissector can be configured for penetration through layers of the vascular anatomy. In some embodiments, the sloped side walls in combination with the expansion of the lobes are configured to produce a plurality of longitudinally oriented lines through the intimal layer. In some embodiments, the sloped side walls in combination with the expansion of the lobes are configured to produce a plurality of longitudinally oriented lines through the internal elastic lamina layer. In some embodiments, the sloped side walls in combination with the expansion of the lobes are configured to produce a plurality of longitudinally oriented lines into the medial layer. In some embodiments, the sloped side walls in combination with the expansion of the lobes are configured to provide lumen gain independent of the arterial dimension. In some embodiments, the sloped side walls in combination with the expansion of the lobes are configured to produce a plurality of longitudinally oriented lines to the medial layer, enabling greater arterial expansion that increase volumetric blood flow. In some embodiments, the sloped side walls in combination with the expansion of the lobes are configured to produce a plurality of longitudinally oriented lines to the medial layer that improves stenosis. In some embodiments, the sloped side walls in combination with the expansion of the lobes are configured to causes positive vessel remodeling. In some embodiments, the sloped side walls in combination with the expansion of the lobes are configured to maintain the generally perpendicular orientation of the wedge dissectors as the wedge dissector induce nodes of separation in the intima. In some embodiments, the sloped side walls in combination with the expansion of the lobes are configured to change the pressure distribution at a vessel wall allowing the wedge dissectors to further penetrate the vessel wall. In some embodiments, the balloon is configured to deliver energy. In some embodiments, the strips increase trackability and pushability by translating forces longitudinally along the balloon.

In some embodiments, an intravascular device is provided. The intravascular device can include a balloon. The intravascular device can include a plurality of strips. In some embodiments, each strip of the plurality of strips includes a plurality of wedge dissectors spaced apart along a surface of each strip. In some embodiments, each strip extends along an outer surface of the balloon. The intravascular device can include a prefabricated covering. In some embodiments, a combinate of the prefabricated covering and the balloon with the plurality of strips is formed by inflating the balloon with the plurality of strips within the prefabricated covering and applying heat to the plurality of strips such that the prefabricated covering softens and the plurality of wedge dissectors extend through the prefabricated covering.

In some embodiments, the prefabricated covering hardens around the plurality of wedge dissectors. In some embodiments, each strip is bonded to the outer surface of the balloon or a base coat of the balloon with an adhesive. In some embodiments, the balloon with the plurality of strips is configured to be pleated before insertion into the prefabricated covering. In some embodiments, adhesive is configured to be applied to the balloon with the plurality of strips before insertion into the prefabricated covering. In some embodiments, the plurality of wedge dissectors are configured to rotate from a generally tangential orientation to a generally perpendicular orientation when the balloon with the plurality of strips is inflated within the prefabricated covering. In some embodiments, the plurality of wedge dissectors comprise an unhoned radially outward facing surface that does not poke through the prefabricated covering during inflation of the balloon. In some embodiments, the expansion of the balloon uniformly distributes adhesive between the balloon and the prefabricated covering. In some embodiments, the prefabricated covering provides a thicker layer surrounding the wedge dissectors. In some embodiments, the prefabricated covering near the wedge dissectors limits the ability of the prefabricated covering to tear in the spaces between adjacent wedge dissectors. In some embodiments, only individual wedge dissectors extend through the prefabricated covering. In some embodiments, prefabricated covering remains intact along the longitudinal spaces between adjacent wedge dissectors. In some embodiments, prefabricated covering comprises rehardened material extending longitudinally along sloped side walls of the wedge dissectors. In some embodiments, prefabricated covering comprises rehardened material extending laterally along the proximal and/or distal edges of the wedge dissectors. In some embodiments, prefabricated covering, the balloon, and the plurality of strips are bonded together. In some embodiments, prefabricated covering, the balloon, and the plurality of strips are pleated. In some embodiments, prefabricated covering facilitates retention of the plurality of strips relative to the balloon. In some embodiments, the wedge dissectors are configured to rotate from a generally tangential orientation to a generally perpendicular orientation within a blood vessel. In some embodiments, the prefabricated covering and the balloon are configured to function unitarily to apply a tensile force on the vessel wall to create linear dissected lines.

In some embodiments, an intravascular device is provided. The intravascular device can include a balloon. The intravascular device can include a plurality of strips. In some embodiments, each strip of the plurality of strips includes a plurality of dissectors spaced apart along a surface of each strip. In some embodiments, each strip extends along an outer surface of the balloon. In some embodiments, the dissectors comprise a base surface, an outward facing surface, and side walls extending from the base surface to the radially outward facing surface. In some embodiments, the balloon is configured to expand and create lobes between the plurality of strips. In some embodiments, the lobes apply a force to the sloped side walls of the dissectors to rotate the dissectors from a generally tangential orientation to a generally perpendicular orientation.

In some embodiments, the intravascular device is bidirectional to allow the plurality of strips to rotate clockwise or counterclockwise. In some embodiments, the plurality of strips point counterclockwise in the generally tangential orientation before inflation and after inflation. In some embodiments, the plurality of strips are at least partially covered by a pleat of the balloon in the generally tangential orientation. In some embodiments, the intravascular device allows for more effective control of the generally perpendicular orientation of the wedge dissectors. In some embodiments, the intravascular device is configured to contact a vessel wall while creating little to no separation of plaque from the vessel wall. In some embodiments, the lobes are configured to exert a tensile force on a vessel wall. In some embodiments, the lobes are configured to exert a force on a vessel wall causing tissue to pull away from the dissectors. In some embodiments, the intravascular device is configured to create serrations in the vessel wall. In some embodiments, the intravascular device is configured to create linear dissected lines.

In some embodiments, a method is provided. The method can include providing an intravascular device for angioplasty treatment comprising a balloon and a strip comprising a plurality of microperforators. The method can include expanding the balloon to rotate the microperforators from a first position to a second, more perpendicular position, wherein the strip is disposed between lobes of the balloon. The method can include expanding the balloon to create serrations, indentations, and/or microperforation in the vessel wall by moving the strip radially outward and applying a force to a vessel wall. The method can include expanding the balloon at higher pressure to cause crack propagation along the serrations, indentations, and/or microperforation in the vessel wall to the medial layer.

In some embodiments, the method can include pleating the balloon. In some embodiments, the method can include disposing the strip within the fold of the balloon. In some embodiments, the intravascular device is provided with the strip in a tangential orientation. In some embodiments, the intravascular device is provided with the strip at least partially covered with balloon material. In some embodiments, expanding the balloon to rotate the microperforators occurs with pressure under 4 atm. In some embodiments, expanding the balloon to rotate the microperforators further comprises uncovering the strip by pulling back balloon material. In some embodiments, expanding the balloon to rotate the microperforators further comprises expanding the vessel wall. In some embodiments, expanding the balloon to creates serrations, indentations, and/or microperforation further comprising holding the balloon at pressure between 2 atm and 4 atm for 60 seconds. In some embodiments, expanding the balloon at higher pressure further comprising holding the balloon at pressure between 4 atm and 6 atm for a short period of time of 60 seconds or less. In some embodiments, expanding the balloon at higher pressure produces stable and more repeatable lumen gain independent of the arterial dimension. In some embodiments, expanding the balloon at higher pressure produces improved lumen gain and blood flow. In some embodiments, expanding the balloon at higher pressure improves final stenosis by about 50% over POBA alone. In some embodiments, expanding the balloon at higher pressure produces stable and more repeatable lumen gain independent calcification. In some embodiments, expanding the balloon at higher pressure can lead to positive vessel remodeling, where the vessel diameter returns to a non-diseased diameter over time. In some embodiments, the method can include positioning the balloon near the treatment site, wherein the strip translates forces along the axis of the balloon during positioning. In some embodiments, the method can include plasma functionalization of the strip. In some embodiments, the method can include applying ultra-sound waves toward the vessel wall. In some embodiments, the method can include subsequent angioplasty with a drug coated balloon.

In some embodiments, an intravascular device is provided. The intravascular device can include a balloon configured to reversibly expand and collapse within a vessel. The intravascular device can include a strip comprising a plurality of microperforators. In some embodiments, each microperforators comprising an unhoned tip, the strip comprising spaces between adjacent microperforators. In some embodiments, the balloon is configured to expand to create serrations, indentations, and/or microperforation in the vessel wall by moving the strip radially outward and applying a force to a vessel wall.

In some embodiments, the intravascular device is configured to create predicable and repeatable crack propagation along the serrations, indentations, and/or microperforation. In some embodiments, the intravascular device is configured to increase arterial diameter while minimizing vessel injury. In some embodiments, the intravascular device is configured to increase volumetric flow. In some embodiments, the intravascular device is configured to require minimal atmospheric pressure to achieve improvements in blood flow. In some embodiments, the intravascular device is configured to promote the angioplasty energy to follow along the serrations, indentations, and/or microperforation to separate the intima and medial tissue. In some embodiments, the intravascular device is configured to improve one or more of compliance, flow dynamics, and internal diameter of the vessel. In some embodiments, the intravascular device is configured to serrate the internal elastic lamina. In some embodiments, the intravascular device is configured to allow the treated diseased region to become less turbulent by creating fewer interruptions or perturbations in the flow stream. In some embodiments, the intravascular device is configured to improve residual stenosis by about 50% over POBA alone. In some embodiments, the intravascular device is configured to improve the trackability, pushabilty, and translation of force across the balloon with the strip. In some embodiments, the strip improves column strength when the strip is transversely oriented. In some embodiments, the method can include a plasma functionalization layer on the strip. In some embodiments, the balloon is configured to produce consistent lumen gain. In some embodiments, the method can include an energy source configured to disrupt a calcium deposit. In some embodiments, the balloon is configured to create serrations, indentations, and/or microperforation at pressures under 4 atm.

In some embodiments, a medical catheter with embedded serrated metal is provided. The catheter can include an outer shaft comprising an elongate member comprising an inner diameter and an outer diameter. The catheter can include an inner member. The catheter can include a balloon blown with metal embedded in the balloon material such that a section of the metal is raised above the surface of the balloon diameter:

In some embodiments, the metal raised above the balloon diameter has raised sections and unraised sections. In some embodiments, the inner member comprises a guidewire lumen. In some embodiments, the metal comprises a plurality of strips, each strip comprising a plurality of wedge dissectors thereon. In some embodiments, the wedge dissectors are configured to create serrations in a vessel without cutting the vessel. In some embodiments, the height or amount of metal raised above the balloon surface to form the wedge dissectors of the plurality of strips is less than the thickness of the healthy tissue wall, thereby limiting or preventing puncture through the entire the vessel wall. The height of the wedge dissectors can limit penetration through the layers of tissue. The height of the wedge dissectors can be above the threshold to start crack propagation. The height of the wedge dissectors can form tiny pricks that are limited in depth of penetration. The height of the wedge dissectors can be selected to facilitate the slow, steady crack propagation through the tissue. In some embodiments, the wedge dissectors are configured to cut through a portion of a vessel through crack propagation. In some embodiments, the catheter can include spaced-apart ridges on an outer balloon surface configured to inhibit the metal from damaging the balloon.

In some embodiments, a method of blowing a balloon with embedded metal is provided. The method can include positioning a balloon extrusion with respect to a balloon die, the die comprising a plurality of detached segments and open spaces between the plurality of detached segments. The method can include positioning metal elements in the detached segments of the die. The method can include positioning a retention material over the metal elements. The method can include heating the balloon. The method can include expanding the balloon. In some embodiments, the metal elements comprises strips and micro wedges.

In some embodiments, an intravascular device is provided. The intravascular device can include a base balloon. The intravascular device can include a plurality of strips, each strip of the plurality of strips including a plurality of wedge dissectors spaced apart along a surface of each strip. The intravascular device can include a prefabricated covering. In some embodiments, the base balloon comprises a lower compliance and the prefabricated covering comprises a higher compliance.

In some embodiments, the base balloon comprises a non-compliant balloon. In some embodiments, the base balloon comprises a semi-compliant balloon. In some embodiments, the base balloon is configured to expand to a specific diameter. In some embodiments, the base balloon is configured to exert a specific pressure on a vessel wall without additional radial expansion. In some embodiments, the prefabricated covering is configured to minimize surface tearing along a portion of a strip of the plurality of strips. In some embodiments, the prefabricated covering is configured to minimize surface tearing between adjacent wedge dissectors. In some embodiments, the prefabricated covering is configured to minimize surface tearing by the wedge dissectors. In some embodiments, the prefabricated covering is configured to minimize surface tearing by calcified atherosclerosis. In some embodiments, the prefabricated covering is configured to retain the plurality of strips between the base balloon and the prefabricated covering.

In some embodiments, a method of manufacturing an intravascular device is provided. The method can include selecting a first extruded tube and blow molding a base balloon. The method can include selecting a plurality of strips, each strip of the plurality of strips including a plurality of wedge dissectors spaced apart along a surface of each strip. The method can include selecting a second extruded tube and blow molding a prefabricated covering. The method can include modifying the compliance of the base balloon, the prefabricated covering, or both the base balloon and the prefabricated covering during the process of manufacturing.

In some embodiments, modifying the compliance comprises modifying a molecular orientation of polymer chains. In some embodiments, modifying the compliance comprises changing a process of producing the first extruded tube or the second extruded tube. In some embodiments, modifying the compliance comprises a change in a forming process. In some embodiments, modifying the compliance comprises a change in a balloon modeling process. In some embodiments, modifying the compliance comprises orienting polymer chains biaxially. In some embodiments, modifying the compliance comprises increasing the tear resistance of the prefabricated covering. In some embodiments, the base balloon comprises a lower compliance and the prefabricated covering comprises a higher compliance. In some embodiments, modifying the compliance comprises changing the temperature of the heating jaws. In some embodiments, modifying the compliance comprises changing a pre-pressure and/or warm-up time. In some embodiments, modifying the compliance comprises changing a forming pressure and/or forming time. In some embodiments, modifying the compliance comprises changing a distal and/or proximal stretching load. In some embodiments, modifying the compliance comprises changing a distance between extrusion tooling and a cooling bath. In some embodiments, modifying the compliance comprises changing a speed of a gear pump during an extrusion process. In some embodiments, modifying the compliance comprises changing an inner and/or outer diameter of the first extruded tube or the second extruded tube. In some embodiments, modifying the compliance comprises changing a drawdown and die heads of the first extruded tube or the second extruded tube. In some embodiments, modifying the compliance comprises changing a final molecular orientation of polymer chains.

In some embodiments, a method is provided. The method can include providing an intravascular device. In some embodiments, the intravascular device can include a base balloon. In some embodiments, the intravascular device can include a plurality of strips, each strip of the plurality of strips including a plurality of wedge dissectors spaced apart along a surface of each strip. In some embodiments, the intravascular device can include a prefabricated covering. The method can include expanding the intravascular device within a vessel, wherein a ratio between a reference vessel diameter and a diameter of the expanded intravascular device is greater than 1:1.

In some embodiments, the ratio between a reference vessel diameter and a diameter of the expanded intravascular device is greater than 1:1.1. In some embodiments, the ratio between a reference vessel diameter and a diameter of the expanded intravascular device is greater than 1:1.2. In some embodiments, the ratio between a reference vessel diameter and a diameter of the expanded intravascular device is greater than 1:1.3. In some embodiments, expanding the intravascular device enables greater arterial growth. In some embodiments, expanding the intravascular device enables better residual blood flow. In some embodiments, expanding the intravascular device provides low residual stenosis.

In some embodiments, systems and methods can include any number of features of this disclosure.

BRIEF DESCRIPTION OF THE DRAWINGS

These and other features, aspects and advantages are described below with reference to the drawings, which are intended to illustrate but not to limit the invention. In the drawings, like reference characters denote corresponding features consistently throughout similar embodiments.

FIG. 10 shows an embodiment of a strip retained by a plurality of rings with the wedge dissectors protruding from the plurality of rings.

Figure 23A:
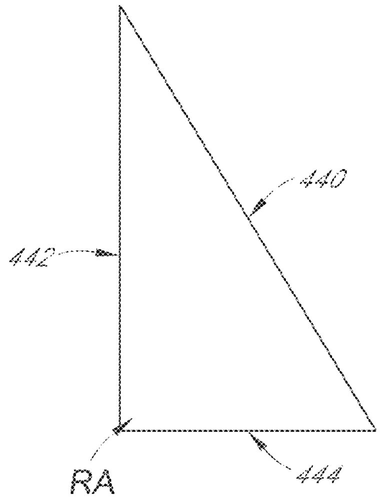
FIGS. 23A-23D illustrate respective end and isometric views of various asymmetric wedge dissector geometries, according to some embodiments.
Figure 23B:
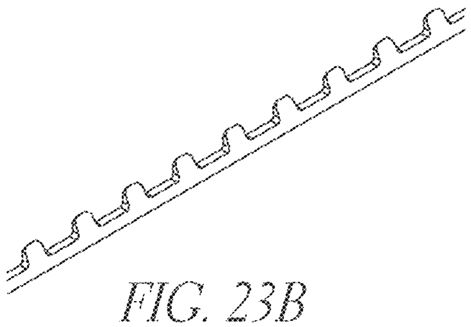
Figure 23C:
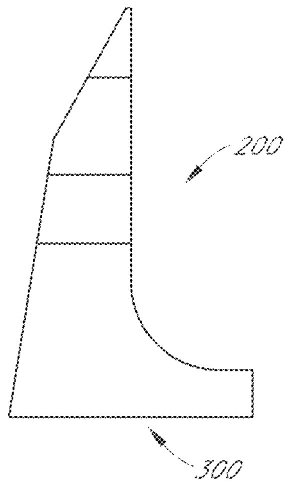
Figure 23D:
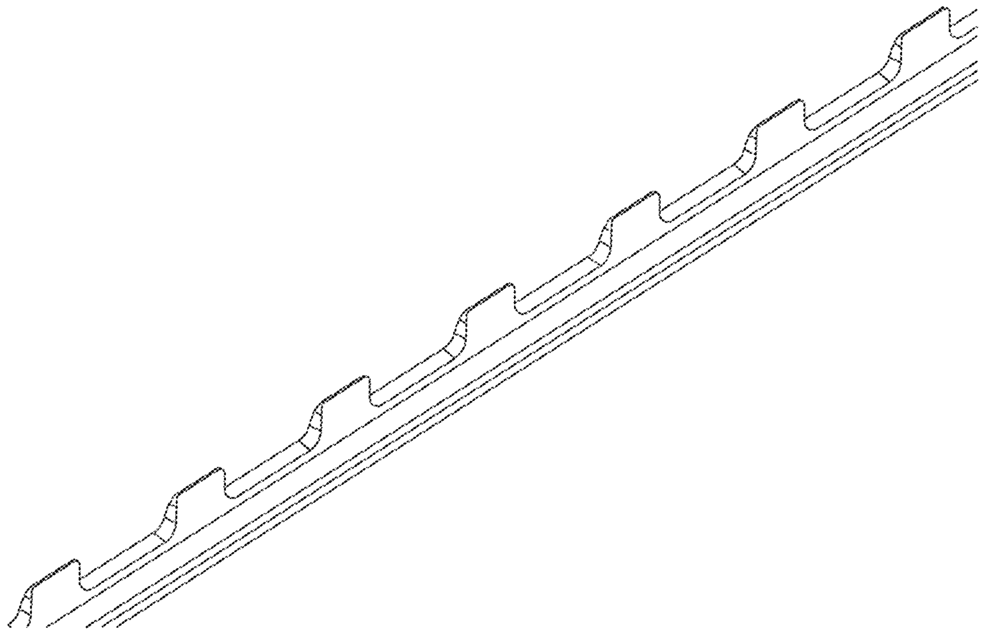
Figure 23E:
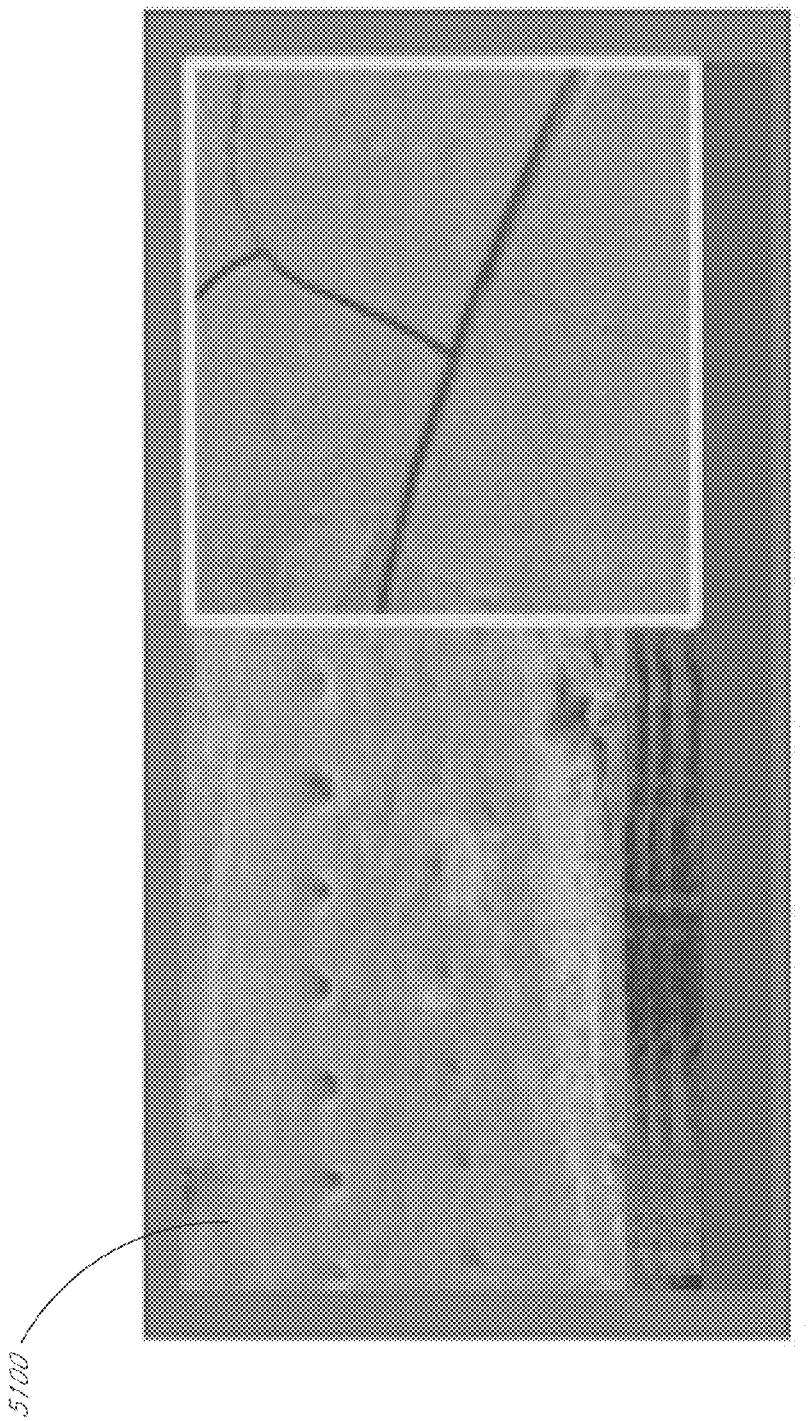
Figure 23F:
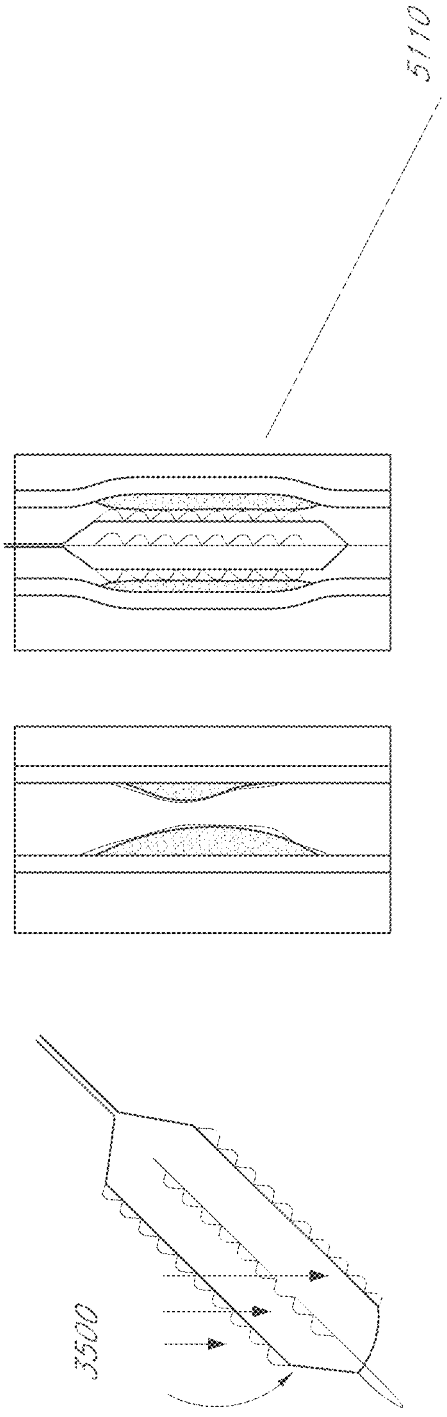

Not to be limited by theory, FIGS. 23E, 23F, and 23F.1 show potential mechanisms of actions of a serration device.

Figure 24:
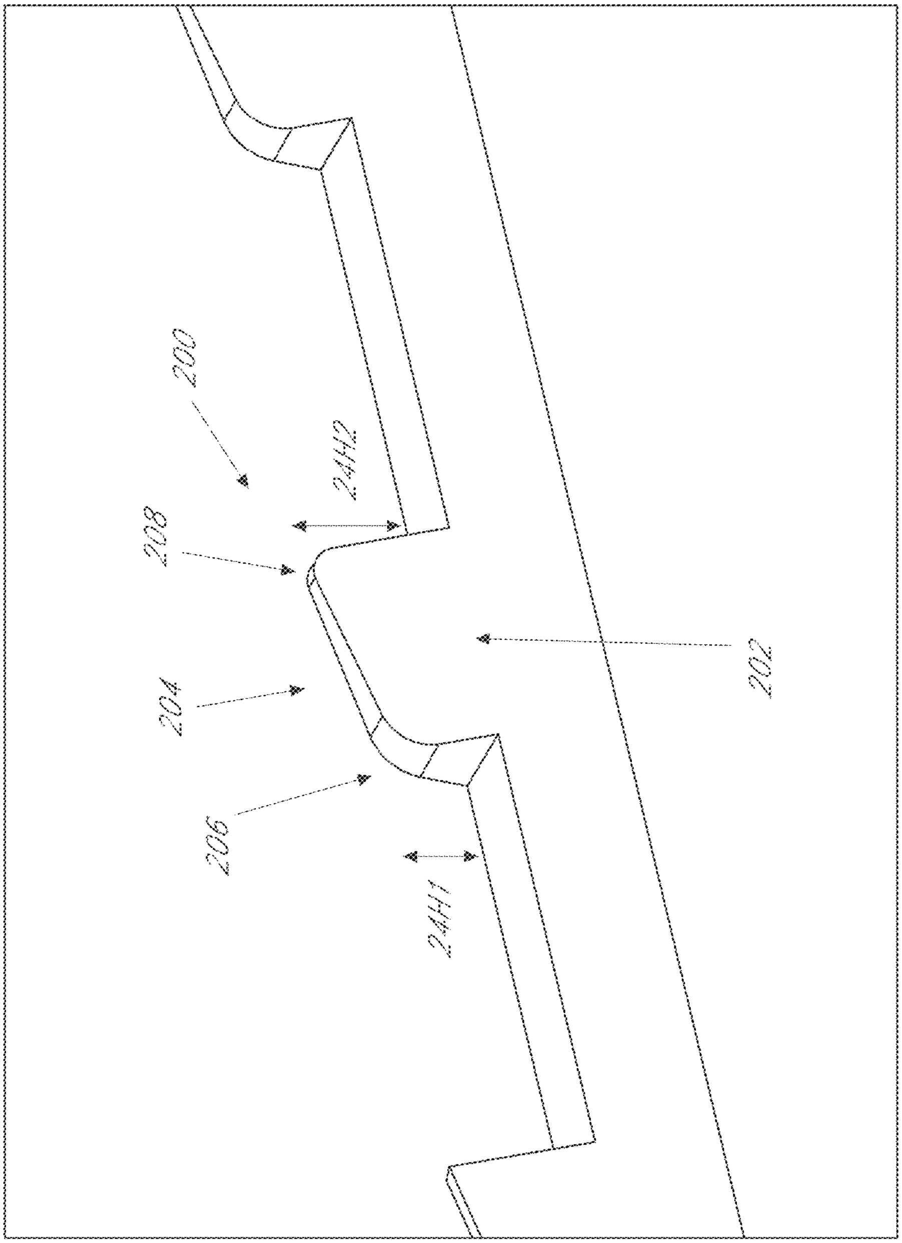

FIG. 24 illustrates an embodiment illustrating how the unbounded surface 204 may have a varying height, according to some embodiments.

FIGS. 25A-25K illustrate various embodiments of strips with reliefs in various locations.

FIGS. 25L-25Q illustrate embodiments of method of stabilizing strips during the laser cutting manufacturing process and involving temporary tabs, according to some embodiments.

Figure 26:
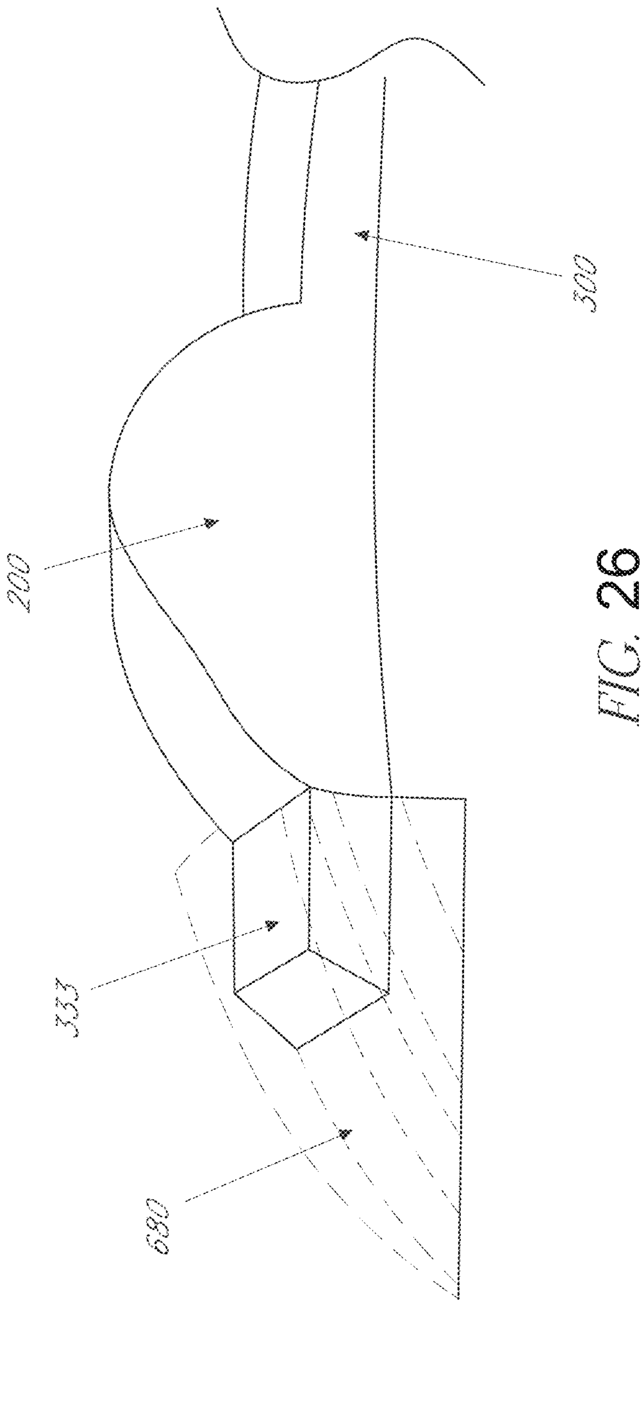
Figure 26A:
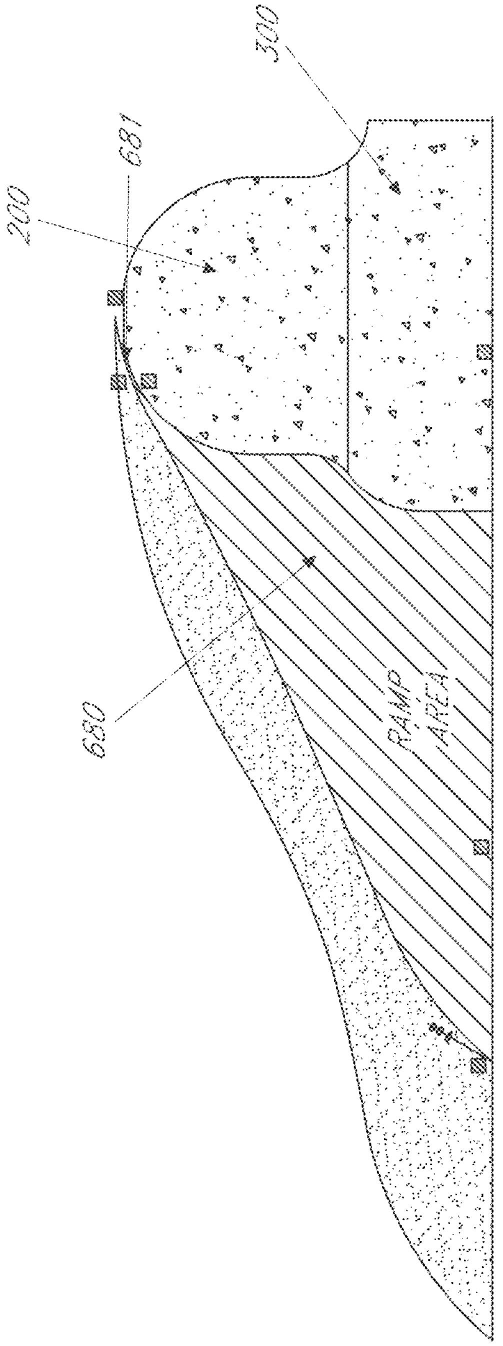

FIG. 26 illustrates embodiments of an adhesive ramp for bonding lateral ends of a strip to the balloon surface, according to some embodiments. FIG. 26A shows another image of a ramp feature shown in a side view to illustrate the distance away from the strip edge where a ramp extends.

Figure 27:
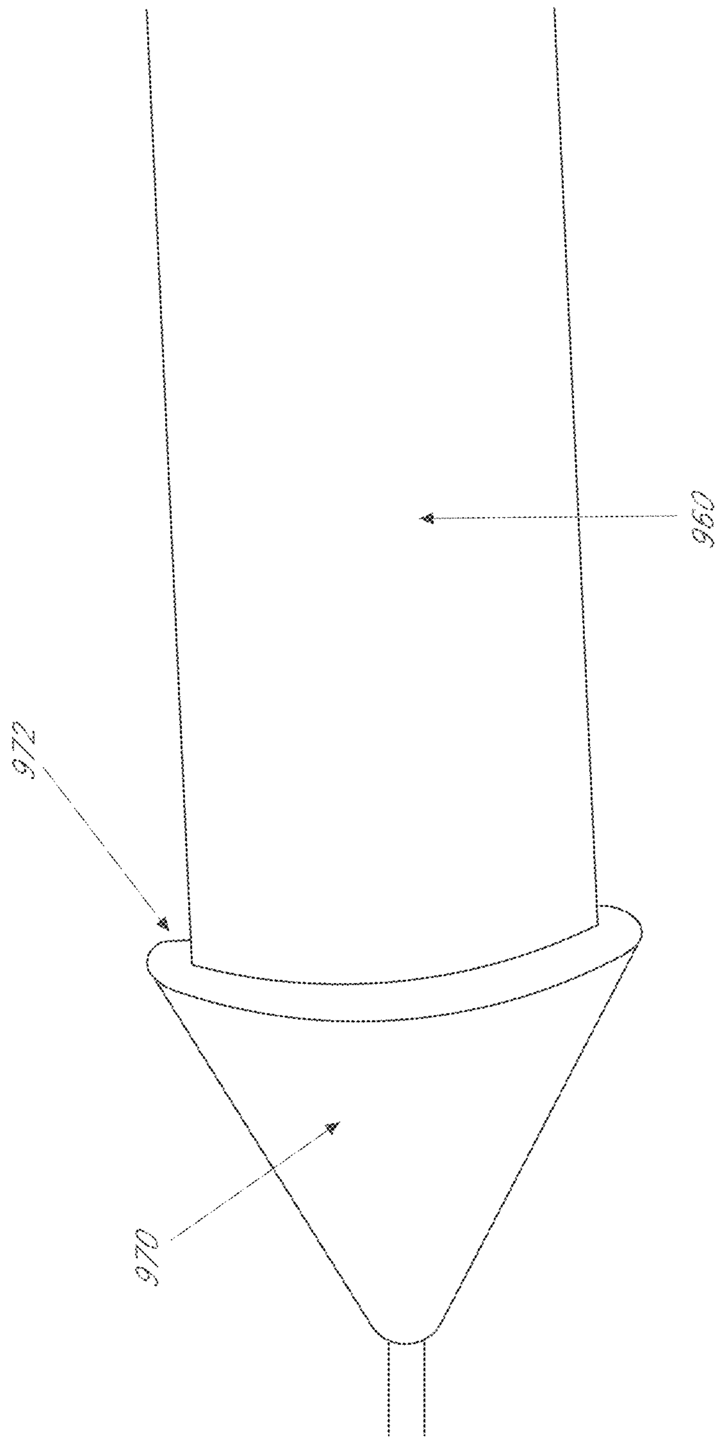

FIG. 27 illustrates a cone ramp for a balloon, according to some embodiments.

Figure 28:
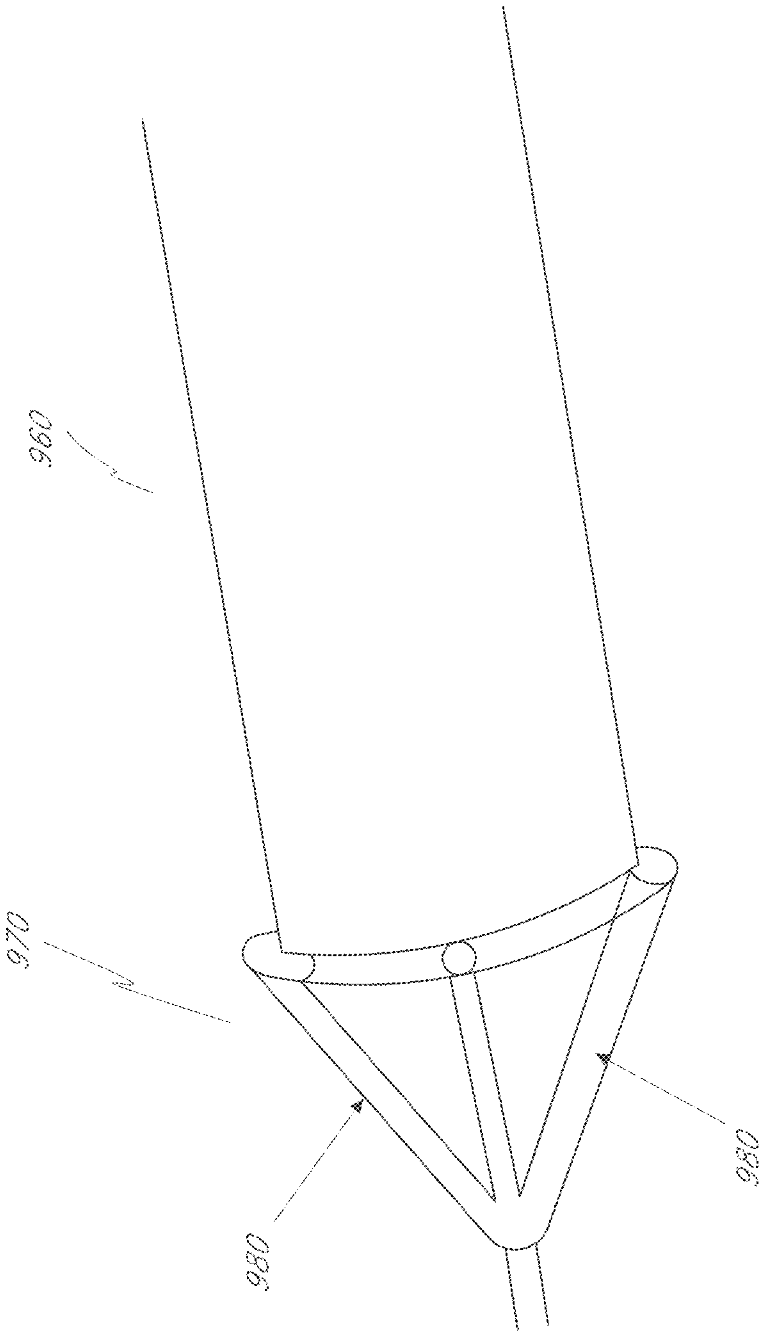

FIG. 28 illustrates a series of cone rails or struts, according to some embodiments.

Figure 29:
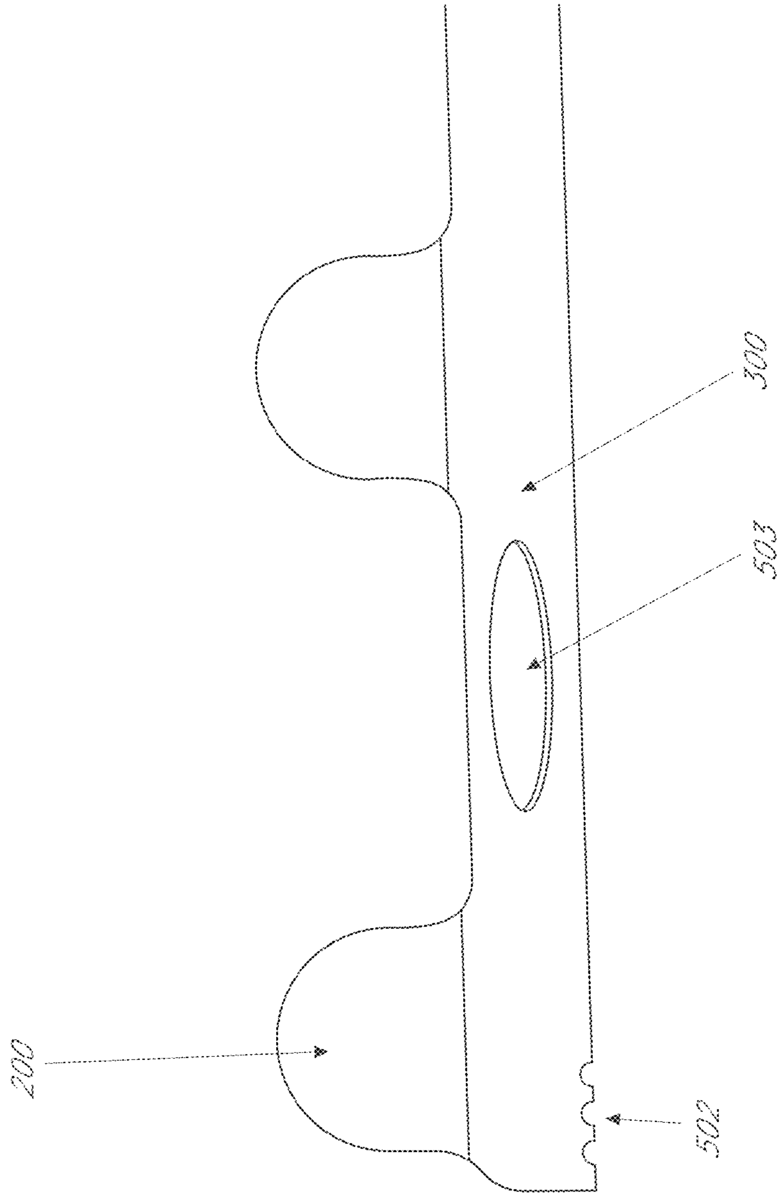

FIG. 29 illustrates another embodiment of strips having reliefs, according to some embodiments.

Figure 30A:
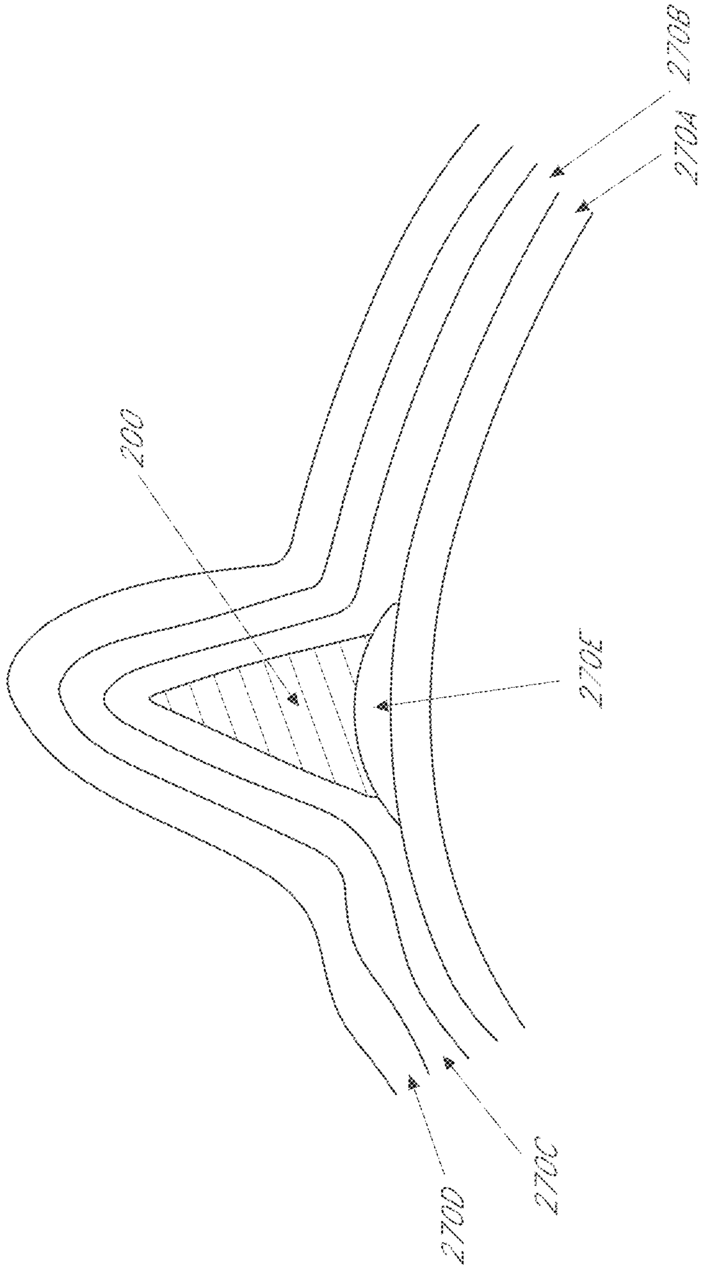
Figure 30B:
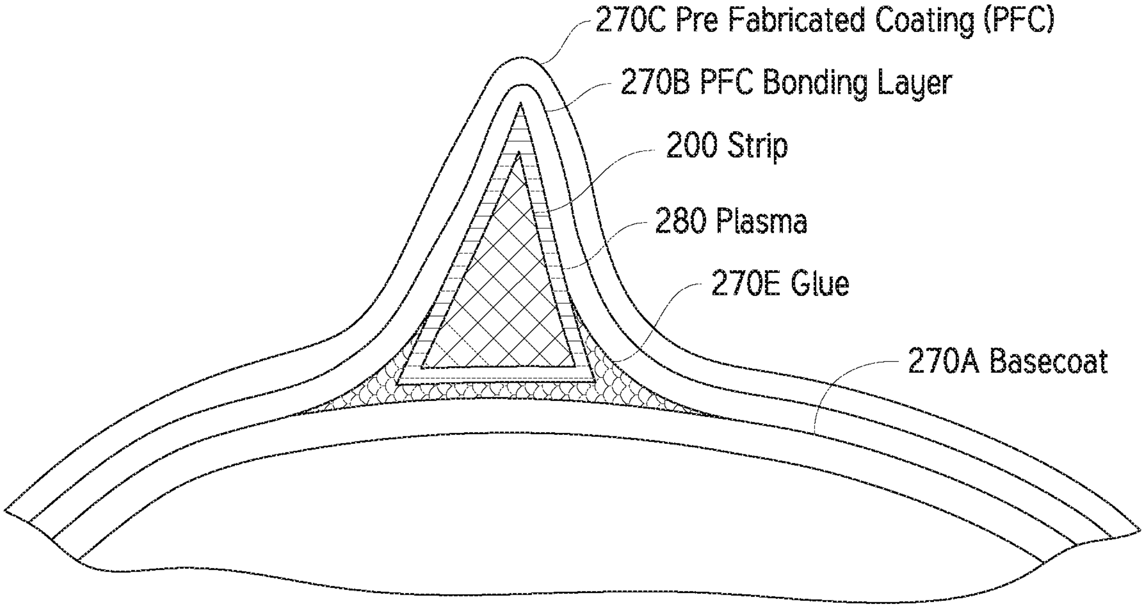

FIGS. 30A-30B illustrates a schematic cross-section of a balloon with wedge dissector and intervening layers.

Figure 31:
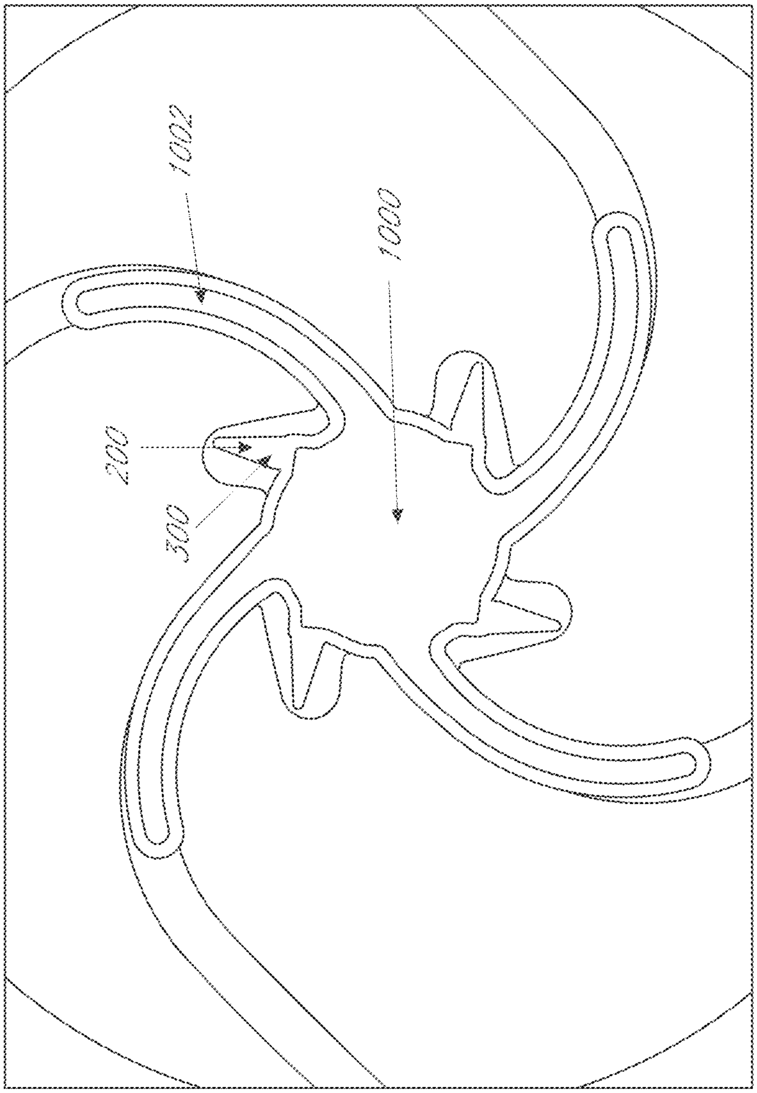

FIG. 31 illustrates an embodiment of a pleated balloon with strips and wedge dissectors in between pleats.

Figure 32:
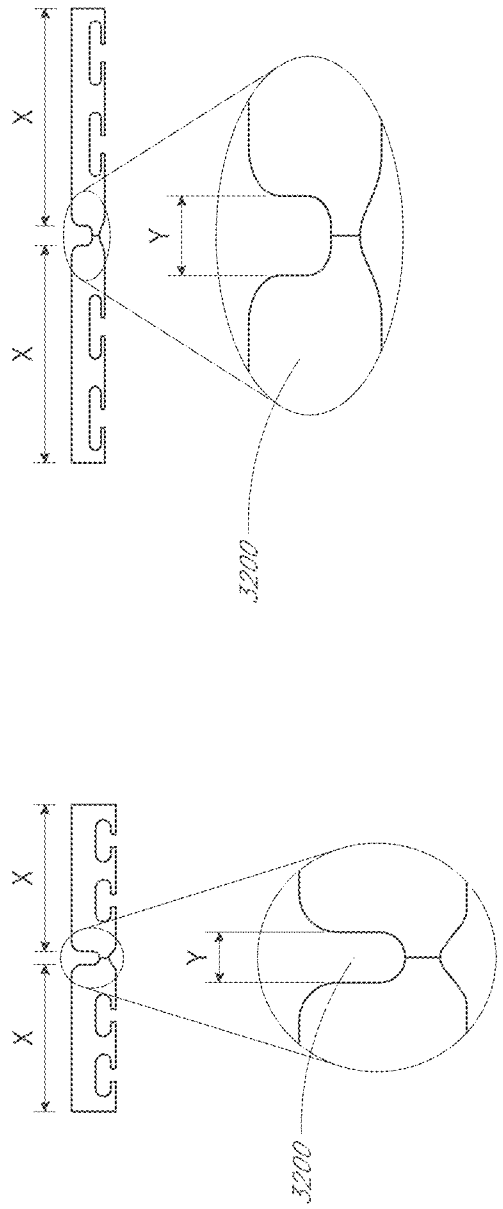

FIG. 32 illustrates an embodiment of a modified cutting balloon to produce serrations.

Figure 33:
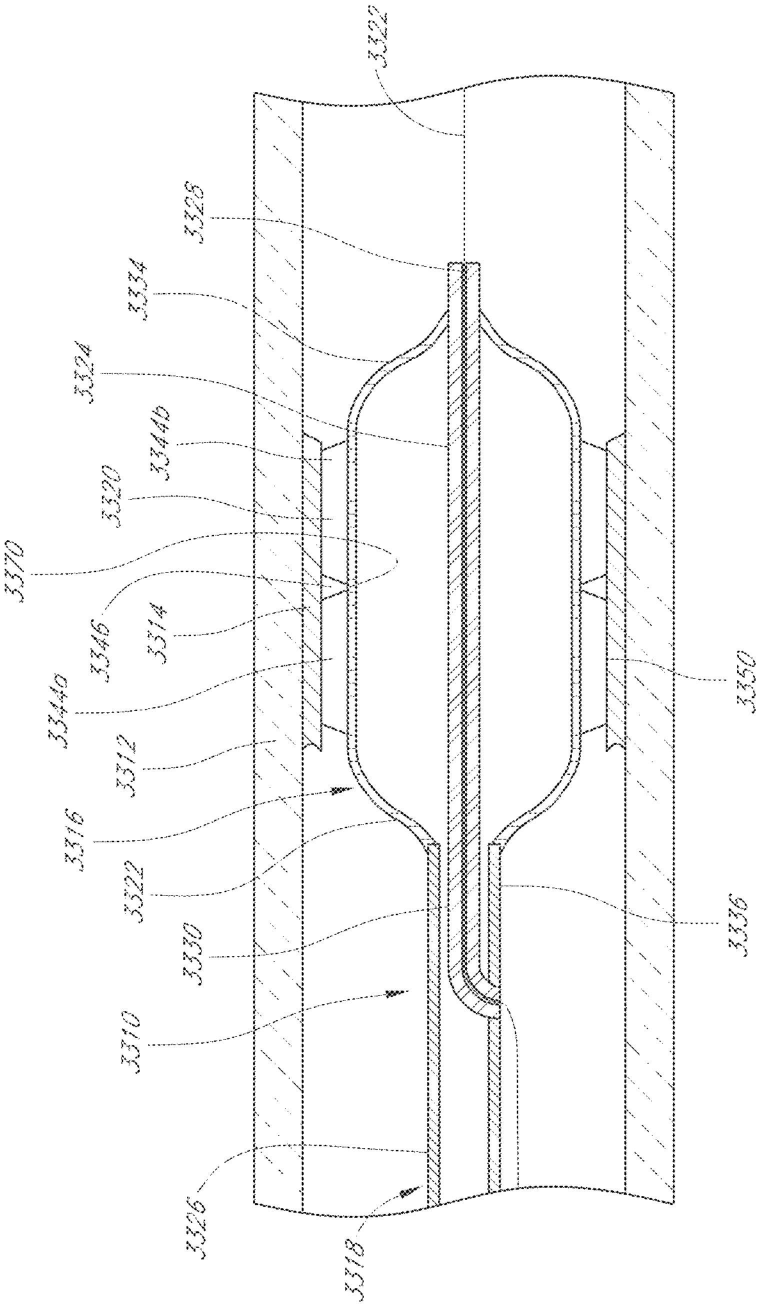
Figure 34:
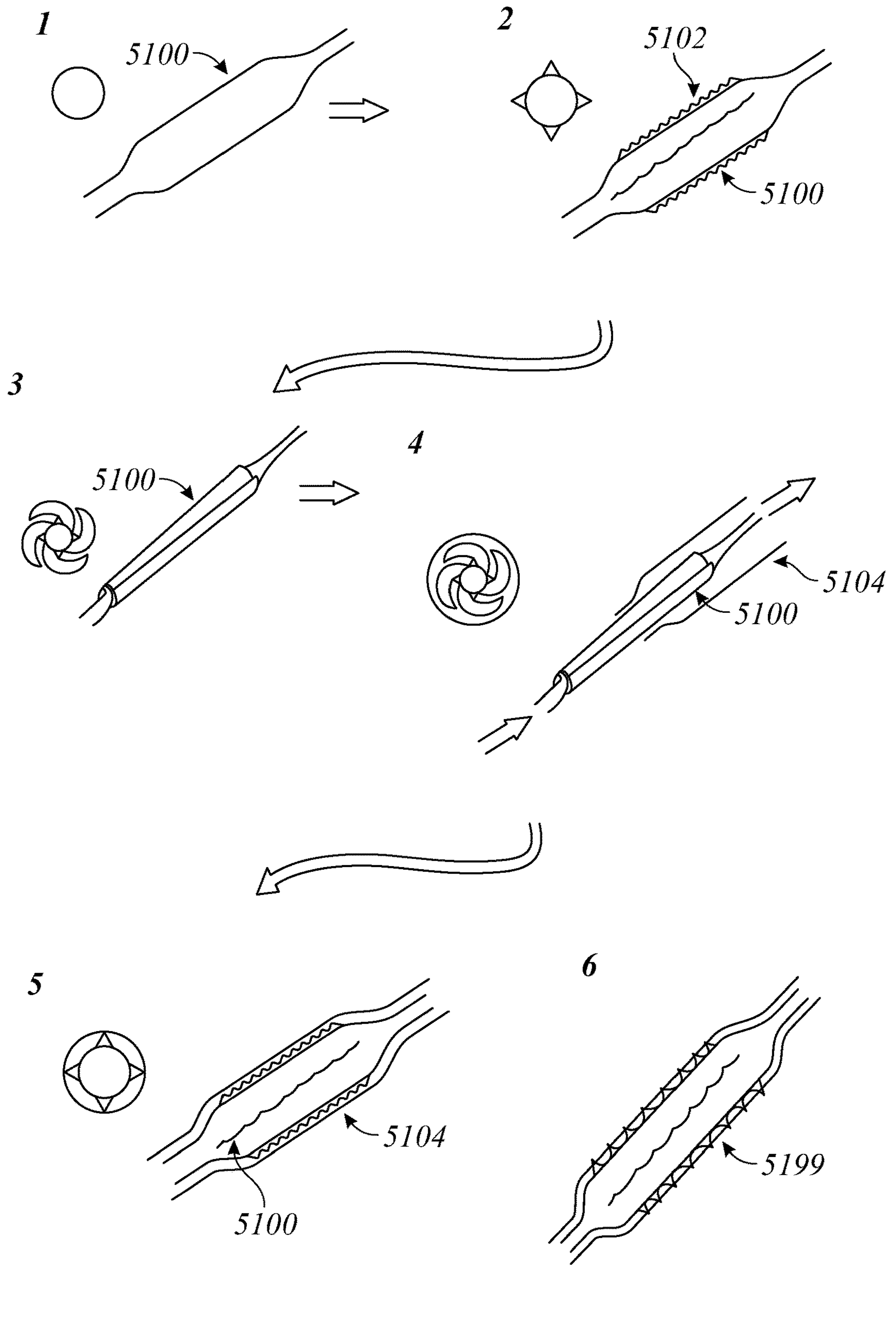

FIG. 33 shows an illustration of a modified cutting balloon where flexibility is further enhanced and the cutting is either completely or partially replaced with a serrated blade pattern FIG. 34 illustrates schematically an embodiment of a method for producing a balloon-in-balloon design.

Figure 35A:
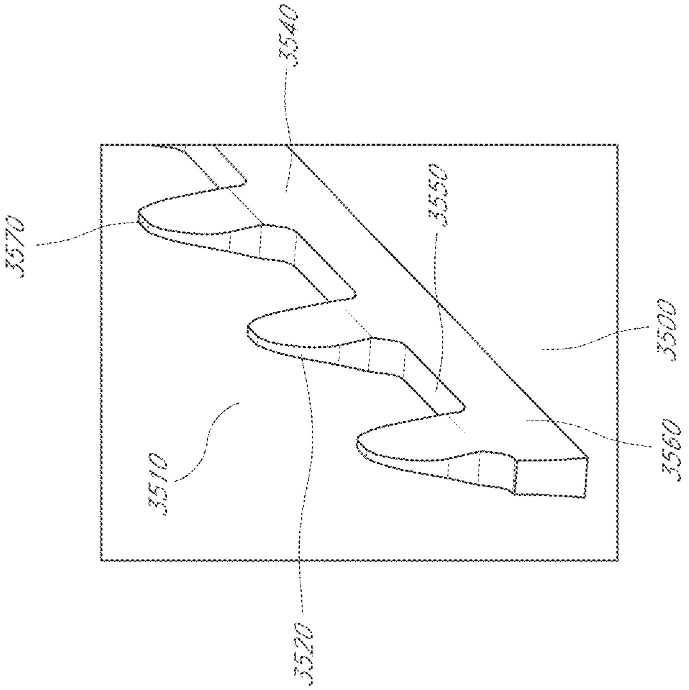
Figure 35B:
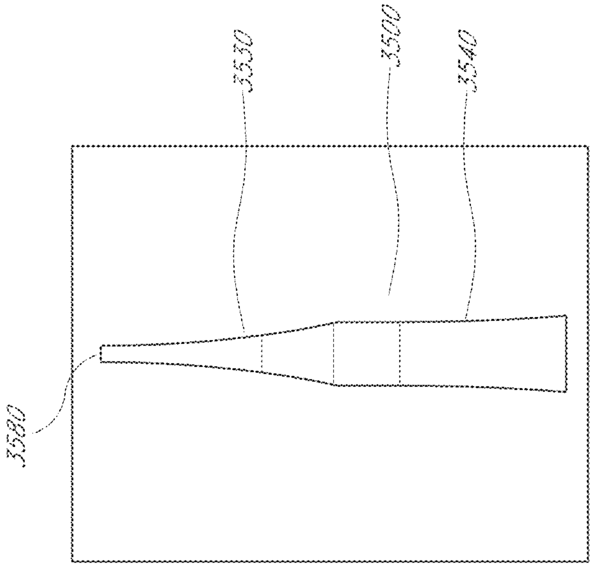

FIGS. 35A-B illustrates an embodiment of a strip with wedge dissectors where the wedge dissector has a sloped non-linear edges.

Figure 36:
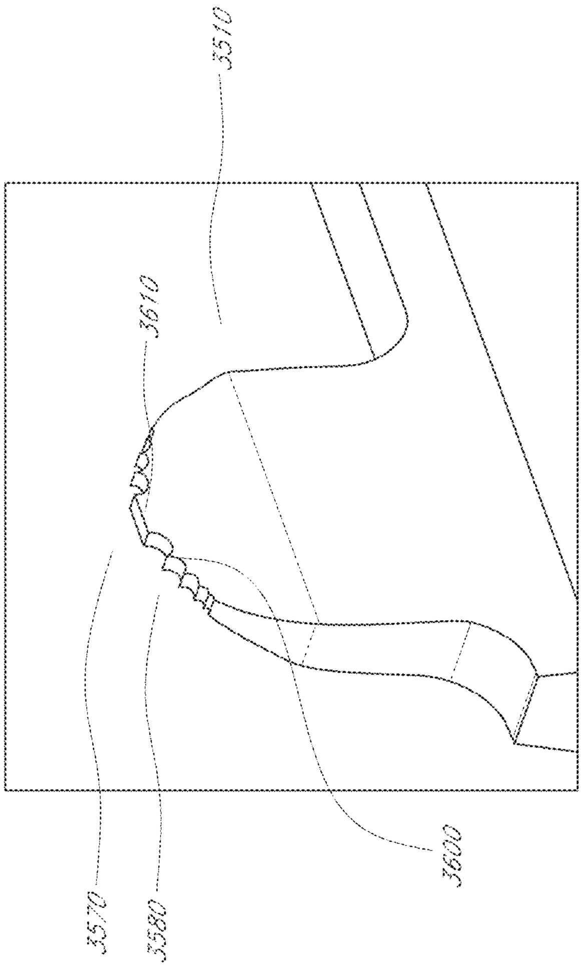

FIG. 36 illustrates the top of the wedge dissector can have a variety of the unique features on the tip (e.g., radially outward facing surface) that contacts the tissue.

Figure 37:
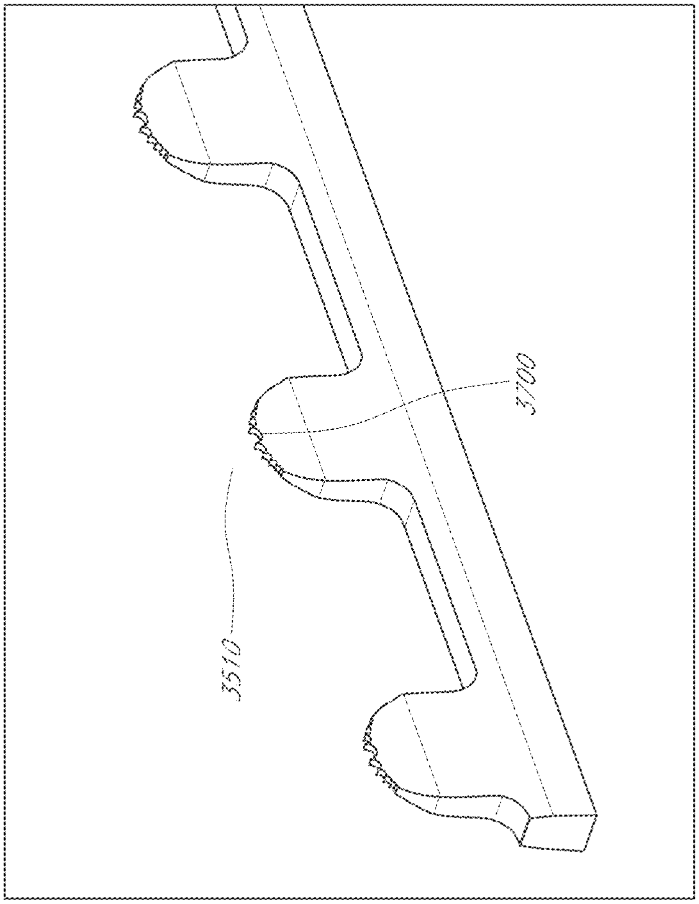

FIG. 37 is another design illustrating an alternate variation of the serrated edge of the wedge dissector, where the central segment can include a small depression as shown.

Figure 38:
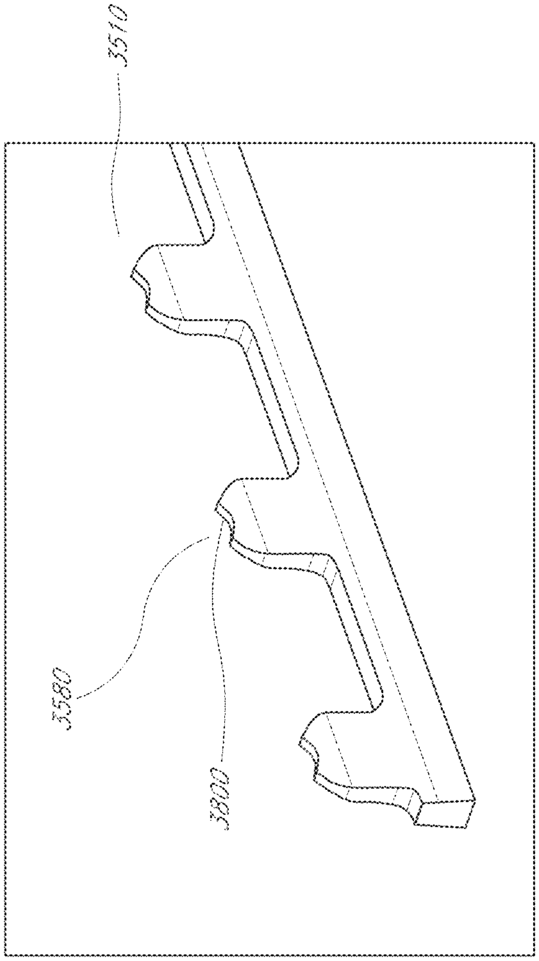

FIG. 38 illustrates the wedge dissectors having rounded double-hump like contacting surfaces at the tip that can provide effective tissue penetration.

Figure 39:
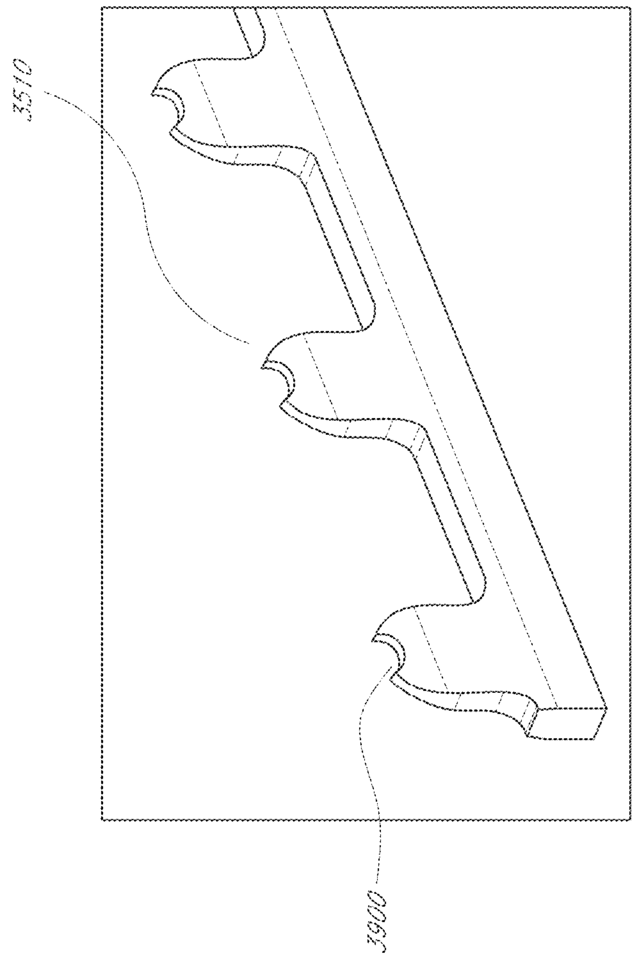

FIG. 39 illustrates variations on a design that provides a relatively sharp, pointed double contacting surface at the tip of each wedge dissector providing effective tissue penetration.

Figure 40:
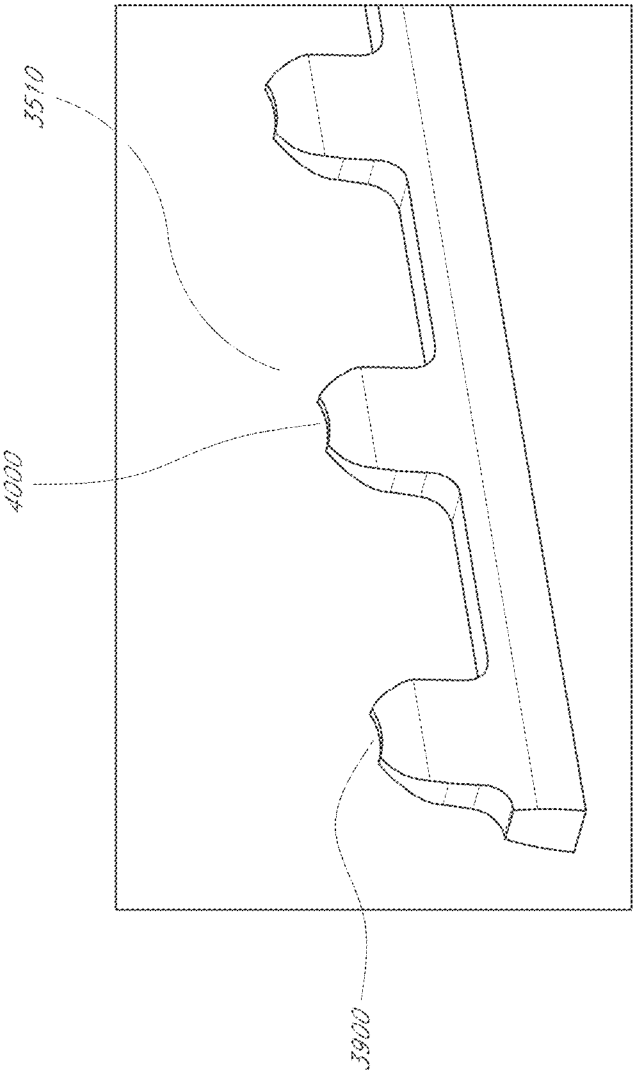

FIG. 40 illustrates a similar design that provides a relatively sharp, pointed double contacting surface at the tip of each wedge dissector which provides effective tissue penetration, that abut a central deeper, and more shallow valley/depression respectively.

Figure 41A:
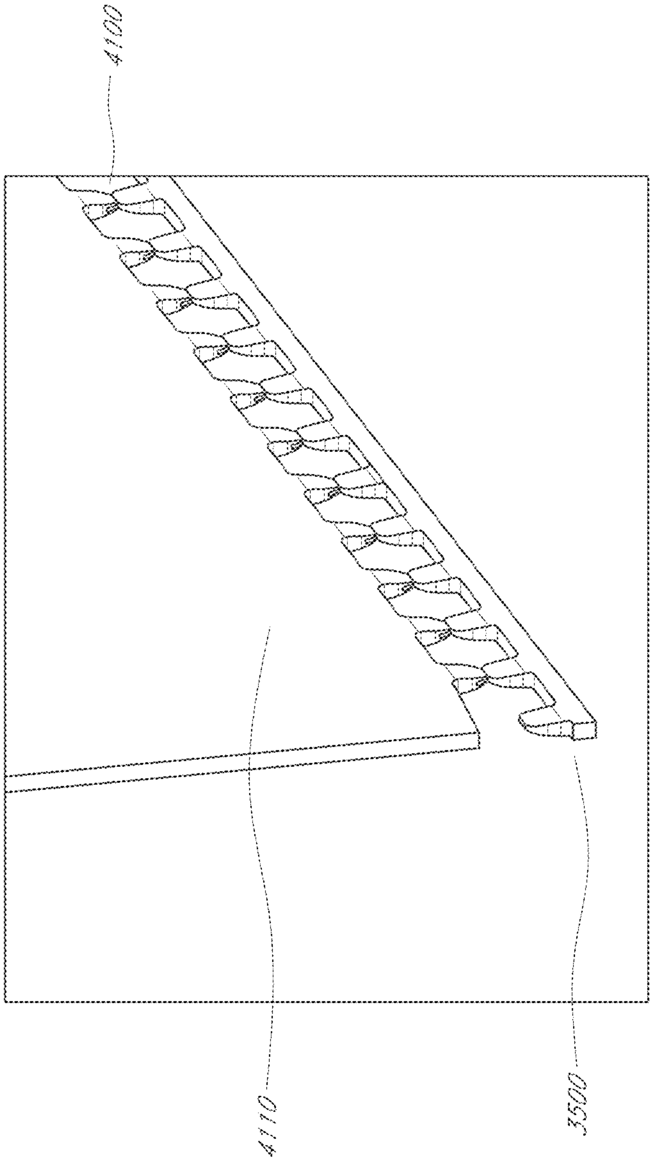

FIG. 41A illustrates that a strip can be fabricated that includes a plurality of strips (e.g., two identical strips) touching tip to tip in a wedge dissector frame.

Figure 41B:
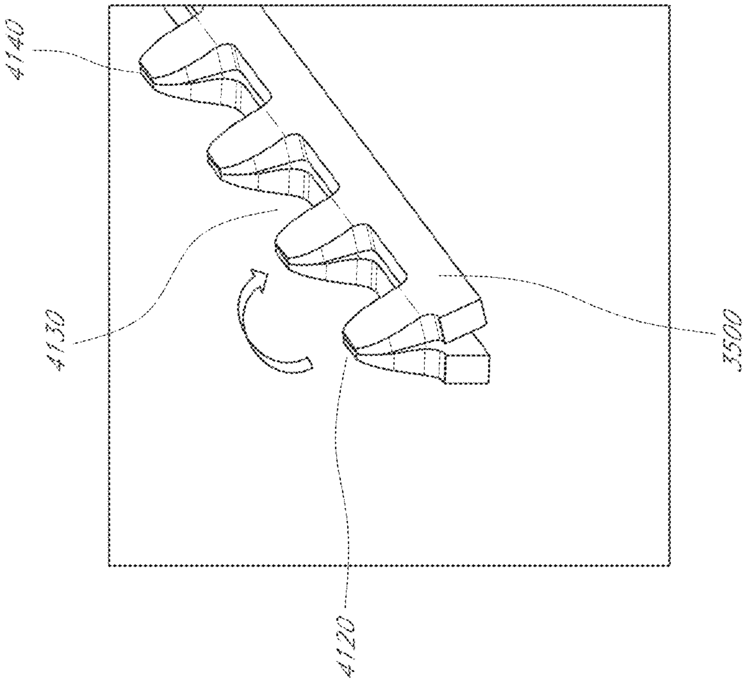
Figure 41C:
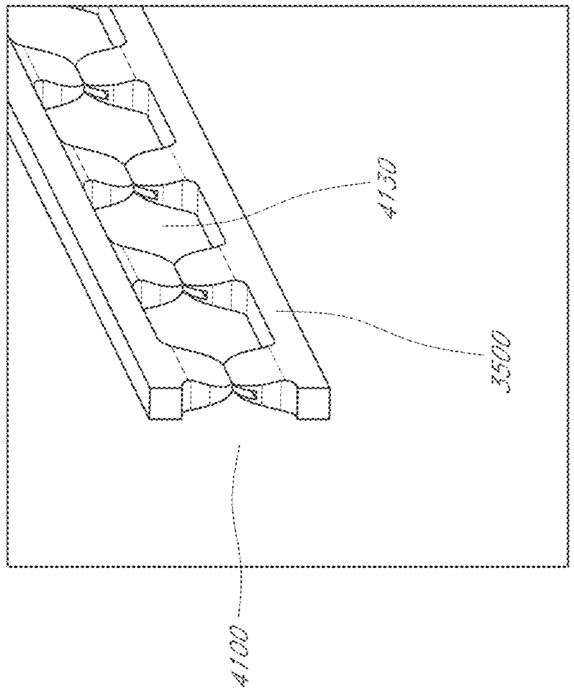

FIGS. 41B and 41C illustrate that in some embodiments, a plurality of strips can be bent or folded over into a bent form.

Figure 41E:
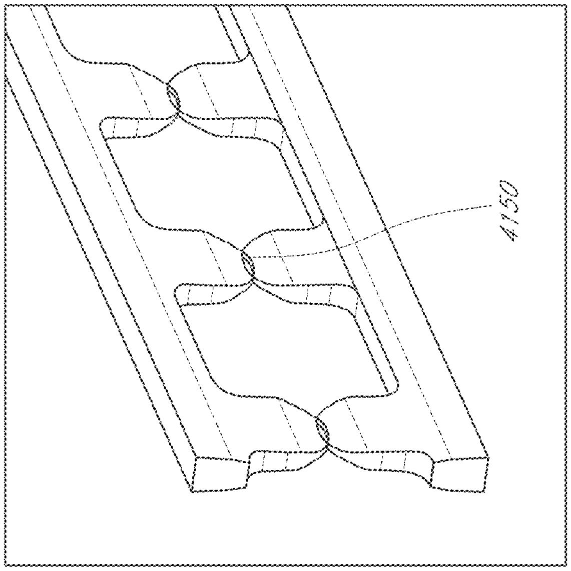
Figure 41D:
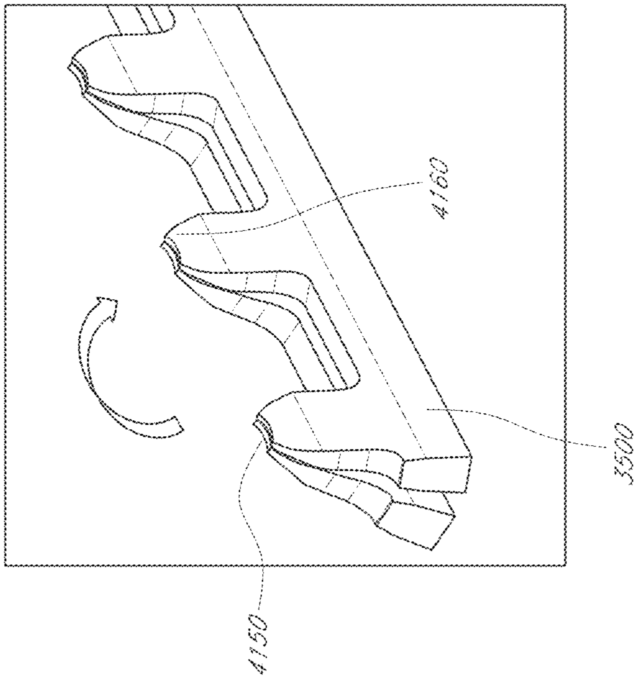

FIGS. 41D and 41E illustrate an alternative embodiment with serrated tips that include a plurality of pointed surfaces with a central concave segment there between.

Figure 42:
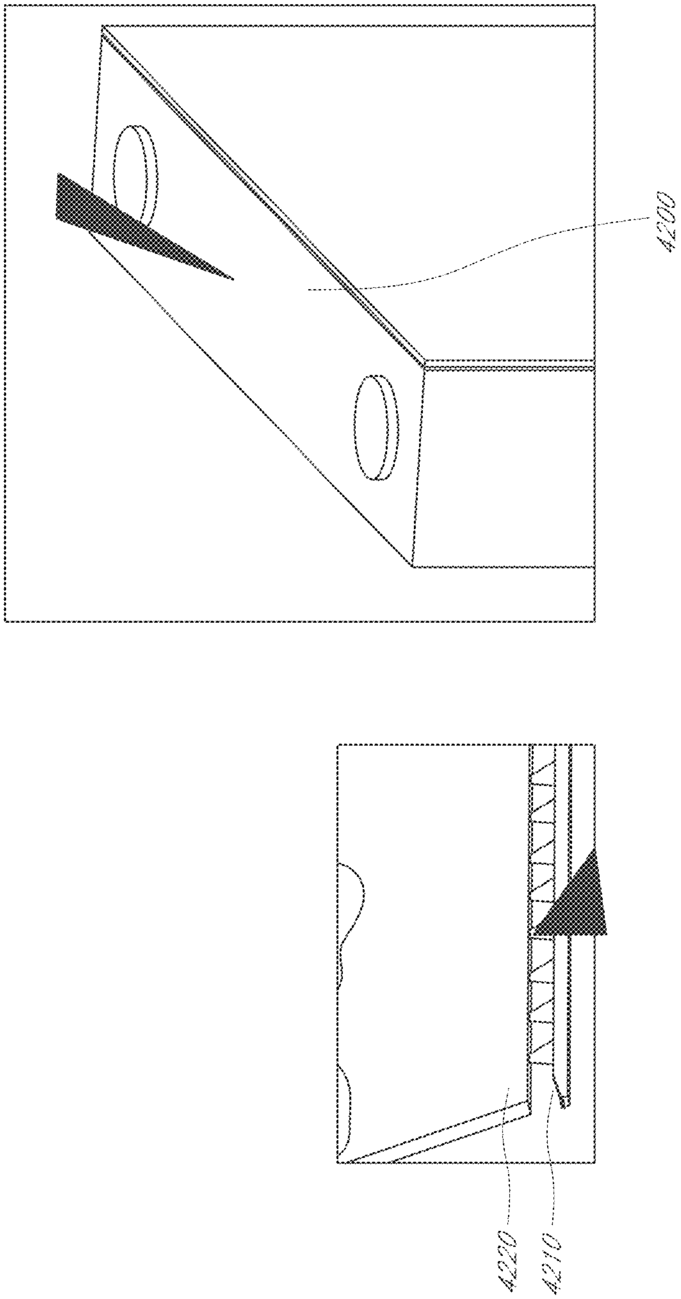

FIG. 42 illustrates an illustration series that shows the ability to take a stack of strips connected to a blank that can be discarded at any point in the strip attachment process. The radial distal tips are abutted against continuous edge for easy breaking off.

Figure 43:
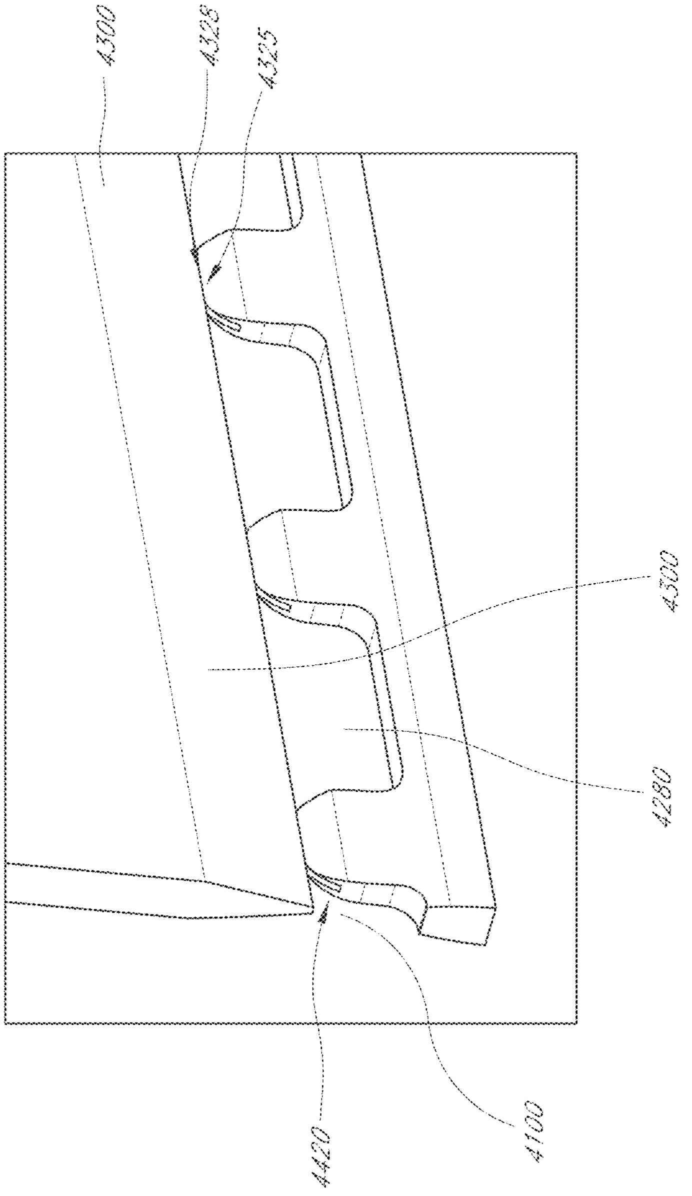

FIG. 43 illustrates an embodiment of a close-up drawing of the attachment of the strip tip to the blank.

Figure 44A:
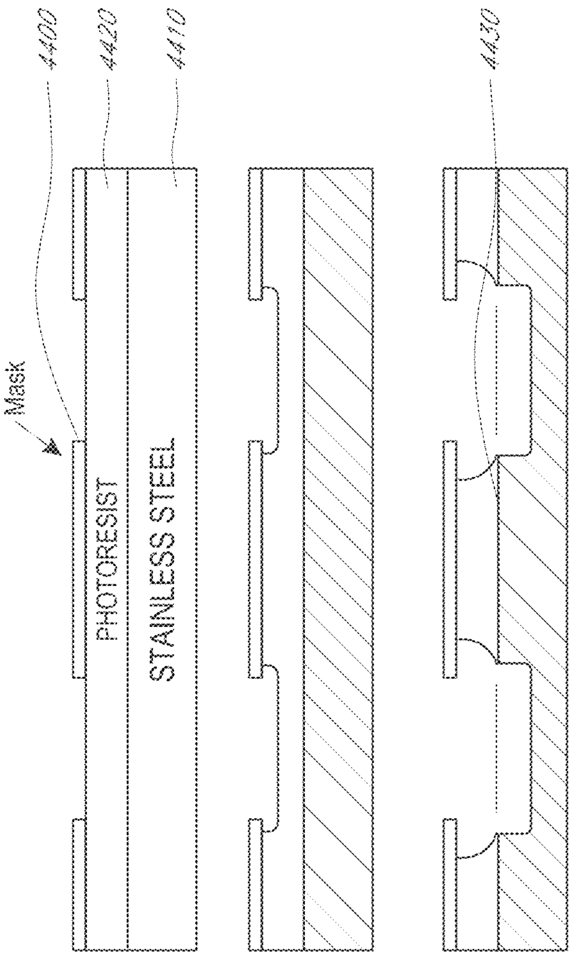
Figure 44B:
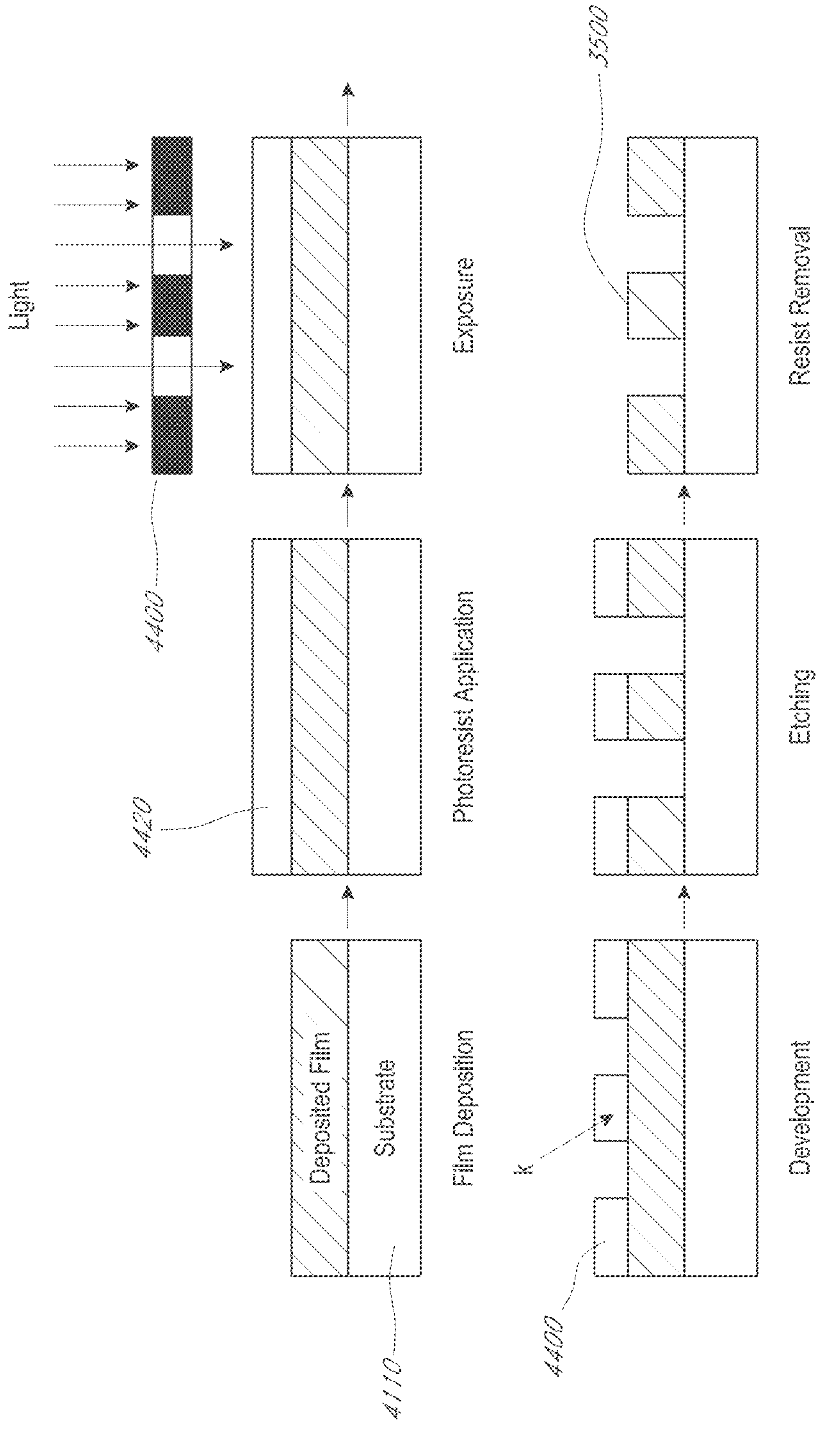

FIGS. 44A and 44B illustrate an isotropic etching where the etch occurs in more than one direction (both vertically and horizontally under the mask).

Figure 45B:
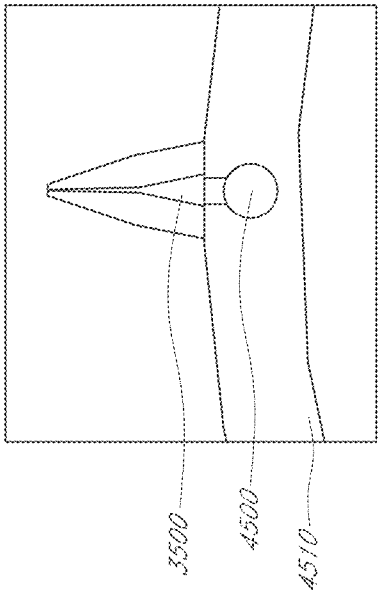
Figure 45A:
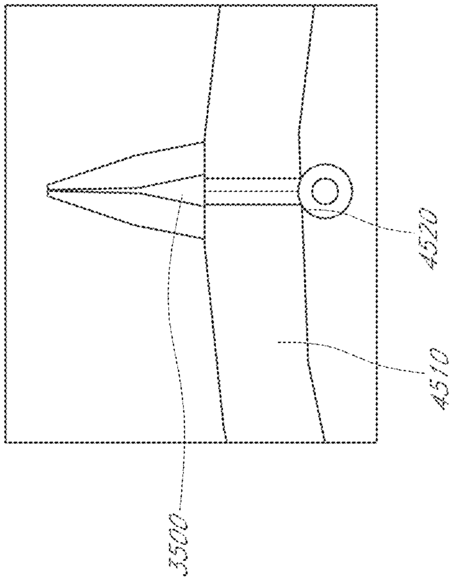
Figure 46:
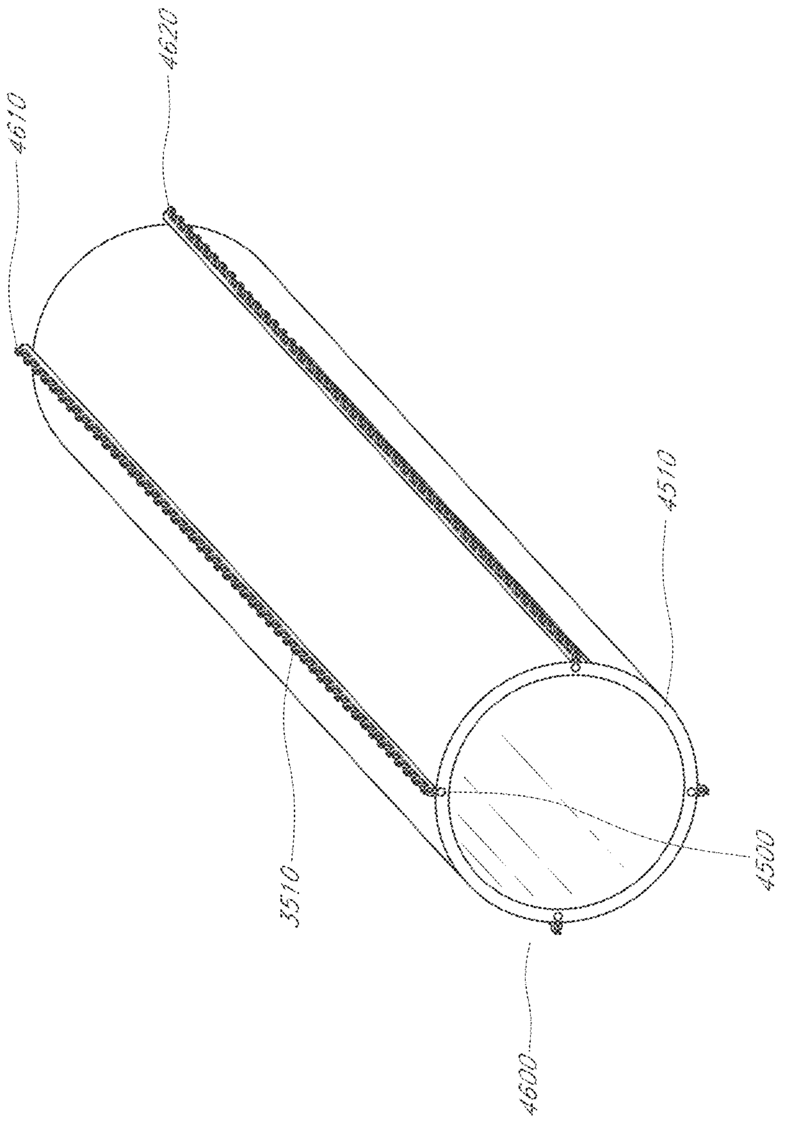

FIG. 45A shows the strip can be placed over a through hole embedded in the balloon. FIG. 45B shows the strip can be placed over a through hole embedded in the balloon wall FIG. 46 illustrates in some embodiments, a series of 4 A-frame strips can be placed over through holes embedded in the balloon wall.

Figure 47:
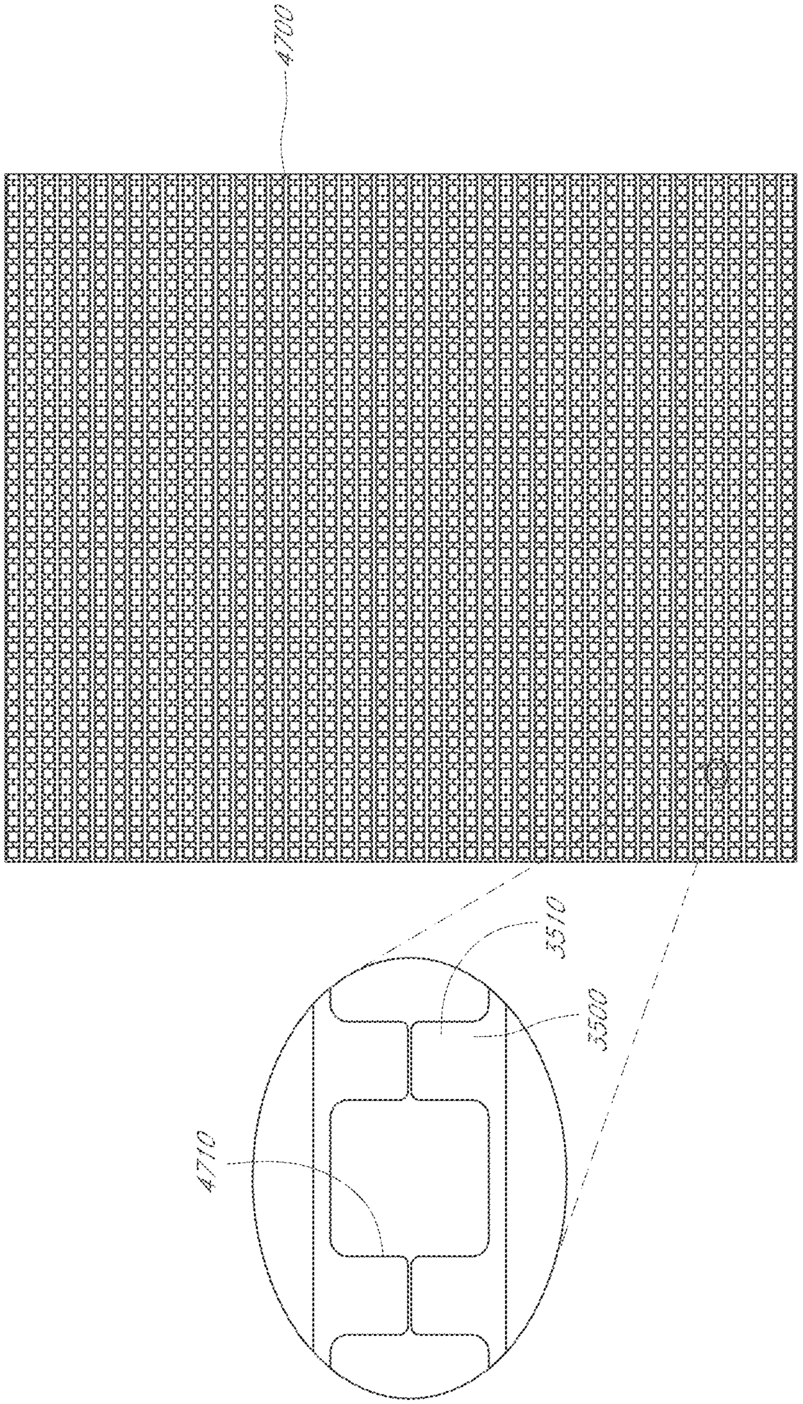

FIG. 47 illustrates an embodiment (with a close-up insert) of what an array of strips might look like on a mask set prior to chemical etching.

Figure 48B:
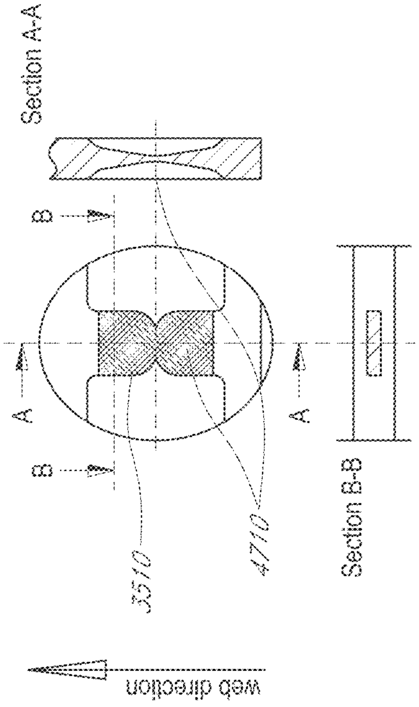
Figure 48A:
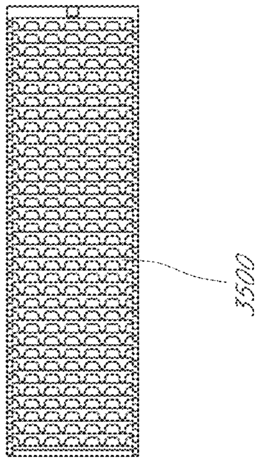
Figure 48C:
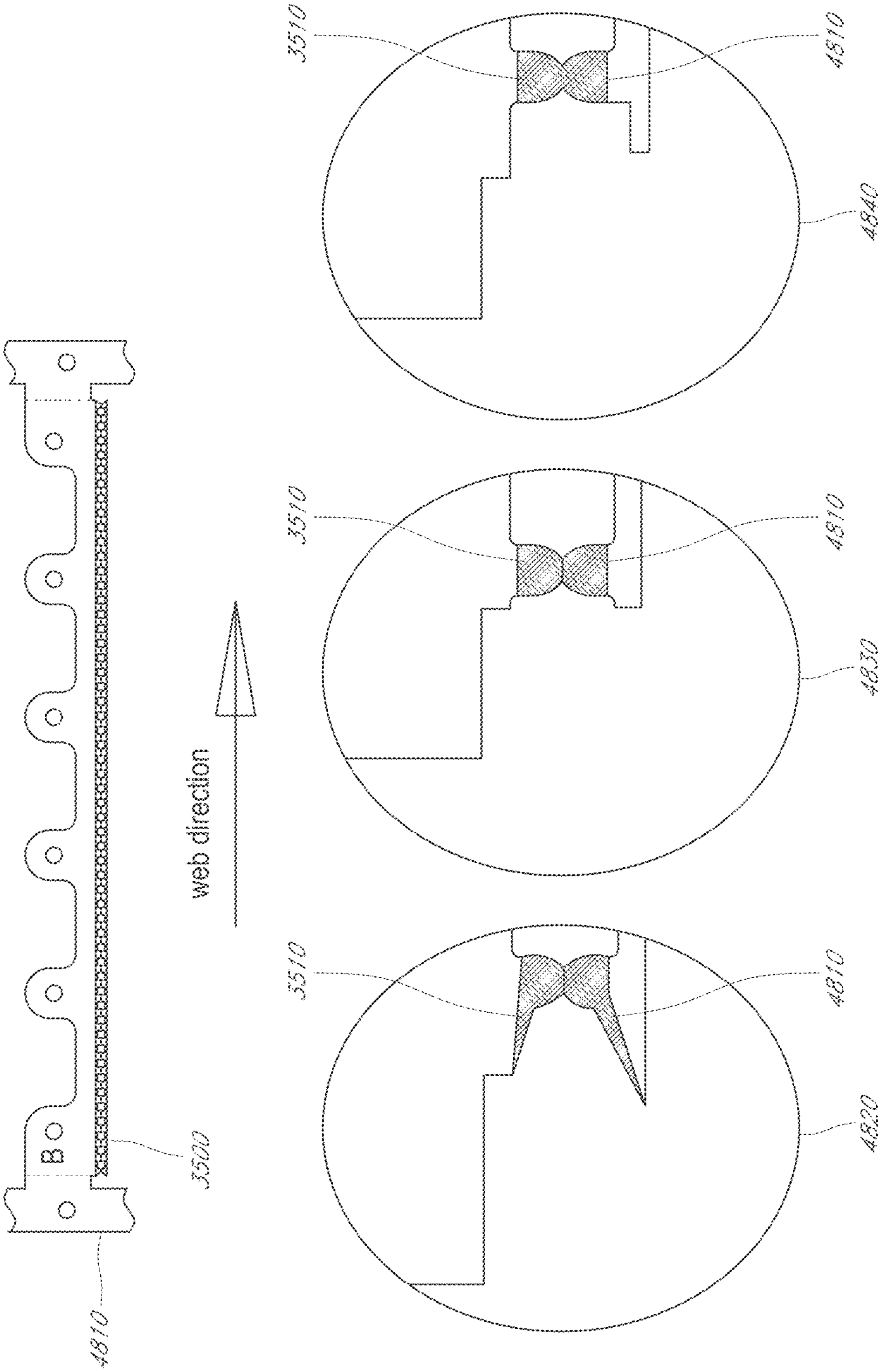
Figure 48D:
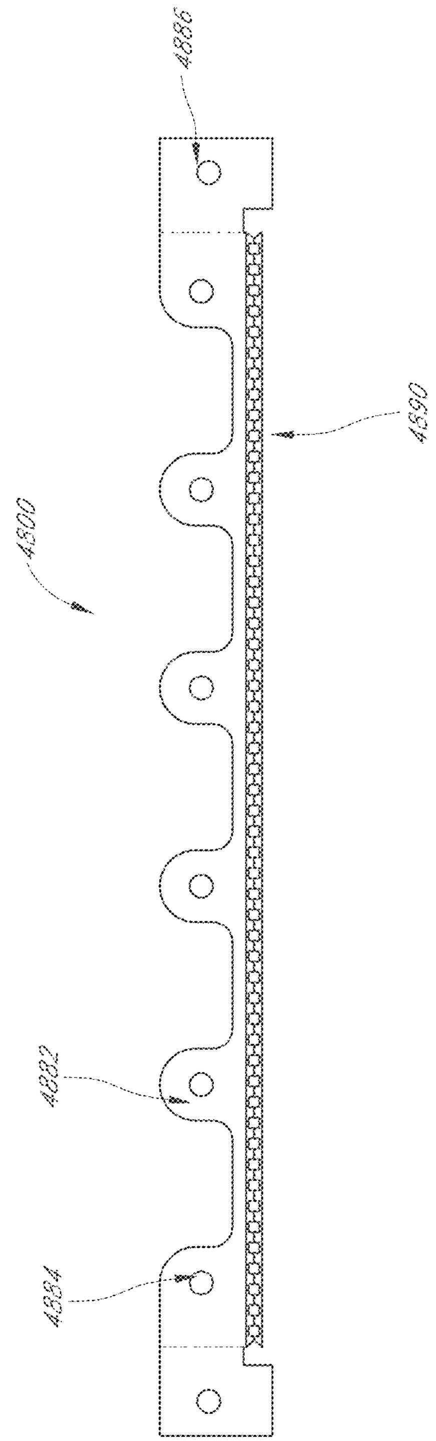

FIG. 48*a* shows a strip array. FIG. 48*b* shows a detailed close up image of the adjacent wedge dissectors with detachable zones. FIG. 48*c* shows serration strips connected to a strip carrier for alignment, control, placement, and ease of manufacturing. FIG. 48*d* illustrates an embodiment of a strip carrier reversibly attached to a strip.

Figure 49:
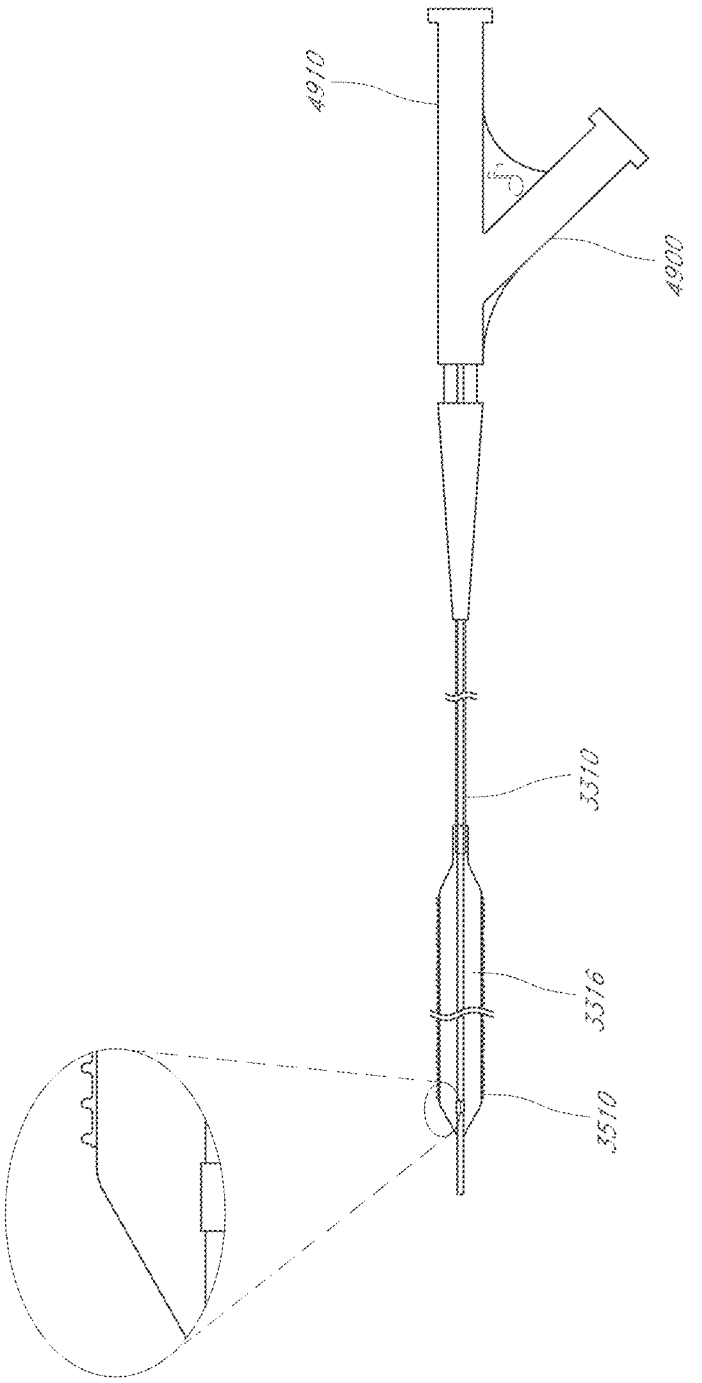
Figure 49A:
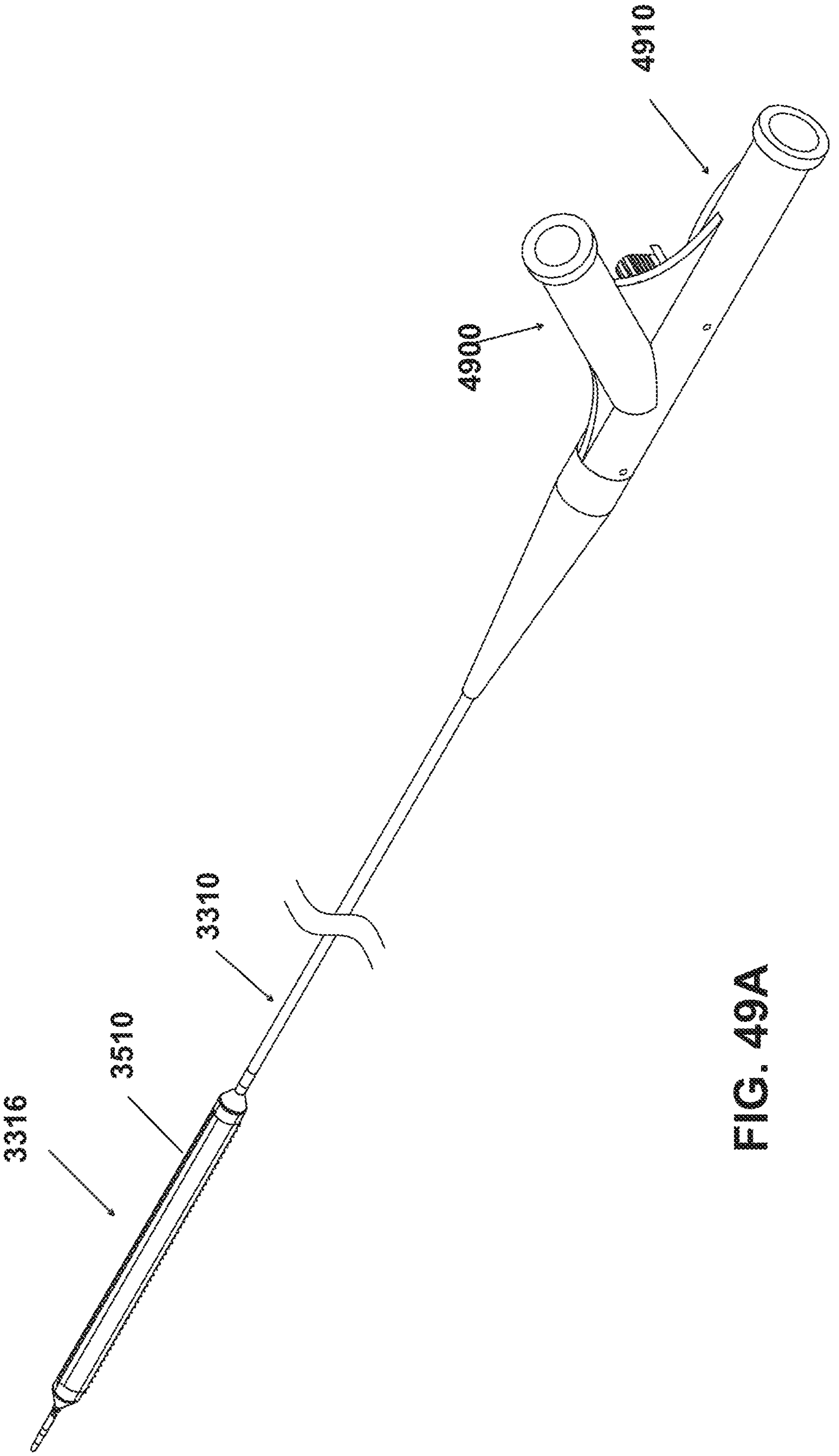
Figure 49B:
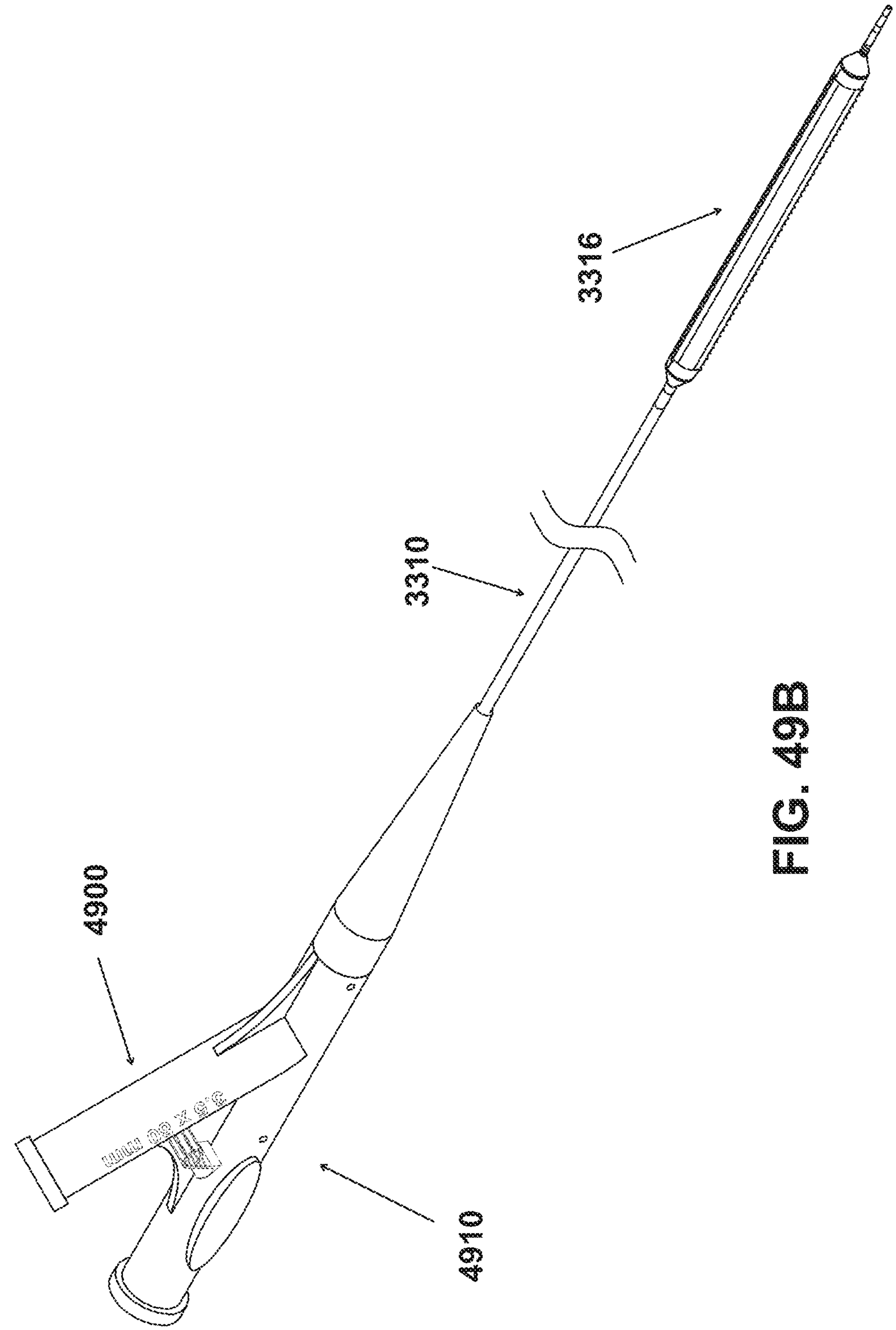
Figure 49C:
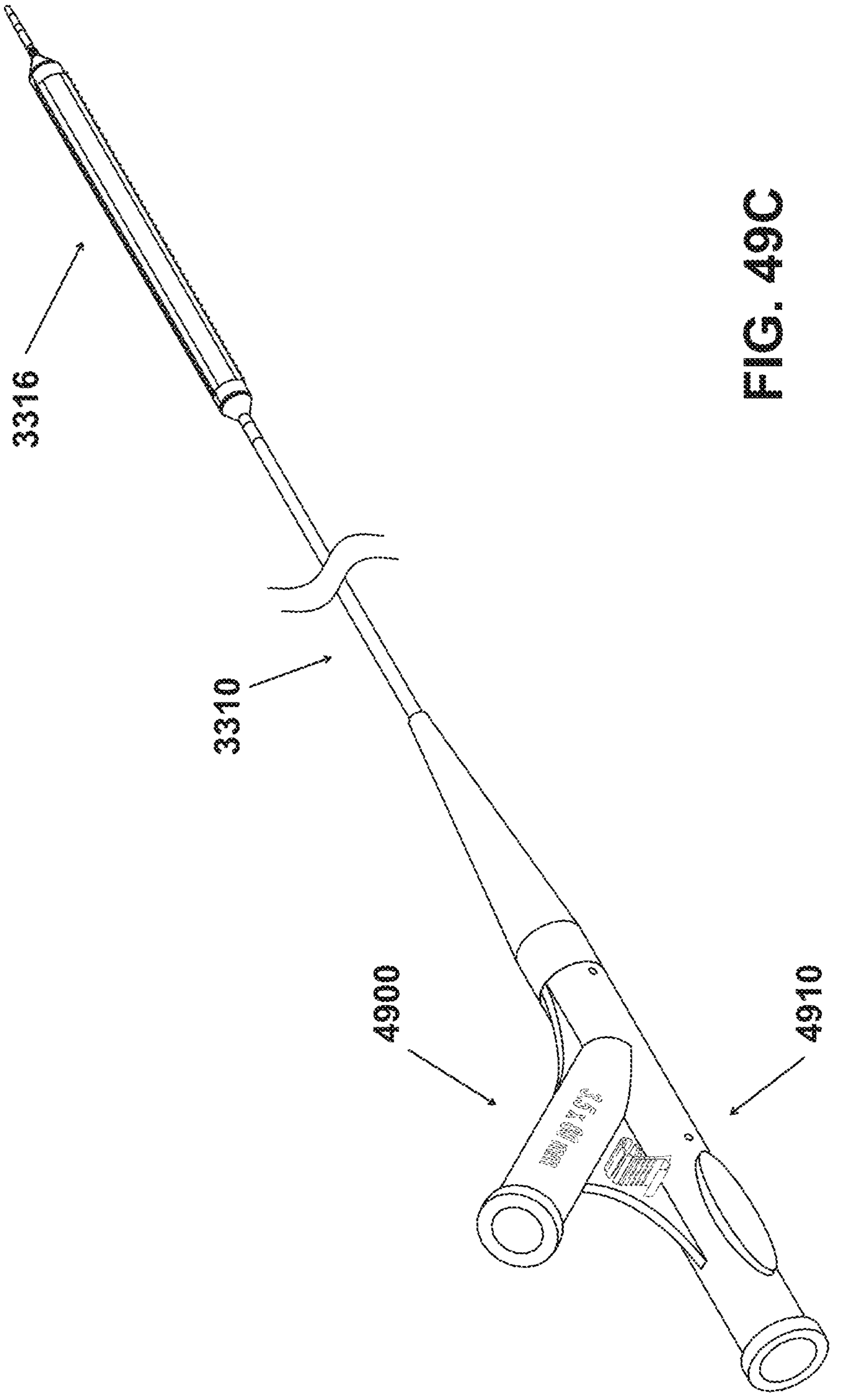
Figure 49D:
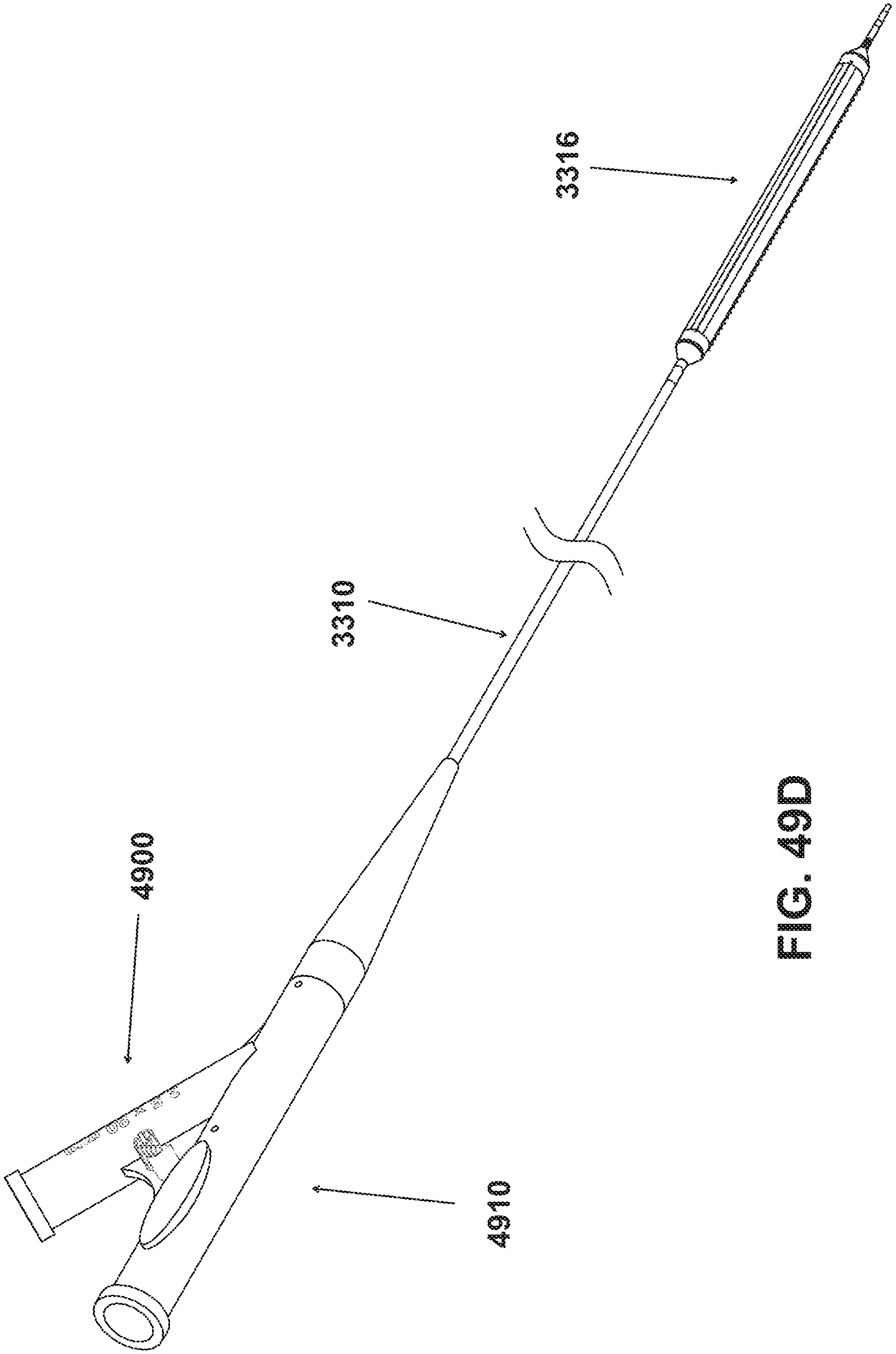
Figure 49E:
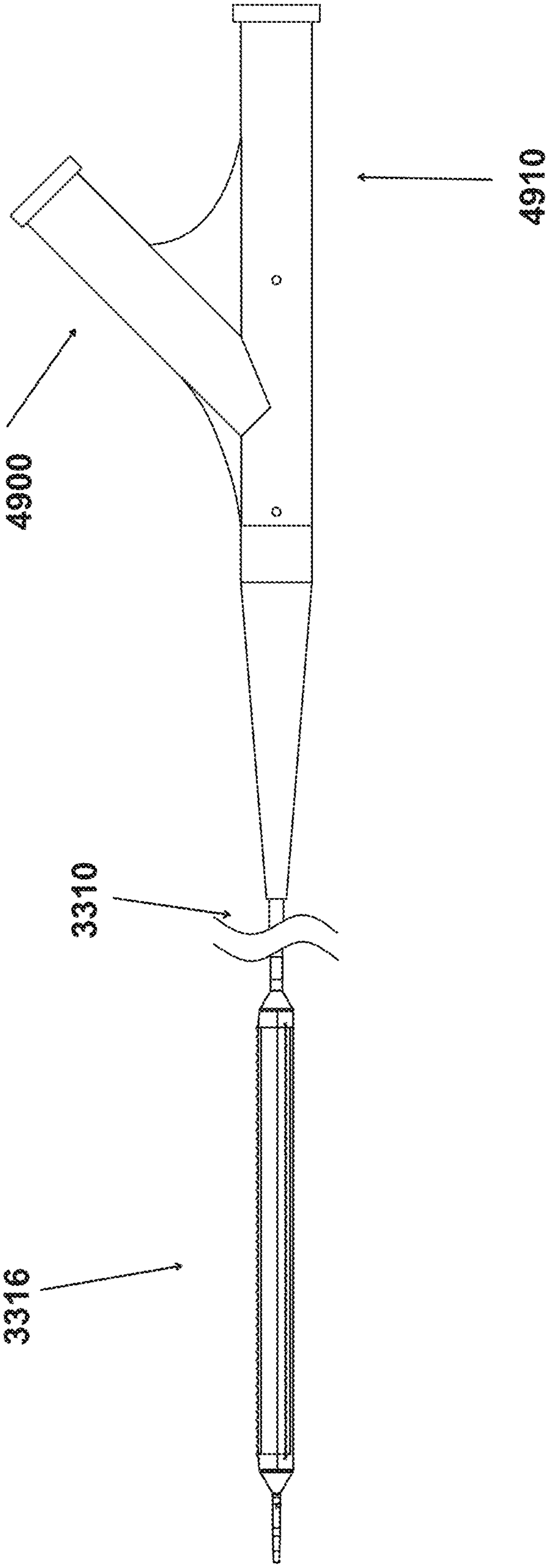
Figure 49F:
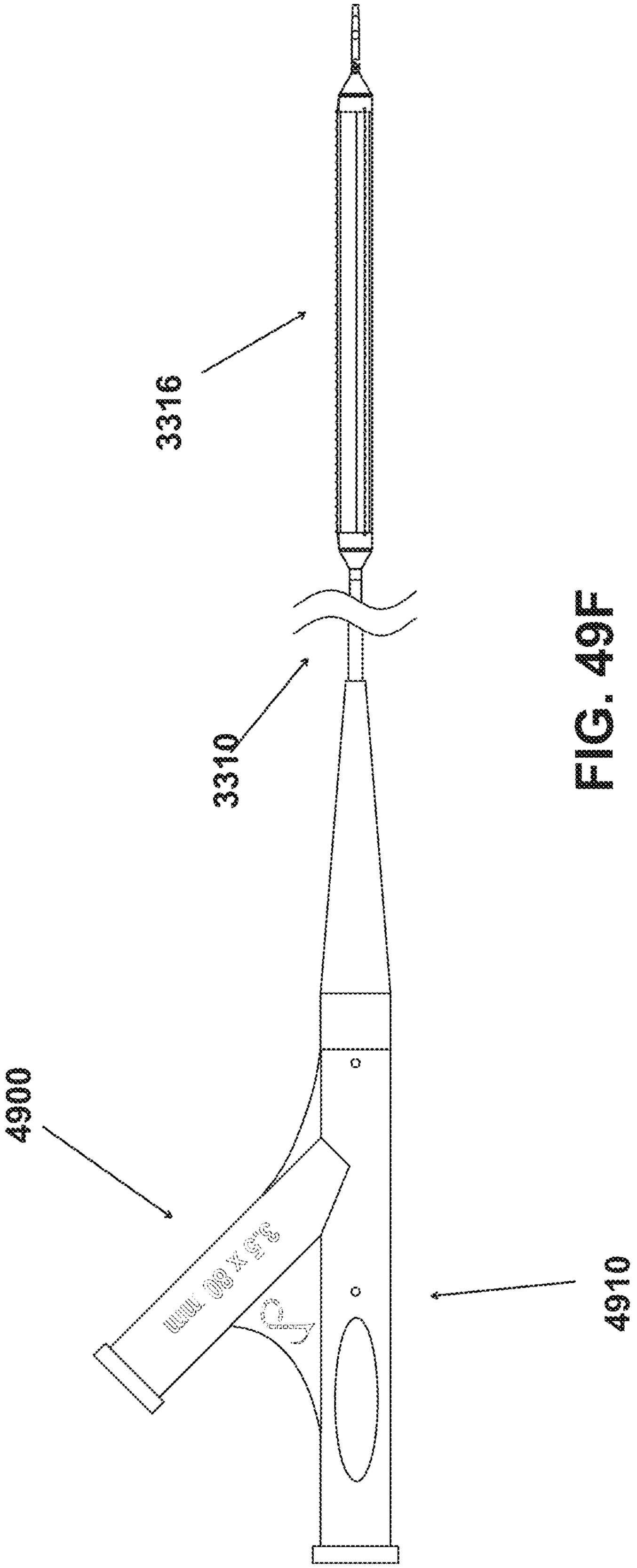
Figure 49G:
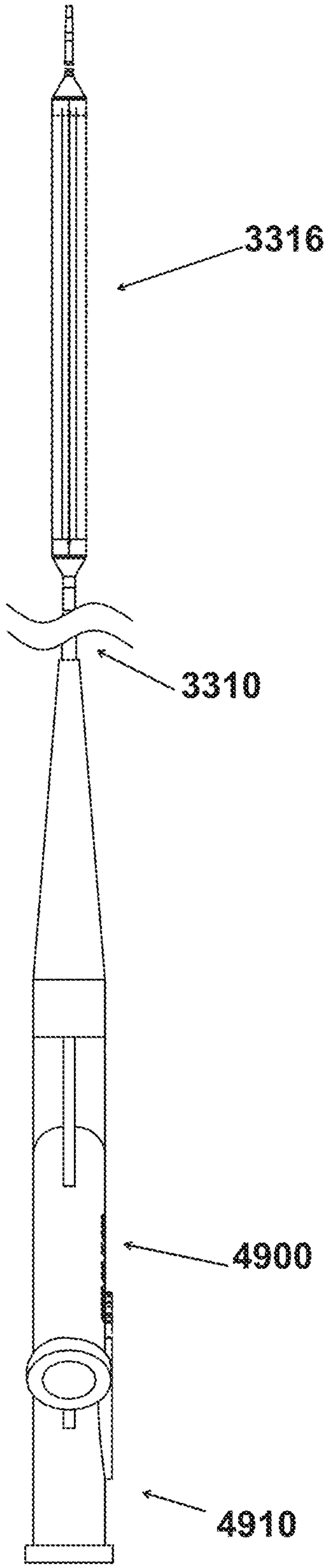
Figure 49H:
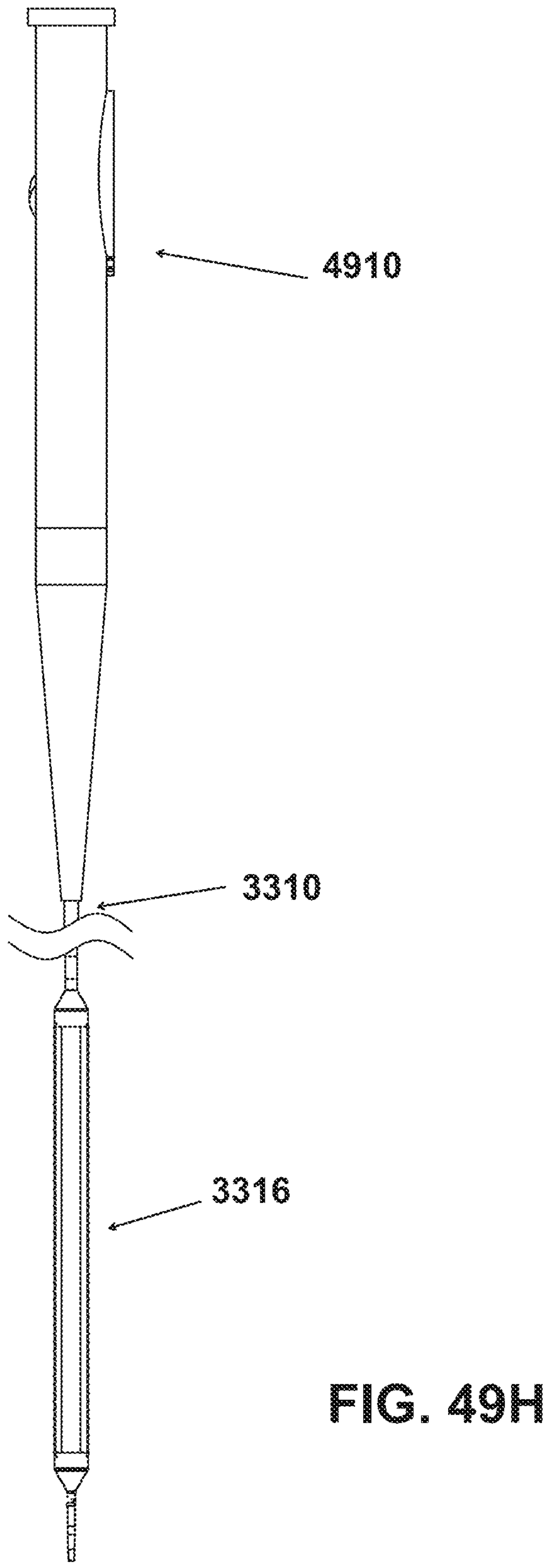
Figure 49J:
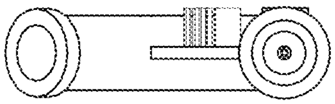
Figure 49I:
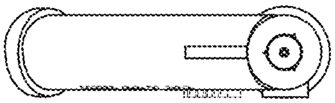

FIGS. 49-49J illustrate various views of one embodiment of an overall system for producing serratoplasty showing a series of serrating or scoring wedge dissectors on the outer diameter of the catheter attached to a catheter with a guidewire hub and balloon inflation hub.

Figure 50:
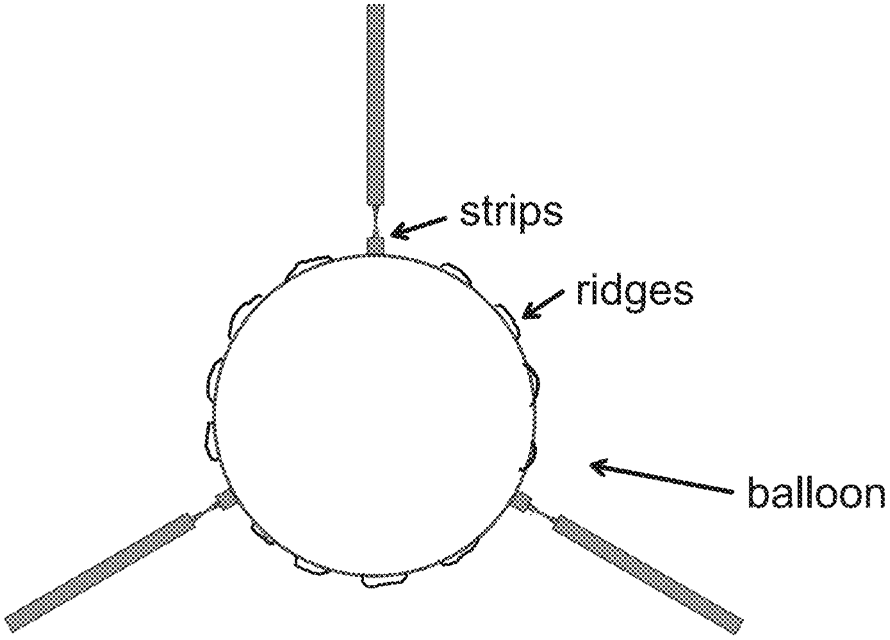

FIG. 50 schematically illustrates a balloon his blown from an extrusion that has a set of longitudinally oriented ridges of material, according to some embodiments.

Figure 51:
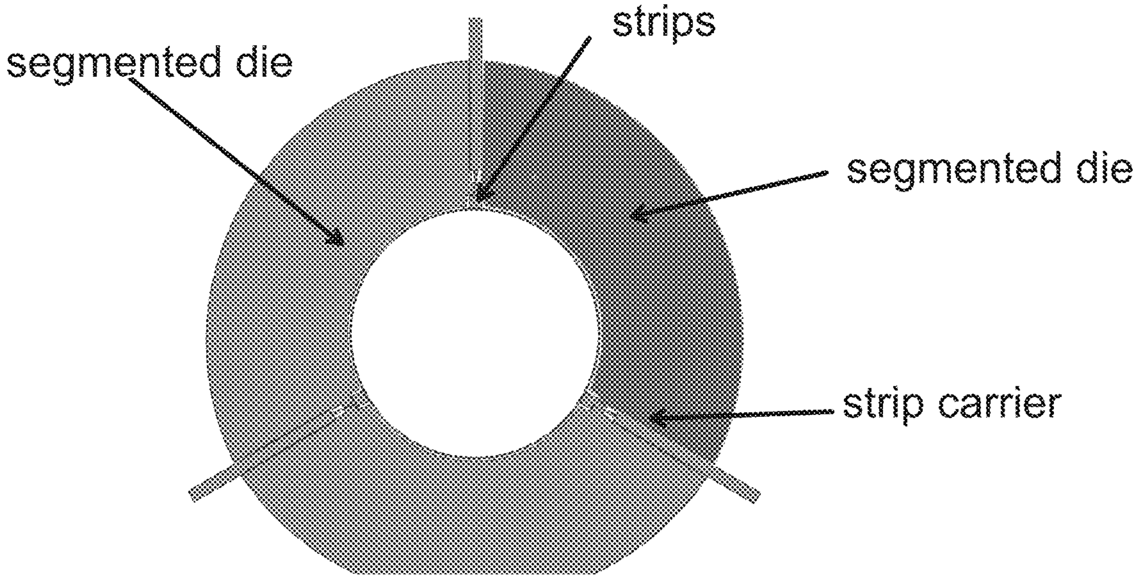

FIG. 51 schematically illustrates the sets of strips placed in the balloon blowing dies prior to the balloon blowing process, according to some embodiments.

Figure 52:
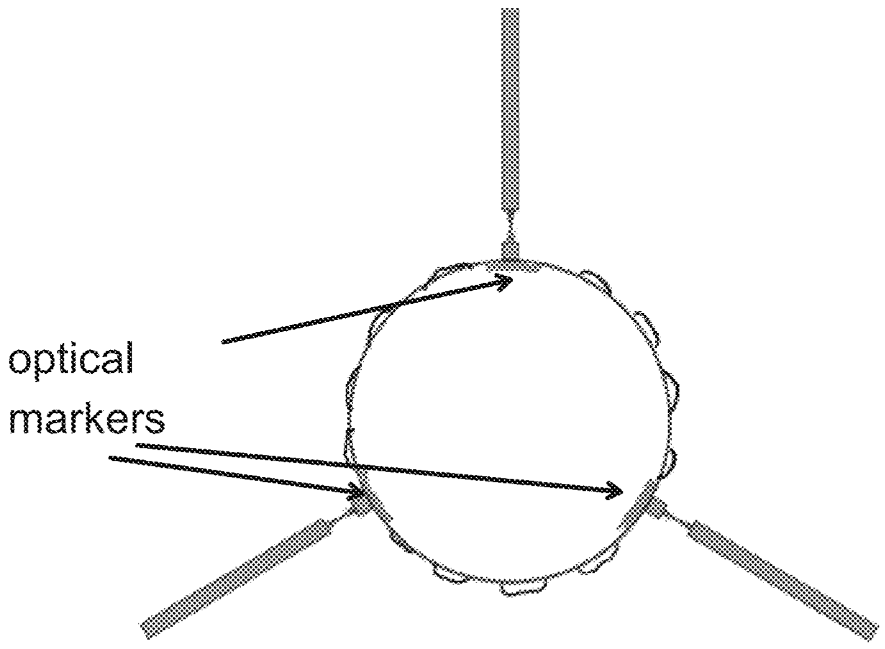

FIG. 52 schematically illustrates the extrusion including optical markers to aid in orientation of the extrusion in the balloon blowing process, according to some embodiments.

Figure 53:
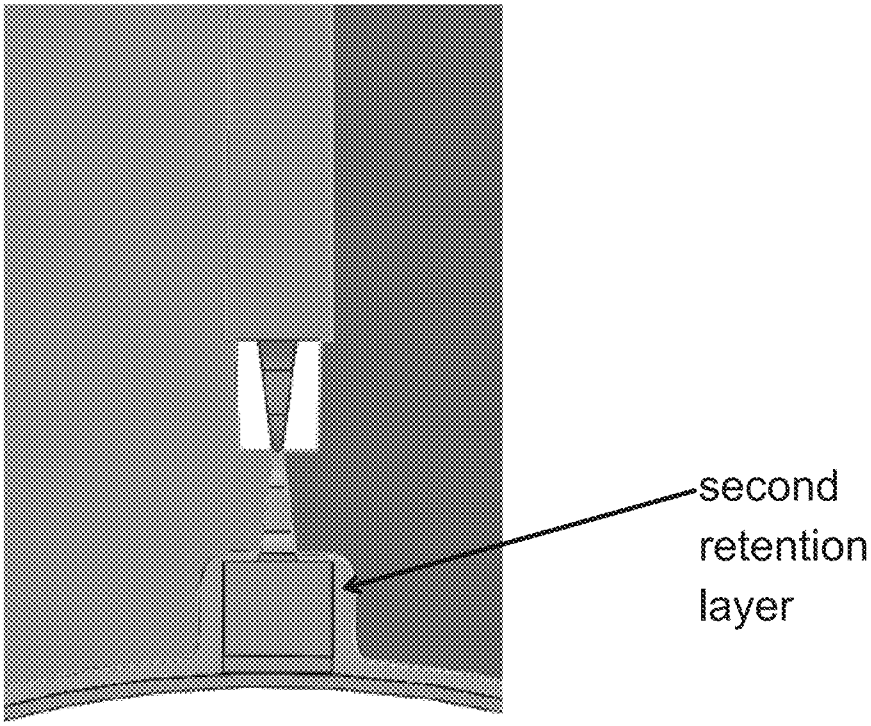

FIG. 53 illustrates an embodiment where the extrusion used to blow the balloon has a second retention layer with a slightly lower glass transition temperature than the balloon itself.

Figure 54:
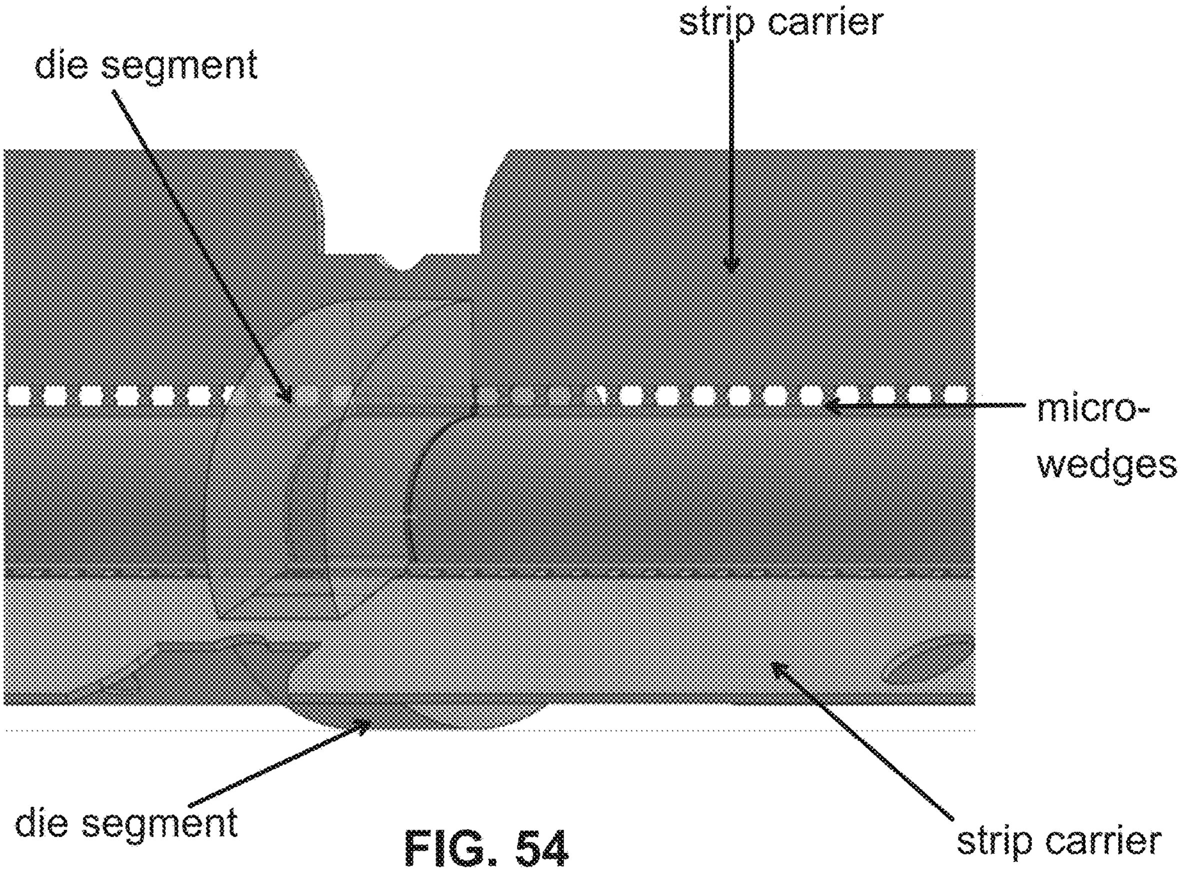

FIG. 54 schematically illustrates a perspective view of the dies (shown only partially and transparently) with a series of strips shown clamped into a modified balloon blowing machine, according to some embodiments.

Figure 55:
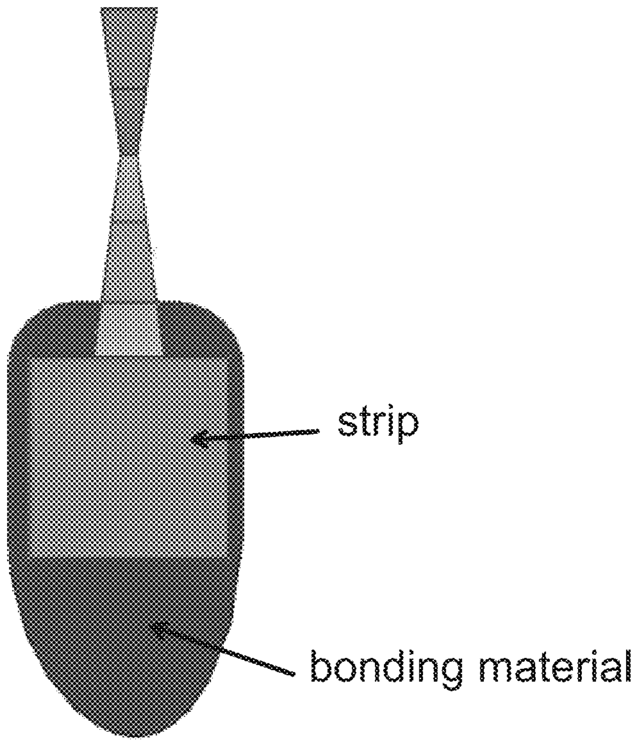

FIG. 55 schematically illustrates a strip and bonding material surrounding the base of the strip, according to some embodiments.

Figure 56:
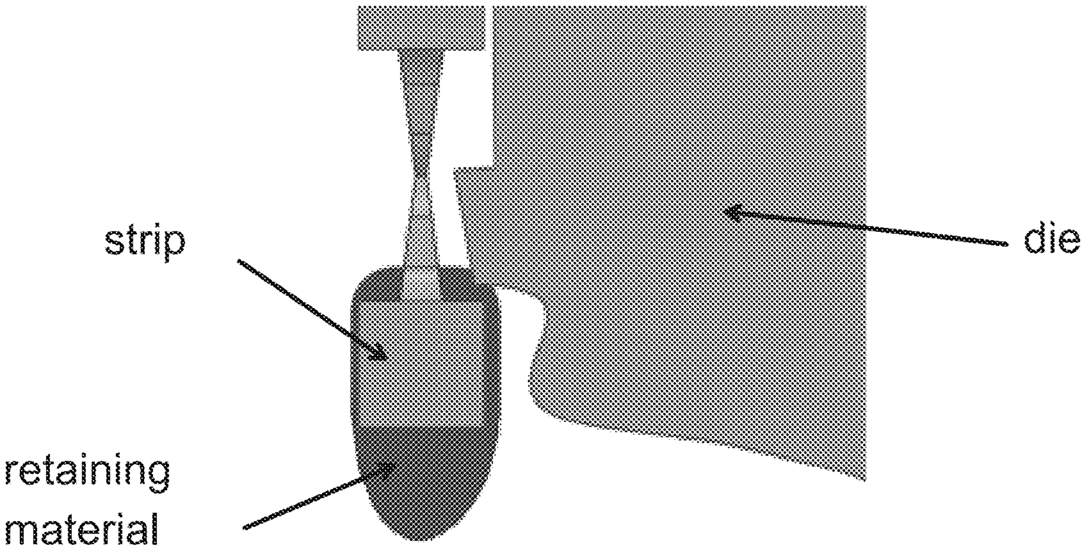

FIG. 56 schematically illustrates a sectional view of the strip and the strip retaining material being placed into one side of a single balloon blowing die, according to some embodiments.

Figure 57:
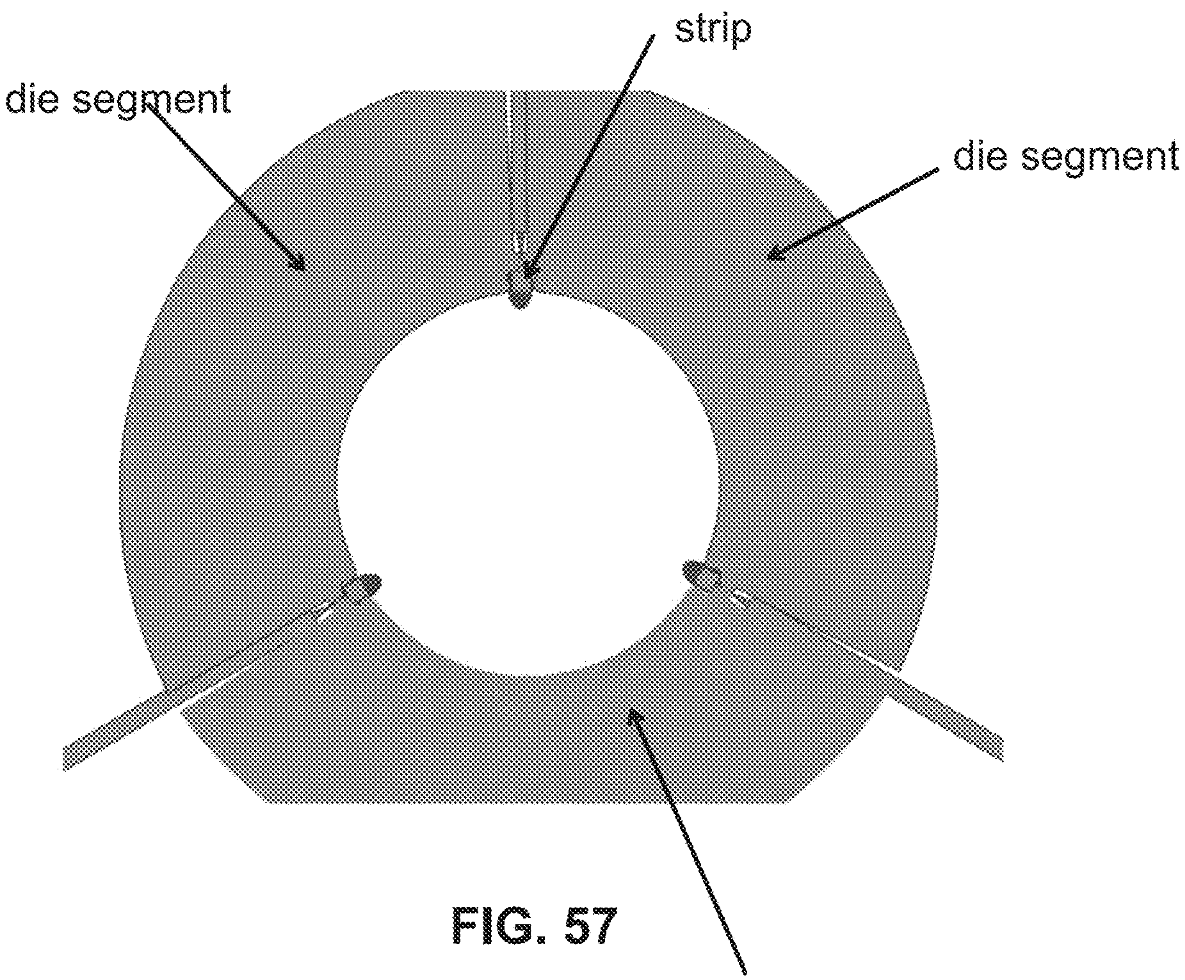

FIG. 57 schematically illustrates 3 strips captured within a set of three dies at 120 degrees from each other, according to some embodiments.

Figure 58:
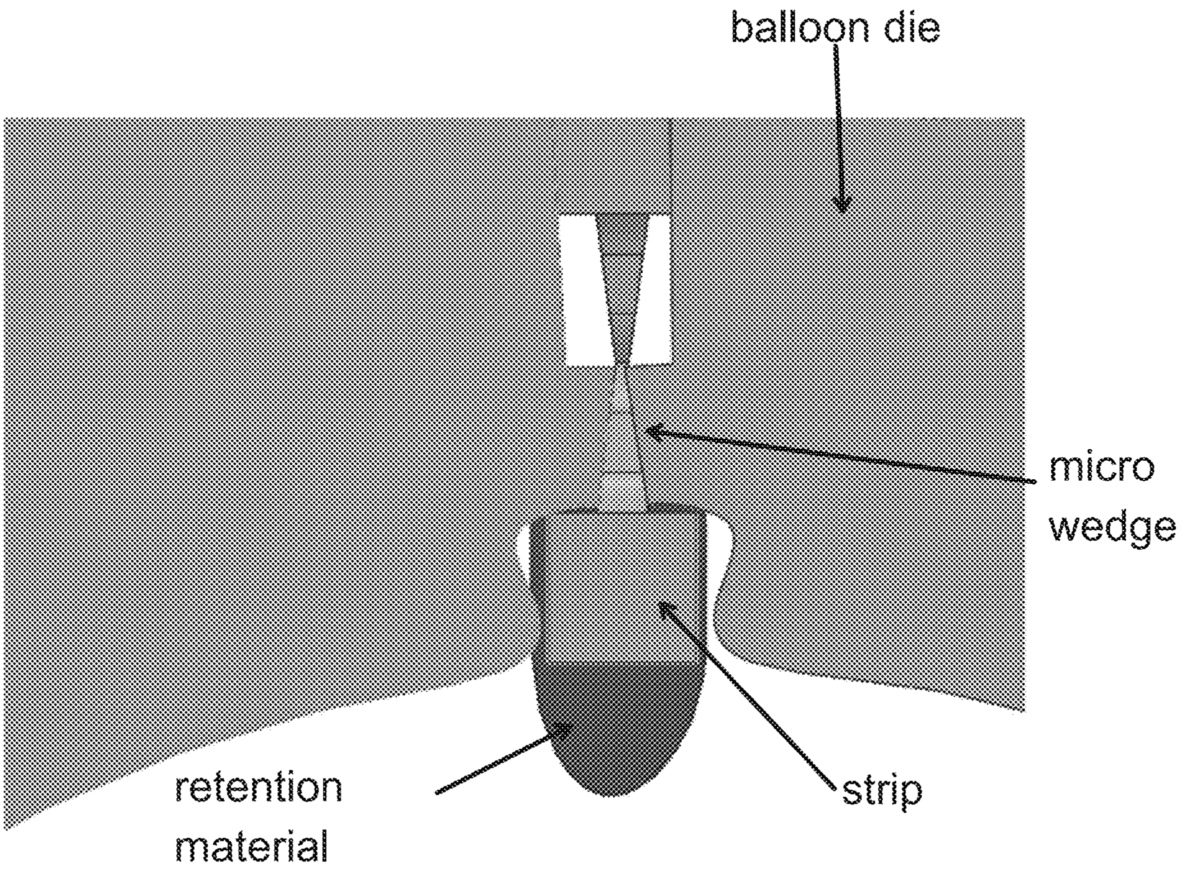

FIG. 58 schematically illustrates a magnified view of the strip and retention material captured between two sides of the balloon dies, according to some embodiments.

Figure 59:
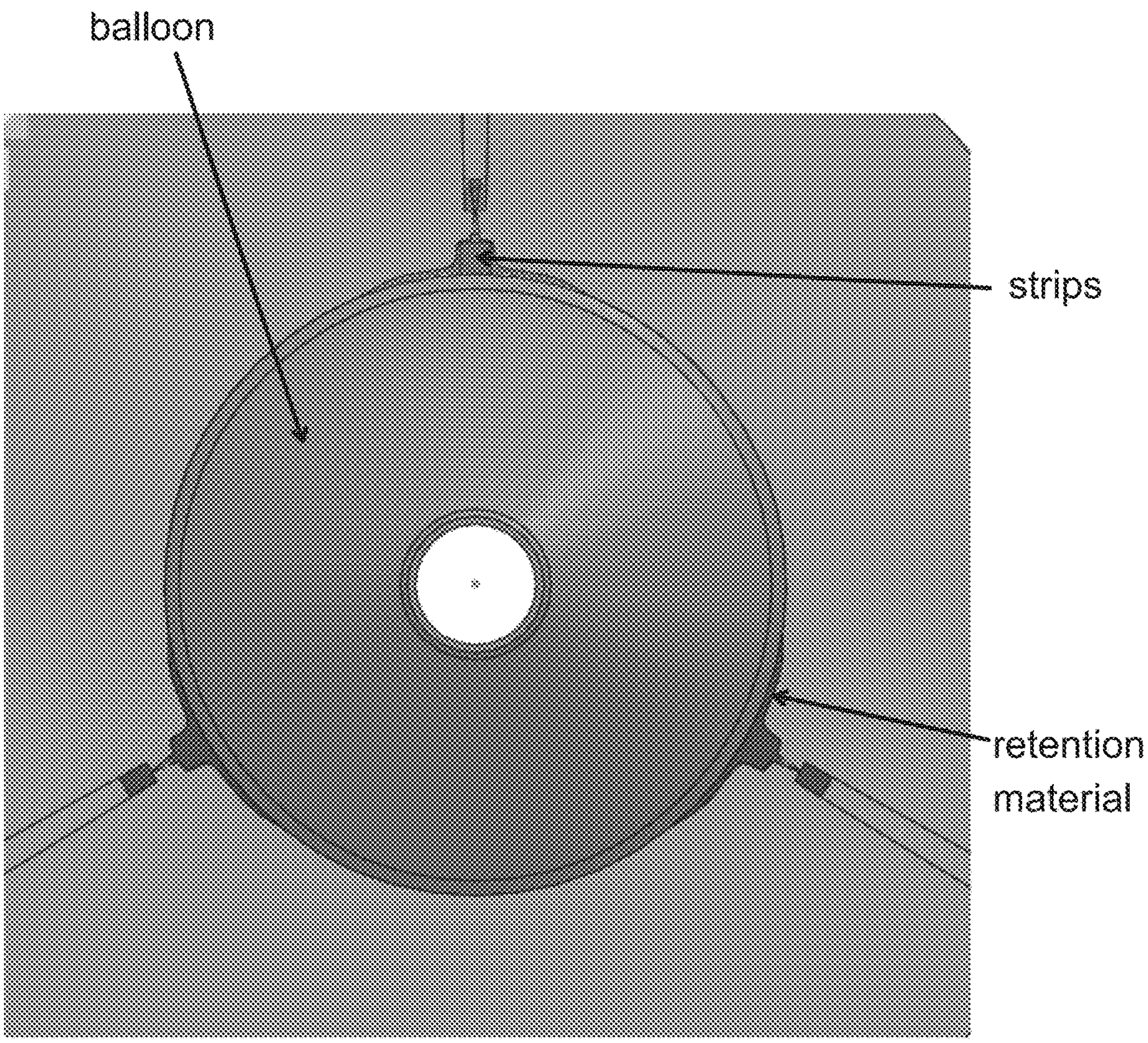

FIG. 59 schematically illustrates a cross section of the balloon with the strips and the retention materials bonded together and removed from the balloon blowing machine, according to some embodiments.

Figure 60:
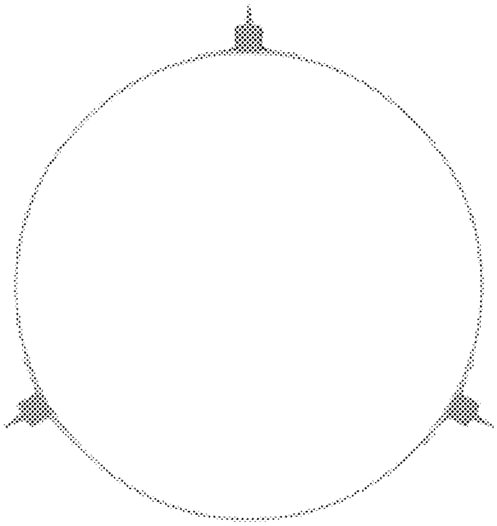

FIG. 60 schematically illustrates three strips are bonded to the balloon surface with the retention layer, according to some embodiments.

Figure 61:
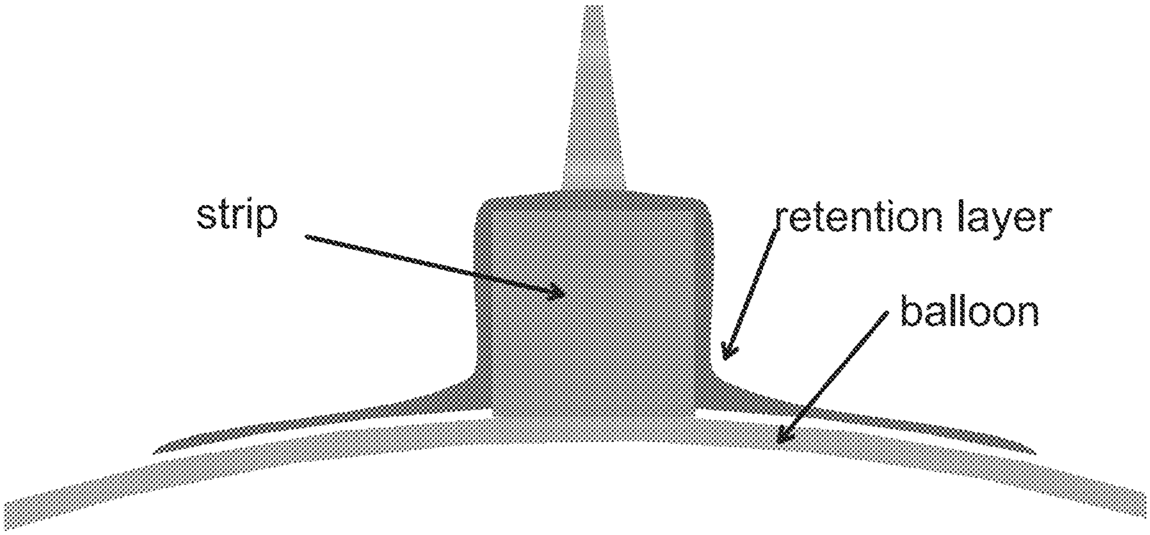

FIG. 61 schematically illustrates a magnified view of this strip after the retention layer has been bonded to the balloon surface, according to some embodiments.

Figure 62:
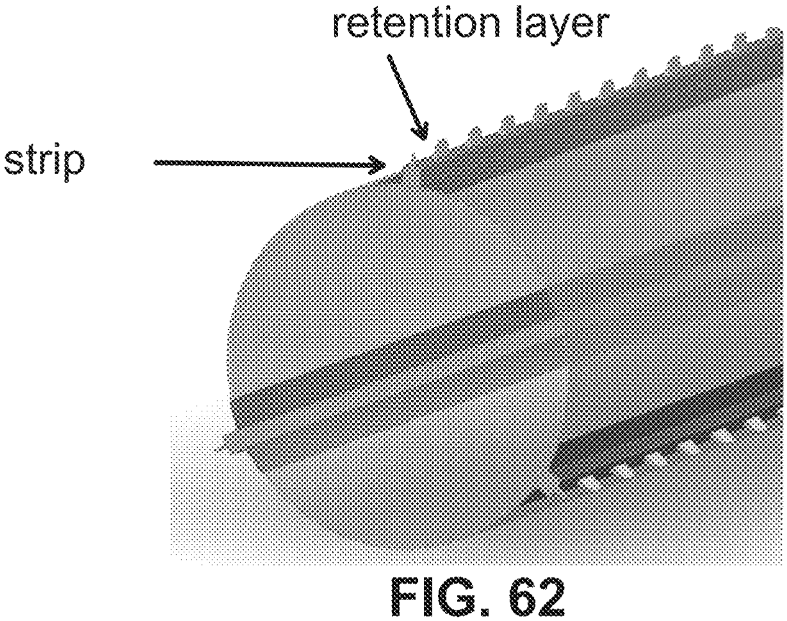

FIG. 62 schematically illustrates a perspective view of the three strips with the retention layer bonded showing the minimal surface area that the retention layer covers on the outer balloon surface relative to the entire balloon surface, according to some embodiments.

Figure 63:
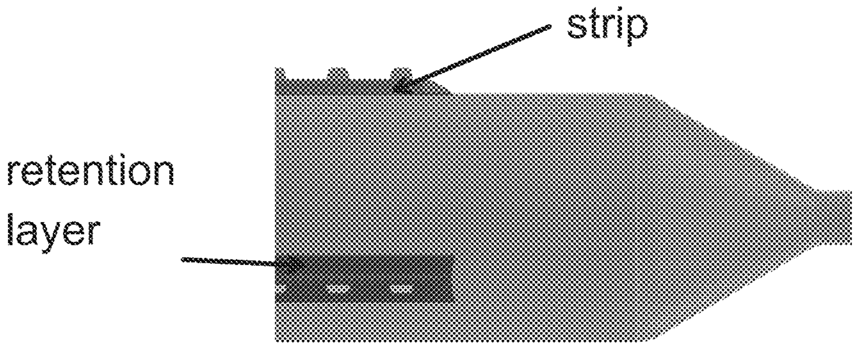

FIG. 63 schematically illustrates a top view illustration where the retention layer is shown covering the top of the strip, between each of the wedge dissectors, and outward some fraction of the balloon surface such that a footing is placed on the balloon to aid in strip retention.

Figure 64:
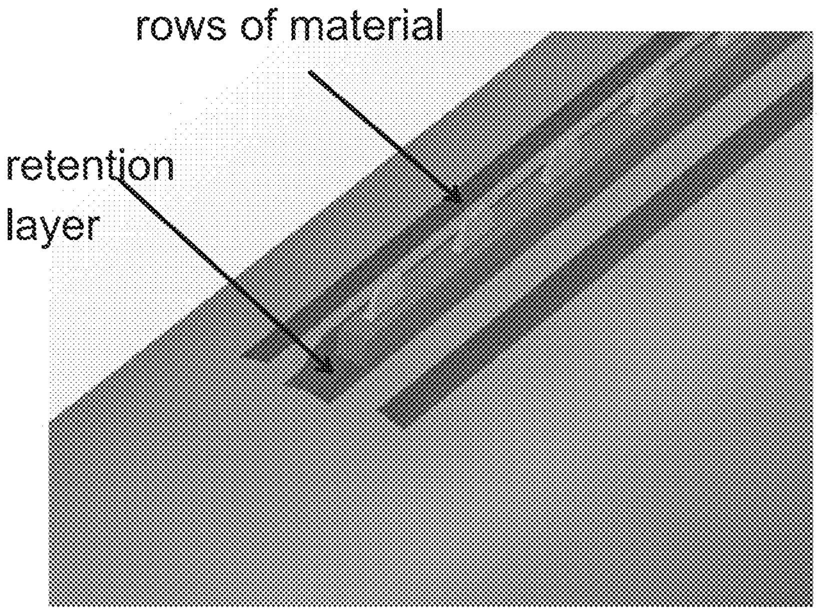

FIG. 64 schematically illustrates a retention layer that is minimized with no footprint on either side of the strip along the balloon surface.

Figure 65:
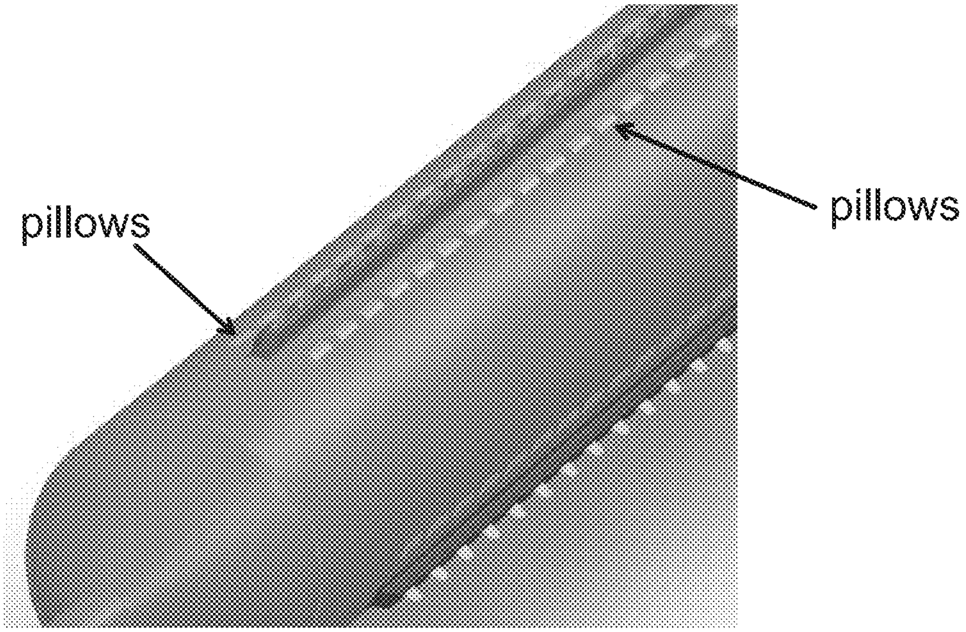

FIG. 65 schematically illustrate the pillows that adjoin the retention of the strips are shown in a dotted pattern similar to the spacing of the tips of the strip.

Figure 66:
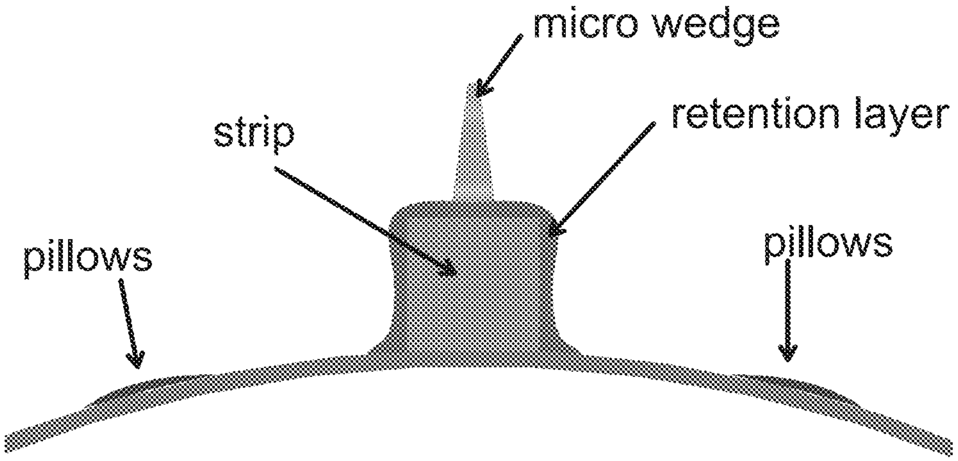

FIG. 66 schematically illustrates a cross section view of the retained strip with retention layer over it with minimal retention material and accompanying pair of balloon protection pillows on either side as protective zones to minimize strip puncturing of the balloon.

Figure 67:
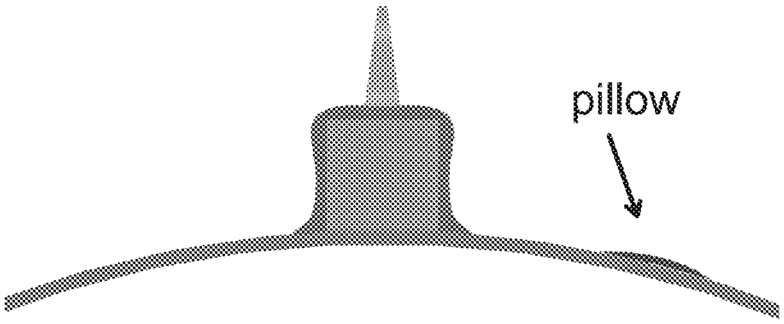

FIG. 67 schematically illustrates an embodiment with only a single pillow as shown in the zone where the strip lays down, but no contralateral pillow.

Figure 68:
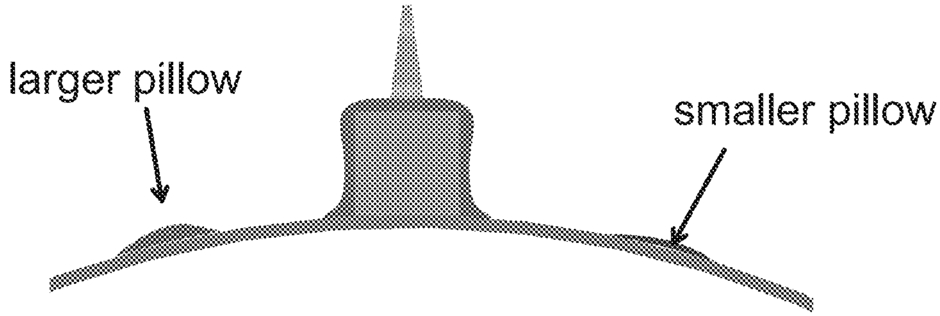

FIG. 68 schematically illustrates a variation of the same concept of minimal retention zone for the strip while on one side the pillow region is contains less material then the pillow region on the opposing side of the strip.

Figure 69:
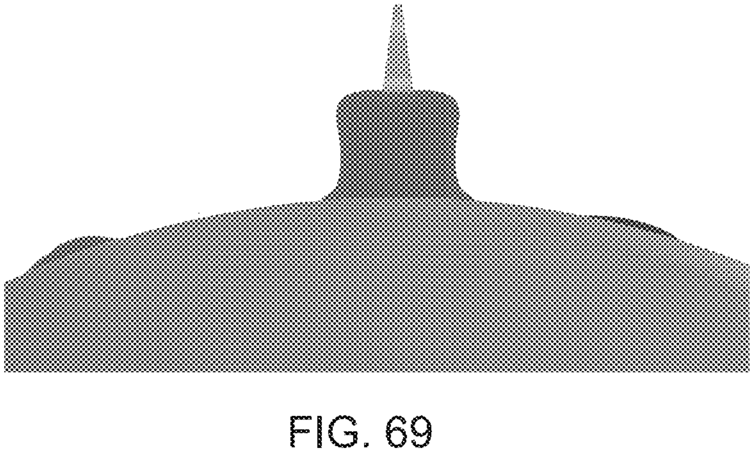

FIG. 69 schematically illustrates a variation of the same concept of minimal retention zone for the strip, but additional material is shown on the proximal edge of the strip.

Figure 70:
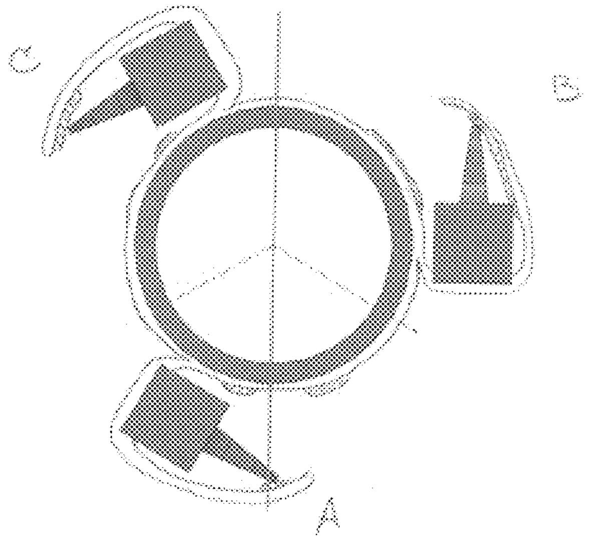

FIG. 70 schematically illustrates a variation of how protection zones (raised pillow regions) integrated into the balloon offer protection of the balloon during the folding and crimping of the balloon.

Figure 71:
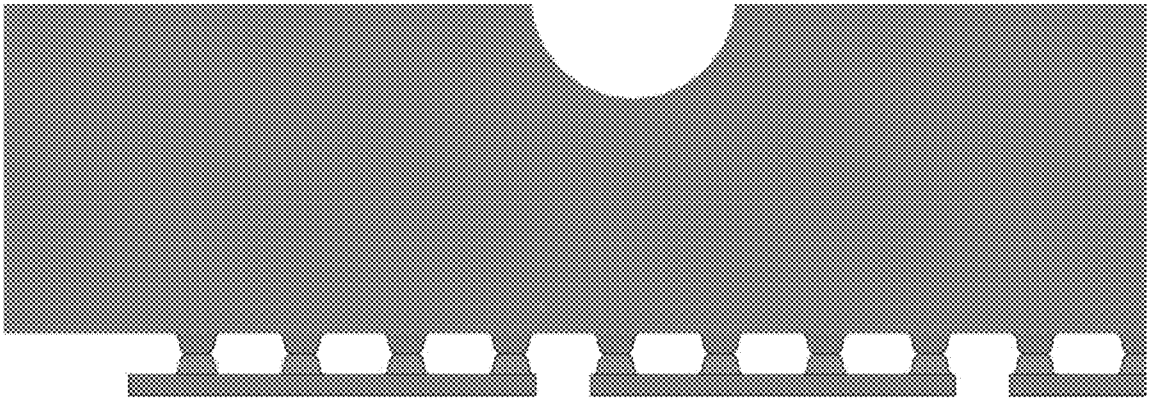

FIG. 71 schematically illustrates an embodiment with an array of smaller strip sections with four wedge dissectors connected by a base followed by a gap and another set of arrays of four wedge dissectors.

Figure 72:
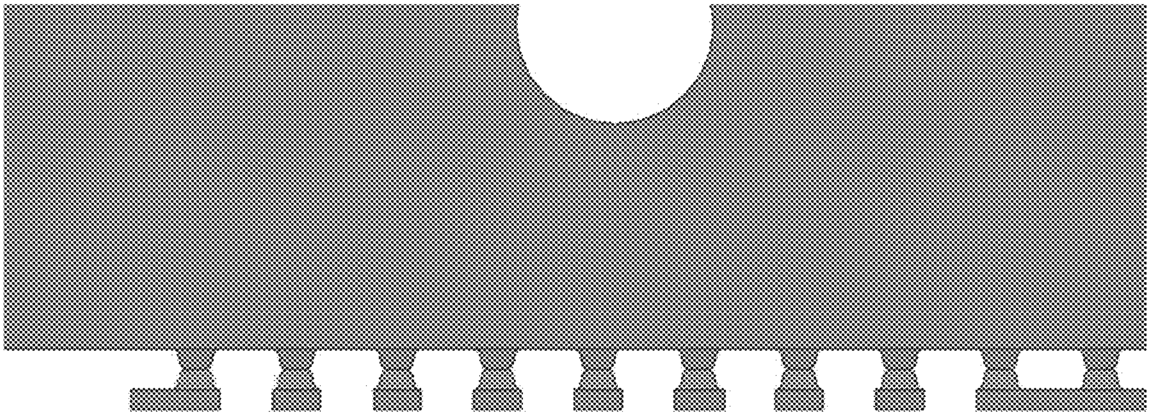

FIG. 72 schematically illustrates an embodiment with individual wedge dissectors unconnected.

Figure 73:
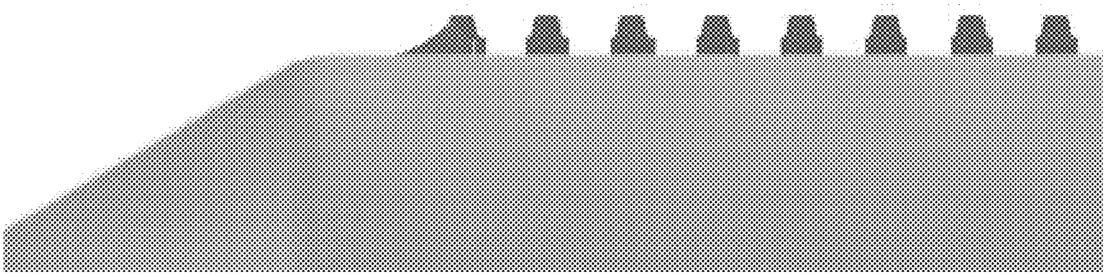

FIG. 73 schematically illustrates a side view of the strips integrated onto the balloon surface.

FIG. 74A-74E is a series of illustrations showing the mechanism for serrated strip elements to turn from a tangential orientation to being uncovered and orienting perpendicularly.

Figure 75:
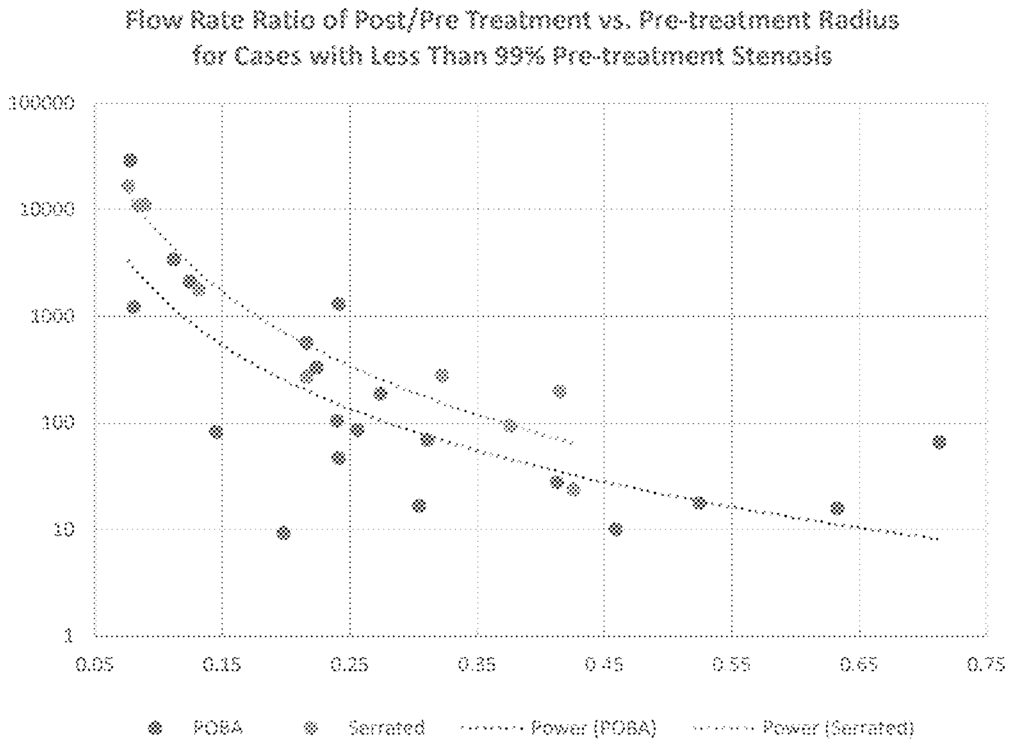

FIG. 75 is plot of data of flow rate ratio of post/pre-treatment versus pre-treatment radius.

Figure 76:
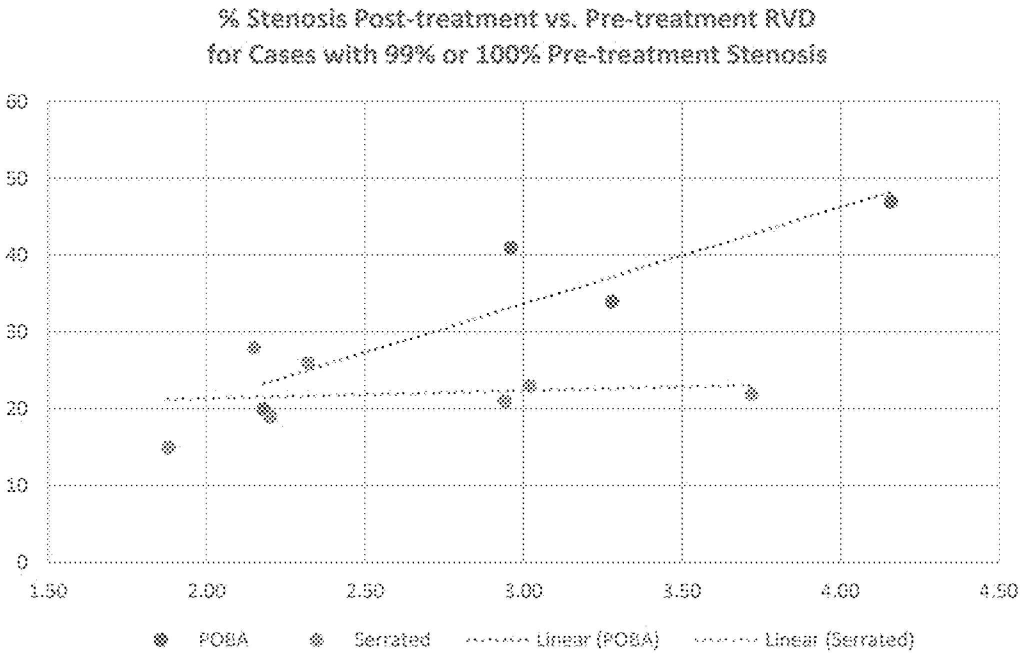

FIG. 76 is graph comparing post-treatment percentage stenosis of plain balloon versus serrated balloon.

Figure 77A:
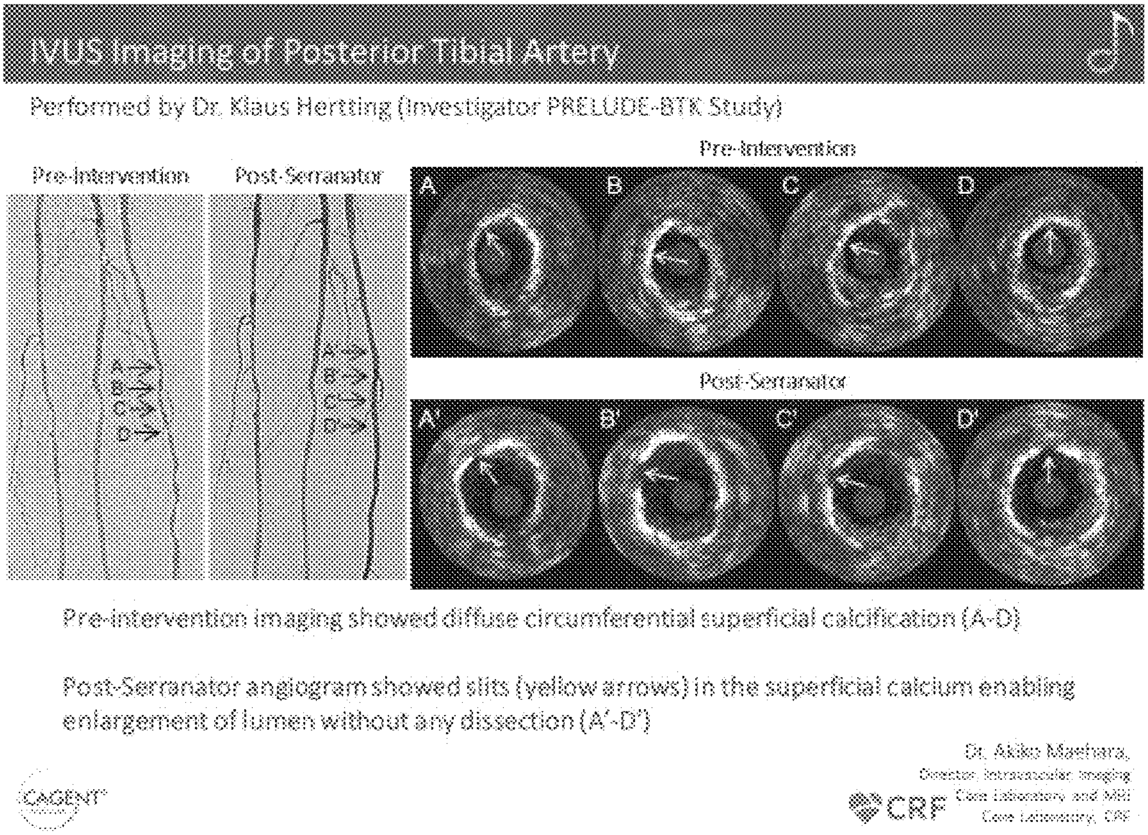
Figure 77B:
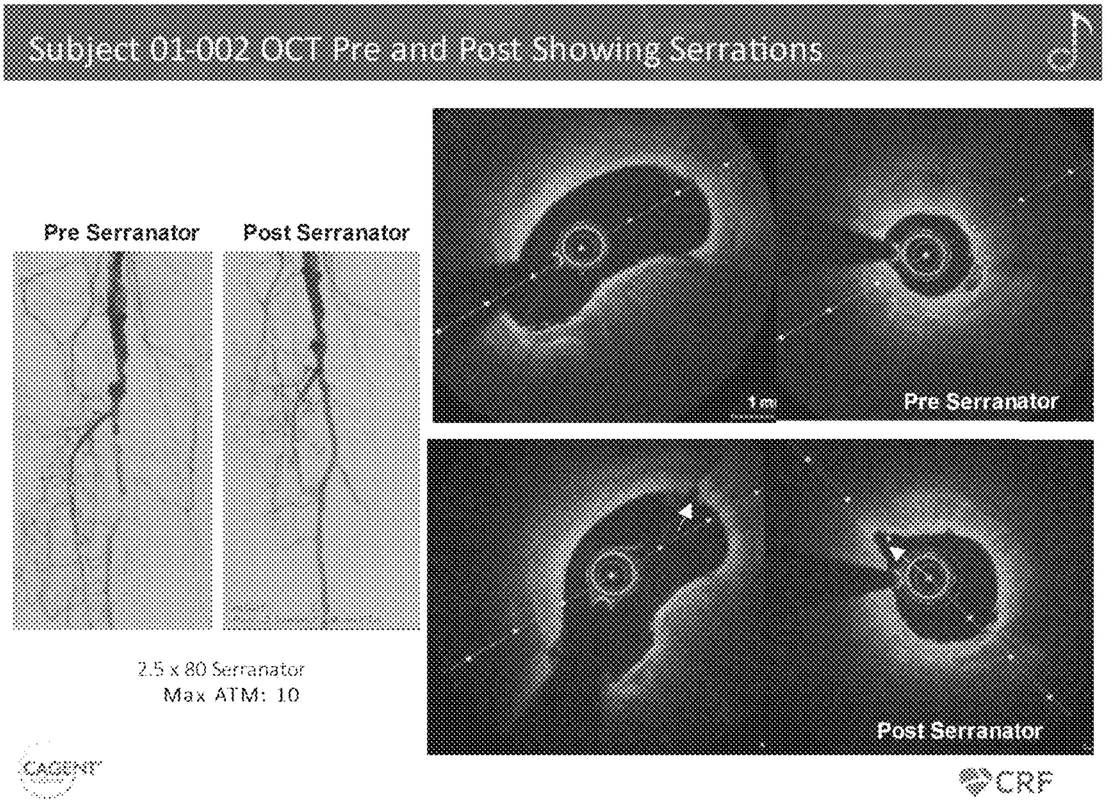

FIG. 77A-77B is a set of images taken from within the artery pre and post treatment with a serrated balloon technology.

Figure 78A:
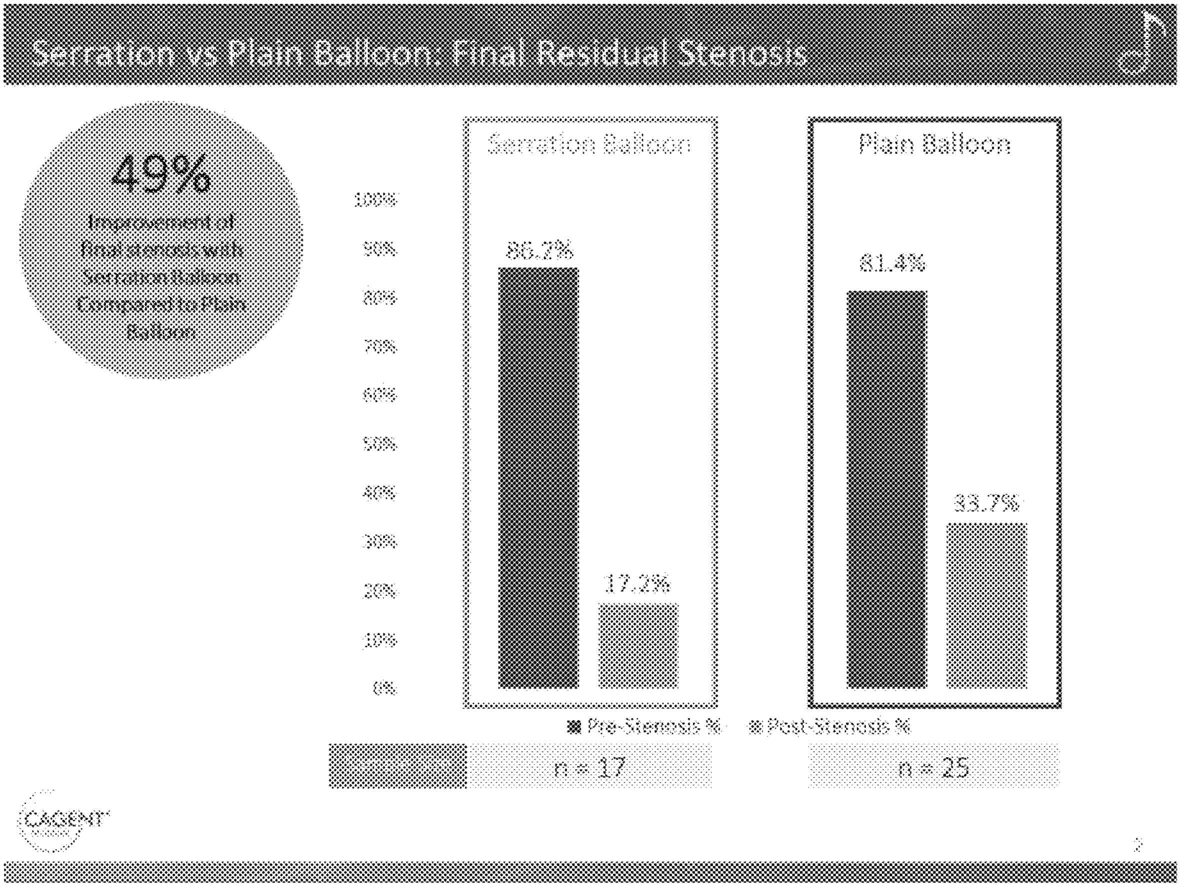
Figure 78B:
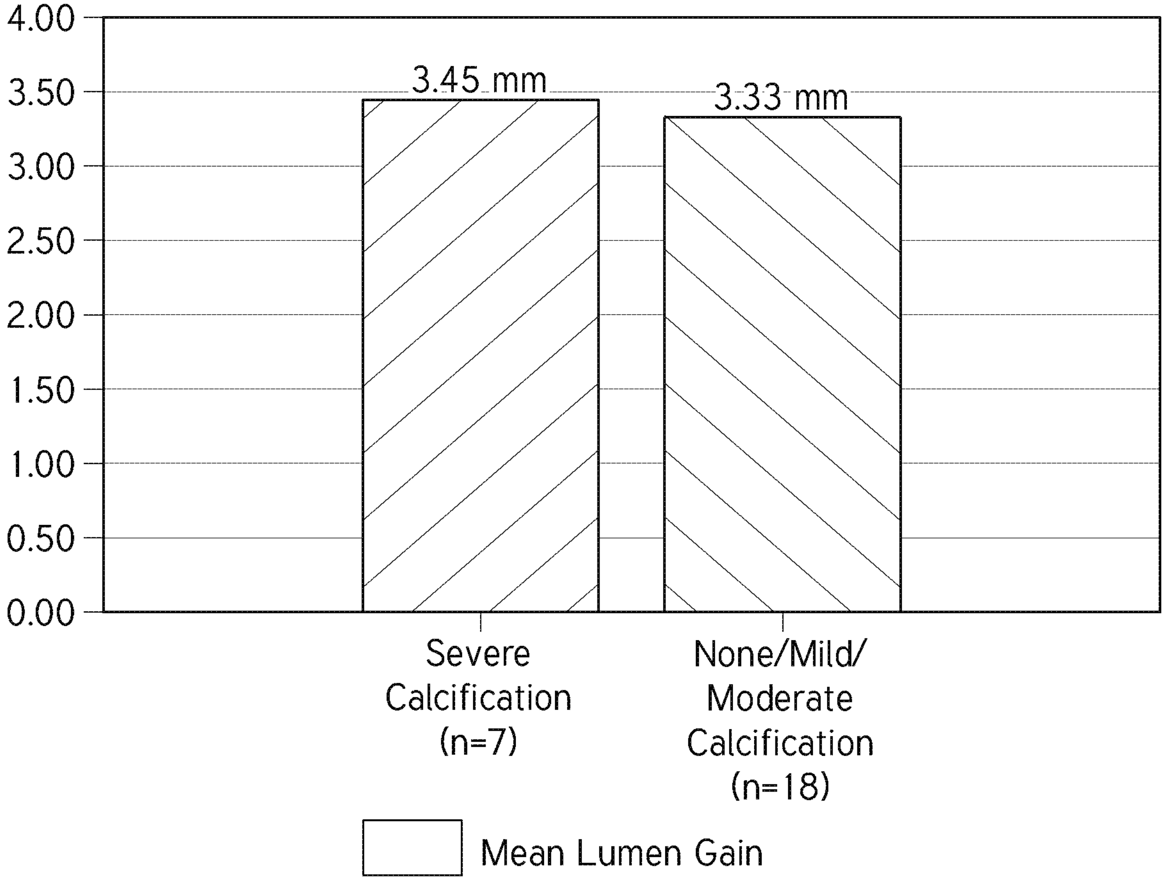

FIGS. 78A-78B are graphs showing a comparison of the lumen gain between the effects of plain balloon and serration balloon.

Figure 79:
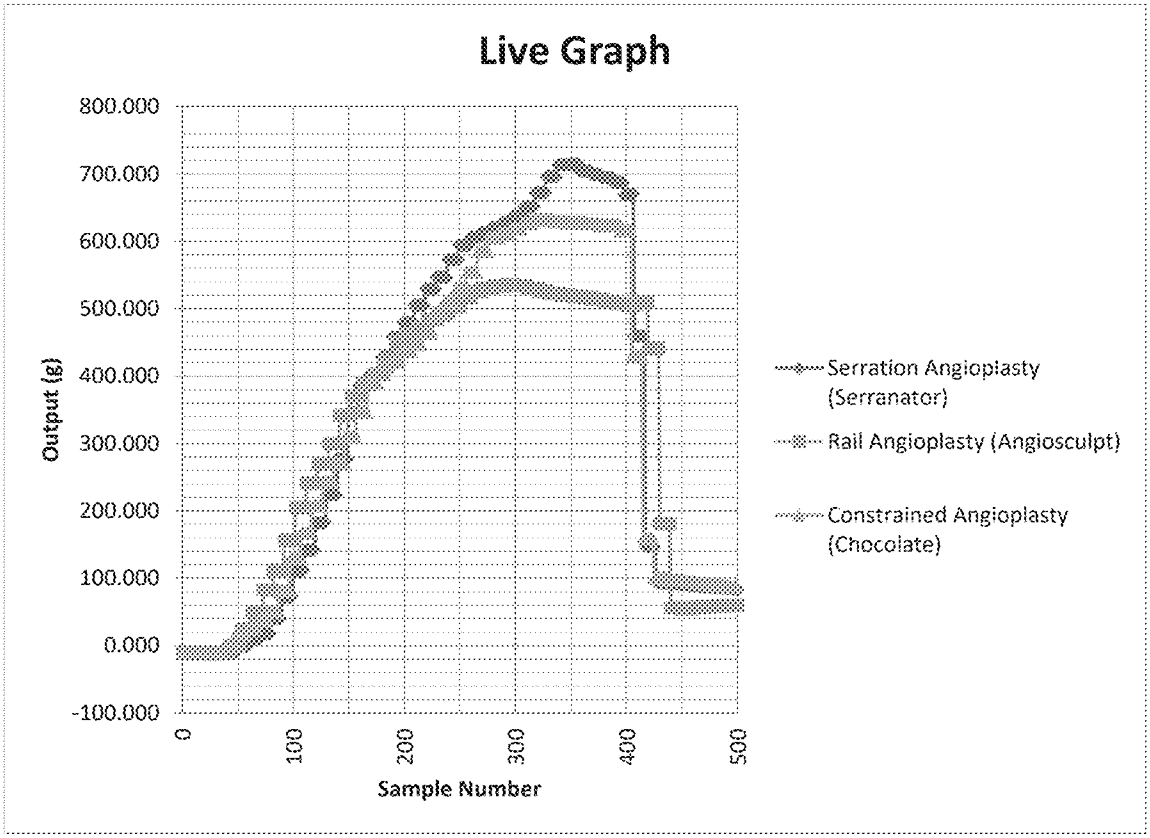

FIG. 79 is a graph comparing the translation of force originating at the hub of the catheter to the tip of the catheter.

Figure 80:
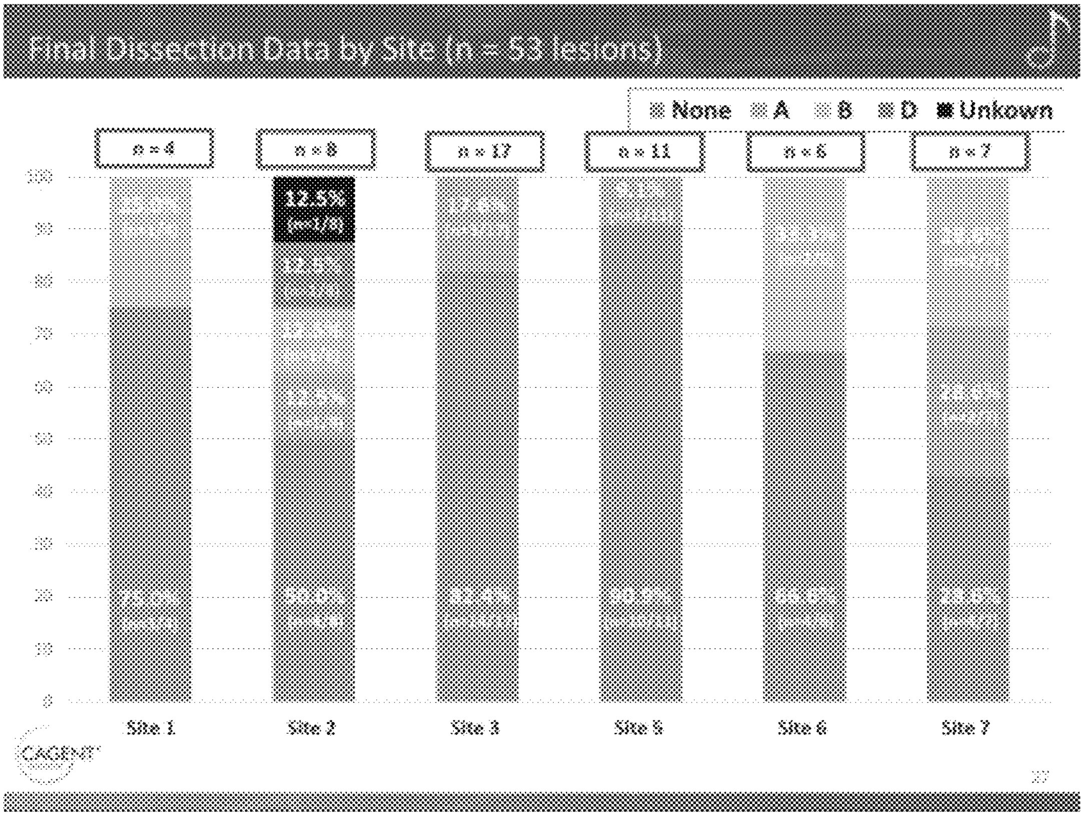

FIG. 80 shows the low incidence of dissections of the serration balloon catheter at different clinical sites.

Figure 81:
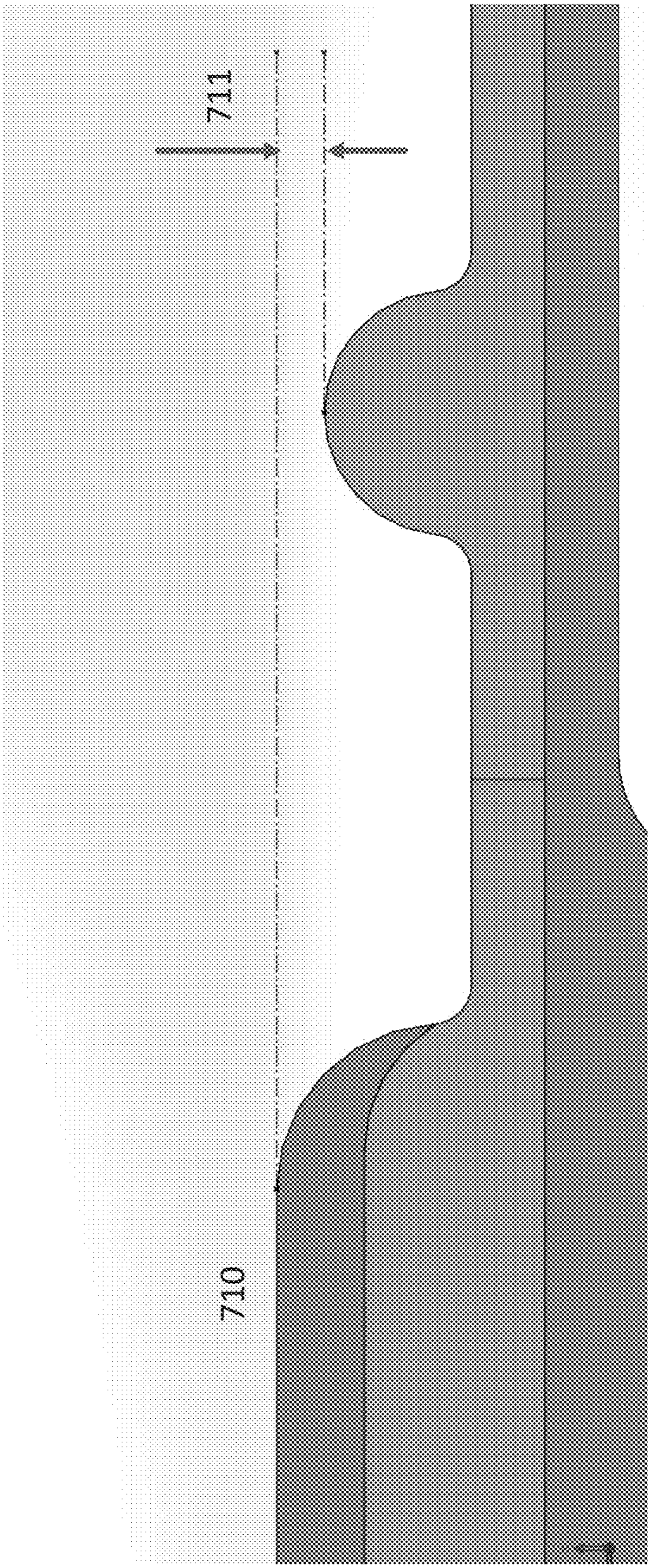

FIG. 81 illustrates a schematic view of the manufacturing process producing a wedge dissector, with an unhoned edge, from a razor blade, according to some embodiments.

DETAILED DESCRIPTION

Spikes can be positioned on the strips in any number of different orientations and configurations as will be described further below. The spikes can be any of the spikes discussed in U.S. Pat. No. 8,323,243 to Schneider et al., issued Dec. 4, 2012 and incorporated by reference herein in its entirety. The spikes and cage can also be used in accordance with the plaque serration methods and other methods also described therein.

Figure 1:
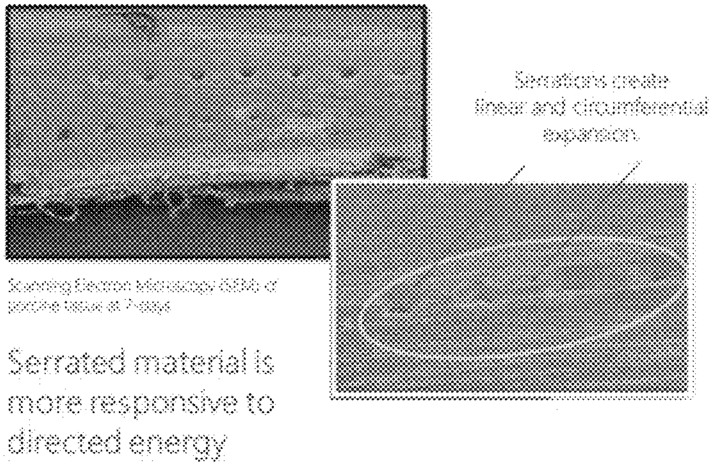
FIG. 1 illustrates examples of serrations under electron microscopy.
Figure 2:
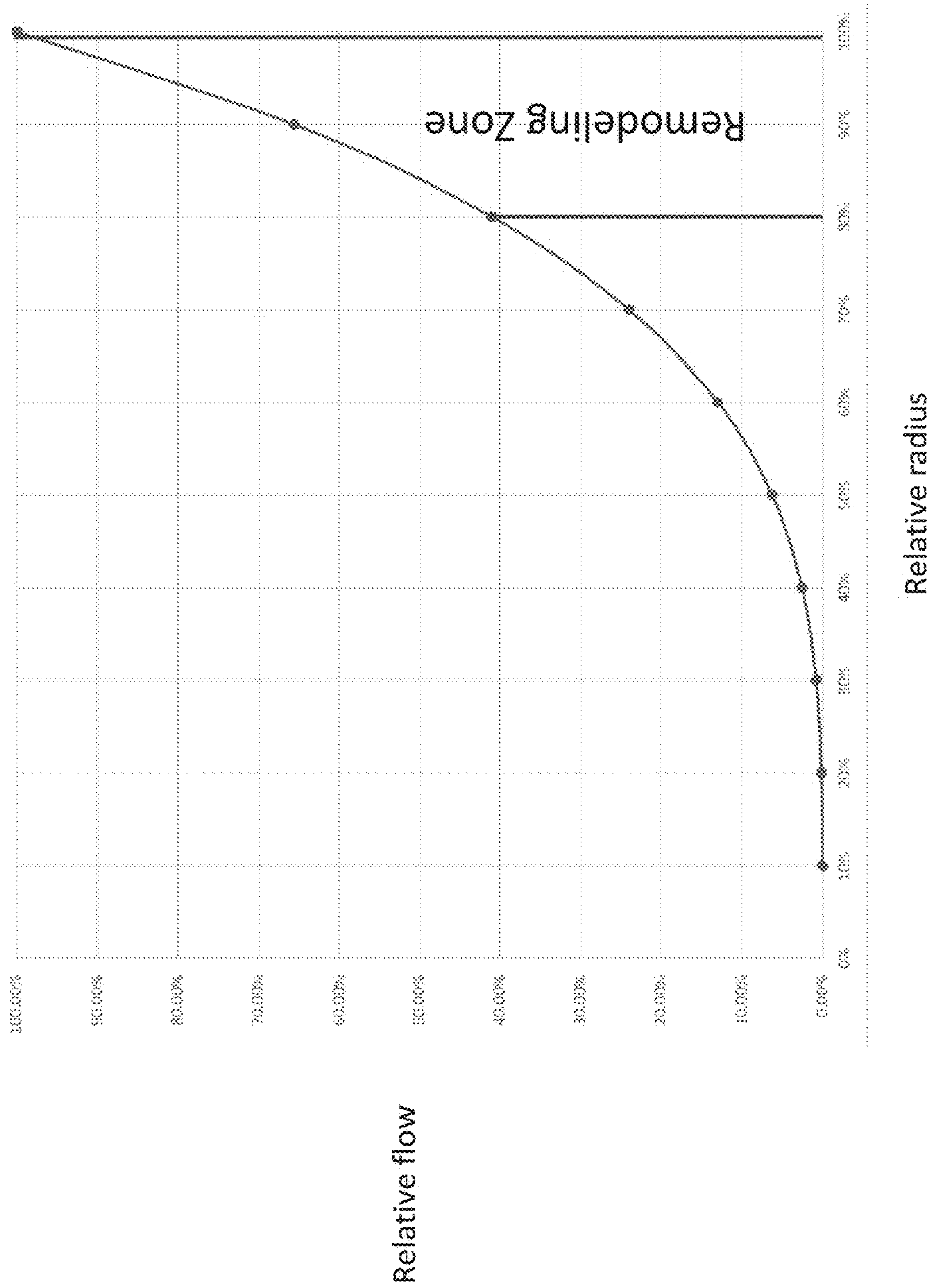
FIG. 2 shows the maximum distal flow in peripheral arteries as a percentage of vascular reduction assuming pressure within the vessel were held constant.
Figure 3:
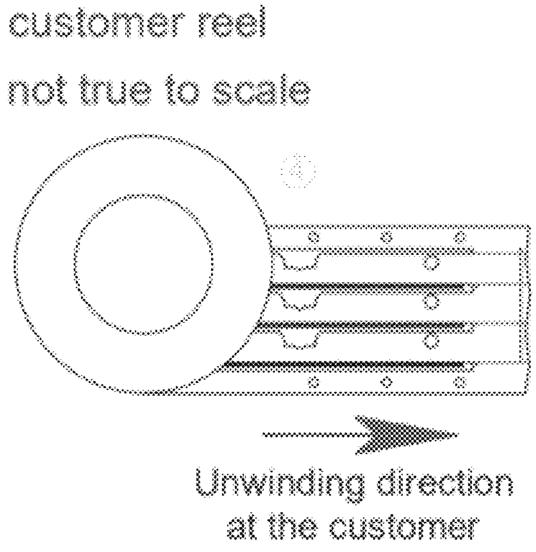
FIG. 3 shows an example of unwinding a reel.
Figure 4:
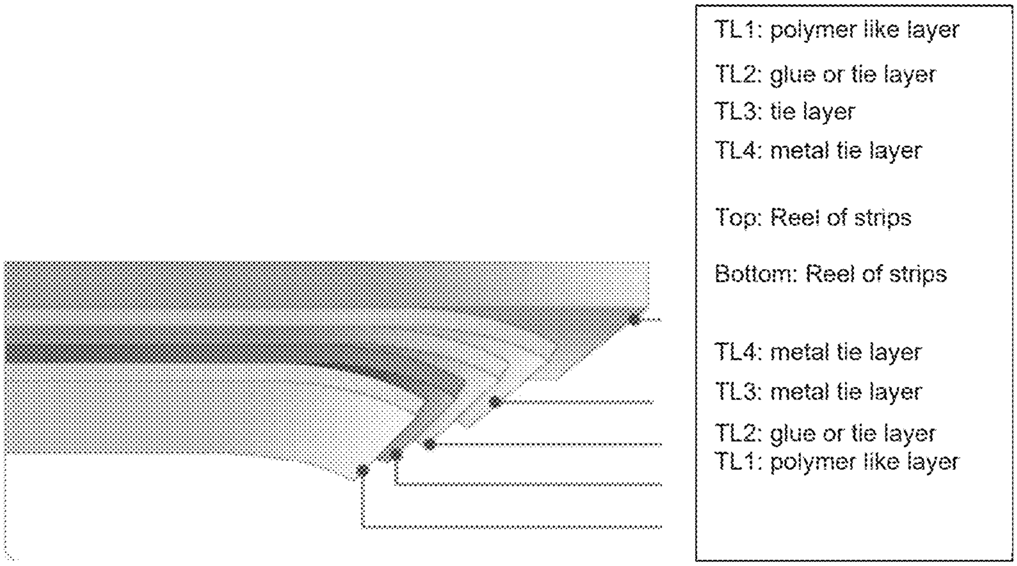
FIG. 4 illustrates an example of a multi-layer strip.
Figure 5:
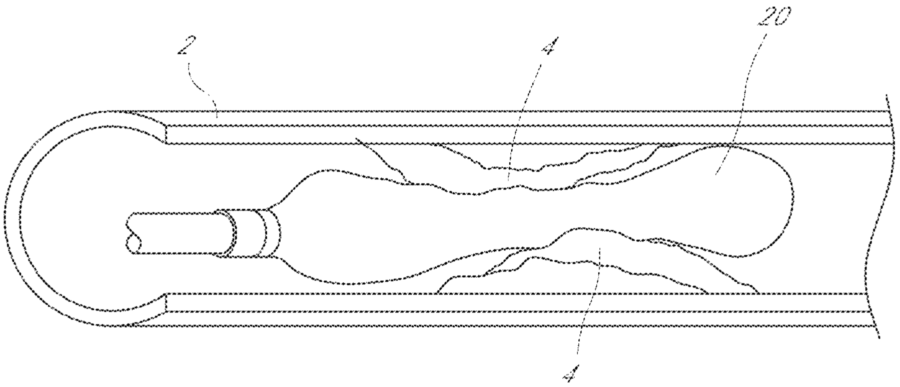
FIG. 5 shows an angioplasty balloon within a vessel at a treatment site that is experiencing dog boning.
Figure 6:
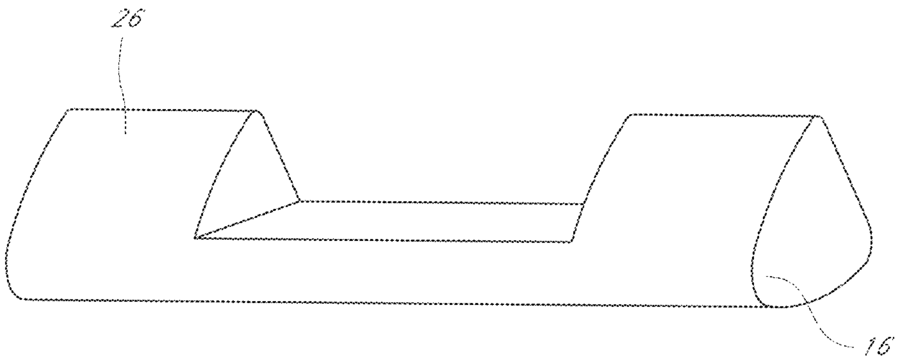
FIG. 6 shows a detail view of a portion of another embodiment of cage.
Figure 7:
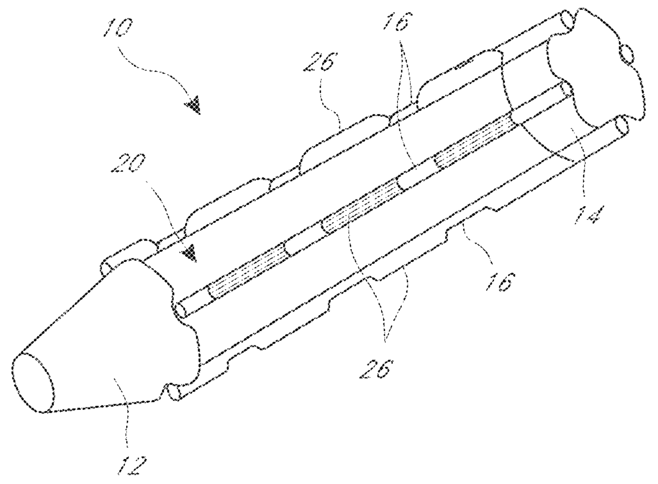
FIG. 7 is another embodiment of cage with a conical ring.
Figure 8:
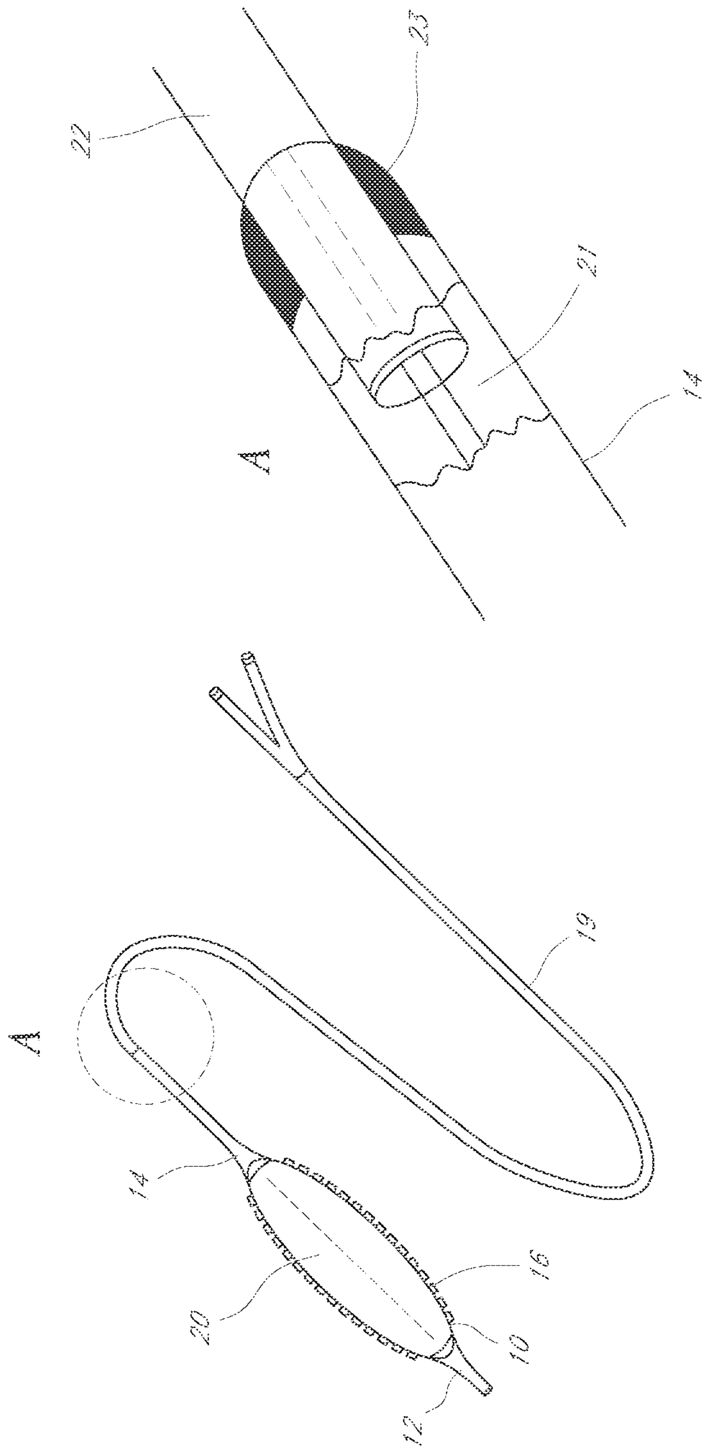
FIG. 8 illustrates a view of a conical distal ring retaining a plurality of strips.
Figure 9B:
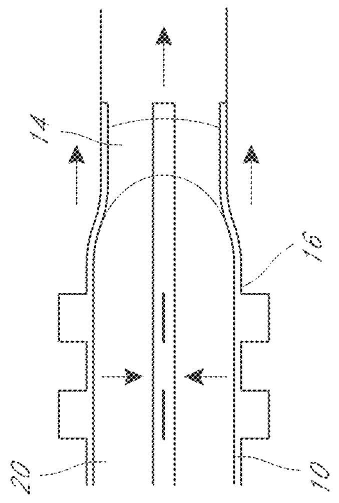
FIGS. 9A-9B show a view of one end of a balloon with a cage disposed about the balloon and the forces applied to the balloon during inflation and deflation.
Figure 9A:
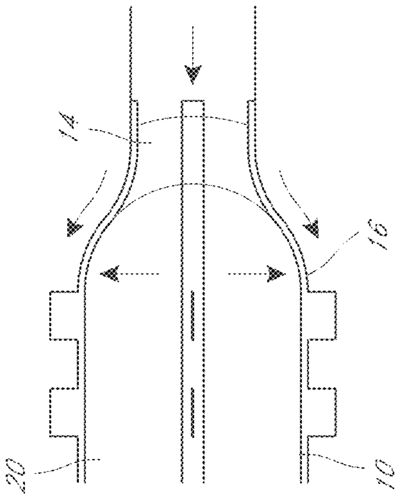

Looking now to FIG. 6, an enlarged detail view of a portion of a cage is shown. In this embodiment, the strip 16 has been formed with a plurality of spikes or wedge dissectors 26. In some embodiments, from the base of the unfinished cage, a slit can be cut in the tube to form adjacent strips. The wedge dissectors 26 can be shaped like a tent or axe head with an elongated tip and base, both of which extend longitudinally, along the longitudinal axis of the tube. The wedge dissectors 26 can assist with cutting and/or perforating plaque before or during an angioplasty procedure. The space between the wedge dissectors 26 can be machined or otherwise formed to remove material and increase the flexibility of the strip. The space between the wedge dissectors 26 is shown as being twice the length of the wedge dissector 26, though other spacing can also be used. Typically spacing length can be 4:1 to 3:1 space to length and more commonly 2:1 to 1:1 space to length.

In some embodiments, rows of strips and/or strip segments can be placed around the balloon 20. Some rows may extend over the entire length of the balloon 20 and other rows may not. In some examples, a row may include a plurality of strips in series that are separated by gaps. Placing strips in a series on the balloon can provide greater flexibility which can improve deliverability through tortuous anatomy.

As shown herein many of the strips 16 have a flat bottom. This can help the strips 16 sit on the surface of the balloon and to maintain the orientation of the wedge dissectors. This can prevent rotational movement of the strips 16 on the surface of the balloon 20.

Unique functional characteristics that some embodiments of embedded strip configurations aim to achieve include any number of 1) perpendicularity of the wedge dissectors to the balloon surface, 2) maintaining flat and low profile of the strips on the balloon in the deflated state, and 3) aiding in limiting the wedge dissectors from damaging the balloon or tissue during delivery or retraction. Design features that contribute to these functional characteristics include: strips that have flat bottoms enabling stable orientation of the wedge dissectors but are thin enough to be laid down tangential to the balloon or contained in a fold of the balloon during folding, regions on the balloon surface with slightly increased thickness to limit puncturing, and spacing between the wedge dissectors which does not have a raised region or cutting edge. It will be understood that other benefits and advantages can also be provided.

A method of progression of a method of blowing a balloon catheter with metal (including serrated strips) on the outside can include any of the following: Laminating a reel of strips with a layer stack of materials positioned to allow deposition of polymers to the base of the strips. Positioning the laminated strips into a series of dies designed to accommodate the strips. The strips typically include wedge dissectors as previously described. The strips can be positioned equally spaced around a center point where a balloon will be blown. The strips are typically oriented to extend primarily longitudinally. Especially in longer balloons, the strips may be positioned serially in rows, such as 1-8 rows, each with 1 to up to 25 strips or more. In some embodiments the base region of the strips are pre dipped, laminated, or coated with a material that has a similar or lower glass transition temperature as the balloon material. In some embodiments the coating is a series of one or more materials. In cases of more than a single material the collected material stack can be designed to offer adhesion between the elastic balloon surface and the inelastic strip surface. Once all strips are placed between the balloon blowing dies in such a manner as to allow the coating below the base to be positioned into the diameter of the balloon blowing dies. The design of the dies and the strips being attached. The intravascular device can include a prefabricated covering as described herein. The prefabricated covering can be formed by a second balloon blowing process. In some embodiments, a combinate of the prefabricated covering and the balloon with the plurality of strips is formed by inflating the balloon with the plurality of strips within the prefabricated covering and applying heat to the plurality of strips such that the prefabricated covering softens and the plurality of wedge dissectors extend through the prefabricated covering. Alternately, a secondary balloon blowing like process is envisioned to offer a unique mechanism to fuse the strip to the balloon. In this alternate process the strip may have a polymer, extrusion, laminate or other fusing material on it. The strip with the fusing material is strategically placed into the secondary balloon blowing like machine to allow for accurate positioning of the strip to the balloon. A base balloon is inflated in the secondary machine and a form of energy, such as heat or ultraviolet light is applied. The energy can be applied throughout the entire region or to specific regions in the machine where the strips are placed. The energy is capable of allowing the fusing material to move towards the elastic phase of the material and enabling a fusing event between the base balloon and the base material. The fusing material is designed to flow through regions both between the interface of the balloon and the strip. In some embodiments the fusing material flows along some portion of the outer balloon surface providing a more durable attachment region and a buffer zone to protect the base balloon from the serrated teeth as they are captured in the wings of the balloon in pleating and folding.

A method of retrofitting a balloon catheter with a series of metal strips can include any of the following steps. Positioning strips around an inflated balloon or during the balloon blowing cycle. The strips may include wedge dissectors. The strips can be positioned equally spaced around the inflated balloon. The strips can extend primarily longitudinally. The strips may be positioned individually, or serially in rows, such as 2, 3, 4, 5, 6, or 7 rows, each with anywhere between a single strip up to a row of 2, 3, 4, 5, 6, 7, 8, 9 or more segmented strips, with any number of arrays of wedge dissectors, or even up to a hundred or more individual wedge dissectors separated from each other. In some embodiments it is envisioned that individual wedge dissectors are placed on the balloon surface unbound to neighboring wedge dissectors. When more than one wedge dissector are connected they can form a strip of wedge dissectors. In some embodiments, the strip and the wedge dissectors comprise the same material. In some embodiments, the strip and the wedge dissectors are monolithically formed. In some embodiments, the strip and the wedge dissectors comprise the different material. In some embodiments, the strip and the wedge dissectors are separately formed. In some embodiments, the spaces between the wedge dissectors are non-metallic. The individual wedge dissectors or the strips can be attached either permanently or temporarily to the balloon with an adhesive. The intravascular device can include the prefabricated covering as described herein. The prefabricated covering can be formed by a second balloon blowing process. In some embodiments, a combinate of the prefabricated covering and the balloon with the plurality of strips is formed by inflating the balloon with the plurality of strips within the prefabricated covering and applying heat to the plurality of strips such that the prefabricated covering softens and the plurality of wedge dissectors extend through the prefabricated covering.

Figure 11:
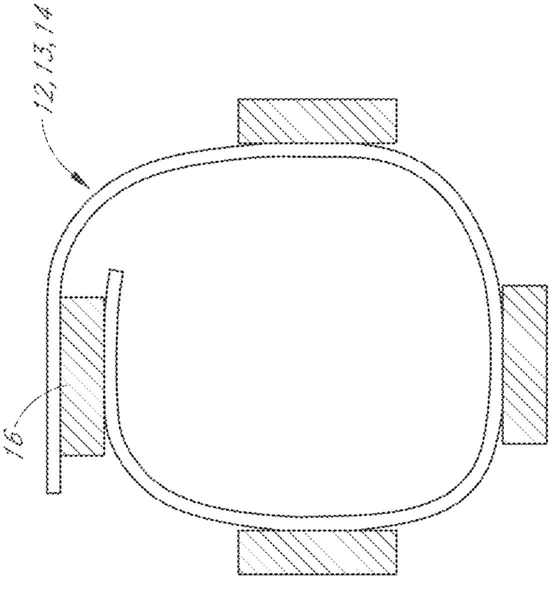
FIGS. 11-13 show a plurality of embodiments of strips secured by a ring.
Figure 12:
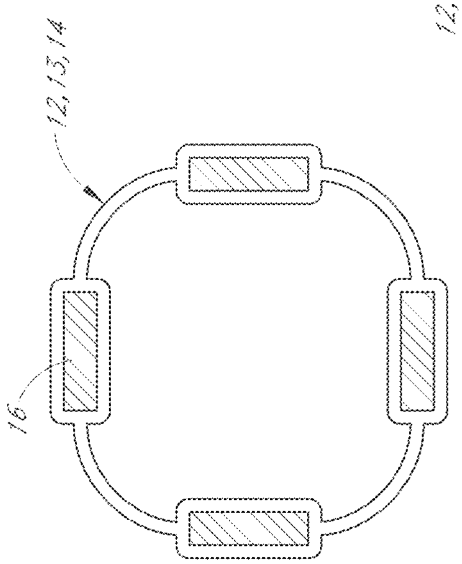
Figure 13:
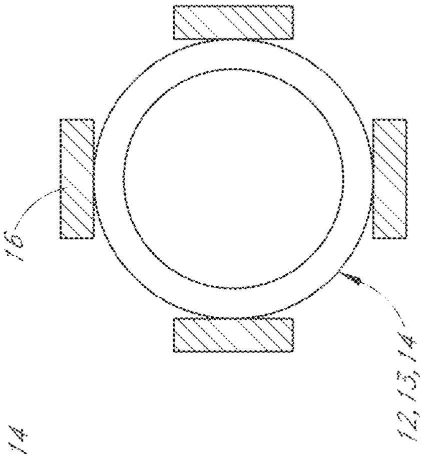

The rings 12, 13, 14 can be attached to the strips 16 in a variety of ways. FIGS. 11-13 shows examples of the rings 12, 13, 14 secured to the strips 16. FIG. 11 shows a material wrapped around the balloon to form rings 12, 13, 14 such that the material of the ring can be secured to more than one strip. In some examples, as illustrated in FIG. 12, the ring 12, 13, 14 can be wrapped about a portion of each strip. This can be accomplished in the same way as illustrated in FIG. 10, where each of the rings can have an upper layer and bottom layer that wraps around a portion of the strip 16. FIG. 13 illustrates a solid ring 12, 13, 14 that can be attached to a portion of the balloon. A portion of the strip can be secured to the ring.

Heat shrink material can be positioned around the ends of the strips as a ring. Individual rings of heat shrink material can connect to or cover ends of multiple strips positioned circumferentially around the balloon. Individual rings of heat shrink material can also connect to or cover ends of adjacent strips positioned serially in a row. Heat can then be applied to shrink the heat shrink material. The balloon can be deflated and then sterilized in preparation for use.

Systems and methods as disclosed herein can deploy the cages and wedge dissectors in any body lumen, including vascular lumens such as arteries and veins. The arteries could be coronary arteries, peripheral arteries, or carotid or other cerebral arteries, for example, iliac, femoral, superficial femoral, popliteal, anterior and posterior tibials, peroneal, or other peripheral vasculature, for example. The device may also be used in any lumen or transportation vessel found in any of the vascular, respiratory, digestive, urinary, reproductive, lymphatic, auditory, optical, or endocrine systems. It is understood that a device for generating serrations in anyone, two, or more of these anatomical regions, might have slightly different catheter bodies and features. In some systems the design may include feature like those found in a monorail design while other systems may offer rapid exchange like design features. Other design features may also be included and each may take slightly different forms. Independent of the location where the device might be used, some embodiments of devices include spikes (also herein referred to as wedge dissectors, or serrating elements) that may be joined together on a supporting spline, and an expandable mechanism to increase and decrease the diameter of the spike features (such as a balloon). Together the serration portion and the balloon produce a serrated balloon element. The serrated balloon element is then attached to a base catheter-like device.

Figure 14:
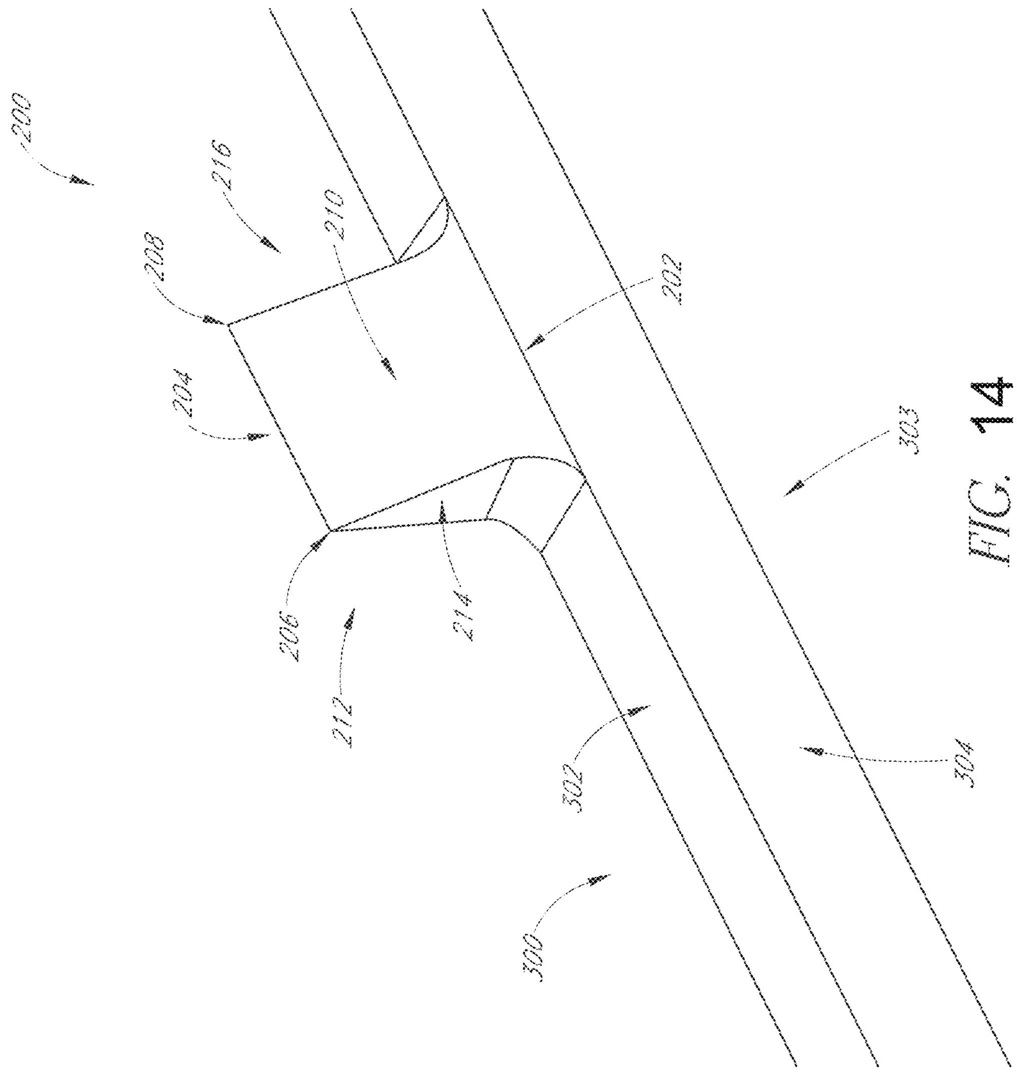
FIG. 14 is a close-up detail view of an embodiment of a wedge dissector on its associated strip.

In some embodiments, as illustrated for example in FIG. 14 which is a close-up detail view of an embodiment of a wedge dissector 200 on its associated strip 300, a wedge dissector 200 can include a strip-facing base surface 202 (which may also be referred to herein as a bounded surface). The strip-facing base surface 202 of the wedge dissector 200 can be defined by the base where the wedges 200 protrude outward and directly continuous with a surface of the strip at the interface between the wedge dissectors and the balloon. The strip could be a spline 300 or other strip-like structure. In some embodiments, this strip-facing base surface 202 has a relatively narrow width made of a hard material capable of holding a sharp edge. In some embodiments, the preferred material is martensitic stainless steel, with a hardness as low as 48 and as high as 70 but more typically between 52 to 64 on the Rockwell C-scale (HRC) although other materials including a polymer or co-polymer including but not limited to polyolefin, fluoropolymer (including fluorinated ethylene-propylene (FEP), polytetrafluoroethylene (PTFE) or polyvinylidene fluoride (PVDF)(e.g. KYNAR)), polyvinyl chloride (PVC), neoprene, silicone, elastomer or synthetic rubber and fluoropolymer elastomer (e.g. VITON), or a combination thereof can be utilized. The strip and wedge dissectors can have hardness on the Rockwell C-scale (HRC) of 48, 49, 50, 51, 52, 53, 54, 55, 56, 57, 58, 59, 60, 61, 62, 63, 64, 65, 66, 67, 68, 69, 70, or any range of the foregoing values. In some embodiments, the strip is about or no more than about 0.004", 0.005", or 0.006" wide (oriented circumferentially). In some cases, the width can be between about 0.006" and about 0.020" or between about 0.004" and about 0.030". In some embodiments, the strip 300 typically runs longitudinally the length of the working balloon edge, but can also be oriented in angles up to and including 90 degrees from the longitudinal axis of the balloon (or other expandable structure), or in a helical fashion at varying pitches. In some embodiments, the height of the base strip 300 can be between about 0.004" and about 0.010", or between about 0.002". and about 0.020" in some embodiments.

Still referring to FIG. 14, a wedge dissector 200 can also include a radially outwardly facing surface 204 (which may be referred to herein as an unbounded surface) that can define a top surface of the wedge dissector 200 from first (e.g., proximal) edge 206 to second (e.g., distal) edge 208 and be configured to contact tissue, plaques, or other structures within the body. Also shown are anterior surface 210, posterior surface 212, and opposing lateral surfaces 214 and 216. In some embodiments, the lateral surfaces 214, 216 extend upward generally perpendicular to the longitudinal axes of the strips, and the radially outward facing surface extends between the lateral surfaces as a linear, curved, or other geometry as described elsewhere herein at an angle to the lateral surface/lateral surface axis. Also illustrates are strips or splines 300 having an unbounded (e.g., superior-facing) surface 302 that can be coextensive with the strip-facing surface or boundary 202 of the wedge dissector 200, as well as side surfaces (e.g., 304), and inferior-facing surface 303.

Figure 15:
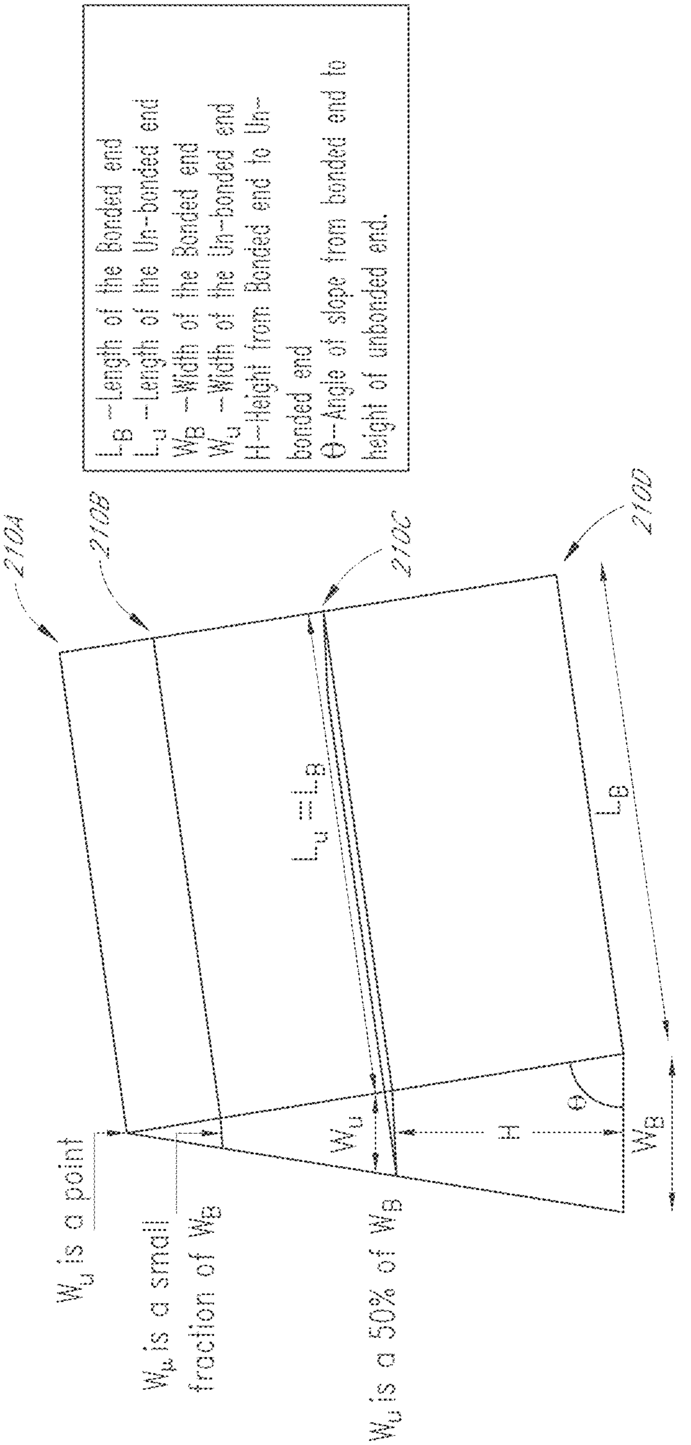
FIG. 15 illustrates a schematic perspective view of various dimensions and terminology of a wedge dissector, according to some embodiments.

FIG. 15 is a schematic illustrating several possible non-limiting embodiments of a wedge dissector. In some embodiments, the length of the radially outwardly facing surface $L_U$ (e.g., radially outwardly facing surface 204 between first edge 206 and second edge 208 of FIG. 14) is between about 30%, 20%, or 10% less than the total length of the strip-facing surface $L_B$ (of strip-facing surface 202 in FIG. 14). In some embodiments, the radially outwardly facing surface length $L_U$ can be from about 50% to about 20% less than the strip-facing surface length $L_B$, and sometimes as large as the strip-facing surface length $L_B$. The radially outwardly facing surface width $W_U$ is in some cases equal to or less than the strip-facing surface width $W_B$, and typically between or less than about 10%, 20%, 30%, 40%, or 50% of the strip-facing surface width $W_B$, or between about 20% and about to 50% less than the strip-facing surface width $W_B$, and sometimes about or up to about 50%, 60%, 70%, 75%, or 80% of the strip-facing surface width $W_B$. The radially outwardly facing surface width $W_U$ is in some cases equal to or less than 0.01 inch. The radially outwardly facing surface width $W_U$ is in some cases equal to or between 0.005 inch and 0.002 inch, or 0.002 inch and 0.001 inch, or 0.0012 inch and 0.0002 inch. The radially outwardly facing surface width $W_U$ is in some cases equal to 0.0011 inch, 0.0009 inch, 0.0008 inch, 0.0007 inch, 0.0006 inch, 0.0005 inch, 0.0004 inch, or 0.0003 inch. In some embodiments, the radially outwardly facing surface area ($L_U \times W_U$) can be from about 30% to about 10% less than the strip-facing surface area ($L_B \times W_B$). Therefore, in some embodiments there is an angle θ that is equal to or less than about 90 degrees that defines the slope from the strip-facing surface width $W_B$ to the radially outwardly facing surface width $W_U$ on at least one of the strip-facing surface width $W_B$ edges. While in some embodiments the radially outwardly facing surface width $W_U$ is constant from edge to edge, in some embodiments the radially outwardly facing surface width $W_U$ varies along the radially outwardly facing surface length $L_U$ as described elsewhere herein, such as decreasing from a first lateral edge to a point or segment in between the first lateral edge and the second lateral edge of the radially outwardly facing surface segment, and then increasing, from the point or segment in between the proximal edge and the distal edge, to the distal edge. In some embodiments, the relatively central segment in between the proximal edge and the distal edge has a constant width, while the lateral segments surrounding relatively central segment have variable, such as tapered widths.

Figure 22:
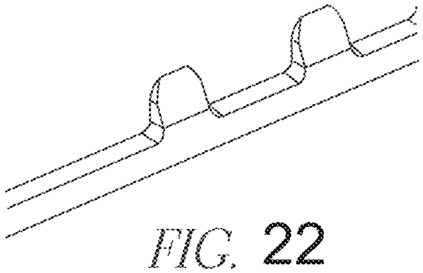
Figure 22A:
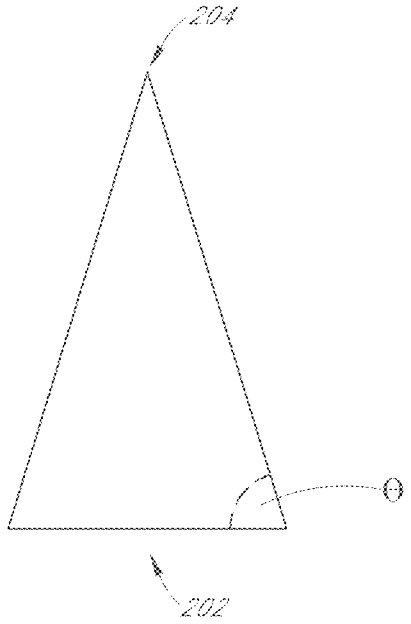
FIGS. 22A-22F illustrate respective end and isometric views of various wedge dissector geometries, according to some embodiments.
Figure 22B:
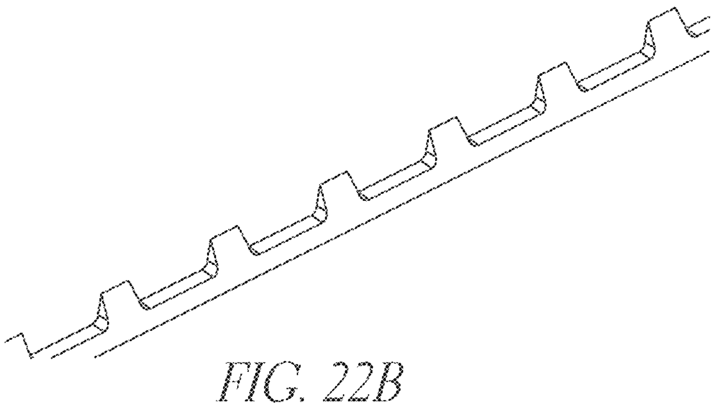
Figure 22C:
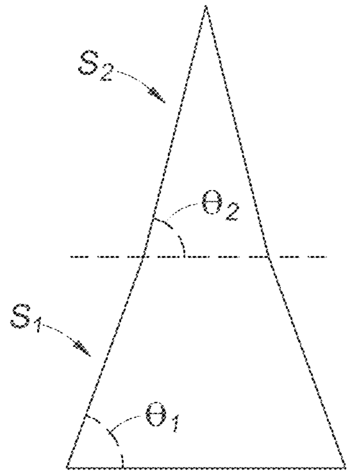
Figure 22D:
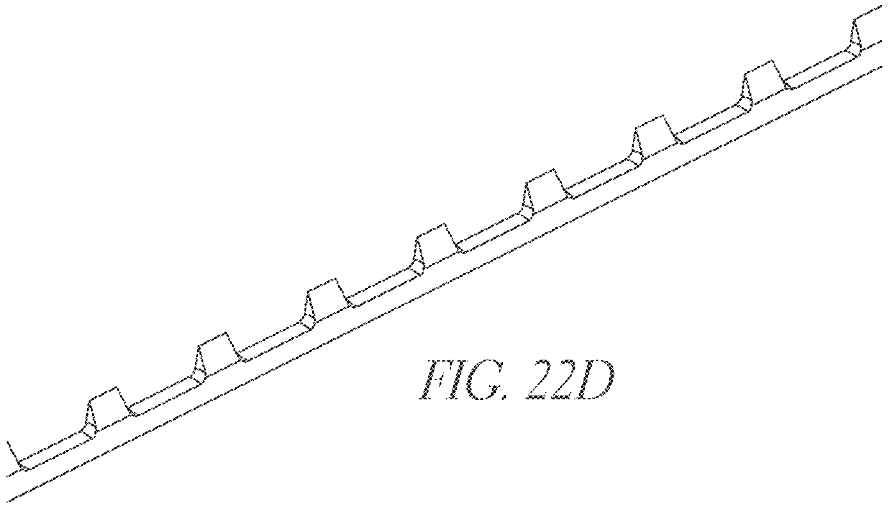
Figure 22E:
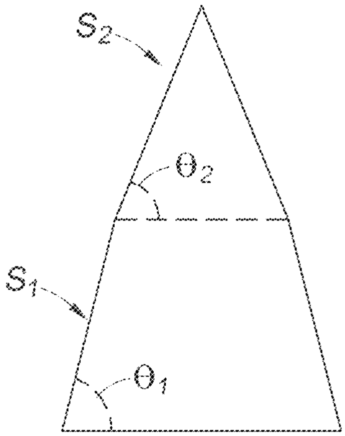
Figure 22F:
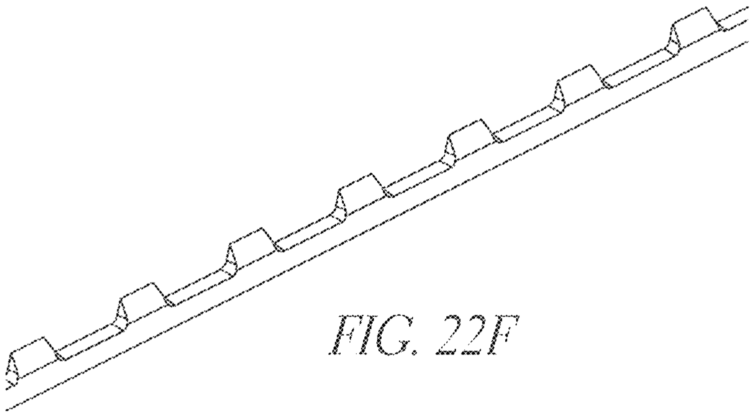

Although the radially outward facing width $W_U$ can come to a point, sloping from the strip-facing base width $W_B$ of the strip-facing base surface 202 to the radially outward facing width $W_U$ of the radially outward facing surface 204 in a single, constant sloped angle θ or bevel such as shown in FIG. 22A (end view resembling an isosceles triangle) and FIG. 22B (isometric view), it can also in some embodiments include a plurality of different angles, such as more than a single slope angle such as a double, triple or more bevel (e.g., a first angle for a first segment of the height, a second angle for a second part of the height that can be less than or greater than the first angle, and in some cases a third angle for a third part of the height that can be less than or greater than the first angle, and less than or greater than the second angle). FIG. 22C illustrates an end view and FIG. 22D illustrates an isometric view of a wedge dissector with a plurality of differing slopes and associated angles from the strip-facing base surface to the radially outward facing surface, where the angle θ2 between horizontal and an upward slope after a transition point is greater than an angle θ1 between the horizontal strip-facing base edge and the intersecting upward slope (in other words, the first slope S1 from the strip-facing base edge base is less steep than a second slope S2 higher up after a transition point). FIGS. 22E and 22F illustrate an embodiment similar to FIGS. 22C and 22D except the angle θ2 is less than the angle θ1 (in other words, the first slope S1 from the strip-facing base edge base is steeper than a second slope S2 higher up after a transition point).

Alternately, some embodiments may also include a series of steps at different heights where the width transitions to a narrower width and then continues to climb in height. When a series of steps is used in place of the bevel it can sometimes be due to fabrication limitation when methods other than a reel of stainless steel is honed to an edge. For instances where chemical etching is used to form the steps from the strip-facing surface width $W_B$ to the radially outward facing width $W_U$ the shape of the side walls may not have a single slope. The side wall may tend towards a concave shape with one or more series of concave etch regions transitioning from the strip-facing surface width $W_B$ to the radially outward facing width $W_U$.

The shapes of the radially outward facing edge or surface (e.g., radially outward facing surface 204 of FIG. 14) can in some embodiments be the same height from one edge 206 of the radially outward facing length or width to the other edge 208. In some embodiments, the height along the radially outward facing surface 204 can vary from one edge 206 to the other edge 208. When the radially outward facing edge or surface 204 varies, typically the radially outward facing edge has a series of raised features herein referred to as wedge dissectors, spikes, or serrating elements 200. In some embodiments, the midpoint of these raised features along the radially outward facing length 204 between edges 206, 208 is the highest point of the radially outward facing surface. However, in some embodiments, the highest point is offset from the midpoint, and there may be a plurality of highest points interspersed by lower point relative to the bounded/base surface 202. The maximal variation of height between edges 206, 208 of the radially outward facing surface 204 of the wedge dissectors 200 and the radially outward facing surface 302 of the base strip 300 between the wedge dissectors 200 can in some embodiments be less than about 80%, 70%, 60%, 50%, 40%, 30%, 20%, 10%, or less than the total height of the wedge dissector 200.

In some embodiments, the base strip 300 has a roughened or otherwise textured inferior surface to aid in adhesion to an outer surface of the underlying balloon. The base strip can have any desired geometry such as square, rectangular, or in some embodiments trapezoidal with the bottom surface having a greater width, such as about or at least about 10%, 20%, 30%, 40%, 50%, 60%, 70%, 80%, 90%, 100%, or more of the top surface. In some embodiments between about ⅓ and ½ of the top surface of the strip 300 is covered by wedge dissectors (also referred to as micro wedges) 200, while between about ½ and ⅔ of the top surface are free of wedge dissectors 200.

Figure 21:
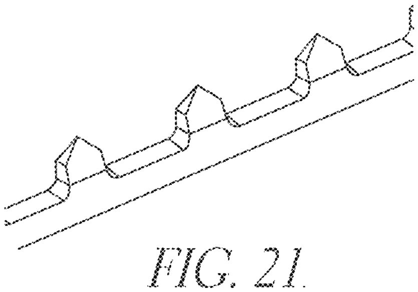

Referring to FIG. 21, in some embodiments, the radially outward facing surface viewed from the top can be seen as a line extending from one edge of the radially outward facing length to the other edge of the radially outward facing length (e.g., where $W_U$ is a point assuming 210A is the radially outward facing surface of the device). This would be analogous to a honed or "razor-sharpened" edge with no apparent width. In other embodiments, the top view appears as an unhoned surface that is slightly blunt resembling a rectangle (e.g., if 210B or 210C is the top of the device, and assuming everything above those lines were cut off) with the width of the radially outward facing surface $W_U$ being less than the strip-facing base surface $W_B$ but directly correlated with the slope or slopes between the width edge and height from the strip-facing base surface to the radially outward facing surface. In some embodiments, the top or the radially outward facing surface can be a line, a flat rectangle, a rounded or mounded surface (that might appear to be a rectangle or square in a 2-dimension point of view), or take a pyramidal, wedge, trapezoidal, or other polygonal shape.

In some embodiments, an unhoned width can be a width, for example, that is about or a combination of about 1 nm, 5 nm, 10 nm, 50 nm, 100 nm, 500 nm, 1 μm, 2 μm, 5 μm, 7 μm, 10 μm, 15 μm, 20 μm, 25 μm, and 30 μm, measured at the radially outward facing edge or surface. In some embodiments, unhoned radially outward facing surfaces of wedge dissectors can be advantageous as being slightly blunt/relatively less sharp than honed edges, in situations for example where creating serrations, indentations, and/or microperforations in a wedge dissector target, for example, is desirable rather than making cuts through the entire luminal wall. In some embodiments, the entire radially outward facing wedge dissector surface has an unhoned width.

Figure 16:
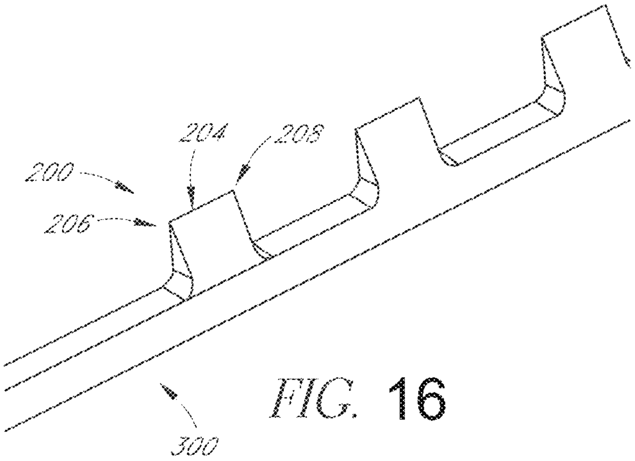
FIGS. 16-22 illustrate various embodiments of wedge dissector geometries.
Figure 17:
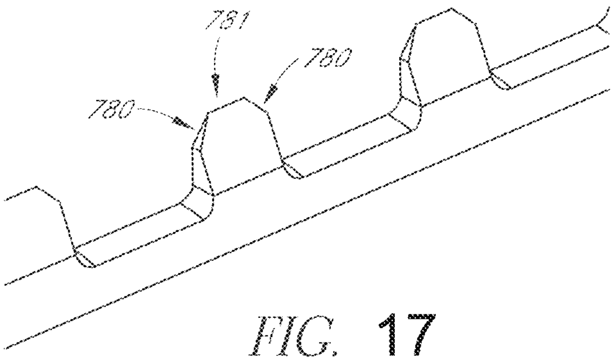
Figure 18:
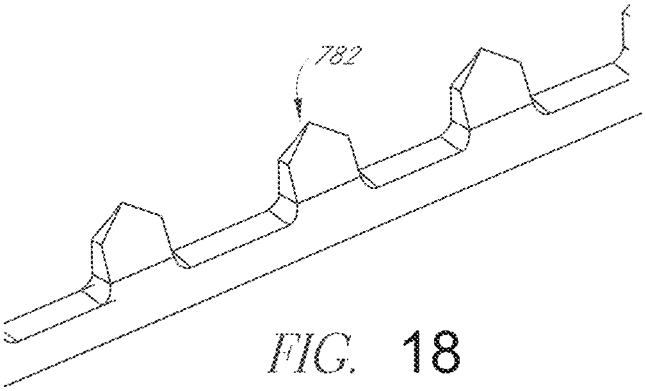
Figure 19:
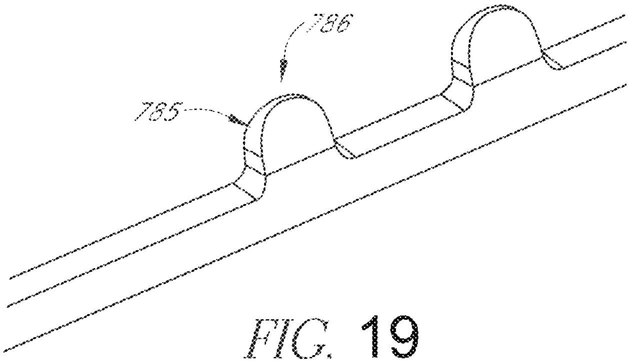

The shape of the wedge dissectors can take many forms, including further non-limiting embodiments as those shown in FIGS. 16-22. For example, FIG. 16 illustrates wedge dissectors 200 rising from a base strip 300 with a honed/sharp radially outward facing surface 204 from edge 206 to edge 208. FIG. 17-18 illustrates wedge dissectors with chamfered segments 780 of a radially outward facing surface on both lateral edges that slope or otherwise ramp upward to a honed central single point 782 or edge having a length 781. The slope could be a straight line ramp, or follow a curve as seen in FIG. 19 below. As illustrated in FIG. 17, the wedge dissector includes lateral segments 780 of radially outward facing surface that increases in height, but decreases in width from a first edge to a central mid-portion 781 having a length with minimal/negligible width, and then increases in width and decreases in width from the midpoint to the second edge. FIG. 18 illustrates a wedge dissector similar to FIG. 17 except that the mid-portion is a single honed apex point 782.

FIG. 19 illustrates a wedge dissector with a radiused radially outward facing surface 785 that increases in height from an edge along a first curved length but decreases in width from a first edge to a central zone such as a midpoint 786, then decreases in height and increases in width along a second curved length to another edge.

Figure 20:
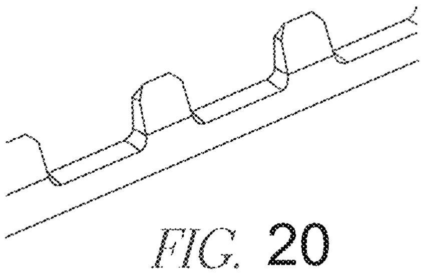

FIGS. 20-22 illustrate embodiments of wedge dissectors with an unhoned, radially outward facing surface that do not include a sharp honed point or edge (e.g., having a width that is larger than that of a honed edge). FIG. 20 illustrates an embodiment of a wedge dissector somewhat similar to that of FIG. 17, except the radially outward facing surface is completely unhoned along its length. FIG. 21 illustrates an embodiment of a wedge dissector somewhat similar to that of FIG. 18, except the radially outward facing surface is completely unhoned along its length. FIG. 22 illustrates an embodiment of a wedge dissector somewhat similar to that of FIG. 19, except the radially outward facing surface is completely unhoned along its length.

One commonality of the embodiments of FIGS. 17-22 is that the widths of the radially outward facing surfaces are greater (wider) at the lateral edges, and narrower/less wide more centrally, either at a central point or longer central segment. The height of the radially outward facing surface from one edge to the other edge can be arched or otherwise variable, e.g., with a highest point more centrally and the shortest height at one or more edges when viewed from the side. In these embodiments, the orientation of the narrowest or thinnest (least wide) section of the radially outward facing surface can be along the longitudinal axis of the strip, which may or may not be aligned with the longitudinal axis of the balloon.

In other embodiments, the narrower point or segment need not be symmetric about the midpoint of the length of the radially outward facing surface, but can be asymmetrical/offset from the midpoint of the length in some cases.

Independent of the geometry of the wedge dissectors, some embodiments are characterized by having a bounded end 202 or base (e.g., the spikes have a base the spikes are "attached" to, whether it is a spline (or strip), a balloon, or a molded element of some sort) with a length and width and an radially outward facing surface 204, end or tip with a length and width. In some embodiments, the width of the radially outward facing end is about, or less than about 90%, 85%, 80%, 75%, 70%, 65%, 60%, 55%, 50%, 45%, 40%, 35%, 30%, 25%, 20%, or less than the width of the strip-facing base end, or ranges incorporating any of two of the foregoing values. The width of the strip-facing base end of the wedge dissector (as well as the spline/strip) can be fixed/constant, or alternatively variable in some embodiments.

The wedge dissectors can be a number of different sizes and shapes. In some embodiments, the wedge dissectors are about or less than about, for example, 0.10", 0.09", 0.08", 0.07", 0.06", 0.05", 0.04", 0.03", 0.02", or 0.01" in length at the strip-facing base end or ranges incorporating any of two of the foregoing values, or between about 0.01" and about 0.06", or between about 0.01" and about 0.04" in length. In some embodiments, the wedge dissectors can be about or less than about 0.05", 0.04", 0.03", 0.025", 0.02", 0.015", 0.01", or 0.005" in height as measured from the unbonded edge of the base strip, or between about 0.005" and about 0.025" or between about 0.01" and about 0.025", or between about 0.005" and about 0.015" in some embodiments.

The wedge dissectors (or micro wedges) can, in some embodiments, have a wedge strip-facing base length of about, or less than about 25 mm, 20 mm, 15 mm, 14 mm, 13 mm, 12 mm, 11 mm, 10 mm, 9 mm, 8 mm, 7 mm, 6 mm, 5 mm, 4 mm, 3 mm, 2 mm, or 1 mm long, or ranges incorporating any two or more of the foregoing values. In some embodiments the wedge dissectors have a wedge strip-facing base length of 2 mm, 2.5 mm, or 3 mm long, or between about 1 mm and about 5 mm long, or between about 1.5 mm and about 3.5 mm long. The wedge dissectors can be spaced apart in a regular or irregular fashion to increase the flexibility of the device. For example, the space between adjacent wedge dissectors can be, for example, between about 2 times to about 10 times the wedge strip-facing base length of the wedge dissectors, with the wedge dissectors positioned lengthwise. For example, in some embodiments, wedge dissectors with a wedge strip-facing base length about 2.5 mm long can have about 5 mm spaces between them, or about 25 mm spaces between them. In some embodiments, groups of wedge dissectors can be spaced apart with a first smaller ratio of, for example, about 1-4 times the strip-facing base length of the wedge dissectors and then a group can be spaced apart by a second larger ratio, for example, about 8-10 times the strip-facing base length of the wedge dissectors. For example, a first group of wedge dissectors with a strip-facing base length of 2.5 mm can have 5 mm spaces between them and then a second group of wedge dissectors can be spaced 20 mm from first group. The second group can have the same or a different size, shape, and or spacing as the first group.

The location of the radially outward facing surface relative to the strip-facing base surface is not always centered or symmetric in some embodiments. In other words, the midpoint of the radially outward facing surface can be offset from the midpoint of the strip-facing base surface. FIGS. 23A-B and 24 illustrate an asymmetric radially outward facing surface as an alternate embodiment of the spikes. An asymmetric radially outward facing surface can be off center with respect to the alignment of a radially outward facing width edge directly over the strip-facing base width edge. In this configuration only one of the strip-facing base width edges has a tilted edge 440 climbing in height off of the radially outward facing surface while the other height edge 442 is perpendicular, at a 90 degree (right) angle RA to the strip-facing base surface 444, seen best in FIG. 23A. In addition, the edges of the radially outward facing surface in one or both of the width ends and/or in one or both of the length ends can be chamfered or beveled or have a radius. In some variations, the radially outward facing surface location is limited to the area projected upward over the strip-facing base surface. The radially outward facing surface can be a sharp line (e.g., honed edge) or any of the described unhoned edge variations for example. FIG. 23C-D illustrates an embodiment where the total volume or substantially the total volume of the wedge dissector rises/is present over less than the entire width (or surface area) of the base of the strip, such as about or less than about 70%, 60%, 50%, 40%, or 30% of the width or surface area of the strip, for example, and are thus the wedge dissectors are asymmetrically offset either anteriorly or posteriorly from the longitudinal axis of the strip.

FIG. 24 illustrates an embodiment illustrating how the radially outward facing surface 204 may have a varying height (increasing from first height 24H1 at first edge 206 to second height 24H2 at second edge 208) from the strip-facing base surface 202 and may include edge profiles that are rounded with a radius of curvature of the radially outward facing length edges 206, 208. Here, a wider radius of curvature at one edge 206 is shown that has a shallow height 24H1 measured from the strip-facing base surface 202 while the radius of curvature of the opposite edge 208 is narrower and has a longer height 24H2 measured from the strip-facing base surface 202.

In some embodiments, the various wedge dissector features described herein can offer unique advantages to aid in delivery of the device, including but not limited to reducing vessel trauma if the radially outward facing surface is positioned outside of the delivery apparatus and/or can contact the luminal wall and has the potential to scrape the vessel wall during movement through the artery. This can be the case, for example, in embodiments with wedge dissectors with unhoned, radially outward facing surfaces.

In addition, not to be limited by theory, certain shapes may offer more effective penetration into the tissue. For instance, wedge dissectors that include chamfered or rounded radially outward facing edges can potentially enter the vessel wall with less force (requires less pressure to penetrate tissue) while still maintaining an effective micro channel 5100 to weaken the tissue and enable tissue expansion with minimal vessel trauma and cellular injury.

Furthermore, while there have been prior proposals for providing blades or sharp edges or scoring wire on a balloon during angioplasty or other procedure for cutting or scoring the plaque in conjunction with balloon expansion, these prior methods are deemed to have problems or disadvantages which are eliminated or avoided by systems and methods as disclosed herein. Cutting or scoring a luminal wall, such as, for example, the plaque during angioplasty can be performed at high pressures that can result in high injury to the blood vessel. The cutting blades, edges or scoring wire can be forced into the wall of the blood vessel at the same time that the angioplasty balloon is expanded to dilate the plaque. During this process the cutting blades, edges, or scoring wire can be forced into the vessel wall at oblique angles and can plow up the plaque potentially increasing the tendency for dissections and the potential need for implants like stents. In contrast, in some embodiments, wedge dissectors employ can be expanded into the plaque at low pressures so as to form precise microperforations, serrations, and/or indentations in a radially outward direction that form precise indentations, cleavage lines or planes in the plaque or other location in the luminal wall, or other target. The radially outward facing surface of the wedge dissector can push into the plaque or other luminal surface in small surface areas, thereby being much less likely to plow up the plaque or luminal surface.

Wedge dissectors can be designed, in some embodiments, to provide a series of oriented punctures or serrations into (but not completely through in some cases) a diseased vessel wall, which can create in some cases predictable and controlled lumen expansion along the serrated lines with minimal injury, and without cutting with blades with honed/sharp edges. The perforations can serve as a pathway such as micro-channels for pharmaceutical or other agents as shown in FIG. 23E. The pharmaceutical or other agents could be delivered using a drug-coated balloon, incorporated either with the device disclosed herein, or on a separate device that is used following the usage of the disclosed device. In some embodiments, the wedge dissectors can be detachable from the base strip, and/or be coated or otherwise impregnated with one or more pharmaceutical agents for drug delivery. The wedge dissectors can produce a linear line of weakness or perforations without cutting a continuous axial segment of the vessel wall that can enable more effective and gentler vessel lumen expansion 5110 as shown in FIGS. 23F and 23F.1. One can see the examples of stages of gradual expansion and serration in 5110, 5130, 5140, 5150. The balloon can be inflated and while the pressure in the balloon increases the following series of events can occur: the balloon unfolds in the artery and the strips are exposed from their resting place within the folds; the tips (e.g., radially outward facing surface) of the wedge dissectors on the strips contact the wall; the tips' relatively narrow profile penetrate the wall generating nucleation sites for the fissuring event; the fissures quickly produce cracking along the intra-luminal surface; due to the proximity and alignment of the cracks, the cracks join to become a long crack along the intra-luminal surface that can extend along the entire length of the strip, or less of the strip length, or greater than the strip length; the depth of the penetration of the crack has been found to be typically similar to the depth of medial tissue.

To reduce potential rigidity of the spline, or base strip, it is envisioned that a series of reliefs on the spline can be added in some embodiments, as illustrated in FIGS. 25 and (or through) 29. The relief elements can be produced in many different ways with the intent to have material removed and offer a more pliable spline for the wedges to be strip-facing base to. Relief can be made in the base of the spline opposite the wedge dissector strip-facing base surface, at the top of the spline directly adjacent the wedge dissector strip-facing base surface, or in both locations, e.g., a combination of top and bottom. The relief can also be made on the side of the spline, or apertures strip-facing base by other areas of the spline can be added to the spline. Any combination of top, bottom, side or through apertures can be added to the spline to offer relief.

In some embodiments, as illustrated in FIGS. 25-20, the strip 300 can have relief holes or slits located at the top, bottom, centered or off center that are either circular, rectangular, linear, triangular, or elliptical or combinations thereof (See FIGS. 25-29). The strips offer a supporting base infrastructure, intended to be flexible and follow the movement of the balloon, for the wedges to be oriented correctly.

The relief holes illustrations as shown in FIGS. 25-29 can be specifically designed to offer a pathway for balloon-based pharmacological agents to migrate through; in addition, they offer strain relief in the surface to enhance the deliverability of the device in tortuous anatomy. FIGS. 25A-C illustrate embodiments of wedge dissectors with reliefs 502 on the inferior surface 500 of the strips 300 opposite the bounded surface of the wedge dissectors 200. FIG. 25A illustrates an embodiment where the reliefs 502 are regularly spaced apart approximately a length of the bounded surface of each wedge dissector 200. FIG. 25B illustrates an embodiment where the reliefs 502 are regularly spaced apart 50% or less of the length of the bounded surface of each wedge dissector 200. FIG. 25C illustrates an embodiment where each relief 502 is spaced apart 50% or less of the length of the bounded surface of each wedge dissector 200, but the reliefs 502 are grouped only under the wedge dissectors and are not present under the strip sections in between the wedge dissectors. In other embodiments, the reliefs 502 are grouped only under the strip sections in between the wedge dissectors, but not under the strip sections directly below the wedge dissectors.

Figure 25A:
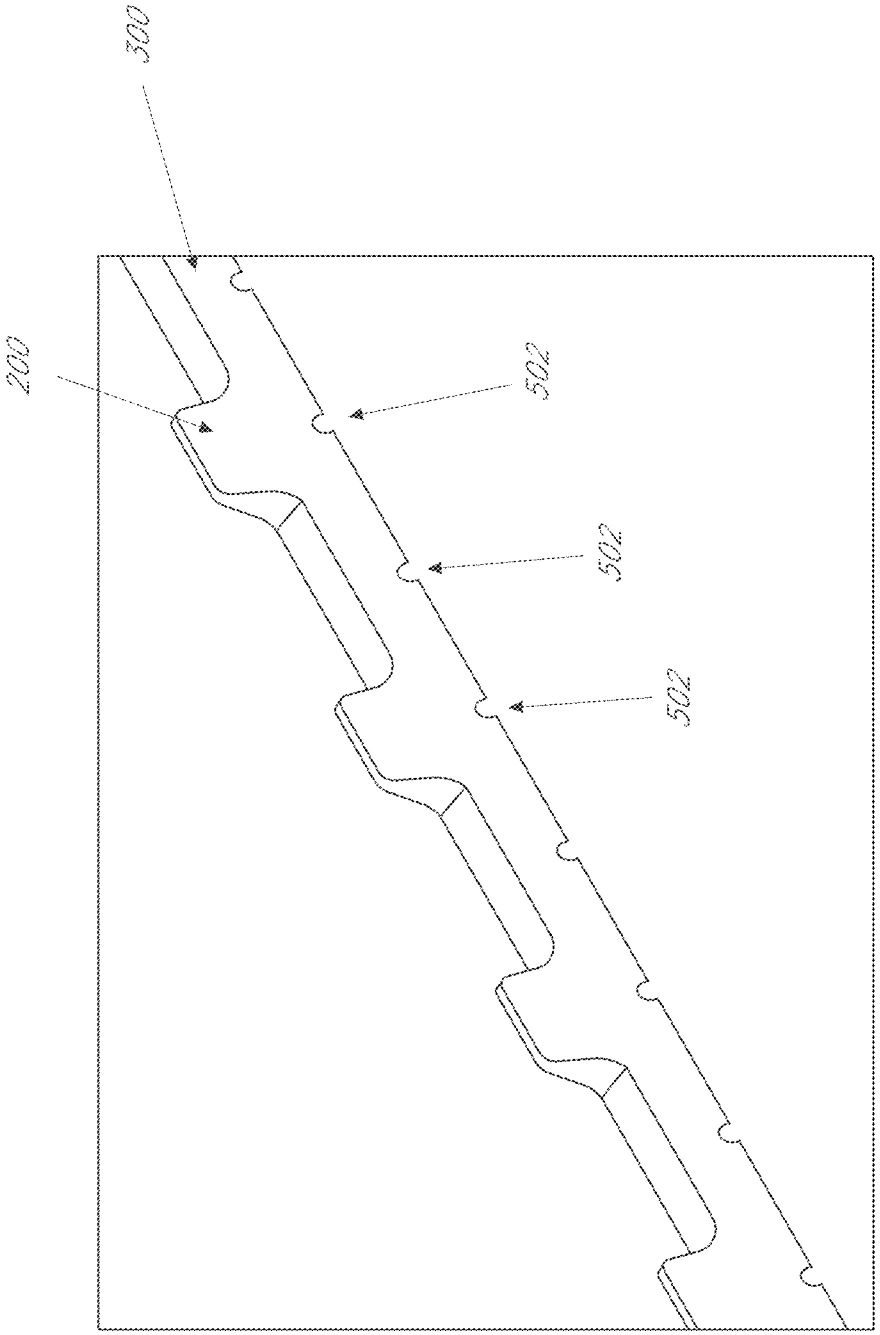
Figure 25B:
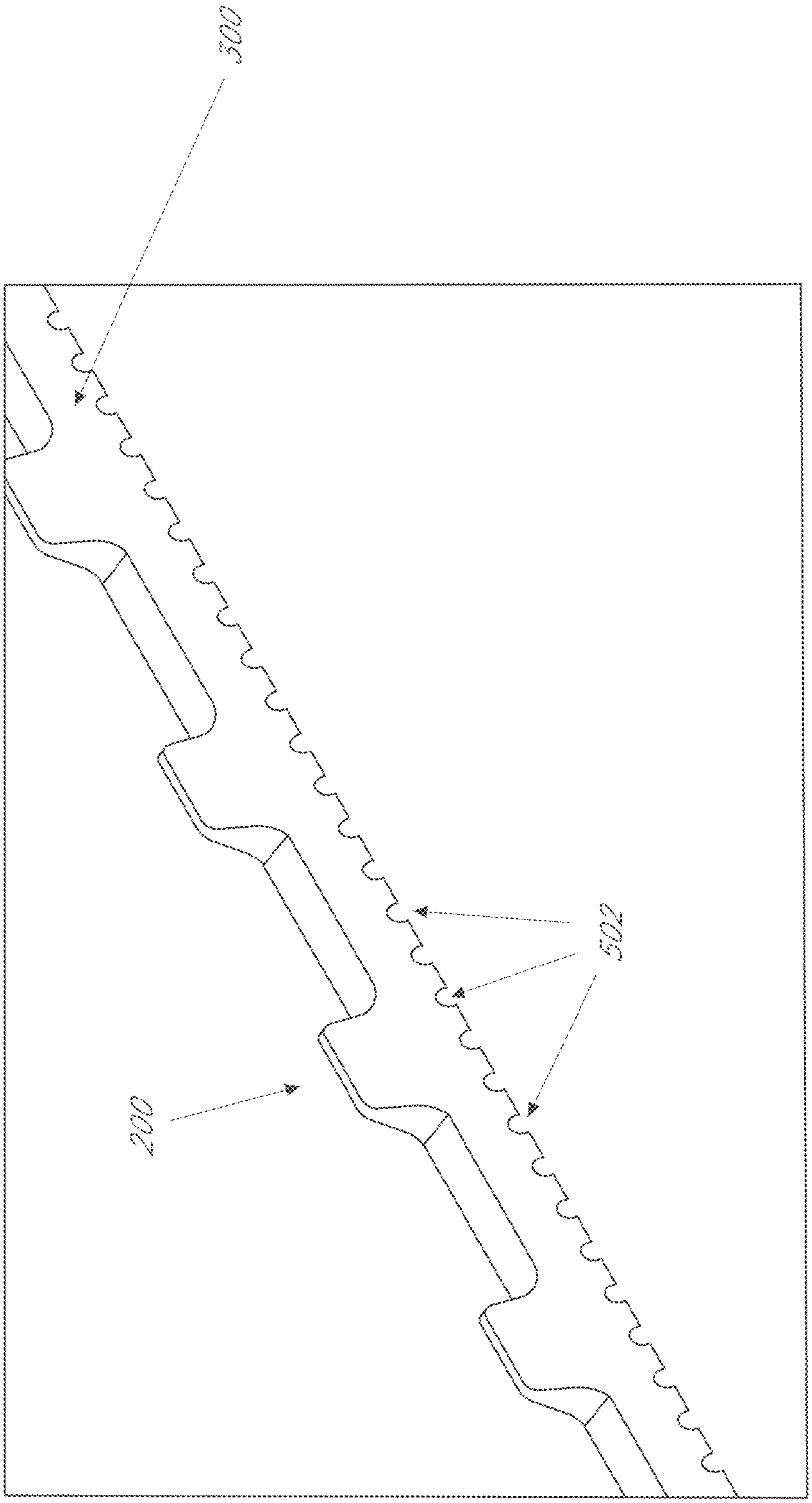
Figure 25C:
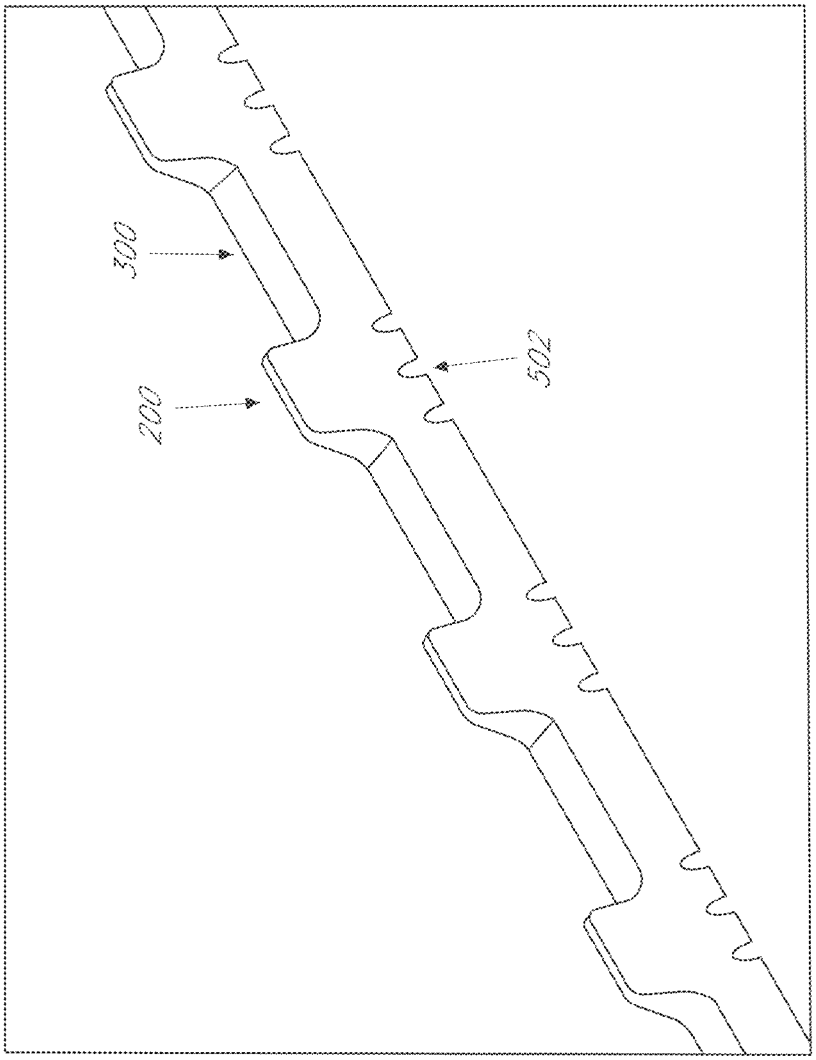
Figure 25D:
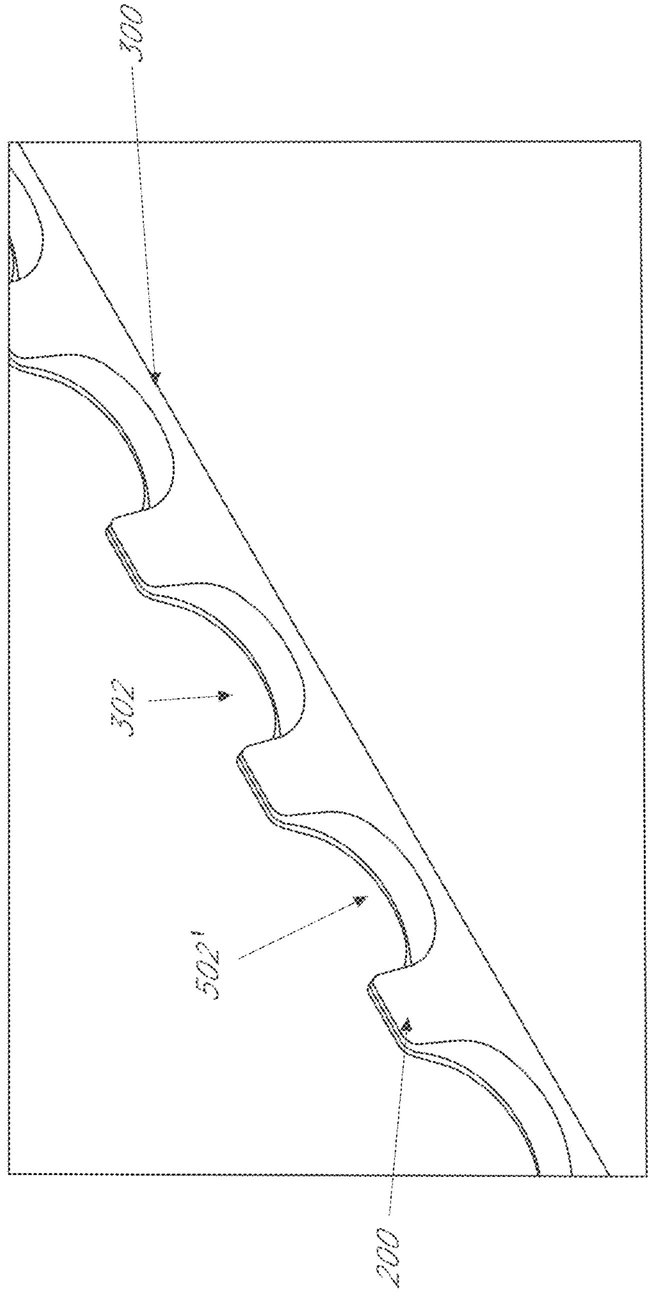
Figure 25E:
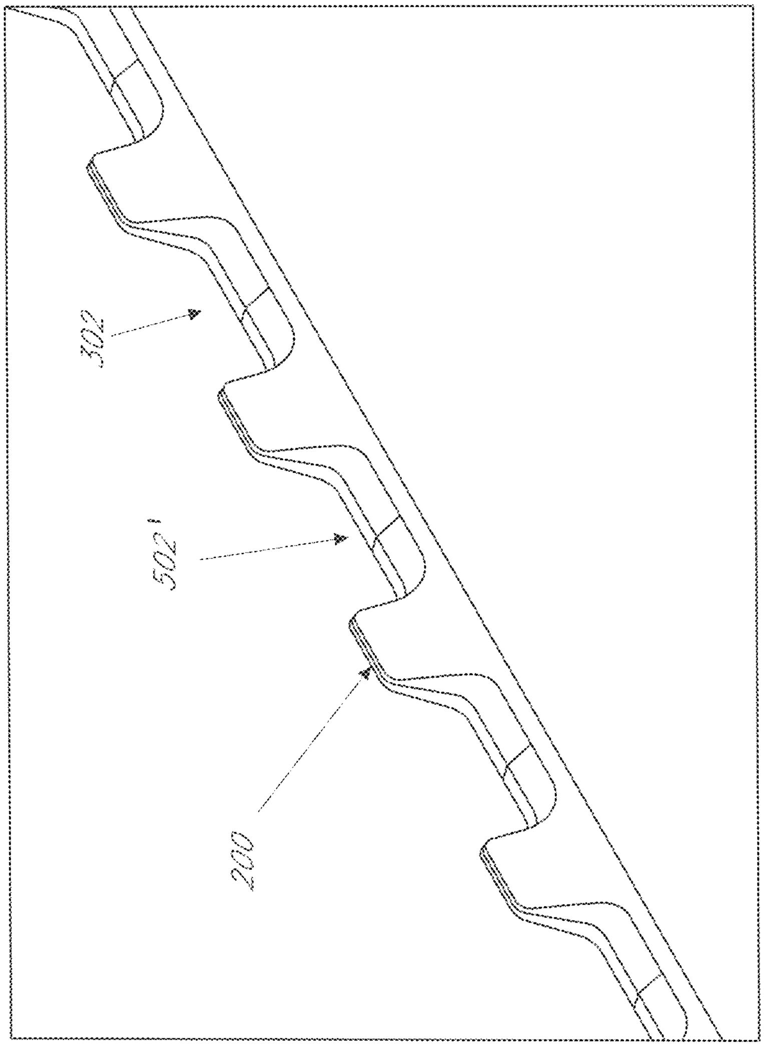
Figure 25F:
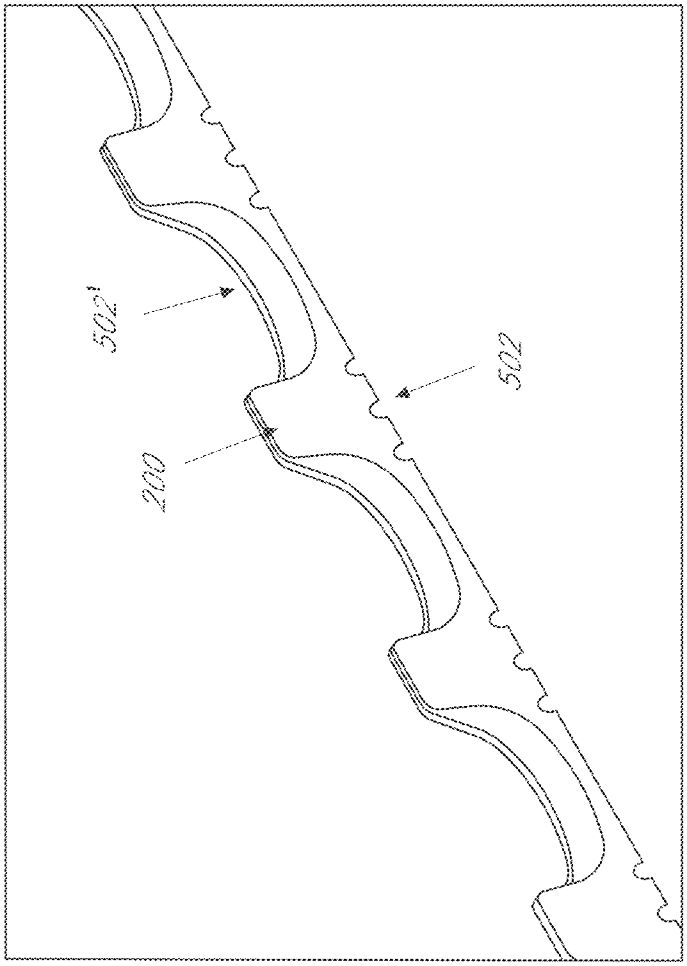
Figure 25G:
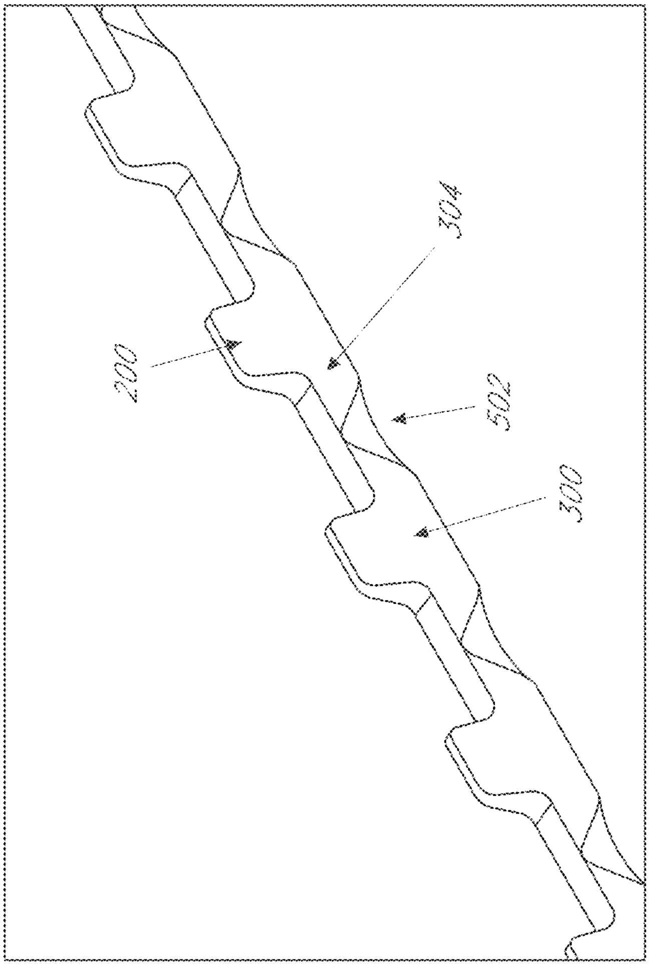
Figure 25H:
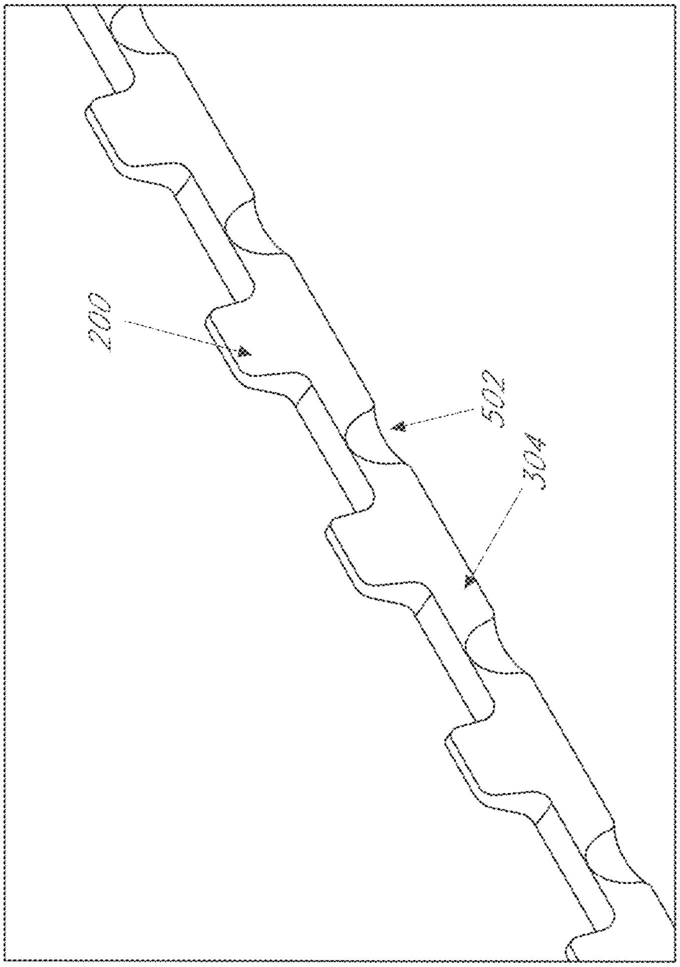
Figure 25I:
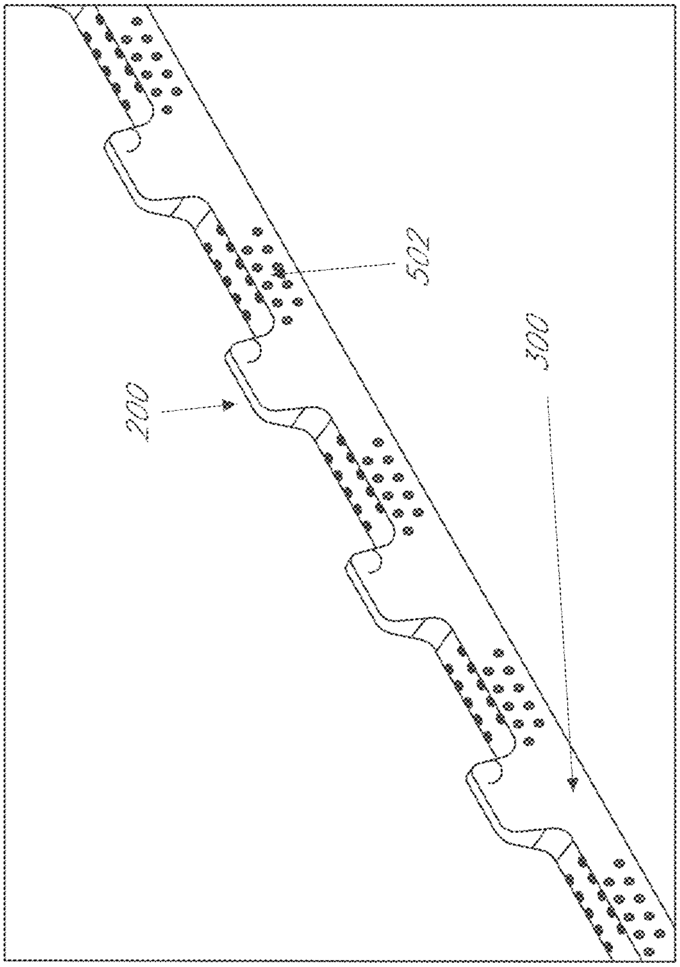
Figure 25J:
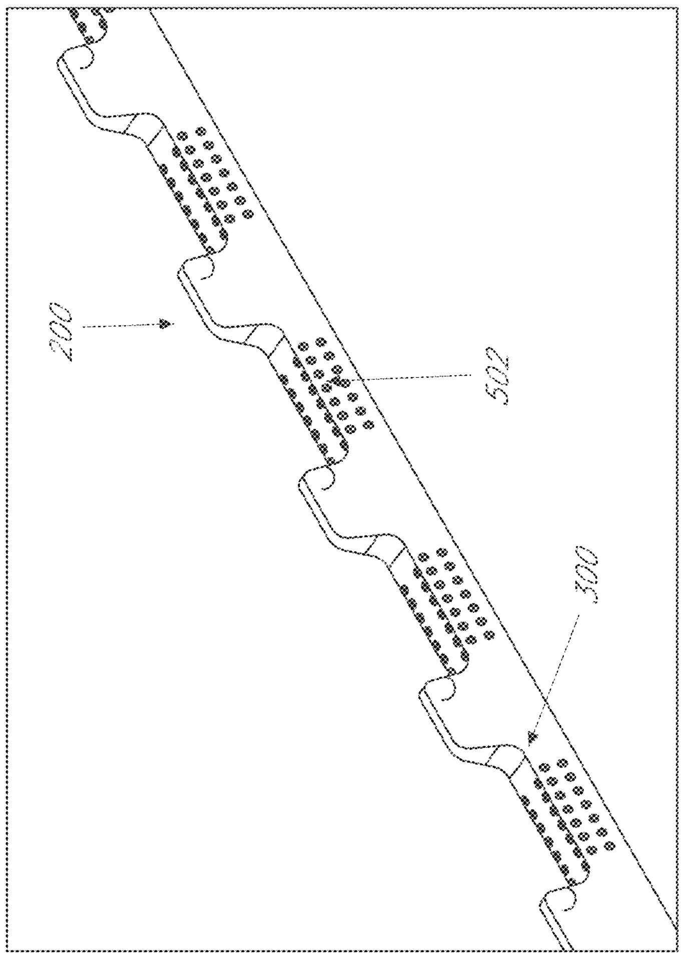
Figure 25K:
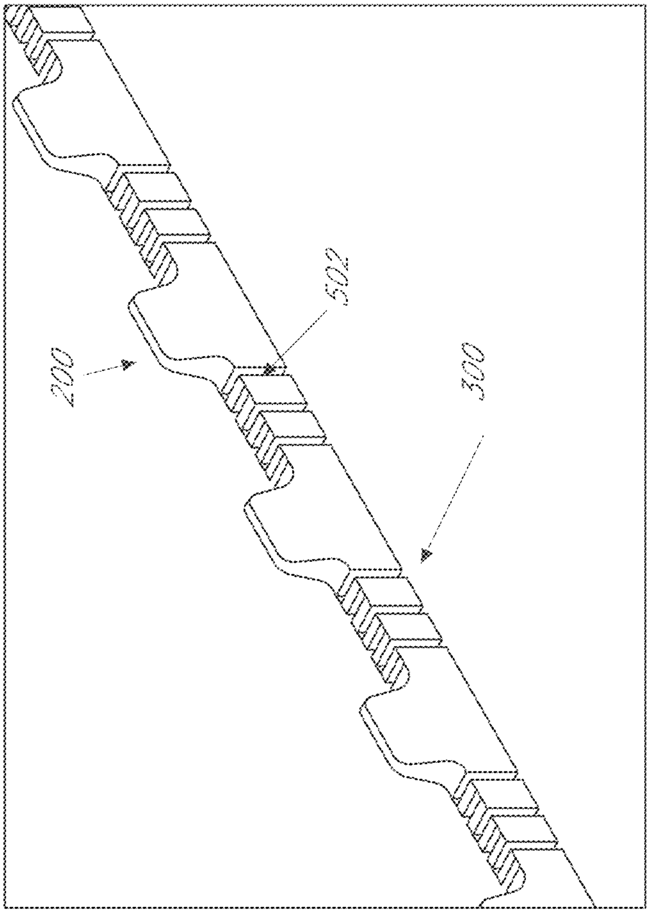
Figure 25L:
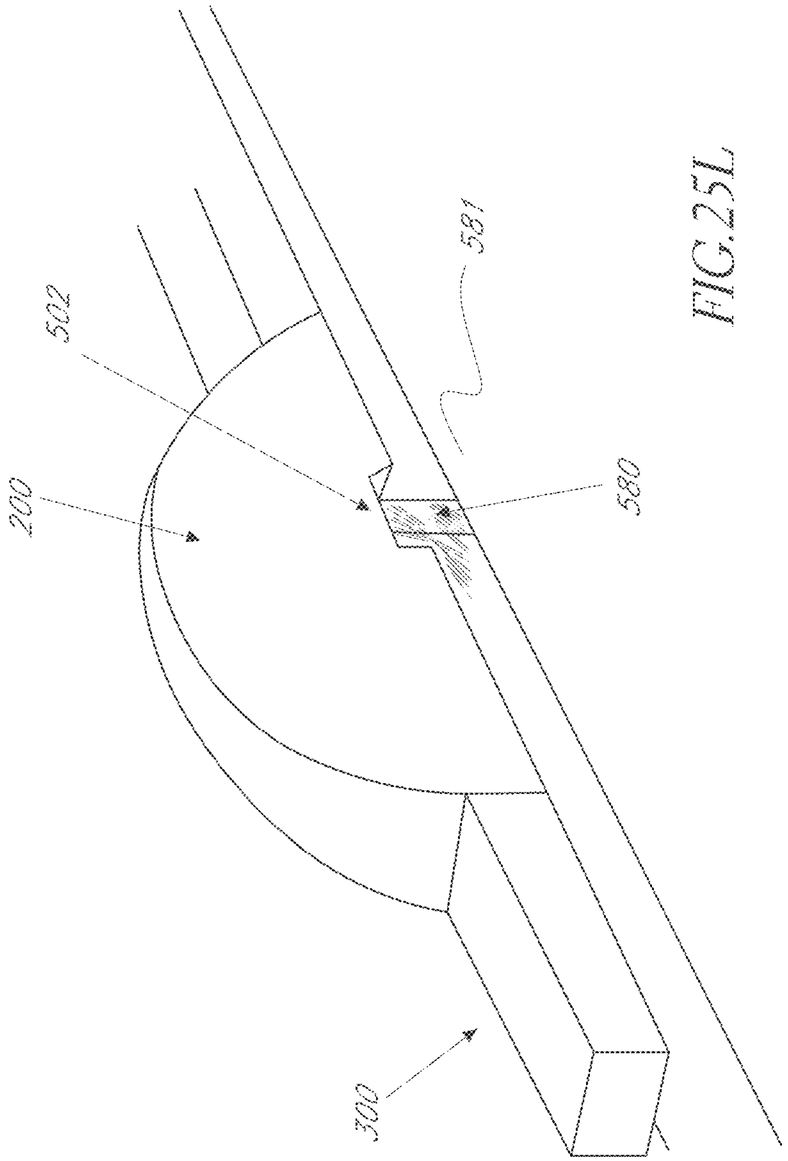
Figure 25M:
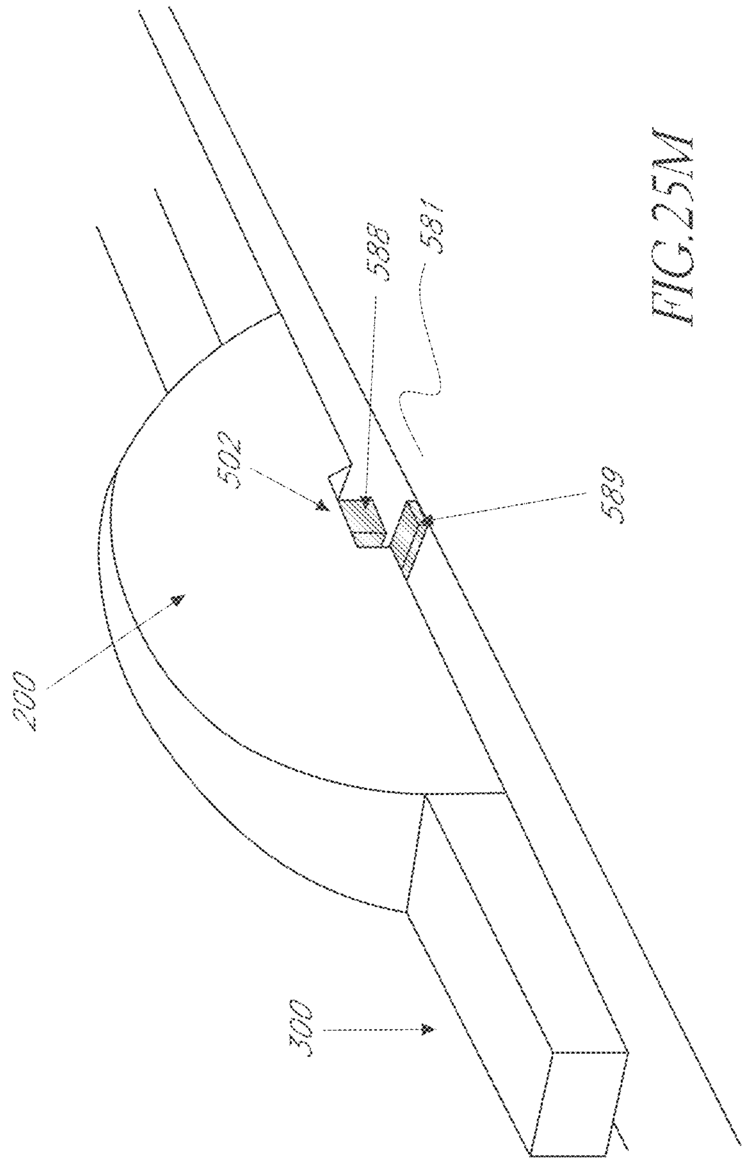
Figure 25N:
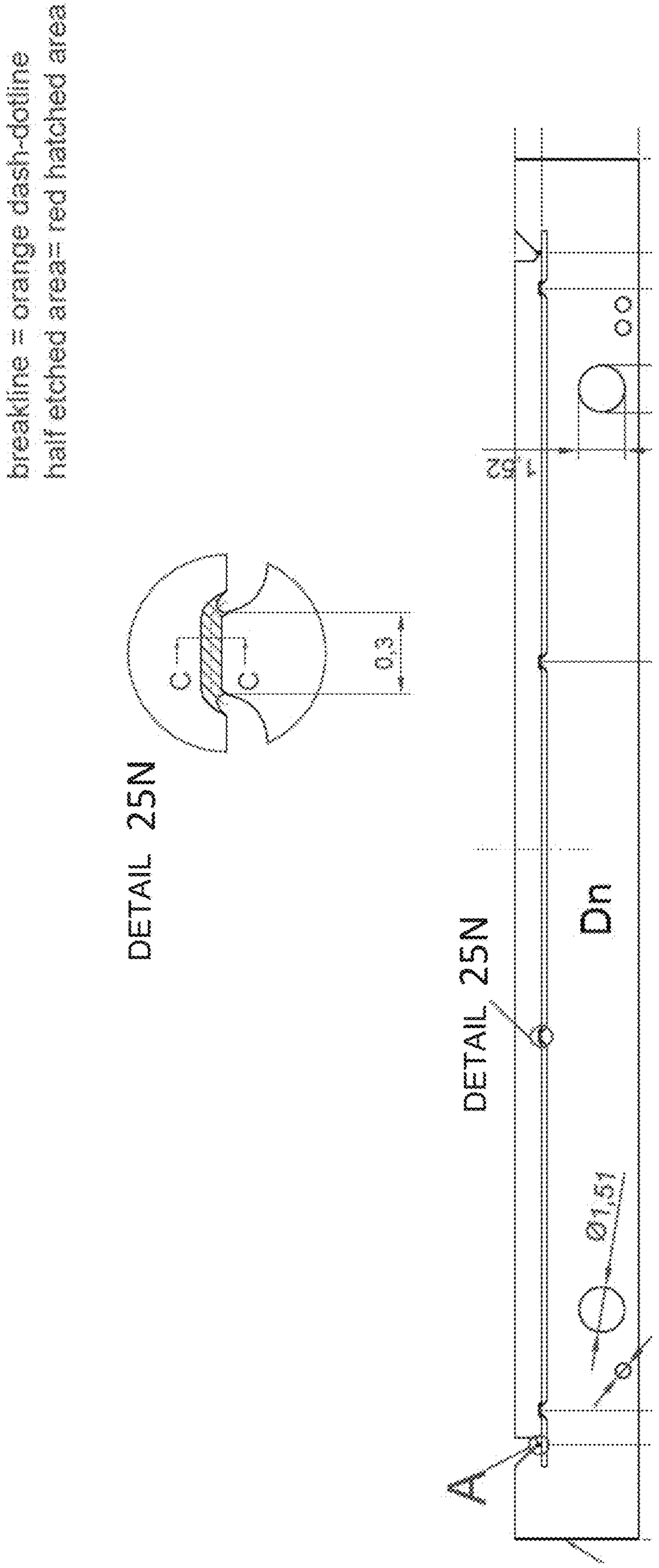
Figure 25O:
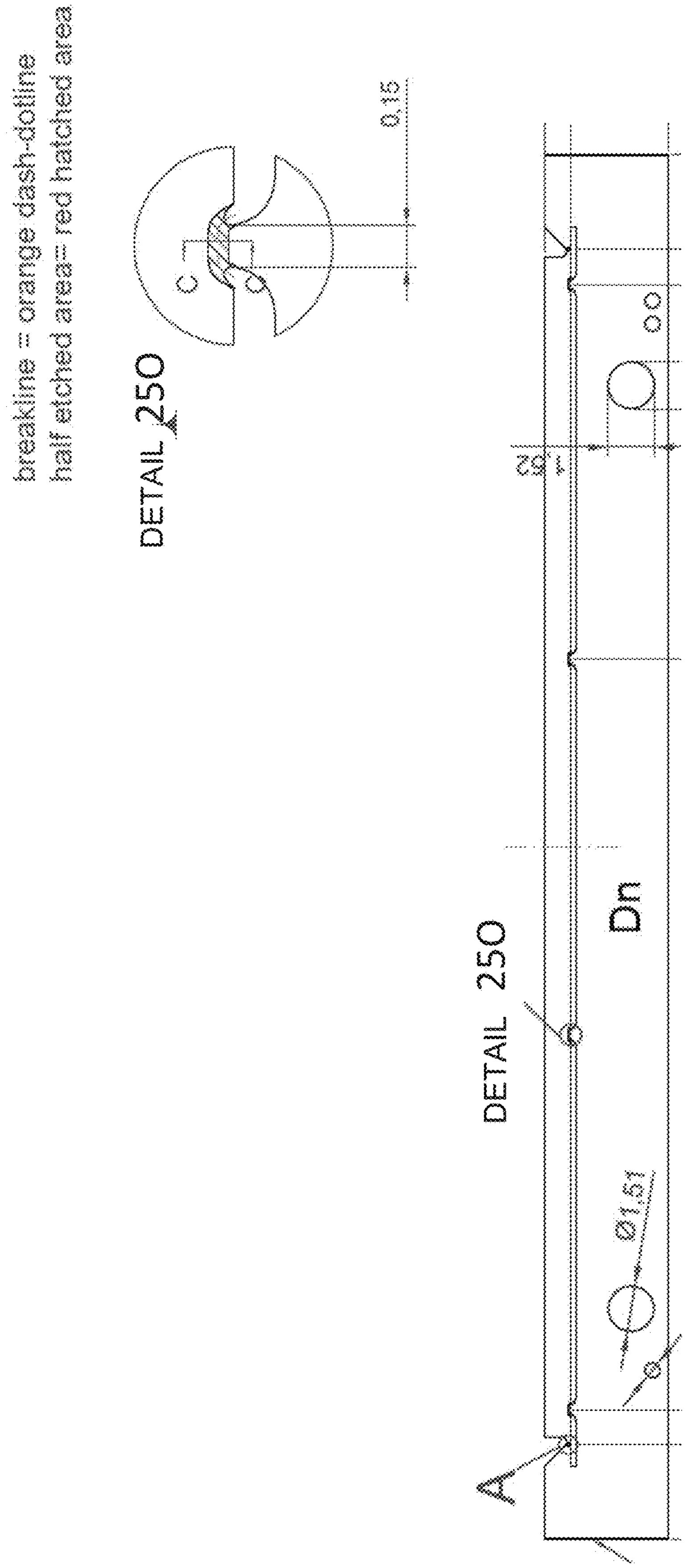
Figure 25P:
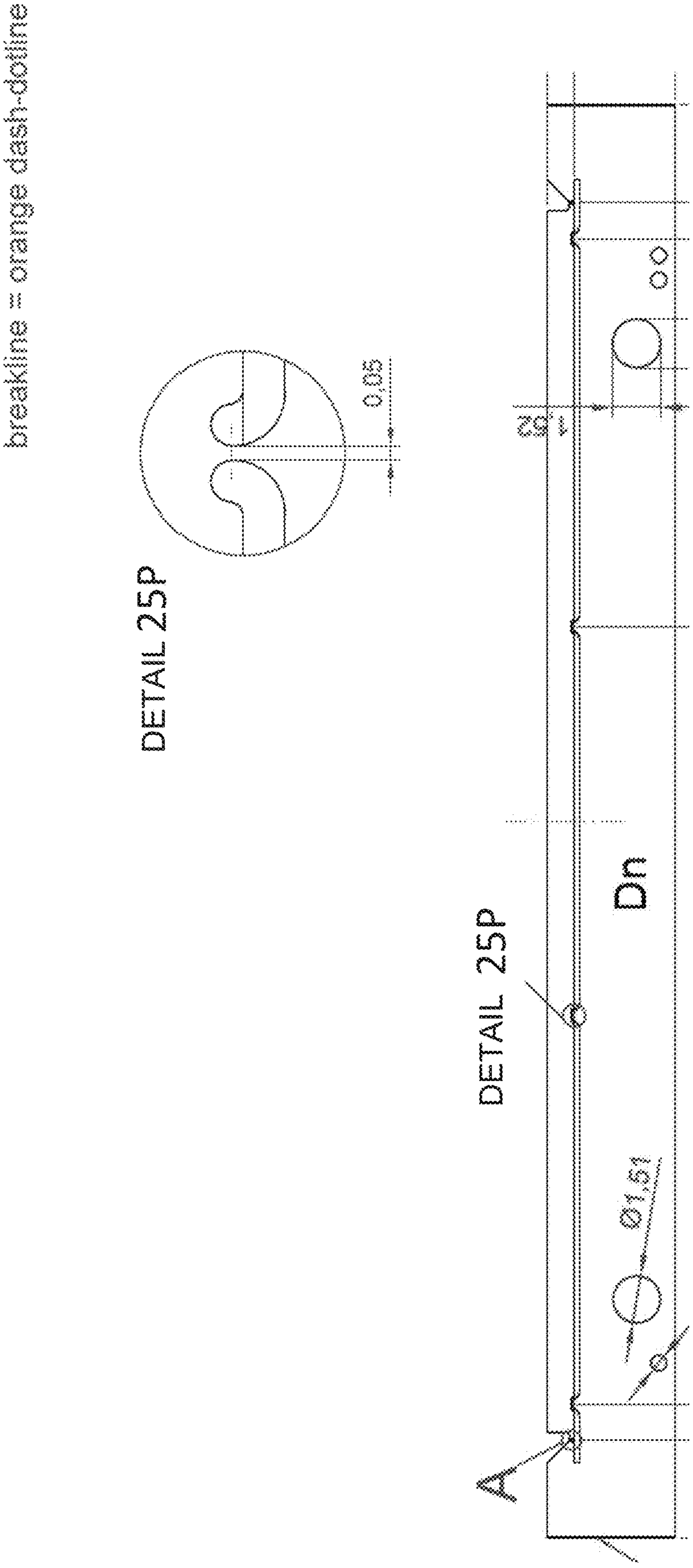
Figure 25Q:
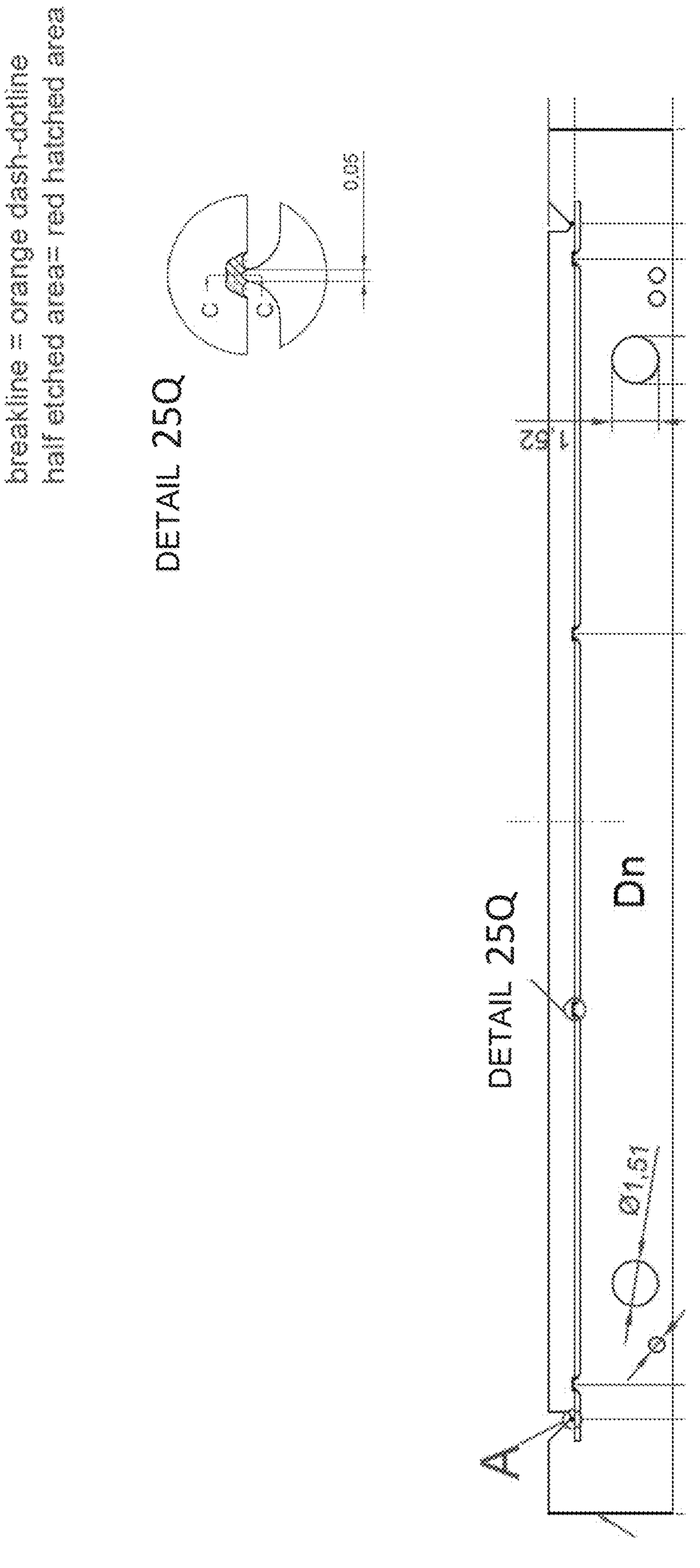

FIGS. 25D-25E illustrates an embodiment where the reliefs 502 are present on the top (bounded or superior-facing surface 302) of the strip in between the wedge dissectors. In FIGS. 25D and 25E, the reliefs form depressions in the superior-facing surface 302 of the strips in between wedge dissectors with a generally curved based as illustrated in FIG. 25D, and a relatively more square or rectangular base as illustrated in FIG. 25E, with or without rounded edges. FIG. 25F is an embodiment combining two different kinds of reliefs 502 found in the embodiments of FIGS. 25C and 25D. Other permutations of combinations are also possible, depending on the desired clinical result. FIGS. 25G and 25H illustrate other embodiments where the reliefs 502 are on an anterior 304 and/or posterior side surface of the strip 300. FIG. 25G illustrates generally pyramidal-shaped reliefs 502, while FIG. 25H illustrates generally arcuate reliefs 502. The reliefs can be spaced axially apart from the wedge dissectors as shown, and/or spaced axially aligned with wedge dissectors in other embodiments. FIGS. 25I and 25J illustrate embodiments where the reliefs 502 take the form of vertically (FIG. 25I) or horizontally (FIG. 25J) oriented through-channels, which can be spaced axially apart from the wedge dissectors as shown, or in another configuration. In some embodiments, the reliefs can be oriented at an oblique angle to the longitudinal axis of the strip. FIG. 25K illustrates an embodiment where the reliefs 502 take the form of slots on the anterior and/or posterior side surfaces, bounded base surface, and/or other locations. FIG. 25L illustrates bridges or tabs under the functional part or wedge dissector 200. These bridges or tabs connect the functional part 200 to the bulk material. In cases where the functional parts are removed from the bulk material using a technology where the radially outwardly facing surface 204 of a wedge dissector 200 is unbound, the functional part typically requires a series of bridges to the bulk material. Bridge features can be made using a variety of manufacturing processes. In some processes the bridges are made by remove the base material with a laser or other spot line of energy that precisely removes predetermined material leaving the bridges to the working part remaining. In other processes the bridges can be made using other forms of material removal including chemical etching. Alternate bridges made using chemical etching are illustrated in FIGS. 25N-25Q. The bridges shown in FIGS. 25N-25Q can include partial etching through the base material as indicated by the hatched area shown on the base of the strip (e.g., the inferior most surface configured to be attached to the outer surface of the balloon). Independent of the bridge design all bridges are designed to be snap broken where the break of the bridge is always above the base of the strip (e.g., the inferior most surface configured to be attached to the outer surface of the balloon).

In some embodiments, balloons can be pleated and crimped down to the very narrow profile allowing the device to be delivered through and introducer sheath with a narrow diameter. Once the balloon has been deployed and deflated, the post-inflated balloon profile can be larger than its original pleated and crimped down diameter. This new profile may have strips that sit proud of the balloon profile potentially scraping the arterial wall or snagging on the opening of an accessory device such as an introducer sheath. The following elements, which are in general described as ramps, can address this potential issue, according to some embodiments.

FIG. 26 illustrates schematically an embodiment of a ramp 680 of adhesive or other material is placed at (e.g., over) one, as shown, or both lateral ends 333 of some or all of the strips 300. When the strips is embedded in the balloon the ramps can be, in some cases, additional material either in the balloon mold, or an adhesive alone, additional material adhesively bonded, or material from the laminate that is placed at other locations such as the distal and proximal ends of the strips. The ramp 680 can offer an effective flexible interface between the edge of the flexible balloon (not shown) and the semi-rigid strip 300, as the ramp 680 can be made of a material (e.g., an adhesive, a layer stack of materials) that is relatively more flexible than that of the strip 300. The ramp 680 can be designed in some embodiments to gently slope from the balloon surface (not shown) to the edge of strip. In some embodiments, the adhesive ramps 680 can advantageously both retain strips and offer protection from undesired strip interaction 300 with ancillary devices during a procedure.

In some embodiments, the lateral edges of the strips can include glue ramps 680 to retain strips 300 and offer protection from strip interaction with ancillary devices during a procedure. Ramps may be produced with UV glues using repeat deposition and curing steps in a series of laying down and building up layers until a ramp is produced as seen in FIG. 26A. Alternatively, ramps maybe prefabricated into the desired shape and then bonded to the surface with cyanoacrylate, UV glue, or other material or method offering a chemical, mechanical, or electromagnetic bond between the prefabricated ramps to the balloon surface. Note that this embodiment, the top of the adhesive layer is near crest of strip projection (wedge dissector tip) 681. In some embodiments, the ramp can extend laterally past the later edge of the strip a distance of between about 0.008" and about 0.040", between about 0.008" to about 0.012", between about 0.010" and about 0.040", between about 0.020" and about 0.030", or other dimensions depending on the desired result.

In some embodiments, a feature that can be incorporated into the balloon element is a cone ramp. The cone ramp feature can be implemented in several ways. In one embodiment, the cone ramp is fabricated by taking a cone configuration for a larger balloon, for example taking a cone for a 6 mm balloon, or 5.5 mm balloon and incorporating it using known methods to be attached to a 5 mm balloon. One such embodiment is shown schematically in FIG. 27. The cone 970 can have in some cases an outer diameter that is larger than that of the outer diameter of the balloon 960, such as about or at least about 5%, 10%, 15%, 20%, or more than that of the outer diameter of the balloon 960, or between about 5% and about 20% larger than that of the outer diameter of the balloon 960 in some embodiments. The relatively larger cone 970 will sit proud of the balloon 960 generating a lip 972 at the intersection of the balloon body. The lip 972 can be beneficial in reducing the potential of the metal strip edges to be snagged or lifted off when the balloon is deflated and retracted through the introducer catheter.

In some embodiments, illustrated in FIG. 28, included are a series of rails 980 along the cone 970 to serve as support or stiffening structures, and assist in collapsing the balloon 960 as it enters an introducer catheter (not shown). In some embodiments, the rails 980 are oriented/align with the longitudinal axes of the strips, furthering enhancing the function of pushing the strips toward the middle of the balloon as the cone is pulled through the introducer.

In some embodiments, also disclosed herein are balloons that can have depressions in the outer surface of the balloon for strip attachment. A series of depressions can be produced on the surface of the balloon. The depressions can, in some embodiments, configured to be wide enough and long enough to allow the strips to be placed within, such as entirely within the depression. The depths of the depressions can be sized to limit the likelihood that the strips could get caught on the distal opening of the introducer during balloon retraction.

The use of the through-holes or microchannels 5100, as shown in FIG. 23E, either in the spline or on the spline sides can offer a mechanism for a therapeutic agent such as, for example, one or more drugs, nanoparticles, and/or stem cell transport from the balloon surface into the diseased luminal surface through capillary or diffusion action and/or utilization of the balloon pressure forcing the drug, nanoparticles, and/or stem cells through the micro channels 5100 on to the surface or into the diseased site. Alternatively, the microchannels 5100 or modified surfaces can provide a reservoir for drug, nanoparticles, or stem cells or other therapeutics to be placed and protected during transport to the diseased site. In some embodiments, the drug may be any drug known in the art. In some embodiments, examples of drugs that may be suitable for use in the methods and devices of this invention depending, on the specific disease being treated, and with consideration of the physical properties of the drug, include, without limitation, anti-restenosis, pro- or anti-proliferative, anti-inflammatory, anti-neoplastic, antimitotic, anti-platelet, anticoagulant, antifibrin, antithrombin, cytostatic, antibiotic, anti-enzymatic, anti-metabolic, angiogenic, cytoprotective, angiotensin converting enzyme (ACE) inhibiting, angiotensin II receptor antagonizing and/or cardioprotective drugs.

Examples of antiproliferative drugs include, without limitation, actinomycins, taxol, docetaxel, paclitaxel, sirolimus (rapamycin), biolimus A9 (Biosensors International, Singapore), deforolimus, AP23572 (Ariad Pharmaceuticals), tacrolimus, temsirolimus, pimecrolimus, zotarolimus (ABT-578), 40-O-(2-hydroxy)ethyl-rapamycin (everolimus), 40-O-(3-hydroxypropyl)rapamycin (a structural derivative of rapamycin), 40-O-[2-(2-hydroxy)ethoxy]ethyl-rapamycin (a structural derivative of rapamycin), 40-O-tetrazole-rapamycin (a structural derivative of rapamycin), 40-O-tetrazolylrapamycin, 40-epi-(N-1-tetrazole)-rapamycin, and pirfenidone.

Examples of anti-inflammatory drugs include both steroidal and non-steroidal (NSAID) anti-inflammatories such as, without limitation, clobetasol, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone, dexamethasone dipropionate, dexamethasone acetate, dexmethasone phosphate, momentasone, cortisone, cortisone acetate, hydrocortisone, prednisone, prednisone acetate, betamethasone, betamethasone acetate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus and pimecrolimus.

Examples of antineoplastics and antimitotics include, without limitation, paclitaxel, docetaxel, methotrexate, azathioprine, vincristine, vinblastine, fluorouracil, doxorubicin hydrochloride and mitomycin.

Examples of anti-platelet, anticoagulant, antifibrin, and antithrombin drugs include, without limitation, heparin, sodium heparin, low molecular weight heparins, heparinoids, hirudin, argatroban, forskolin, vapiprost, prostacyclin, prostacyclin dextran, D-phe-pro-arg-chloromethylketone, dipyridamole, glycoprotein IIb/IIIa platelet membrane receptor antagonist antibody, recombinant hirudin and thrombin, thrombin inhibitors such as ANGIOMAX® (bivalirudin, from Biogen), calcium channel blockers such as nifedipine, colchicine, fish oil (omega 3-fatty acid), histamine antagonists, lovastatin, monoclonal antibodies such as those specific for Platelet-Derived Growth Factor (PDGF) receptors, nitroprusside, phosphodiesterase inhibitors, prostaglandin inhibitors, suramin, serotonin blockers, steroids, thioprotease inhibitors, triazolopyrimidine, nitric oxide or nitric oxide donors, super oxide dismutases, super oxide dismutase mimetic and 4-amino-2,2,6,6-tetramethylpiperidine-1-oxyl (4-amino-TEMPO).

Examples of cytostatic or antiproliferative drugs include, without limitation, angiopeptin, angiotensin converting enzyme inhibitors such as captopril, cilazapril or lisinopril, calcium channel blockers such as nifedipine; colchicine, fibroblast growth factor (FGF) antagonists; fish oil (ω-3-fatty acid); histamine antagonists; lovastatin, monoclonal antibodies such as, without limitation, those specific for Platelet-Derived Growth Factor (PDGF) receptors; nitroprusside, phosphodiesterase inhibitors, prostaglandin inhibitors, suramin, serotonin blockers, steroids, thioprotease inhibitors, triazolopyrimidine (a PDGF antagonist) and nitric oxide.

Examples of ACE inhibitors include, without limitation, quinapril, perindopril, ramipril, captopril, benazepril, trandolapril, fosinopril, lisinopril, moexipril and enalapril.

Examples of angiotensin II receptor antagonists include, without limitation, irbesartan and losartan.

Other therapeutic drugs that may find beneficial use herein include, again without limitation, alpha-interferon, genetically engineered endothelial cells, dexamethasone, antisense molecules which bind to complementary DNA to inhibit transcription, and ribozymes, antibodies, receptor ligands such as the nuclear receptor ligands estradiol and the retinoids, thiazolidinediones (glitazones), enzymes, adhesion peptides, blood clotting factors, inhibitors or clot dissolving drugs such as streptokinase and tissue plasminogen activator, antigens for immunization, hormones and growth factors, oligonucleotides such as antisense oligonucleotides and ribozymes and retroviral vectors for use in gene therapy, antiviral drugs and diuretics.

In other embodiments, a combination of any two, three, or other number of the foregoing drugs or other therapeutic agents can be utilized depending on the desired clinical result.

One method for laying down drugs, nanoparticles, stem cells or other therapeutics in specific regions such as the relief holes is the use of a direct write process, e.g., MICROPENNING (MICROPEN Technologies, Honeoye Falls, NY), to deposit material onto a surface. In general, the term "direct write" describes a printing or patterning method that employs a computerized, motion-controlled stage with a motionless pattern generating device to dispense flowable materials in a designed pattern onto a surface. MICROPENNING is a flow-based micro-dispensing technique in which printed materials are extruded with a high degree of control through a syringe and a precision pen tip. The pen tip "rides" on the surface of the material, not touching the substrate surface and is capable of place precise amount of materials in precise locations.

FIG. 29 illustrates an embodiment of a strip 500 with reliefs 502 on the inferior surface of the strips 300 opposite the bounded surface of the wedge dissectors 200, with additional relatively larger apertures 503 in between wedge dissectors 200 which can be configured to facilitate bonding of the strip 300 to the underlying balloon, which can be as disclosed, for example in PCT Pub. No. WO 2016/073490 published on May 12, 2016 and hereby incorporated by reference in its entirety. The apertures 503 can be relatively oval shaped, circular, or any other shape depending on the desired clinical result.

In some embodiments, the longitudinal axis of the strips are longitudinally oriented along the balloon and spaced apart from each other. In some embodiments, the strips do not completely cover the length of the balloon. For example, in one embodiment an 80 mm long balloon can have strips that measure 76.6 mm. While the length of the strip can be the same as the defined working balloon length, in some embodiments the length of the strip is shorter than the defined working balloon length to allow for balloon contraction that is typically observed when a balloon goes to rated burst pressure. The length of each strip can in some cases be no more than about 15%, 10%, 9%, 8%, 7%, 6%, 5%, 4%, 3%, 2%, or 1%, or between about 1% and about 7%, between about 1% and about 5%, or between about 1% and about 4% shorter than the overall working balloon length. In some embodiments, the working balloon length does not include the lengths of the cones.

In some embodiments, part of the strip, e.g., the base of the strip (e.g., the inferior most surface configured to be attached to the outer surface of the balloon) can be roughened to aid in adhesion.

Spikes (e.g., serrating elements or wedge dissectors) can be fabricated in many different manufacturing methods and in a large range of shapes. Regarding the manufacturing processes, the devices may be fabricated using one or more additive or subtractive processes. Additive processes such as high energy vapor deposition, for instance laser chemical vapor deposition, self-assembly techniques, polymer/metal 3D printing, selective laser sintering, powder printers, or other stereo lithographic are a few such options but other additive processes may be used. Alternatively, subtractive processes such as etching, CNC milling, laser cutting, water jet, or electrical discharge machining are just a few examples, but other subtractive processes may be used.

In some embodiments, a method of fabrication includes the use of a reel of martensitic stainless steel, such as for example a 300 or 400 series stainless steel with a hardness of as low as 48 and as high as 70 but more typically between about 52 to about 64 on the Rockwell C-scale (HRC) or a broader Mohs range between 4 and 7, although other materials can be used. The reel is either honed or precisely unhoned on one or both sides of one edge of the steel. In some embodiments, the steel is in the form of a thin reel strip between about 0.004" and about 0.020" thick or between about 0.005" to about 0.010" thick, and can be as wide as the processing system can handle. Sometimes this is as large or larger than 36".wide. The edge that is either honed or unhoned can be a single hone or two or more honed angles (as illustrated, for example in FIGS. 15-22). In some embodiments, when the angle of a honed edge is measured as the slope from the bounded end to the height of the unbounded end shown in FIG. 15, the angle of the honed edge can be, for example, greater than about 75 degrees. But when more than one honed angle is used, then the tip angle is can be less than, for example, about 75 degrees. In some embodiments, when a honed edge is measured as the angle between the strip-facing surface width $W_B$ to the radially outward facing width $W_U$ the unhoned edge has an angle of about, at least about, or an amount between 70, 75, 80, 85 degrees or greater as it moves toward the honed edge in a series of bevels. In addition to the honed edge, independent of the number of honed angles, in some embodiments a separate and additional edge is generated at the very tip of the unbound edge of the strips. When added, the additional tip edge height from the honed edge to the unbounded edge is often very short and typically has a much larger angle than the overall honed edge. Independent of the number of honed angles used, the unbounded tip width, $W_U$, can be described as the radius of the tip. The unbounded tip width, $W_U$ is the penetrating edge into the lesion, when the width is, in some cases, less than about 0.015" or 0.006", the surface area is minimized to have a less pronounced contact surface with the vessel enabling a reduced amount of energy requirement for penetration. When the tip is configured for penetration into harder surfaces such as calcium beds, in some cases either a more obtuse angle or the removal of the unbound tip at a greater distance from the unbounded surface can produce a wider tip edge (see FIG. 15, $W_U$). Not to be limited by theory, this wider edge distributes the load across the larger surface area generating a more effective resistance to tip deformation when the tip is pressured into rigid tissue surfaces. Once the reel is sharpened it is stamped to a desired length of blades. In some embodiments, the reel is hardened and then stamped to the desired length. Independent of when the stamping occurs, the blades can in some cases be passivated and hardened above, e.g., about HRC 45. but more typically in a range of from about HRC 58 to about HRC 62. The hardened blade can then be laser cut, stamped, EDM'ed or another precise metal shaping technology with spikes, serrating elements or wedge dissectors utilized. In some cases, the serrated elements are processed on the reel and then hardened and passivated. In some embodiments of strips where the tip is not a sharpened honed edge, the tip of the blade, that was produced during the reel sharpening step, is removed during the wedge dissector and strip manufacturing step. In some cases, the material removal (711) shown in FIG. 81 is design to start a distance, such as from about 0.0001" to about 0.003" below the honed edge (710), or from about 0.0001" to about 0.0005" is removed from the honed edge (710), producing a flat top ($W_U$) as illustrated in FIG. 15 The thinnest edge remaining (now a flat top in some cases) on the previously honed edge side is what will become the unbounded surface of the strip.

In some embodiments, disclosed are methods for attaching the strips. The methods can include any number of processing steps that provides effective strip retention, perpendicular orientation, and structural stability during the fabrication and use. In one embodiment the bounded surface is typically coated with a base coat of an appropriate material, such as a polymer, e.g., polyurethane through a controlled dipping process producing a uniform layer of polyurethane. The coating is dried and typically 3 or 4 strips are aligned with a strip alignment mechanism or jig and glued with a medical grade cyanoacrylate into place at predetermined orientations. The number of strips and the periodicity can vary from, for example, 1 to 8 and is typically associated with the same number of balloon folds but can be less than the number of folds and the periodicity can be non-sequential. Once the strips are bonded to the balloon surface, a single or series of multiple top coats or retention layers, are placed over the metal interrupted scoring elements or wedge dissectors to retain the strips and protect the balloon from the thin tips of the scoring elements. In some embodiments, these layers follow a similar process as the base or pre coat using a controlled dipping process producing one or more uniform layers of urethane or polyurethane. In some embodiments there is no base coat and only 1 top coat. Variations in the numbers of base coats and top coats can be between 0-4 on either base or top coats. Once the retention layer or layers are cured a layer of hydrophilic or other coating may be apply to decrease balloon friction and increase the balloons deliverability and retrievability. When incorporated, the outer slip coating as can increase the functionality of the balloon by reducing the force to insert and retract the device.

FIG. 30A illustrates a schematic cross-sectional view of a strip and wedge dissector operably attached to the outer surface of a balloon, according to some embodiments of the invention. A polymer layer, typically thin (e.g., from 0.0001" to 0.0009"), or about or less than about 0.001" in some embodiments, such as to limit increasing the balloon diameter profile, can be used as a base coat (layer 270A) covering the outer balloon surface. This base coat 270A offers an interface bonding layer for the interrupted scoring element to the balloon surface. This layer 270A can be made of the same or similar polymer chemistry as other layers while offering a chemical, mechanical, or electromagnetic bond to the balloon surface. This base coat layer 270A can be configured to and potentially capable of reducing the interface strain between the balloon outer surface and the bonding surface of the metal scoring element. Strain between the two surfaces is reduced by allowing an adhesive layer 270E and the scoring element 200 to be sandwiched within a polymer matrix independent and somewhat isolated from the balloon strain during balloon expansion and pressure. Although typical base coats 270A are polymers, e.g., urethane or polyurethane this layer can be a variety of other materials. In some embodiments, the coating could include silicone and hydrophilic coatings involving hydrogel polymers or the like, such as polymer networks of a vinyl polymer and an uncross linked hydrogel, for example. Polyethylene oxide (PEO) is an example of a hydrogel. An example of a vinyl polymer is neopentyl glycol diacrylate (NPG). The deposition of the layer can be done by single or a series of dips of a balloon or matrix of balloons into a polymer bath under controlled insertion and extraction conditions at controlled rates in both or in one direction. Alternately, layers can be spray coated or deposited using a variety of known processes including coating of monolayers through self-assembly using known and practiced self-assembly techniques, typically employing surface ionic charging.

Still referring to FIG. 30A, a bonding layer 270E between the metal scoring element, 200 and the basecoat 270A can typically be as thin as 0.0002" to 0.001", but more typically is between 0.0006 inch and 0.001 inch and can be as thick as 0.002" in some embodiments. In some embodiments, the bonding layer is designed to be thin enough such as to limit increasing the balloon diameter profile. The adhesive layer 270E can be a cyanoacrylate but can be made from other bonding materials, such as UV cure glue, that offer a chemical, mechanical, or electromagnetic bond between the basecoat 270A and the bonding surface of the metal scoring element. This layer 270E can be seen as the functional layer at joining the bonding surface of the metal scoring element to the balloon and sometimes is the only layer between the bonding surface of the metal scoring element and the outer balloon surface. This layer 270E can be one or more adhesive products. In one preferred embodiment the adhesive layer 270E is a single adhesive with the low viscosity allowing a wicking of the adhesive along the interface of the bonded surface of the metal scoring element and the base coat. In some embodiments, the adhesive material dries quickly, allowing successive layers to be applied on the top of the adhesive layer with minimal curing delay. In other methods of fabrication, a more viscous adhesive layer can be placed at both ends of the bottom of the strips or periodically between the bonding surface of the metal scoring element and the base layer allowing non-glued sections to be free or unbonded. In still another method more than one adhesive can be used. For instance, a more viscous adhesive can be used on either end of the bonding surface of the metal interrupted scoring elements and then followed by wicking adhesive on some or all of the unbonded sections. In some embodiments, one (e.g., a single layer) two, or more retention layers (two layers shown in FIG. 27) 270B, 270C can be present over the base layer 270A as well as the scoring element. A polymer retention layer can in some embodiments be similar to, and have dimensions as described above for the base layer with enough properties such that the base 270A and retention 270B and 270C layers produce an effective bond between the layers. In some cases, the retention layer(s) can be designed to offer a similar thickness as the base layer while other times it may be useful to have the retention layers slightly thicker than the base layer. Thicker base and/or retention layers can in some circumstances offer greater puncture resistance and increased durability of the balloon against potential puncturing from the metal interrupted scoring elements, any sharp edges from implants left in the body, or from sharp edges found in severely calcified disease vessels for example. In some embodiments, an outer slip layer 270D can also be present, above the retention layer(s) over the balloon and/or scoring elements. A variety of hydrophilic coatings are commercially available to reduce friction and offer increased navigation of balloons through tortuous and narrow anatomical features. In some embodiments, the balloon surface can be fully encased in a hydrophilic coating while in other embodiments the balloon can be coated after pleating or after pleating and crimping and therefore only surfaces that will typically be exposed during delivery are coated with the hydrophilic coat. Typical hydrophilic coats are a few microns thick and can be as thin as about 10 Angstroms in some embodiments.

In some embodiments, the adhesive can be applied separately to the balloon and to the strips and then both components are then bonded together. A template can be used to ensure proper positioning of the scoring elements along the surface of the balloon.

A retention polymer layer 270B, 270C can be typically similar to the base layer with enough properties such that the base and retention layers produce an effective bond between the layers. Sometimes the retention layer(s) can be designed to offer a similar thickness as the base layer while other times it may be useful to have the retention layers slightly thicker than the base layer, such as about or no more than about 20%, 15%, 10%, or 5% thicker in some cases. Thicker base and/or retention layers offer greater puncture resistance and increased durability of the balloon against potential puncturing from the metal interrupted scoring elements, any sharp edges from implants left in the body, or from sharp edges found in severely calcified disease vessels. In some embodiments with a plurality of retention layers 270B, 270C, the layers can be made of the same or differing materials.

In FIG. 30B, the addition of a surface functionalization is applied to the strip 200. The functionalization can be done in a large plasma chamber under vacuum conditions with hundreds of strips 200 placed within the plasma field. The deposited functionalized layer is typically very thin in the order of hundreds of angstroms. The use of surface enhancement or functionalization can produce an effective bonding surface.

The balloon can have any of the features of FIG. 30A. FIG. 30B illustrates a schematic cross-sectional view of a strip and wedge dissector operably attached to the outer surface of a balloon, according to some embodiments. A polymer layer can be used as a base coat (layer 270A) covering the outer balloon surface. A bonding layer 270E, such as glue, can be between the strip 200 and the basecoat 270A. In some embodiments, one (e.g., a single layer), two, three or more retention layers 270B, 270C can be present over the base layer 270A and the strip 200. The retention layer 270B can be a pre-fabricated coating bonding layer. The retention layer 270C can be a pre-fabricated coating. In some embodiments, an outer slip layer 270D can also be present, above the retention layer(s) over the balloon and/or the strip 200. The balloon in FIG. 30B can include a plasma layer 280.

The plasma cleaning can offer advantages to the bonding coefficient between two surfaces. Although plasma cleaning is very effective to improve adhesion under certain conditions, in some embodiments, cleaning the surface is not enough. The use of surface functionalization by coupling amino groups to the surface can offer additional benefits. To achieve an effectively functionalized surface for polymer adhesion to the metallic strip surface 200, plasma technology can be used for applying a preselected amino group. The plasma process has three active plasma steps, i.e., steps where intentional physical or chemical changes to the strip surface take place. The three active plasma steps are 1) cleaning, 2) activation, and 3) functionalization. The plasma process is designed to clean the substrate of the strip 200 (step 1) and populate the stainless steel substrate of the strip 200 with pendant vinyl groups (step 2 and 3) that will readily react with the UV cyanoacrylate adhesive used to bond the stainless steel strip to the bonding layer 270E, the pre-fabricated coating bonding layer 270B, the pre-fabricated coating 270C, and/or the outer slip layer 270D. The functionalization employs the coupling of an acrylic functional organosilane. The functionalization designated as silanization employs two steps, hydroxylation (step 2) which populates the substrate of the strip 200 with an atomically thin (less than 50 Angstroms) hydroxyl groups followed by silanization (step 3) with a thickness in the range of 100 to 500 Angstroms where the organo-silane couples to the pendant hydroxyl group via a condensation reaction. A low power plasma initiates the reaction at conditions much milder than can be accomplished thermally or via catalysis. Although other technologies are known to be able to deposit angstrom thin layers the use of plasma technology has shown effective and repeatable outcomes for purposes of functionalizing of the stainless steel strips 200.

The strip 200 can include a surface treatment applied to the surface of the strip. The surface treatment can include plasma treatment. The process can be completed within a chamber. The one or more strips 200 can be place within the chamber under vacuum. The chamber can be placed in a plasma field. The plasma can be deposited on the entire surface of the strip 200. The plasma can be deposited on one or more surfaces of the strip 200. The plasma can be deposited as a functionalized layer. The outer surface of the strips 200 can include a thin plasma layer. The layer can be 100 angstroms, 200 angstroms, 300 angstroms, 400 angstroms, 500 angstroms, 600 angstroms, 700 angstroms, 800 angstroms, 900 angstroms, or any range of two or more of the foregoing values. The plasma layer 280 can facilitate bonding to other layers. The plasma layer 280 can facilitate bonding between the strip 200 and the basecoat 270A. The plasma layer 280 can facilitate bonding between the strip 200 and the adhesive 270E. The plasma layer 280 can facilitate bonding between the strip 200 and the PFC bonding layer 270B. The plasma layer 280 can facilitate bonding between the strip 200 and the PFC 270C. The plasma layer 280 can be an enhanced bonding surface.

The plasma layer 280 can improve the bonding coefficient between two surfaces, such as the surface of the strip 200 and another layer. In some embodiments, the strip 200 undergoes plasma cleaning. The plasma cleaning can improve the surface of strip 200 to improve bonding. In some embodiments, plasma cleaning is used in combination with surface functionalization. The surface functionalization can include coupling amino groups to the surface. The plasma layer 280 can include one or more amino groups. The amino groups can facilitate adhesion between the metallic surface of the strip 200 and the additional polymer/adhesive layers. The amino groups can function as a bridge to improve adhesion between these different materials. The amino groups can function as a bridge between metallic and non-metallic layers. The plasma process can apply the amino groups. The amino groups can be preselected based on the layers to be bonded. The plasma layer 280 can include amino groups to facilitate adhesion between layers.

The process can include one or more steps. These steps can be considered active plasma steps. The process can include physical changes in the surface of the strip 200. The process can include chemical changes in the surface of the strip 200. The process can include cleaning. The plasma process can be designed to clean the surface of the strip 200. The process can clean the entire outer surface of the strip 200. The cleaning can be a prerequisite for subsequent coating of the surface of the strip 200. The cleaning can be a surface treatment. The cleaning can remove impurities and/or contaminants from the surface of the strip 200.

The process can include activation. Plasma activation can improve surface adhesion properties of the strip 200. The process can populate the surface of the strip 200 with amino acids. In some embodiments, the strip 200 is populated with pendant vinyl groups. The amino acids, such as pendant vinyl groups, are configured to react with adhesive. The amino acids, such as pendant vinyl groups, are configured to react with UV cyanoacrylate adhesive. The UV cyanoacrylate adhesive is applied to one or more layers to bond the strip 200 to the layers. The UV cyanoacrylate adhesive can be used to bond the strip 200 to the basecoat 270A. The adhesive 270E can be UV cyanoacrylate adhesive. The UV cyanoacrylate adhesive can be used to bond the strip 200 to the PFC 270C. The PFC bonding layer 270B can be UV cyanoacrylate adhesive.

The process can include functionalization. Plasma functionalization can improve surface adhesion properties of the strip 200. The process can couple an acrylic functional organosilane. This can be a coupling agent for light cured composites. The process can include hydroxylation. Hydroxylation can populate the surface of the strip 200 with hydroxyl groups. The hydroxyl groups can be less than 50 angstroms, for instance, the layer can be 5 angstroms, 10 angstroms, 15 angstroms, 20 angstroms, 25 angstroms, 30 angstroms, 35 angstroms, 40 angstroms, 45 angstroms, 50 angstroms, or any range of two or more of the foregoing values. The process can include silanization. The silanization can include a layer with a thickness in the range of 100 to 500 Angstroms, for instance 100 angstroms, 200 angstroms, 300 angstroms, 400 angstroms, 500 angstroms, or any range of two or more of the foregoing values. The organo-silane couples to the pendant hydroxyl group via a condensation reaction. The process can result in depositing thin layers of material on the surface of the strip 200. The process can result in uniform cleaning. The process can result in uniform distribution. The process can result in uniform surface functionalization. The process can result in a surface of the strip 200 suitable to bond to other layers. The process can result more effective adhesion between layers. The process can result in effective and repeatable bonding between layers.

FIG. 30B illustrates a modified layer stack of the strip retention. Many of the layers described in FIG. 30A can be included. FIG. 30B illustrates the pre-fabricated coating 270C, the PFC bonding layer 270B, the strip 200, the adhesive layer 270E and the basecoat 270A. This figure also illustrates the plasma layer 280 that covers the entire strip 200. The deposition of a functional siloxane is coupled to the substrate of the strip 200 via condensation with the hydroxyl groups which is primarily dependent on the Nickel, Titanium and Chromium content of the stainless steel of the strip 200. One example (dependent on the type of glue used) of the chemical equation for this process is:

$$\text{Stainless steel-OH} \rightarrow \dot{e} + (CH_3O)_3Si—(CH_2)_3—C(=O)CH=CH_2 \rightarrow S/S—Si—(CH_2)_3—C(=O)C(CH_3)H=CH_2 + CH_3OH$$

A variety of hydrophilic coatings are commercially available to reduce friction and offer increased navigation of balloons through tortuous and narrow anatomical features. In addition, a variety of commercially available methods for coating balloons are available which include dipping, spraying, and other forms of deposition. In some embodiments, layer 270D of FIG. 30A can be a hydrophilic slip layer. In one preferred embodiment the balloon surface can be fully incased in a hydrophilic coating. In other embodiments the balloon can be coated after pleating or after pleating and crimping and, in these embodiments only, the surfaces that will typically be exposed during delivery are coated via one of the deposition methods above. The surface might only be partially coated with the hydrophilic coating covering only the surfaces exposed after the balloon is pleated and folded. In some embodiments, the typical hydrophilic coats are less than a few hundred microns thick and can be as thin as, for example 100 Angstroms and can incorporate more than a single coat.

The height of the wedge dissectors, strips, and layers of the outer balloon encapsulation process can be viewed as a cage for use with an expandable member such as a medical balloon, such as an angioplasty balloon or as part of a medical procedure involving a medical balloon or other expandable member. In order to effectively perform key hole or catheter based surgery, the ability to fold the balloon to a fraction of the diameter of the intended inflation diameter can be of value. Therefore the balloon and in some cases the cage are typically folded where the profile of the folded balloon can be effectively used. In one such embodiment the cage is folded in a manner that offers orientation of the spikes such as to avoid puncturing the balloon or scraping the intima of the lumen during delivery and removal, as illustrated in FIG. 28. FIG. 28 illustrates the balloon 1000 with a plurality of pleats 1002, and strips 300 and associated wedge dissectors 200 in between the pleats, thus allowing a single strip 300 with its plurality of wedge dissectors 200 to lie between two pleats 1002. A pleating tool was designed that offers effective orientation of the spikes and splines. The pleating tool can have a series of pleating wedges where each wedge offers the ability of the crimp the balloon between the wedges as the wedge elements are closed down onto the balloon. Due to the bulk of the spline elements and desire to minimize contact, and potential damage to the wedge heads, the wedges are designed with a series of pockets that run the length of the wedge heads. The pockets in the wedge heads offer the ability of the spline features to rest within said pockets and limits the spline to wedge contact. The pockets can also offer the ability to aid in orientation of the spline and spike features such that the orientation of the features limits contact with the balloon, such as over folding, and limits orientation, such as perpendicular orientation to the balloon, that might produce scraping of the intima of the vessel during transport of the device on said balloon. One such orientation of the spikes might be at a tangential orientation, an apparent lying down, to the balloon surface as illustrated in FIG. 31.

In some embodiments, disclosed herein are systems and methods that produces linear incision through serration preparation in tissue. It is well understood in cardiovascular disease that applying interventional methods to increase lumen size in occluded lesions aids in blood flow and increases the likelihood that the vessel will remain patent longer than when minimal lumen gain is achieved post-procedurally. Methods for increasing lumen diameter have a range of options. On the basic end, Plain Old Balloon Angioplasty (POBA) or the use of percutaneous transluminal angioplasty (PTA) or similar approaches are often used to open the diseased lesion. In addition, more specialty devices such as the cutting balloon, AngioSculpt (Spectranetics), Chocolate (Cordis), and others that provide a mechanism to aid or control the balloon energy. Often products in this general category provide external structures on the surface of the balloon (either attached or not) that are designed to contact the wall first and be pressed into the wall surface with the balloon pressure. The theory is that the structures on the outer surface produce a localized increase in the force on the lumen which in turn is intended to aid in allowing the surface to be incised and along with the balloon expansion enables arterial expansion. While these designs offer some advantages over POBA or plain balloons alone, they all have limitations on their effectiveness and their ability to facilitate lumen expansion especially in the complexity of diseases they might be used in.

An alternative to external structures that produce lines of compression along the intima is producing serrated lines longitudinally along the lumen. The effectiveness of serration to aid in separation of materials (such as paper, stamps, cardboard, granite stone, marble, etc.) is well understood and since disease morphology often involves both soft and hard materials, serration technology can be advantageous to effectively aid in vessel expansion. There are several ways to produce serrations, including those described in U.S. Pat. No. 9,480,826 issued on Nov. 1, 2016, PCT Pub. No. WO 2015/187872 published on Dec. 10, 2015, PCT Pub. No. WO 2016/073511 published on May 12, 2016, PCT Pub. No. WO 2016/073490 published on May 12, 2016, and U.S. patent application Ser. No. 15/268,407 filed on Sep. 16, 2016, each of which is hereby incorporated by reference in its entirety. For example, a series of serration elements can offer features configured to produce serrations or linear serrated scoring at the deployment site.

In some embodiments, the lumen gain from serration angioplasty is better than balloon alone. The improvement of lumen gain has been recorded (FIG. 78) with 49% improvement of final stenosis with serration balloon compared to plain balloon alone. The increased lumen diameter improves flow (FIGS. 75 and 76). Applying Poiseuille's Law to vascular blood flow, the volume flow rate can be calculated. The improvements in the average flow rate ratio can be compared, which is defined as: (radius post intervention/radius pre intervention) to the $4^{th}$ power. The data set comparing plain balloon to serration balloon along with a set of power-fitting curves is shown in FIG. 75. FIG. 75 illustrates that serration balloon angioplasty is able to achieve a greater than two times the average flow rate ratio.

In some embodiments, the inclusion of serration technology can offer advantages to balloons, not only for the preparation of tissue prior to or concurrent with the use of drug coated balloons, but also as a single step drug delivery mechanism. The inclusion of drug coatings on, around, and/or within reservoirs or regions neighboring serration features on a balloon can facilitate the serrations of a serrated balloon to delivery of the desired drug or other therapeutic agent(s) deeper into the desired target location, such as for example the intima, media, or adventitial surface of a luminal wall.

Typically drug coated balloons are coated on their surface. When the non-serrated drug coated balloon expands it contacts the intima and begins to elude the drug residing on its surface which inhibits the ability of the surface of the balloon to provide drug delivery into the deep tissue spaces. The following disclosure includes, in some embodiments, components and methods to use the components that can effectively deliver drug into tissue with the use of serrations independent of design elements, including but not limited to any number of the following:

1) a surface capable of radial expansion (e.g., a compliant or semi-compliant balloon);
2) a series of drug coated strips including a plurality of wedge dissectors spaced apart along a surface of each strip (in some embodiments, spaces between each wedge dissector are not as long as the length of the wedge dissectors themselves, and/or the height of wedge dissectors are a small fraction of the balloon diameter);
3) the protrusions can be in some cases be an A-framed structure angled from their base to their tip and where long wells or spaces within the A-framed structure becomes a drug reservoir region;
4) the side walls of the wedge dissectors on the A-frame can include a series of holes and/or microchannels to allow for drug migration to the interrupted surface directly beneath the serrations;

5) a single or series of wells where drugs, stem cells, or other therapeutics can be placed within each A-frame structure of the strips;

6a) the wells can include either a depression into the balloon surface, or a separate catheter-like channel along the balloon body, that may include finely defined holes (made through laser drilling or other precision method) offering a greater volume of therapeutics to reside;

6a.1) in some cases the catheter channels are incorporated into the inner diameter of the catheter shaft and can run the entire length of the shaft back to the hub, allowing for drug delivery from a port on the hub through channels to the balloon surface;

6b) during balloon inflation the outward balloon pressure can either a) apply a force on the depressed wells thereby displacing the volume where the therapeutics reside or b) expand the finely defined holes and allow for drug to pass through the holes; this in turn displaces the therapeutics outwardly and encourage the therapeutics to be released into the disrupted tissue;

6c) typically upon balloon delivery the wells, strips, elevating elements and the A-frames are captured within folds of the balloon minimizing therapeutic from leaching systemically into tissue;

7) upon expansion of the balloon, the serrated A-frames separate the intima tissue layer exposing the media, and in some cases open the media layer and the adventitia layer allowing for the therapeutic agents, captured within the balloon folds, to be expelled primarily deep into the vessel wall; and/or exposed;

8) allowing therapeutic agents and drugs to elute from the surface of the serrated drug eluting balloon into the incisions and micro fissures generated by the serrated A-frames, through the intima and into the media or adventitia.

The invention relates, in some embodiments, to the use of serration technology in conjunction with endovascular procedures, where the design of the serration technologies includes a novel drug delivery design in combination with: selectively placed drugs on the balloon, with wells of drug contained near or beneath the serrated elements, or with pathways where drugs can travel from a more proximal section of the delivery system to the balloon surface and out into the tissue through access created by the serrated elements.

In some embodiments serration elements can be combined with a multilayer, such as a bi-layer or tri-layer of polymer previously disclosed, for example, in U.S. patent application Ser. No. 15/268,407, where the space between the base polymer and the top layer or layers can be used as a drug reservoir space. In some embodiments the bottom polymer is removed and the space between the surface of the balloon and the top layer or layers can be used as the drug reservoir space. Depositing the drug in this space can be facilitated, for example, by a spray coating, dipping, or utilizing nanotechnology self-assembly techniques where the drug becomes encapsulated between a base and top layers of polymers. The drug reservoir layer is not, in some embodiments, exposed to the environment due to its encapsulation of the top layer(s) thereby limiting the exposure to the body or to the intima layers that are not perforated. The inclusion of drug coating on, around, and/or within the encapsulated layers facilitates the serrations of a serrated balloon to delivery drug primarily into the sub-intima.

FIG. 32 illustrates an embodiment of a modified cutting balloon to produce serrations. In some embodiments, serration or serration-like advantageous effects could be achieved by modifying a cutting balloon catheter as described, for example, in U.S. Pub. No. 2006/0184191 to O'Brien, which is hereby incorporated by reference in its entirety. The balloon catheter can include a catheter shaft having a balloon coupled thereto. One or more cutting members or blades may be coupled to the balloon. The balloon may include one or more discrete points or areas of flexibility 3200 to enhance flexibility of the cutting balloon catheter. A break in the one or more cutting members may be aligned with the one or more discrete points of flexibility in the balloon. In some embodiments, flexpoints can be located every 5 mm on 10 mm and 15 mm lengths (6 mm length=0, 10 mm length=1, 15 mm length=2). Atherotomes with flexpoints can in some cases assist in tracking to lesions that may have been previously out of reach.

FIG. 33 shows an illustration of a modified cutting balloon where flexibility is further enhanced and the cutting is either completely or partially replaced with a serrated blade 3350 pattern. As shown in FIG. 32, cutting members 3320 may vary in number, position, and arrangement about balloon 3316. For example, catheter 3310 may include one, two, three, four, five, six, or more cutting members 3320 that are disposed at any position along balloon 3316 and in a regular, irregular, or any other suitable pattern. The pattern can include a generally helical orientation of the cutting members 3320. Catheter 3310 may include a plurality of cutting members 3320 placed equidistantly about balloon 3316 extending generally longitudinally. In general, cutting members 3320 may be configured to provide variable flexibility or otherwise vary the flexibility of catheter 3310. Increasing the flexibility of cutting members 3320, balloon 3316, and/or catheter 3310 may be desirable, for example, because it may improve the tracking ability and general deliverability of catheter 3310 through the often tortuous anatomy. Additionally, increasing the flexibility may allow catheter 3310 to be navigable to a larger number of intravascular locations, including some that may not be readily reachable by other, less flexible, cutting balloon catheters. In general, the enhanced flexibility may be the result of a structural feature of cutting members 3320, a structural modification to cutting members 3320, and/or a structural feature of the cutting balloon 3316. For example, cutting members 3320 may include a first section 3344*a*, a second section 3344*b*, and a gap or break 3346 disposed between first section 3344*a* and second section 3344*b*. Break 3346 may be configured to provide a region of flexibility such as a space between first section 3344*a* and second section 3344*b*. In some embodiments, break 3346 may be defined by a downward deflection or slot that is formed in the cutting surface of cutting member 3320. Alternatively, break 3346 may not be a physical gap between first section 3344*a* and second section 3344*b*, but rather break 3346 may be a region of cutting member 3320 having a reduced wall thickness or may comprise a material having an increased flexibility relative to the material of first and second sections 3344*a*, 3344*b*. Break 3346 also may comprise an exogenous connector that is connected to both first section 3344*a* and second section 3344*b* in order to bridge sections 3344*a*, 3344*b*. Separation of sections 3344*a*, 3344*b* can increase the flexibility of cutting member 3320 and/or the overall flexibility of catheter 3310.

In some embodiments, a series of cutting elements (or micro atherotomes) as described above can be placed linearly along the surface of the balloon spaced apart by a gap in the upper surface of the blade. In the above schematic illustration, the gap length is approximately one tenth of the length of an individual blade length. In some embodiments, the gap length to blade length ratio can be, for example, between about 1/15 and about 1/1, between about 1/10 and about 1/1, between about 1/5 and about 1/1, between about 1/5 and about 1/2, or about 1/15, 1/14, 1/13, 1/12, 1/11, 1/10, 1/9, 1/8, 1/7, 1/6, 1/5, 1/4, 1/3, 1/2, 1/1, 1/1.5, 2/1, or ranges including any two of the aforementioned values.

A modified cutting member with dimensions that provide for a more flexible, more stable design and that can serrate or approximates serrations in the tissue are described herein. A modified cutting member embodiment can offer, for example, about or greater than about 8, 9, 10, 11, 12, 13, 14, 15, 20, or more degrees lateral flexion with or without sections where the cutting surface is less or not serrated. Some embodiments can include a series of cutting members, either in tandem or with periods of serrated features as described elsewhere herein (for instance elevated elements) between or on the ends of the cutting members. The cutting members (X) when divided into multiple discrete sections can have a length, for example, in the range of 0.01" to about 0.10" in separated by spaces (Y) of, for example, about 0.01" to about 0.08". In some designs the length of the cutting members (X) are divided into multiple discrete sections separated by spaces (Y) of 1:2, 1:2.5, 1:3, 1:3.5, or 1:4, where the space between the cutting members is larger than the length of the cutting members. The entire cutting blade may have discrete sections at any one or any number of locations along the blade. Once pressure is applied by the balloon into tissue the resulting tissue disruption may appear to be a series of dots and dashes or any combination of dots and dashes, produced by the bonded modified cutting members, piercing the tissue only in narrow regions where the discrete cutting members (X) are located. The effect of this discrete localized penetration is that the balloon with modified cutting blades produces a new angioplasty effect, referred to as serratoplasty. For instance, one such serratoplasty design might be small raised features, able to produce dot like effects (or serration like features) in tissue, on the ends of the cutting blade, then longer raised features, able to produce dashes in the center portion of the blade. Other serratoplasty designs might mix small and longer raised features in alternating patterns, or a series of dots spaced by one or more dashes with a repeated pattern or a non-repeated pattern. The embodiment might have 1, 3, 4, 5, 6, or 8 members, e.g., blades (or a combination of these number of members, e.g., blades) on the outside of a balloon with the blade being typically less than the balloon body length. This device, configured for serratoplasty or serration angioplasty, can be used as a standalone angioplasty balloon or as a preparation device prior to a follow-on therapy. Follow-on therapies would include but are not limited to: stenting, placing a drug eluting stent, performing atherectomy, high pressure ballooning or drug coated balloon treatment or other endovascular procedures requiring effective luminal preparation. Whether or not the device is used as a preparation device for follow-on therapy or a stand-alone therapy, through the use of modified atherotomes (serrated features) as disclosed herein, the device effectively manages plaque or calcium by weakening the bonds, initiating cellular or structural disassociation and minimizing cellular or structural compression, typically generated by angioplasty alone. Serratoplasty allows for the diseased lumen to be safely expanded and accurately dilated and stretched, using low pressure, to a desired diameter without creating numerous and substantial dissections and elevated flaps (FIG. 80). The serrations can enable the plaque to be dilated more evenly and smoothly and avoid forming random cracks that may lead to dissection and residual stenosis. The plaque, after it has been treated or pre-treated with serration, in some cases, may also be dilated with lower pressure than that which is used in standard balloon angioplasty. The lower intra-balloon pressure (e.g., less than, equal to or combinations of 4, 3.5, 3, 2.5, 2, 1, 0.5 atm) applied by the balloon, bonded with modified cutting members, causes less disruption of the plaque, fewer dissections, and less injury to the artery wall. This "low pressure" or "minimal injury" serratoplasty is less likely to cause the biological reaction that often follows balloon angioplasty with neointimal hyperplasia or smooth muscle cell replication. In addition, serration can permit the plaque to expand with less fracturing or disruption of the plaque during balloon angioplasty. By preparing the plaque using a balloon with serrations (capable of serrating the inside of the vessel), the number and severity of dissections can be reduced. This decreases the need for stent placement to be used to treat dissection or residual stenosis after balloon angioplasty with serration.

As described herein, the serrated vessel opens with lower pressure and is capable of retaining the affective lumen gain over time. Observations have been made post serration angioplasty at 15 minutes and higher with the appearance of the lumen gain being retained. The concept of vessel recoil or vessel lumen decreasing after being stretched open can occur and there is a need for designs capable of overcoming the vessels tendency to recoil. With serration angioplasty, it has been observed clinically that minimal to no recoil has been recorded. To assess for recoil events, physicians have collected angiographic images after serration angioplasty and again 15 minutes after serration angioplasty. The images have been assessed for changes in vessel diameter or recoil and the results were that minimal to no recoil was detected. These observations are not expected and have encouraged further experimental designs to investigate serration angioplasty embodiments designed for the purpose of reduction in recoil. This reduction in recoil phenomenon is seen in both the arterial system and the venous system, especially in diseases found in anastomosis or near arterial-venous anastomosis. The serration balloon described herein has shown effective outcomes for reducing and in some cases eliminating recoil in the arterial system. It has also been observed that serration angioplasty of balloons smaller than the reference vessel diameter can be used to pre-treat the diseased region.

This pre-treatment can provide equally effective serration angioplasty treatment while in some cases, including a subsequent balloon angioplasty to be performed, at low balloon pressures of about 4 atmospheres or less due to preparation of the plaque with perforations, so as to avoid injury to the arterial wall or its sub-intimal tissues. By performing plaque preparation and then low-pressure angioplasty, there is less likelihood of a dissection occurring that generates deep tissue tearing while still potentially exposing the media layer of the artery. Exposure of deep tissue from within the artery wall can in some cases stimulate thrombus formation by collagen exposure and also stimulates smooth muscle cell growth which later causes neointimal hyperplastic occlusion of the artery. This decrease in number and also decrease in severity of dissection can in some cases be an advantageous differentiating factor in comparison to conventional cutting or scoring devices and other forms of plaque disruption including but not limited to angioplasty delivering ultrasonic energy.

Strips Blown into Balloon Designs

In some embodiments, the use of embedding the strip into the balloon in place of the top coats (as described herein as well as, for example, U.S. Pub. No. 2017/0333686 to Schneider et al. and U.S. Pub. No. 2017/0080192 to Giasolli et al., both of which are hereby incorporated by reference in their entireties), or in place of a pre-fabricated covering or top balloon coats (as described herein as well as, for example, and U.S. Pub. No. 2020/0155815 A1 to Giasolli et al., hereby incorporated by reference in its entirety) can be preferable. The use of an embedded strip can provide a series of additional values such as, for example, ease in manufacturing, precise control of the thickness, increase retention of the strips, uniformity of the outer layer, the ability to crimp the balloon to a lower profile, and/or the ability to use a wider range of materials for use as the balloon and for features that protect the balloon. The range of materials where the strips can be embedded can include nearly any material that is both extrudable and can be blown into a balloon mold. In some embodiments, the embedding balloon might be made of more than a single material or more than a single layer. When more than a single layer is used the top layer is typically made from a more stretchable or pliable material than the base balloon. Since the functional characteristics of the embedding balloon are different from a balloon in balloon design the materials and processes used to build it are typically different. In the case of the outer surface of the embedding balloon the main requirement would be retention of the elevating elements (e.g., wedge dissectors/serrations for example) while allowing the tips to be raised above the base balloon. Independent of the materials and processes used to build the embedding balloon, the dimension of the balloon can be the same or different than that of a regular base balloon. Due to the Laplace formula described above, the tangential stress on the balloon surface is directly proportional to the radius of the balloon and the pressure inside the balloon. Therefore, the material of choice and the dimensions of the embedding balloon may need to vary at different diameters of balloons. Therefore, a 2.5 mm diameter balloon may need a more stretchable material as a 5.0 mm diameter balloon since the tension on the surface of the balloon are 12 as high at the same pressure.

Interface Bonding Between Pre-Fabricated Covering and Base Balloon.

The spacing between the elevated elements or the top surface of the base strip can be thought of as a stretchable membrane that retains the strip and stabilizes the elevated elements to the balloon surface. In some embodiments this space between the elevated elements might be bonded to the base balloon and the strip. In other embodiments the space may not be bonded to the base balloon allowing the pre-fabricated balloon to float free in the strip section while both balloons are selectively bonded elsewhere. In the embodiment where the strip region is not selectively bonded, the inner balloon can in effect fall away during the deflation event. As the system deflates, the outer balloon deflates at slightly different rate than the inner balloon since the balloon system is not completed bonded into a single unit. Due to the variation in deflation rates a regional void between the balloons is generated. The space produced by the regional void enables the serrated strip to retract into the space. As such, the elevated elements of the strip body or recessed the height or profile of the elevating elements that lies above the outer balloon is minimized and in some cases all of the elevating elements are fully recessed into the space between the balloons. Such embodiments can be advantageous to, for example, reduce the risk of the serrations catching on an undesired portion of the anatomy, such as a vessel or bifurcation other than the target treatment location, during insertion or removal of the device for example. However, in some embodiments the pre-fabricated covering or outer balloon is bonded to the base balloon into a single unit.

As illustrated in FIG. 34, in some embodiments, a balloon with serrations bonded to the surface is inflated inside the pre-fabricated covering. FIG. 34 illustrates schematically an embodiment of a method for producing a balloon-in-balloon design. As shown in panel 1, the base balloon 5100 is provided. In some embodiments, the base balloon 5100 can be a Plain Old Balloon Angioplasty (POBA) balloon. The base balloon 5100 provides the desired support for the vessel. The base balloon 5100 provides the desired support for the serrations. The base balloon 5100 can have any characteristics to achieve the methods described herein. The base balloon 5100 can accommodate the pressures described herein. The base balloon 5100 can expand to the diameters described herein. The base balloon 5100 can be disposed typically on a short catheter. The base balloon 5100 can be located at the distal end of the catheter. The base balloon 5100 can be located at any point along the length of the catheter. The base balloon 5100 can be used alone. The base balloon 5100 can be used with only a single base coat. The base balloon 5100 can be used with multiple base coats, in other cases. The base balloon 5100 can comprise any material described herein. The base balloon 5100 can be compliant. The base balloon 5100 can be non-compliant. The base balloon 5100 can be made of polyester or nylon. The base balloon can be designed to expand to a specific diameter. The base balloon can be designed to handle over-inflation diameters without radial expansion. The base balloon 5100 can be semi-compliant. The base balloon 5100 can be made of Pebax or higher-durometer polyurethanes. The base balloon 5100 can be inflated to various diameters based on pressure. The base balloon 5100 can conform to the lumen size. The base balloon 5100 can be elastomeric. The base balloon 5100 can be made of polyurethane, nylon, polyethylene, polyolefin copolymer, polyethylene terephthalate, or silicon, or any combination of materials. The base balloon 5100 can be inflated by an inflation medium that fills a volume.

As shown in panel 2, the strips with wedge dissectors 5102 can be attached to the base balloon 5100. The strips with wedge dissectors 5102 can be attached to the base balloon 5100 can be attached with adhesive along a base of the strip 5102. The strips with wedge dissectors 5102 can be applied longitudinally to the base balloon 5100. The strips with wedge dissectors 5102 can be applied to the outer surface of the base balloon 5100. The strips with wedge dissectors 5102 can be applied as described for example elsewhere herein to create a serrated balloon. In the illustrated embodiment, four strips with wedge dissectors 5102 are applied to the base balloon 5100. The serrated balloon can include any number of strips with wedge dissectors 5102 include one, two, three, four, five, six, seven, eight, or any range of two or more of the foregoing values. The strips with wedge dissectors 5102 can be equally spaced around the circumference of the base balloon 5100. The strips with wedge dissectors 5102 can be unequally spaced around the circumference of the base balloon 5100. Adjacent strips can be separated by 30 degrees, 45 degrees, 60 degrees, 75 degrees, 90 degrees, 105 degrees, 120 degrees, 135 degrees, 150 degrees, 165 degrees, 180 degrees, or any range of two or more of the foregoing values.

As shown in panel 3, the base balloon 5100 with attached strips with wedge dissectors 5102 can then be pleated. The single strip with wedge dissectors 5102 can lie between the surface of the base balloon 5100 and the pleat. The strips with wedge dissectors 5102 can be in the tangential orientation as described herein. The tangential orientation allows the strips 5102 to lie against a surface of the base balloon 5100. The tangential orientation allows the strips 5102 to have a low profile assembly configuration. The wedge dissectors 5102 can be fully covered by the pleats. The wedge dissectors 5102 can be at least partially covered by the pleats. The balloon 5100 can include one or more pleats, for example one pleat, two pleats, three pleats, four pleats, five pleats, six pleats, or any range of two of the foregoing values. The number of pleats can correspond to the number of strips with wedge dissectors 5102.

Once pleated, an adhesive is applied to the outer surface of the pleated base balloon 5100. The adhesive be a series of glue lines that can be applied to the pleated regions on the balloon surface. For balloons with three pleats, three lines of glue can be applied. For balloons with four pleats, four lines of glue can be applied. The same method of applying glue to all pleats would apply for any number of pleats. In some methods, glue lines are applied to all pleats. In an alternate method, the adhesive may be sprayed on or applied through other means. The volume of glue is typically associated with amount of surface area of the inflated balloon. For larger diameter balloons or longer length balloons, a higher volume of glue is applied. The final volume of glue is applied that offers an effective bonding of the inner base balloon to the outer prefabricated covering, as described herein. In some methods, the adhesive is only applied to the outer surface of the pleated base balloon 5100 and the adhesive is not applied to the strips with wedge dissectors 5102. The strips with wedge dissectors 5102 can be covered, or at least partially covered by the pleats while the adhesive is applied. The adhesive can be circumferentially applied, for instance if the strips with wedge dissectors 5102 are fully covered by the pleats. The adhesive can be longitudinally applied if the strips with wedge dissectors 5102 are only partially covered by the pleats.

As shown in panel 4, the pleated balloon 5100 with the applied adhesive and attached strips with wedge dissectors 5102 can then be inserted into a prefabricated covering 5104. The adhesive can function as a lubricant, thereby facilitating the sliding. The base balloon 5100 can be centered within the prefabricated covering 5104. The prefabricated covering 5104 can be a second balloon. The prefabricated covering 5104 can be any outer walled structure. The prefabricated covering 5104 can be any covering. The prefabricated covering 5104 can does not include any serrations/wedge dissectors on its outer surface. The prefabricated covering 5104 can comprise any material described herein. The prefabricated covering 5104 can be a Plain Old Balloon Angioplasty (POBA) balloon. The prefabricated covering 5104 and the base balloon 5100 can comprise the same material. The prefabricated covering 5104 and the base balloon 5100 can comprise the different material. The prefabricated covering 5104 and the base balloon 5100 can comprise the same or similar dimensions. The prefabricated covering 5104 and the base balloon 5100 can comprise different dimensions. The prefabricated covering 5104 can be slightly larger in diameter and/or length than the base balloon 5100. The pleated balloon 5100 can have a low profile assembly configuration for insertion into the prefabricated covering 5104.

As shown in panel 5, the inner serrated base balloon 5100 can then be inflated. The strips with wedge dissectors 5102 can rotate from a tangential orientation under the pleat of the base balloon 5100 to being uncovered by the base balloon 5100 and orienting perpendicularly within the prefabricated covering 5104. The expansion of the base balloon 5100 can cause the strips with wedge dissectors 5102 to turn from a generally tangential orientation to a generally perpendicular orientation. During expansion of the base balloon 5100, the strips with wedge dissectors 5102 begin to rotate within the prefabricated covering 5104. The base balloon 5100 can form lobes. The lobes of the base balloon 5100 can uncover the strips with wedge dissectors 5102 upon expansion of the lobes. The lobes of the base balloon 5100 can expand into contact with the prefabricated covering 5104. The base balloon 5100 can inflate until the lobes rest against the prefabricated covering 5104. The direction that the strips with wedge dissectors 5102 rotates upon inflation can be defined by the orientation of how the base balloon 5100 is pleated. The lobes of the base balloon 5100 can facilitate rotation of the strips with wedge dissectors 5102. The lobes of the base balloon 5100 can apply a torque to the sloped surfaces of the wedge dissectors 5102. The controlled expansion of the lobes of the base balloon 5100, in relation to the shaped side walls and rigidity of the strips 5102, can cause reliable rotation of the strips 5102 to a more perpendicular orientation. The base balloon 5100 can be inflated to high pressures within the prefabricated covering 5104. The base balloon 5100 can be inflated to 4 atm, at least 4 atm, 4.5 atm, up to 4.5 atm, at least 4.5 atm, not more than 4.5 atm, 5 atm, up to 5 atm, at least 5 atm, not more than 5 atm, 5.5 atm, up to 5.5 atm, at least 5.5 atm, not more than 5.5 atm, 6 atm, up to 6 atm, at least 6 atm, not more than 6 atm, 7 atm, up to 7 atm, at least 7 atm, not more than 7 atm, 8 atm, up to 8 atm, at least 8 atm, not more than 8 atm, 9 atm, up to 9 atm, at least 9 atm, not more than 9 atm, 10 atm, up to 10 atm, at least 10 atm, not more than 10 atm, 11 atm, up to 11 atm, at least 11 atm, not more than 11 atm, 12 atm, up to 12 atm, at least 12 atm, not more than 12 atm, between 4 atm and 6 atm, or any range of two of the foregoing values.

As the inner base balloon 5100 with strips 5102 is inflated, the tips of the wedge dissectors can indent the inner diameter of the prefabricated covering 5104. In many cases, the tips of the wedge dissectors do not poke through the prefabricated covering 5104. The tips of the wedge dissectors can be unhoned, as described herein. The design of the unhoned edge of the tips of the wedge dissectors create a blunt or butting force against the pre-fabricated covering 5104. In contrast, honed or sharp edge would poke through the prefabricated covering 5104 upon expansion of the base balloon 5100 and contact with the prefabricated covering 5104. Without a honed or sharp edge, the pre-fabricated covering stretches under the outward force exerted by the inflated base balloon 5100 with the strips 5102. The unhoned surface of the wedge dissectors causes the prefabricated covering 5104 to stretch. The unhoned surface of the wedge dissector does not pierce the prefabricated covering 5104, in some methods.

In some methods, the prefabricated covering 5104 can be altered near the wedge dissectors of the strips 5102. The prefabricated covering 5104 can be altered while the base balloon 5100 is inflated. The prefabricated covering 5104 can be altered when the strips 5102 are in contact with the prefabricated covering 5104. The method can include the use of an opposing mechanical force to weaken the prefabricated covering 5104. The method can include the use of one or more heating sources to weaken the prefabricated covering 5104. The heat source can be a heating iron. The method can include the use of an electric discharge to weaken the prefabricated covering 5104. The method can include the use of any other delivery system to weaken the prefabricated covering 5104. The method can include weakening the prefabricated covering 5104 at the areas where the tips of the strips 5102 are pushing outward on the prefabricated covering 5104. In some methods, a heating iron or other heat source is used. In some methods, a heat higher than the transition temperature of the prefabricated covering 5104 is applied to the tips of the strips 5102. The heat can be applied to the prefabricated covering 5104 near the strips 5102. The heat can be along the length of the strips 5102. The heat can be applied in the vicinity of the strips. The heat can weak the prefabricated covering 5104 near the strips 5102.

As the base balloon 5100 expands and contacts the inner surface of the prefabricated covering 5104, the adhesive that was applied in the pleats is uniformly distributed. The adhesive can be applied to the outer surface of the pleats of the base balloon 5100. The pleats can expand under pressure to form the lobes. The lobes can press against the inner surface of the prefabricated covering 5104. The expansion of the base balloon 5100 can uniformly distribute the adhesive between the base balloon 5100 and the prefabricated covering 5104. In some embodiments, the adhesive is uniformly distributed along the entire inner surface of the prefabricated covering 5104. In some embodiments, the adhesive extends between the tips and the prefabricated covering 5104.

The base balloon 5100 can include one or more base coats. The base coat can be any material described herein including polyurethane. The adhesive can spread out within the inner space between the base balloon 5100 and the prefabricated covering 5104. The adhesive can spread out within the inner space between the polyurethane base coat, covering the base balloon 5100, and the prefabricated covering 5104. The adhesive can provide a uniform thin layer of adhesive material between the layers. The adhesive can provide a uniform thin layer of adhesive material between the base balloon 5100 and the prefabricated covering 5104. The adhesive can provide a uniform thin layer of adhesive material between the one or more base coats, if provided on the base balloon 5100, and the prefabricated covering 5104.

In some embodiments the pairing of the base balloon 5100 and the prefabricated covering 5104 have one or more functions. The first function is that the pairing is designed to hold balloon pressure during the intended use. The base balloon 5100 and the prefabricated covering 5104 can maintain the expanded diameter within smaller tolerances. The base balloon 5100 and the prefabricated covering 5104 can maintain a more consistent balloon pressure.

The second function is that the pairing is designed to limit the prefabricated covering 5104 from tearing, thereby allowing the prefabricated covering 5104 to retain the metal strips while allowing the elevated elements or teeth to penetrate the prefabricated covering 5104 layer. The prefabricated covering 5104 can be designed to prevent tearing longitudinally. The prefabricated covering 5104 can be designed to prevent tearing between adjacent wedge dissectors. The prefabricated covering 5104 can be designed to prevent tearing along the strip. The prefabricated covering 5104 can be designed to prevent tearing to expose the strips. The prefabricated covering 5104 can be designed to retain the strips. The prefabricated covering 5104 can extend over the surface of the strips between adjacent wedge dissectors. The prefabricated covering 5104 can extend circumferentially. The prefabricated covering 5104 can extend around the circumference of the base balloon 5100.

The third function of the pairing is designed to minimize puncture of the base balloon 5100 by the elevated elements on the strips during pleating and crimping of the pairing into a tightly bound diameter. The prefabricated covering 5104 can protect the base balloon 5100 from being punctured. The strips lie down tangentially relative to the base balloon and the prefabricated covering 5104. The wedge dissectors lie against the outer surface of the prefabricated covering 5104. The prefabricated covering 5104 can comprise a material designed to prevent puncturing by the wedge dissectors. The prefabricated covering 5104 can comprise a material designed to prevent tearing along the line of wedge dissectors that are poking through the prefabricated covering. The prefabricated covering 5104 can protect the base balloon 5100 during pleating. The prefabricated covering 5104 can protect the base balloon 5100 during crimping. The prefabricated covering 5104 can protect the base balloon 5100 when the balloon is in the low profile insertion configuration.

Fourth function is to minimize puncture of the base balloon 5100 by native disease (e.g. calcified atherosclerosis) or other external penetrating source. The prefabricated covering 5104 can protect the base balloon 5100 from being punctured. The prefabricated covering 5104 can interact with the lumen of the vessel. The prefabricated covering 5104 can comprise a material designed to prevent puncturing by roughened surface of the plaque. The prefabricated covering 5104 can protect the base balloon 5100 from the plaque during insertion. The prefabricated covering 5104 can protect the base balloon 5100 from the plaque during inflation.

In some embodiments the base balloon 5100 diameter is designed to apply a uniform pressure to the inner diameter of the prefabricated covering 5104 during the manifesting manufacturing process. The balloon 5100 expanding under pressure is used to expel the uncured, liquid adhesive between the base balloon 5100 and the prefabricated covering 5104 through holes in the prefabricated covering 5104 at the locations where the elevated elements penetrate through the prefabricated covering 5104. The balloon 5100 expanding under pressure can distribute the adhesive in a thin layer to cover at least a portion of the elevated elements. The balloon 5100 expanding under pressure can distribute the adhesive in a thin layer to cover at least a portion of the strip. The balloon 5100 expanding under pressure can distribute the adhesive in a thin layer between the base balloon 5100 and the prefabricated covering 5104. The adhesive can be cured, forming a unitary structure between the base balloon 5100 and the prefabricated covering 5104.

The design of the base balloon 5100 in some embodiments has a high expansion ratio which reduces the compliance of the balloon over the nominal pressure ranges intended during the procedure. The base balloon 5100 can be non-compliant. The base balloon 5100 can be semi-compliant. The base balloon 5100 can facilitate the control of the maximum expanded diameter of the balloon. The base balloon 5100 can expand to a specific diameter, or a specific diameter within certain tolerances. The base balloon 5100 can exert a specific pressure on the vessel wall without additional radial expansion. In some embodiments, the prefabricated covering 5104 is designed with a high compliance or low expansion ratio with the intent to minimize surface tearing by the penetration of the serrated elements, native disease (e.g. calcified atherosclerosis) or other external penetrating source. The prefabricated covering 5104 can be compliant. The combination of a low compliant base balloon 5100 with a high complaint prefabricated covering 5104 has several advantages as described herein. The design features function as a system to effectively retain the strip. The design features function to minimize the ability of the prefabricated cover to tear along a portion of the strip, such as between the wedge dissectors. The design features function to minimize the ability of the strip or plaque to puncture the prefabricated coating and the base balloon. The design features function to allow for good pressure retention throughout the procedure.

One method to reduce compliance in the base balloon 5100 or increase the compliance of the prefabricated covering 5104 is to modify the manufacturing processes at the balloon tubing extrusion process and/or balloon molding process. The base balloon 5100 can be formed from an extruded tube that is blown during the balloon molding process. The prefabricated covering 5104 can be formed from an extruded tube that is blown during the balloon molding process. During the process of manufacturing the base balloon 5100 and/or the prefabricated covering 5104, the compliance can be modified. In some embodiments, a method of manufacturing is applied to modify molecular orientation of the polymer chains. The molecular orientation of the polymer chains of the base balloon 5100 can be modified. The molecular orientation of the polymer chains of the prefabricated covering 5104 can be modified. Through a change in the process of producing the extrusion or raw material, used in making either the base balloon 5100 or making the prefabricated covering 5104, a change in the forming process, or a change in the balloon modeling process, the molecules can be encouraged to orient biaxially. The molecular orientation of the polymer chains of the base balloon 5100 can be orient biaxially. The molecular orientation of the polymer chains of the prefabricated covering 5104 can be orient biaxially. In some methods the biaxial orientation produces materials that offer unique properties including tear resistance or limiting or increasing material compliance. The biaxial orientation of the base balloon 5100 can facilitate reduced compliance in the base balloon 5100. The biaxial orientation of the base balloon 5100 can facilitate increased compliance in the prefabricated covering 5104. The biaxial orientation of the base balloon 5100 can facilitate tear resistance.

To influence the base balloon 5100 and/or the prefabricated covering 5104 properties, changes in the blow molding parameters and or the extrusion parameters are envisioned, but are not limited to these two areas of manufacturing processes or to the parameters listed herein. Changes in the balloon molding methods that could be used to influence the behavior of the base balloon 5100 or the pre-fabricated covering 5104 include a set of four blow molding parameters to influence the desired properties including: changing the temperature of the heating jaws, changing the pre-pressure/warm-up time, changing the forming pressure/forming time, and/or changing the distal/proximal stretching load. These blow molding parameters can facilitate the desired molecular orientation. Changing any of these parameters can produce slightly different performance properties of the base balloon 5100 or the prefabricated covering 5104. Additionally, changes in the extrusion parameters that could be used to influence the behavior of the base balloon 5100 or the prefabricated covering 5104, include: changes in the distance between the extrusion tooling and the cooling bath, and changing the speed of the gear pump during the extrusion process, which can both have effect on the performance properties of the base balloon 5100 or the prefabricated covering 5104.

Other properties that are considered to produce desired properties of the base balloon 5100 or the prefabricated covering 5104 include the inner and outer diameter of the extrusion, the drawdown and die heads of the extrusion, and/or the final molecular orientation of the polymer chains. This modification of the balloon in balloon design can provide many advantages. The base balloon 5100 can be designed to have low compliance, such that the base balloon does not radially expand as pressure is increased. The prefabricated covering 5104 can be designed with high compliance, such that the prefabricated covering 5104 avoids tearing.

In some methods, the application of heat and/or force can facilitate alteration of the prefabricated covering 5102. In some methods, a heat and/or force can be applied to the strips 5102 when the strips 5102 are in contact with the prefabricated covering 5104. The heat source such as a heating iron can be rolled over the tips of the strips 5102. In methods where heat is applied to the tips of the strips, the heat from the heating source such as a heating iron can melt or liquefy the pre-fabricated covering 5104. The heat source can be used to melt the material around each tip of the strips 5102. As the material of the prefabricated covering 5104 melts in the regions of the tips of the strips 5102, the tips of the strips 5102 can protrude through the melted holes in the prefabricated covering 5104. The tips of the strips 5102 can rise above the outer surface of the prefabricated covering 5104. The melted material of the prefabricated covering 5104 quickly rehardens in the area surrounding the tips of the strips 5102 when the heat is removed. The rehardened material provides a thicker, more durable, and tougher layer of the pre-fabricated covering 5104. The melted and rehardened material of the prefabricated covering 5104 surrounds the tips of the strips 5102. The additional material around each tip of the strip 5102 increases the tear resistance of the prefabricated covering 5104. The additional material around each tip of the strip 5102 limits the ability of the prefabricated covering 5104 to tear in the spaces between the strips.

In some embodiments, the prefabricated covering 5104 is melted along the unhoned surface of the wedge dissectors. The strip 5102 can have longitudinal spaces between adjacent wedge dissectors along a single strip. The prefabricated covering 5104 can be melted along only the unhoned surface, such that only the individual wedge dissectors extend through the holes in the prefabricated covering 5104. The prefabricated covering 5104 can remain intact along the longitudinal spaces between adjacent wedge dissectors. The prefabricated covering 5104 can remain intact along the circumferential spaces between adjacent wedge dissectors. The rehardened material can surround the wedge dissectors that extends through the prefabricated covering 5104. The rehardened material can extend longitudinally along the sloped surfaces of the wedge dissectors. The rehardened material can extend laterally along the proximal and/or distal edges of the wedge dissectors. The rehardened material can strengthen the prefabricated covering 5104 near the wedge dissectors. In some methods, the wedge dissectors can only extend through the prefabricated covering 5104 under the application of force and/or heat that creates opening in the prefabricated covering 5104. The unhoned surface cannot poke through the prefabricated covering 5104 until heat or force is applied, and the prefabricated covering 5104 stretches under pressure from the base balloon 5104. The application of force and/or heat weakens the prefabricated covering 5104 in the vicinity of the wedge dissectors. The prefabricated covering 5104 melts around the wedge dissector, forming a thickened material around the wedge dissector. The force and/or heat allows the wedge dissector to extend through the prefabricated covering 5104. The force and/or heat reinforces the prefabricated covering 5104 near the wedge dissector to prevent or reduce tearing of the prefabricated covering 5104. The rehardened material is more difficult to tear in between each wedge dissector. The rehardened material is more difficult to tear in the regions near the wedge dissectors. The rehardened material is more difficult to tear in regions that are the most vulnerable to tearing. The method of melting the material of the prefabricated covering 5104 around the extruding tips of the strips 5102 t increase tear resistance in the regions that are most vulnerable to tearing, thus increases the robustness and durability of the system.

The prefabricated covering 5104 can facilitate retention of the strips 5102 relative to the base balloon 5100. The prefabricated covering 5104 can reinforce the attachment of the strips 5102. One important feature of the prefabricated covering 5104 is to prevent the strip 5102 from falling free from the balloon during an endovascular procedure. The strips 5102 can experience great forces within the vasculature during expansion and the interaction with plaque. The prefabricated covering 5104 provides a retention layer between the strips 5102 and the base balloon 5100. Methods aiding in tip protrusion, for instance by the application of force and/or heat to weaken the prefabricated covering 5104, can have the added benefit of regional material thickening near the wedge dissectors. The material thickening of the prefabricated covering 5104 can be designed to increase the functional effect of the prefabricated covering 5104 as a strip retention feature.

As shown in panel 5, the inner serrated base balloon 5100 is inflated. The wedge dissectors extend through openings in the prefabricated covering 5104. The openings in the prefabricated covering 5104 surround individual wedge dissectors. The prefabricated covering 5104 is continuous between the individual wedge dissectors. The opening in the prefabricated covering 5104 can have a thickened wall surrounding the wedge dissectors. In some methods, the adhesive can be distributed into the opening of the prefabricated covering 5104. The adhesive can form a thin layer between the hardened, thickened material of the prefabricated covering 5104 and the wedge dissector.

In some embodiments, the entire space between the base balloon 5100, the strips with the wedge dissectors 5102, and the outer pre-fabricated covering 5104 are bonded together. The adhesive can form a thin layer between the base balloon 5100, the strips with the wedge dissectors 5102, and the outer pre-fabricated covering 5104. The base balloon 5100, the strips with the wedge dissectors 5102, and the outer prefabricated covering 5104 can be exposed to UV light to cure the adhesive. The final balloon-in-balloon construct 5199 can be seen in panel 6. The bonding of the two layers is typically done with, for example, a UV curable glue or other adhesive that is uniformly applied to the surface of the inner base balloon 5100 prior to sliding the outer prefabricated covering 5104 over the inner base balloon 5100, shown in panels 3 and 4. The inner base balloon is then inflated, such as to high pressures (for example, above about 5, 6, 7, 8, or more ATM), as shown in panel 5, and then exposed to UV light and allowed to cure. The contact of the two surfaces of the base balloon 5100 and the prefabricated covering 5104 under the pressure loading disperses the adhesive uniformly. The contact and pressure between the base balloon 5100 and the prefabricated covering 5104 allows for uniform coating thickness on the balloon body and balloon cone surfaces prior to the curing cycle. The final balloon-in-balloon construct 5199 can be pleated. The final balloon-in-balloon construct 5199 can be utilized in any method described herein. The final balloon-in-balloon construct 5199 is a serrated balloon. The wedge dissectors of the strips 5102 can rotate from the tangential orientation to the perpendicular orientation within the vessel. The prefabricated covering 5104 and the base balloon 5100 can function unitarily to form lobes to contact the vessel wall. The prefabricated covering 5104 and the base balloon 5100 can function unitarily to rotate the strips into a perpendicular orientation. The prefabricated covering 5104 and the base balloon 5100 can function unitarily to apply a tensile force on the vessel wall to create linear dissected lines.

The final balloon-in-balloon construct 5199 can have several advantages. The strips 5102 can be attached to the base balloon 5100. The prefabricated covering 5104 can functionally reinforce this attachment of the strips. The adhesive can be applied to the pleats of the base balloon 5100. The adhesive can serve as a lubricant for sliding the base balloon 5100 into the prefabricated covering 5104. The strips 5102 can right themselves within the prefabricated covering 5104 as the base balloon 5100 is inflated. The strips 5102 can rotate to a perpendicular orientation within the prefabricated covering 5104. The wedge dissectors do not poke through the prefabricated covering 5104 under the application of pressure from the base balloon 5100. The prefabricated covering 5104 can be a durable, pliable material. The prefabricated covering 5104 can be penetrated by the wedge dissectors by the application of heat. The heat interacts with the prefabricated covering 5104 to melt the prefabricated covering 5104 in the vicinity of the wedge dissectors. The wedge dissectors poke through the prefabricated covering 5104 under the application of heat and a ridge is formed from softened material of the prefabricated covering 5104 around the wedge dissector. The prefabricated covering 5104 surrounds each individual wedge dissector. The unhoned surface extends from the prefabricated covering 5104. The height of the wedge dissector is largely exposed. The prefabricated covering 5104 can be a thin layer, such that the majority of the height of the wedge dissector extends from the prefabricated covering 5104. The prefabricated covering 5104 forms a hardened ridge around the wedge dissector when the heat is removed. The adhesive previously applied to the pleats of the base balloon 5100 can distribute through the space between the wedge dissector and the hardened ridge of the prefabricated covering 5104. The balloon-in-balloon construct 5199 can be exposed to light to cure the adhesive. The final balloon-in-balloon construct 5199 can be a new serrated balloon. The final balloon-in-balloon construct 5199 advantageously includes the prefabricated covering 5104 which forms a thin layer over the base balloon 5100 and over the longitudinal spaces between the wedge dissectors of the strip 5102. The prefabricated covering 5104 can be a thin, durable layer. In some embodiments, the prefabricated covering 5104 can support the strips 5102 attached to the base balloon 5100 better than only an adhesive layer between the base balloon 5100 and the strip 5102. In some embodiments, the prefabricated covering 5104 can reinforce the connection between the strip 5102 and the balloon 5100 to keep the strip 5102 in place. In some methods, the dynamics of the arterial geometry can act to dislodge the strip 5102 from the base balloon 5100. Such dynamics can be overcome by the prefabricated covering 5104 which reinforces the connection between the strip 5102 and the base balloon 5100. The prefabricated covering 5104 can uniformly extend over the base balloon 5100 and between the wedge dissectors, exposing only the wedge dissectors from openings in the prefabricated covering 5104. The prefabricated covering 5104 can provide a consistent retention of the strip 5102.

As illustrated in FIG. 41A, a strip 3500 can be fabricated that includes a plurality of strips (e.g., two identical strips) touching only tip to tip 4100, in a wedge dissector frame or carrier 4110. This wedge dissector frame 4110 can be potentially created via a mechanical removal process such as chemical etching. In some embodiments, the strip 3500 can be easily and cleanly detached from the frame 4110 and mirror image strip via a mechanical force or other means without modifying the geometry of the wedge dissectors of the strip 3500. In some embodiments, the frame or carrier 4110 can remain attached to the strip 3500 until a surface of the strip opposite the base of the wedge dissectors is bonded or otherwise attached to a surface of a balloon as described elsewhere herein.

FIGS. 41B and 41C illustrate that in some embodiments, a plurality of strips 4100 can be bent or folded over into a bent form 4120 leaving the tips 4100 intact and producing an A-frame 4130 with an open gap or well within the radially-outward facing surface of the combined A-frame wedge dissector 3510 assembly.

FIGS. 41D and 41E illustrate an alternative embodiment with serrated tips 4160, that include a plurality of pointed surfaces with a central concave segment therebetween 4150 (compared with the central flat segment 4140 in FIGS. 41B and 41C). A strip 3500 with serrated tips 4160 can be bent over leaving the serrated tips 4160 intact and producing an A-frame with serrated tips 4160 with an open gap or well.

In some embodiments, the distance between adjacent base strips at the base is between about 30 μm and about 260 μm, between about 60 μm and about 190 μm, or between about 90 μm and about 130 μm. In some embodiments, a dimension, e.g., width of the gap at the apex of the "A" of the A-frame can be, for example, between about 10 μm and about 150 μm, between about 25 μm and about 100 μm, or between about 50 μm and about 75 μm. In some embodiments, the angle creating the apex of the "A" of the A-frame defined by the intersection of distal portions of the two wedge dissectors can be, for example, between about 5 degrees and about 45 degrees, such as between about 10 degrees and about 30 degrees, or between about 15 degrees and about 22 degrees.

FIG. 42 illustrates an illustration series that shows the ability to take a stack of strips 4200 connected to a blank or carrier 4300 that can be discarded at any point in the strip attachment process (prior to placement on the balloon, during balloon placement, or post gluing of the strip to the balloon). This process offers an aid to automation, picking up and placing the strip, and facilitates the precision in aligning the strip and balloon. The radial distal tips 4210 can abut against continuous free edge 4220 or other continuous or discontinuous surfaces to allow for simple detachment of the strip. In some embodiments, a carrier system for attaching wedge dissectors to a medical balloon can include a strip including a plurality of wedge dissectors spaced longitudinally apart along a surface of the strip. Each of the wedge dissectors can include a strip-facing base surface directly adjacent a first surface of the strip, an unhoned radially outward facing surface having a length between a proximal edge of the radially outward facing surface and a distal edge of the radially outward facing surface and defining a height of each wedge dissector, and lateral surfaces between the strip-facing base surface and the radially outward facing surface. The strip can also include a second surface opposing the first surface of the strip and a strip carrier that includes a free edge. The unhoned radially outward facing surface of each of the wedge dissectors can be reversibly attached to the free edge of a strip carrier at attachment zones. The areas between attachment zones can define voids, and be configured to be detached upon application of a mechanical force. In some embodiments, the second surface of the strip can be attached to a surface of the medical balloon, and the strip carrier detached from the strip after the second surface of the strip is attached to the medical balloon. In some embodiments, the strip carrier can be integrally formed with the strip, and created using a process such as chemical etching. The strip carrier can be made of the same, or a different material than that of the strips.

FIG. 43 illustrates an embodiment of a close-up drawing of the attachment of the radially outward facing surfaces 4325 of the wedge dissectors 4100 to the free edge 4220 of the blank or carrier 4300. Also shown are voids 4280 between attachment zones 4328 where the base surface of the strip does not contact the corresponding free edge 4420 of the blank or carrier. In some embodiments, each void or all of the voids 4280 have a surface area that is about, at least about, or about or more than about 110%, 120%, 130%, 140%, 150%, 160%, 170%, 180%, 190%, 200%, 250%, 300%, or more of the surface area of a wedge dissector or each of the wedge dissectors of each strip. In some embodiments, the proximal-most free edge 4420 of the blank or carrier 4300 contacts (e.g., is the only contact edge) to the distal-most edge or surface of the wedge dissector 4325 such that the intersection or points of contact between the strip/wedge dissector 4100 and the blank 4300 are along a straight line only, and there is no or substantially no overlap in a dimension, such as a height dimension as shown in FIG. 43 between any part of the strip or wedge dissector of the strip and the blank or carrier. In some embodiments, this can advantageously allow for simple detachment of the strip and associated wedge dissectors from the carrier. In other embodiments, there can be overlap in one or more dimensions between the attachment zone of the carrier and the strip and associated wedge dissectors, e.g., via a slot or groove in a free edge of the blank. In other embodiments, the attachment zone need not be along a continuous free edge of the blank or carrier, but rather at spaced apart intervals between projections of the blank or carrier and the wedge dissectors. The projections can be mirror images of the wedge dissectors, or another pattern.

FIGS. 44A and 44B shows a description of an embodiment of a fabrication process for the manufacturing of serratoplasty strips, cutting members, or wedge dissectors 3510 which utilizes a reel of an appropriate material, such as a metal, e.g., stainless steel material stock 4410. The stock 4410 can be shaped or ground with or without honed edges. The honed edge 4430 can be fabricated with a single or multiple facets on its edge and can be either ground to a fine tip (e.g., honed) or with a narrow but flat side (e.g., unhoned). The cross-sectional view of ground honed stock 4430 in some embodiments can be a triangle like shape with potentially multiple slopes on the rising side of an equilateral triangular slope.

In addition to the material grinding fabrication technique described above, the fabrication of stainless steel serrated blades can be achieved with other bulk processing techniques.

As such grinding, stamping, etching, electro chemical machining, and electrical discharge machining or a combination of these processes are bulk processing techniques envisioned to be used alone or in combination to achieve low cost manufacturing of serrated tips.

A description of the fabrication steps that would be included in chemical etching can in some embodiments include some or all of the following.

A mask or mask set 4400 that includes the information and design details to produce a series of serrated blades, cutting members, or wedge dissectors can be placed on top of a photo resistant layer 4420. Each mask 4400 is a series of openings to allow light to shine through the mask 4400. The mask set 4400 can be the same or can be slightly different from each other to allow partial etching through of a single side of the stainless steel material 4410.

Chemical etching of stainless steel reel or sheets 4410 using masks, photoresist, and etching materials can be advantageously applied to allow for large volumes of material to be etched at low costs.

Bulk chemical etching can allow for extremely repeatable and low cost parts to be fabricated in volume. Traditionally, chemical etching produces rounded edges with gentle slope side walls through the material at angles approximating 90 degrees. To achieve more gentle sloped angles grayscale masking was considered with poor results. In place of grayscale new masking techniques utilized relatively narrow hole along with narrow slit like patterns to control etch rates with success. By controlling the etch material flow through the resist layer, angles for blade-like structures have been achieved.

Two-sided mask exposure can enable etching through the material from both sides. With dual side exposure the edge profile produces greater control mirror imaging profiles on either side of the stainless-steel material.

FIG. 45B shows the strip 3500 can be placed over a through hole 4500 embedded in the balloon wall 4510. The through hole can be a hole that was extruded prior to the fabrication of the balloon, thus providing a conduit through which a volume of therapeutic agent(s) can be passed and delivered to the serrated tissue. Similarly in FIG. 45A, in some embodiments, the strip 3500 can be placed over a series of through holes 4520 laser cut or other method to puncture the balloon wall 4510, down to a separate conduit produced in the extrusion process thus providing a conduit through which a volume of therapeutic agent(s) can be passed and delivered to the serrated tissue.

FIG. 46 illustrates in some embodiments, a series of a plurality, such as 4 A-frame strips 3500 (or non A-frame strips with wedge dissectors as disclosed herein) can be placed over through holes 4600 embedded in the balloon wall 4610. The A-frame strips 3500 above can be spaced regularly apart as illustrated above, or irregularly in other embodiments.

In other words, in some embodiments the “A-frame” strip 3500 design includes a first strip 3510 and a second strip 3520 spaced apart at their respective bases, each strip comprising wedge dissectors 3510 having radially-outward facing surfaces having a perimeter, the wedge dissectors 3510 of the first strip 3510 and the second strip 3520 contacting each other at part of the perimeters of each of the radially-outward facing surfaces, wherein an apex gap is present at a location where the first strip 3510 of wedge dissectors 3510 and second strip 3520 of wedge dissectors 3510 do not touch each other, wherein the gap is configured to house a drug reservoir hole 4500 therethrough.

FIG. 47 illustrates an embodiment (with a closeup insert) of an array of strips 3500 on a mask 4700 set prior to chemical etching. Each array of strips 3500 can include a detachable zone 4710 between adjacent wedge dissectors 3510.

FIG. 48*a* shows a strip array 3500. FIG. 48*b* shows a detailed close up image of the adjacent wedge dissectors 3510 with detachable zones 4710. FIG. 48*c* shows serration strips 3500 reversibly connected to a strip carrier 4810 for alignment, control, placement, and ease of manufacturing. Three chemical etch variations of connection of a strip carrier 4810 to strips 3500 with different geometries are shown in Etch 1 4820, Etch 2 4830, and Etch 3 4840. The close-ups illustrate how the wedge dissectors 3510 on the side are connected to the strip carrier 4810. FIG. 48*d* illustrates another embodiment of a strip carrier 4480 reversibly attached to wedge dissectors of a strip 4890. The strip carrier 4880 can have any appropriate geometry, and in some cases have rounded or other tabs 4882, apertures 4884, lateral tabs 4886, or other features for alignment, control, placement, and ease of manufacturing. In some embodiments, the strip carrier includes projections that can be mirror images of the wedge dissectors of the strip to allow for ease of removal, such as after the strip has been bonded or otherwise secured to a balloon (not shown).

FIG. 49 above is an illustration of one embodiment of an overall system for producing serratoplasty showing a series of serrating or scoring wedge dissectors 3510 on the outer diameter of the balloon 3316 attached to a catheter 3310 with a guidewire hub 4900 and balloon inflation hub 4910. FIGS. 49A-49J illustrate additional views of one embodiment of a serratoplasty system.

FIG. 50 schematically illustrates a balloon blown from an extrusion that has a set of longitudinally oriented ridges of material, according to some embodiments. The ridges of material may be the same as the balloon or may be different. The number and location of the ridges typically corresponds to the position of the strip tips when they lay down in the pleat and crimp position. The ridges offer regions where the blown balloon is thicker than the non-ridged regions. The thicker regions act as buffer zones or pillows to limit and prevent accidental balloon popping due to the retained strips on the balloon surface.

FIG. 51 schematically illustrates the sets of strips placed in the balloon blowing dies prior to the balloon blowing process, according to some embodiments. In this design the strips offer the ability to be accurately placed within the die set through the inclusion of alignment elements integrated into the carrier part for the strip. The die (e.g., in a plurality, such as 3 detached segments as shown) allows for proper positioning of the strip to allow adequate height of the base of the strip to coincide with the intrended location to allow for embedding of the strip into the balloon matrix during the heating and balloon blowing process.

FIG. 52 schematically illustrates the extrusion including optical markers to aid in orientation of the extrusion in the balloon blowing process, according to some embodiments. In some embodiments as shown, there are three zones (highlighted) used as optical reference planes to orient the extrusion in the balloon blowing process to allow the strips to be positioned properly to align for the ridges to be accurately positioned as pillow (e.g., protection) zones four protection of the balloon during the pleat and fold process.

FIG. 53 illustrates an embodiment where the extrusion used to blow the balloon has a second retention layer with a slightly lower glass transition temperature than the balloon itself. The second layer offers a slightly more forgiving effective zone of material to allow the strip to be embedded within. During the heating and blowing of the extrusions into the balloon mold the top retention layer flows more readily into cavities designed in the die of the balloon mold providing space to encapsulate the strip as shown. Again, in this design the control of the depth of the strip is achieved by the design of the die and strip carrier allowing for a more effectively position the strip with a high level of tolerance and minimal control effort.

FIG. 54 schematically illustrates a perspective view of the dies (shown only partially and transparently) with a series of strips shown clamped into a modified balloon blowing machine, according to some embodiments. The partial and transparent dies are shown in three sections covering approximately 120 degrees per section of the balloon surface. A series of features on the strip carrier are seen including a hole and a cut out in the center of the carrier. These features are designed to align and assist in accurate positioning of the strip to narrow ranges of positions aligned with a zone at the balloon surface during the blowing cycle.

FIG. 55 schematically illustrates a strip and bonding material surrounding the base of the strip, according to some embodiments. In this cross-sectional illustration, the bonding material is a single material but can be more than one layer of materials, such as 2, 3, or more layers. The bonding material is designed to offer effective strip retention to the balloon. Therefore, the material is designed to offer flexibility and durability of retention of the strip while under the various force loading conditions of the system while being delivered, inflated, disrupting the diseased tissue, and retrieval.

FIG. 56 schematically illustrates a sectional view of the strip and the strip retaining material being placed into one side of a single balloon blowing die, according to some embodiments. It is noted that that the shape of the die for the balloon blowing system can be made to align with the shape of the taper of the strip. When the die is designed this way the alignment enables control of the position of the strip on the balloon and reduces the possibility of the retaining material from flowing over the tip of the strip.

FIG. 57 schematically illustrates 3 strips captured within a set of three dies at 120 degrees from each other, according to some embodiments. Prior to the balloon blowing process the strips are placed within the dye cavities allowing the retention material to be protruded into the balloon blowing cavity control of the depth a penetration into the cavity is achieved through the die design. Other embodiments can include 2 strips 180 degrees apart, 4 strips 90 degrees apart, or strips that are spaced irregularly apart in other embodiments.

FIG. 58 schematically illustrates a magnified view of the strip and retention material captured between two sides of the balloon dies, according to some embodiments. The balloon dies show a contoured shape to allow the retention material to flow into. As the dies are heated to enable the balloon forming to occur the retention materials are also heated. The heating can be sufficiently high enough to be near or above the glass transition temperature of both the balloon material and the retention material enabling the materials to flow together effectively becoming a single composite material.

FIG. 59 schematically illustrates a cross section of the balloon with the strips and the retention materials bonded together and removed from the balloon blowing machine, according to some embodiments. Here the strips are effectively bonded to the balloon surface with the retention material bonded or fused together with the balloons outer surface. It should be noted that the balloon and the retention material can be made of multiple layers. In some cases, the retention materials outer most layer and the balloons outermost layer are the same material or made of materials that are designed to fuse effectively at the balloon blowing temperatures. The design of the retention layer can include multiple layers such that some layers have a higher level of elasticity while other layers are more inelastic. By combining elastic and inelastic layers the retention layer can offer greater retention of both the highly elastic balloon and highly inelastic strip.

FIG. 60 schematically illustrates three strips are bonded to the balloon surface with the retention layer, according to some embodiments. The carriers are removed in this step and the balloon is fully inflated to show the orientation of the strips during deployment.

FIG. 61 schematically illustrates a magnified view of this strip after the retention layer has been bonded to the balloon surface, according to some embodiments. The retention layer is shown as being wrapped around the strip under the strip and spread out on either side of the strip a distance far enough to allow the strip to lay down on the retention layer when folded.

FIG. 62 schematically illustrates a perspective view of the three strips with the retention layer bonded showing the minimal surface area that the retention layer covers on the outer balloon surface relative to the entire balloon surface, according to some embodiments.

FIG. 63 schematically illustrates a top view illustration where the retention layer is shown covering the top of the strip, between each of the wedge dissectors, and outward some fraction of the balloon surface such that a footing is placed on the balloon to aid in strip retention. The height of the retention layer is typically minimal above the strip, according to some embodiments.

FIG. 64 schematically illustrates a retention layer that is minimized with no footprint on either side of the strip along the balloon surface. In this embodiment it is envisioned that an additional two rows or more of material that may or may not be the same as the retention layer run horizontal to the strip at a distance that allows a protective zone (pillow regions) in the region where the tip of the strips lay down on the balloon during pleat and fold.

FIG. 65 schematically illustrate the pillows that adjoin the retention of the strips are shown in a dotted pattern similar to the spacing of the tips of the strip. These individual pillows offer minimal surface area retention zones to protect the balloon and while minimizing additional bulk to the balloon.

FIG. 66 schematically illustrates a cross section view of the retained strip with retention layer over it with minimal retention material and accompanying pair of balloon protection pillows on either side as protective zones to minimize strip puncturing of the balloon.

FIG. 67 schematically illustrates an embodiment with only a single pillow as shown in the zone where the strip lays down, but no contralateral pillow.

FIG. 68 schematically illustrates a variation of the same concept of minimal retention zone for these strip while on one side the pillow region is contains less material then the pillow region on the opposing side of the strip.

FIG. 69 schematically illustrates a variation of the same concept of minimal retention zone for the strip, but additional material is shown on the proximal edge of the strip. The additional region of material offers a more structured retention region typically found at the ends of the strip.

FIG. 70 schematically illustrates a variation of how protection zones (raised pillow regions) integrated into the balloon offer protection of the balloon during the folding and crimping of the balloon. These design variations can, in some embodiments, offer the ability to more tightly fold and crimp the series of micro wedges into the balloon while minimizing the potential to make a hole in the balloon from the sharp edges of the individual micro wedges. Three non-limiting variations for pillow regions are illustrated as A, B, and C. In each illustration, the strip can lie within the balloon folds. In variation A one short pillow is placed on the over folded material of the balloon while two short pillows are placed on the inner circumference of the balloon fold to protect the balloon against puncture. In variation B one long pillow is placed on the over folded material of the balloon while one long pillow is placed on the inner circumference of the balloon fold to protect the balloon against puncture. In variation C one long pillow is placed on the over folded material of the balloon while one short pillow is placed on the inner circumference of the balloon fold to protect the balloon against puncture. Any variation of pillow length and number is envisioned on either the over folded material of the balloon or on the inner circumference of the balloon fold to protect the balloon against puncture.

FIG. 71 schematically illustrates an embodiment with an array of smaller strip sections with four wedge dissectors connected by a base followed by a gap and another set of arrays of four wedge dissectors. This design variation can have any number of lengths of the wedge dissectors bonded together and separated from neighboring arrays. For instance array of five, six, or more as well as arrays of two or three are envisioned. Retention and pillowing designs can follow any of the previously described design patterns.

FIG. 72 schematically illustrates an embodiment with individual wedge dissectors unconnected. In some embodiments some balloon regions may have unconnected wedge dissectors while other regions of the balloon may be connected as illustrated on the right side of the illustration. Retention and pillowing designs can follow any of the previously described design patterns.

FIG. 73 schematically illustrates a side view of the strips integrated onto the balloon surface. An additional retention zone is shown at the last wedge dissector nearest the cone body of the balloon. The cones of the balloon can have more stress on them during delivery and retraction; in addition it is commonly known in the field of balloon blowing that they may have a gentle slope in the region near the cone edge. For this reason and other reasons not listed here, additional material being placed at the most distal end wedge dissectors independent of the strips being collectively bonded together or not can be advantageous.

FIG. 74A-74E is a series of illustrations showing the mechanism for serrated strip elements 200 to turn from a tangential orientation under the wing of the balloon material to being uncovered and orienting perpendicularly within a very tight stenotic lesion. This series of illustrations shows the delivery configuration of the balloon and subsequent expansion. As an overview, the strips 200 rotate during expansion of the balloon 100. The strips 200 are delivered in a tangential orientation. The strips 200 can be at least partially or fully covered by the balloon 100 during delivery. The strips 200 lie down during delivery. The expansion of the balloon can cause the strips 200 to turn from the tangential orientation to the perpendicular orientation. Additionally, the deflation of the balloon can cause the strips 200 to turn from the perpendicular orientation to the tangential orientation. The strips 200 can rotate within vessels with very small diameters. The strips 200 can rotate within small diameter stenotic lesions. The mechanics of the expansion of the balloon 100 facilitate the serration and subsequent crack propagation. These figures illustrate how the balloon expansion occurs.

Figure 74A:
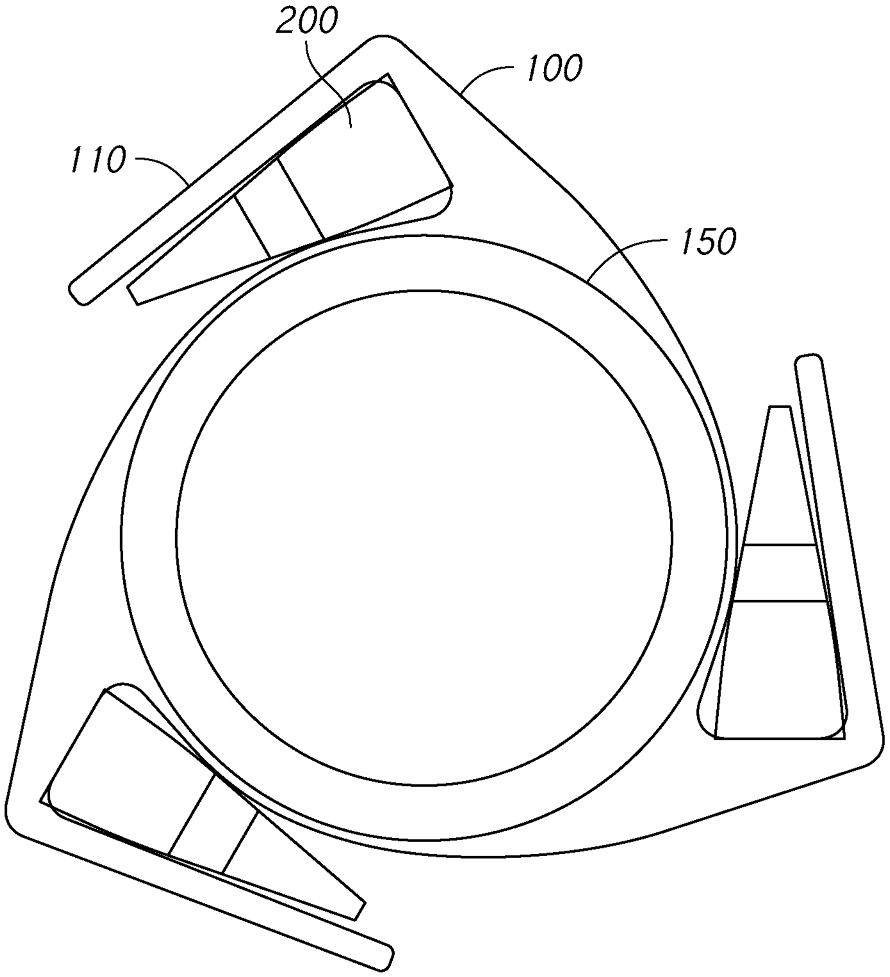

FIG. 74A illustrates the pleated and wrapped balloon 100. The balloon can be folded to a low profile. The balloon 100 can include one or more pleats, for example one pleat, two pleats, three pleats, four pleats, five pleats, six pleats, or any range of two of the foregoing values. The number of pleats can correspond to the number of strips 200. In the illustrated embodiment, the balloon 100 includes three strips 200 and the balloon 100 includes three pleats. The pleats can be designed to at least partially cover the strip 200. The pleat can cover the height of the strip 200. The pleat can cover the tip of the strip 200. The pleat can overhang the strip 200. The strip 200 can be disposed between the pleat and a surface of the balloon. The strip 200 can be disposed within a pocket. The strips 200 can be contained within the folds of the balloon 100. The pleat can form a wing 110. The wing 110 can a portion of the balloon 100 that overlies a portion of the strip 200. The wing 110 can be a flap of material of the balloon 100. The wing 110 can be configured to be inflated as described herein.

The strips 200 can be at least partially covered by the balloon 100 during insertion. The balloon 100, in particular the wing 110, can serve as a buffer between the vessel lumen and the strips 200 during delivery or retrieval. The balloon 100 can cover the tip of the strip 200. The tip of the strip 200 can be covered to protect the unhoned tip of the strip 200. The tip of the strip 200 can be covered to protect the vessel wall during insertion and retrieval.

The strip 200 are delivered in a tangential orientation. The tangential orientation allows the strips 200 to lie against a surface of the balloon. The tangential orientation allows the strips 200 to have a low profile delivery configuration. The tangential orientation allows the unhoned tip to be covered by the wing 110. The tangential orientation reduces the diameter of the catheter for delivery and retrieval. The tangential orientation contains the strips 200 within the folds or pleats of the balloon 200. The tangential orientation allows the strips 200 to lie flat. The strips 200 can be near or against an inner member of the balloon catheter 150. The low profile diameter of the catheter includes the thickness of the strips 200. The low profile diameter of the catheter does not include the height of the strips 200. The low profile diameter of the catheter can be smaller due to the tangential orientation of the strips 200 for delivery. The delivery diameter would be greater if the strips 200 were oriented perpendicularly. The delivery diameter can be smaller than the vessel diameter.

The location of the strips 200 within the fold of the balloon 100 offers an advantage during the inflation cycle as described. The location of the strips 200 within the fold of the balloon 100 enables the strips 200 to rotate from their tangential orientation illustrated here in FIG. 74A. The strip 200 rotates once the balloon is located within the treatment site. The strip 200 rotates once the balloon 100 inflates. The strips 200 have a tangential orientation for delivery. The tangential orientation for delivery allows the strips 200 to be tucked within the fold the balloon 100.

The wings 110 of the balloon 100 offers an advantage during the inflation cycle as described. The balloon material 100 can overlie the strip 200. The balloon material can overhang the tip of each strip 200. The balloon material that forms the pleats or wings 110 is shown. In some embodiments, the wing 110 can extend beyond the strip tip 200. in some embodiments the wing 110 does not to extend past the neighboring strip 200. The wing 110 only covers one or a portion of one strip 200. The wing 110 does not fully cover another strip.

Figure 74B:
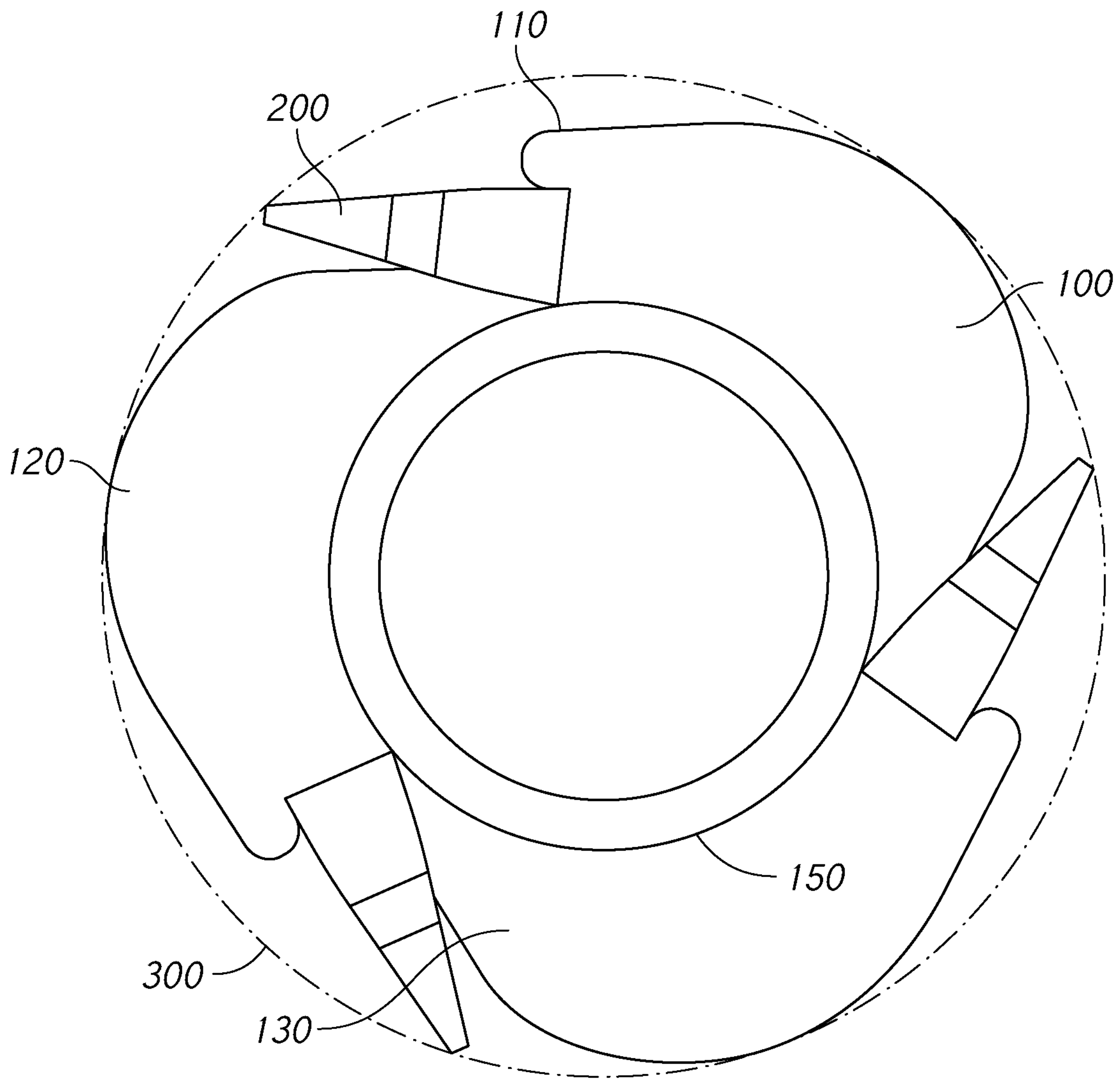

FIG. 74B illustrates the initial expansion event with fluid entering the balloon 100 and expanding the balloon structure. During this phase of the expansion, the strips 200 begin the rotation to the perpendicular orientation. A circle 300 illustrating an occlusion with a 2 mm inner diameter is shown to represent a surface that might limit expansion and limit rotation of the strip elements 200. As the balloon 100 fills with contrast material, the pressure within the balloon 100 is negligible but enough to begin to unfold. As the balloon 100 unfolds, the wings 110 of balloon 100 that buried the strip 200 peel back. At the same time the regions between the strips 200, where minimal resistance to filling is present, begin to fill and begin to apply gentle pressure to the inside wall of the strips 200 facing the inner member of the balloon catheter 150.

This figure illustrates the initial expansion of the balloon 100. The balloon 100 is positioned within a vessel 300. The vessel wall 300 is illustrated as a circle, but the vessel wall can have any cross-sectional shape. The fluid can begin to enter the balloon 100. The fluid can expand the balloon 100. The balloon 100 can form lobes 120. The lobes 120 can be located between the strips 200. The balloon can have any number of lobes, for example one lobe, two lobes, three lobes, four lobes, five lobes, six lobes, or any range of two of the foregoing values. The lobes 120 can expand. The lobes 120 can expand from a position not in contact with the vessel wall 300 to a position contacting the vessel wall 300. The balloon 100 can inflate until the lobes 120 rest against the vessel wall 300. Continued filling of the balloon 100 can cause a greater surface area of the lobes 120 to contact the vessel wall 300. The fluid enters the balloon 100 and expands the lobes 120. The lobes 120 can uniformly expand. The lobes 120 can simultaneously expand. The lobes 120 can non-uniformly expand. The lobes 120 can sequentially expand. The lobes 120 can passively expand based on the geometry of the vessel wall 300. The lobes 120 can expand based on areas of the balloon 100 with low resistance.

The strips 200 can rotate. The strip 200 can rotate as the balloon 100 expands. The strips can rotate as the balloon deflates, as described herein. The direction the strips 200 rotate can be defined by the orientation of how the balloon 100 and strips 200 are pleated. The direction the strips 200 rotate can be determined by whether the balloon 100 is being inflated or deflated. For the following description, in relation to FIGS. 74A-74E, the strips 200 are oriented tangentially pointing counterclockwise. In the series from FIG. 74A to FIG. 74E, the balloon is undergoing inflation and the strips 200 rotate from the transverse orientation to the perpendicular orientation by rotating clockwise during inflation. The strips 200 rotate from the perpendicular orientation to the transverse orientation by rotating counterclockwise during deflation. In other embodiments, the strips 200 are oriented tangentially pointing clockwise. In that embodiment, the strips 200 rotate from the transverse orientation to the perpendicular orientation by rotating counterclockwise during inflation. The strips 200 rotate from the perpendicular orientation to the transverse orientation by rotating clockwise during deflation. The strips 200 are able to rotate in either direction due to the orientation of the pleats placed during the manufacturing process. The pleats can help to define the direction the strips point either clockwise or counterclockwise. The pleats can help reliably unfold and rotate the strips during inflation. The pleats can help reliably refold and rotate the strips during deflation. The strips 200 can rotate clockwise or counter-clockwise. The strips 200 rotate out and back during the inflation and deflation cycles. The strips 200 rotate in a first direction during inflation. The strips 200 rotate in a second, opposite direction during deflation. The strips 200 reliably and repeatedly rotate from the transverse orientation to the perpendicular orientation, and vice versa. The inflation and deflation cycles can occur more than once during a procedure. The repositioning of the strips 200 under the pleat or the balloon wing 110 can occur many times in a single procedure.

The strips 200 can rotate from the tangential orientation to a less tangential orientation. The strips 200 can rotate from the tangential orientation to a more perpendicular orientation. The strips 200 can rotate relative to the inner member of the balloon catheter 150. The strips 200 can rotate under the influence of the expansion of the balloon 100. The strip 200 can begin rotation to the perpendicular orientation. The strip 200 can rotate to the vessel wall 300. The tip of the strip 200 can be unhoned. The tip of the strip 200 can rotate until the tip contacts the vessel wall 300. The vessel wall 300 can have any diameter. The lobes 120 can be against the vessel wall 300. The unhoned tip can be against the vessel wall 300. The vessel wall 300 can limit expansion of the lobes 120. The vessel wall 300 can limit rotation of the strips 200.

The balloon 100 continues to fill with fluid. The fluid can be any fluid, such as liquid or gas. The fluid can be contrast material. The pressure in the balloon 100 can be low, e.g., negligible, less than 0.5 atm, less than 1 atm, less than 2 atm. The low pressure can allow the balloon 100 to unfold. The balloon 100 forms bigger lobes 120 as the balloon fills. The wings 110 of the balloon 100 begin to pull back as the balloon fills. The wings 110 of the balloon 100 fill with fluid. The wings 110 of the balloon 100 begin to merge with the lobes 120. The wings 110 of the balloon 100 uncover the unhoned tip of the strip 200. The wings 110 of the balloon 100 uncover the side or height of the strip 200. The wings 110 of the balloon 100 uncovers the strip 200.

The lobes 120 continue to expand. The lobe 120 is the region of the balloon 100 between adjacent strips 200. The lobes 120 experience minimal resistance to filling. The filling of the lobes 120 is not constrained by the strips 200. The lobe 120 has less resistance to filling than the wing 110. As the wing 110 merges with the lobe 120 the wing 110 fills becoming the lobe 120. The wing 110 migrates to the region between adjacent strips 200. The wing 100 migrates to uncover the strip 100. The fluid fills the areas with minimal resistance to filling. The lobes 120 apply a pressure to the inside wall of the vessel 300. The lobe 120 applies a pressure to the strip 200. The lobe 120 applies a pressure to the inside wall of the strip 200. The lobe 120 applies pressure to the inside wall of the strip facing the inner member or lumen of the balloon catheter 150. The lobe 120 applies pressure to rotate the strip 200. The lobe 120 applies pressure to orient the strip 200 perpendicular to the inner member or lumen of the balloon catheter 150.

While not to be limited by a theory, there may be a portion of the lobe 130 that causes rotation. The portion 130 can be locate between the surface of the strip 200 and the inner member of the balloon catheter 150. As the portion 130 of the lobe 120 expands, the portion 130 can apply a force or torque on the strip 200. The pressure of the expansion of the lobe 120 can overcome the rigidity and resistance to twist of the strip 200, thereby rotating the strip 200. The rigidity of the strip keeps the strip 200 in a transverse orientation during delivery. The pressure of the lobes 120 must overcome this rigidity to rotate the strip 200. The expansion of the lobes 120 can cause the rotation to occur. The directionality of the rotation of the strips 200 can be influenced by the pleating. The pleating can direct the expansion of the lobes 120. The controlled expansion of the lobes 200, in relation to the shaped side walls and rigidity of the strips 200, can cause reliably and predicable rotation. The rotation is bi-directional. The strips 200 can rotate one direction with inflation and rotate the other direction with deflation. The strips 200 can reversibly change between configurations. The shape of the lobes 120 can be load centering. The lobes 120 can allow the strips 200 to rotate to a perpendicular orientation. The lobes 120 can allow the strips 200 to repeatedly return to the perpendicular orientation. The lobes 120 can allow the strips 200 to repeatedly return to the transverse orientation.

Figure 74C:
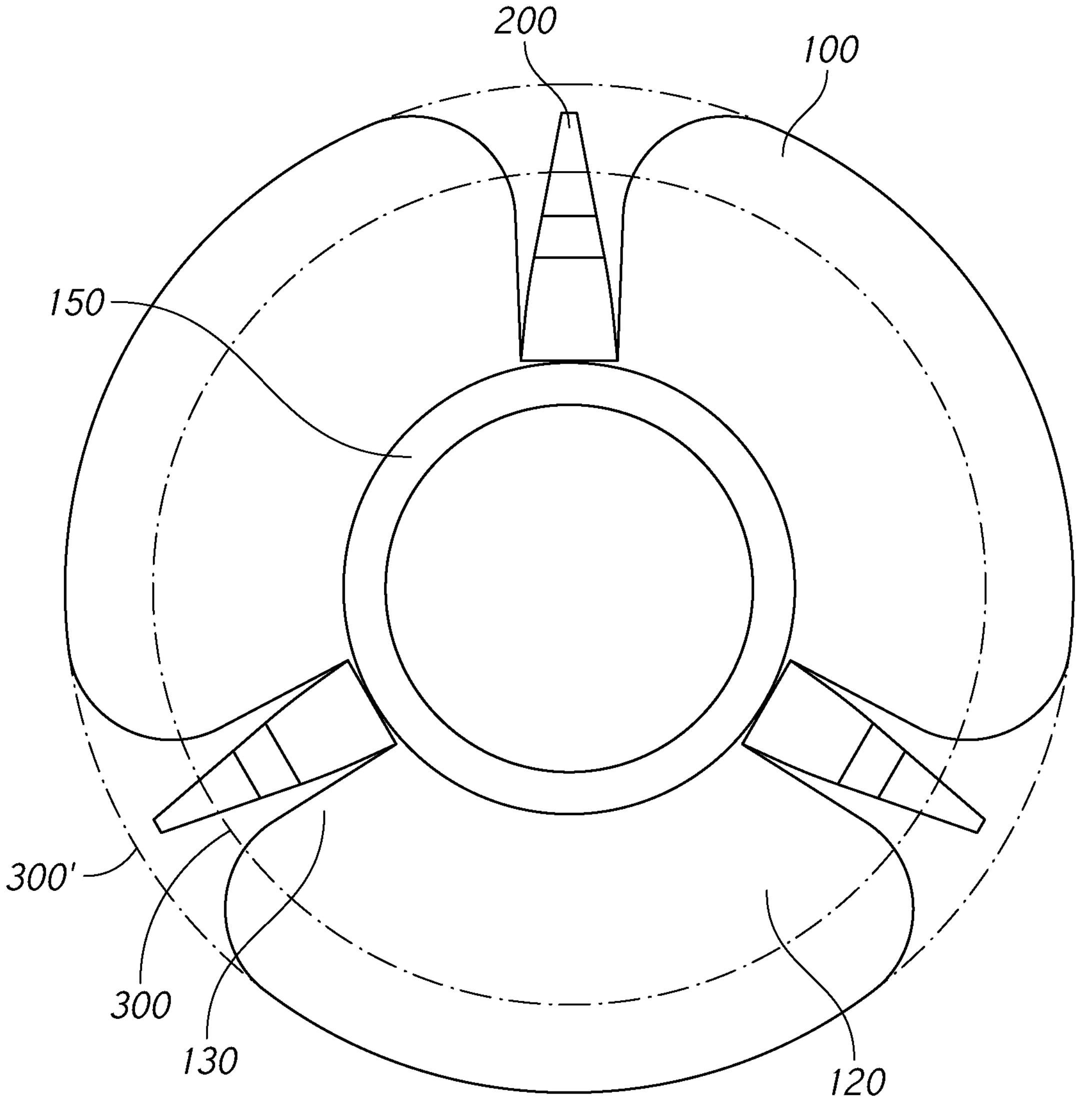

FIG. 74C illustrates the continued expansion event with fluid filling the majority of the balloon 100 and expanding the balloon structure 100 to contact nearly all of the diseased vessel 300. During this phase of the expansion, the pressure is still low (below 2 atmospheres) but enough to force the strips 200 into a perpendicular orientation. Note the circle 300 illustrating an occlusion with a 2 mm inner diameter is shown below the expanded balloon surface 100. The balloon 100 in this phase is behaving like that of plain balloons with minimal serration effects occurring. The rigidness of the strips 200 and the tightly bound disease limit the serrated strips 200 from penetrating the wall. The balloon 100 is able to push the diseased vessel outward while the lobes 120 of the expanding balloon 100 between the strips 200 continue to align the strip 200 upward and perpendicular to the vessel wall.

The balloon 100 can exert a pressure on the vessel wall. The pressure can be low, such as under 2 atm. The diameter of the vessel can expand, in some methods. The expanded diameter can be slight. The circles illustrate the vessel diameter 300 from FIG. 74B and the expanded vessel diameter 300'. The vessel diameter 300 can be 2 mm and the increased vessel diameter can be greater than 2 mm. The balloon 100 in this phase exerting a pressure on the vessel wall 300' based on the pressure of the fluid within the balloon 100. The balloon 100 continues to expand. The fluid can fill the majority of the balloon 100. The lobes 120 continue to expand. The surface area of the lobes 120 in contact with the vessel wall increases. The lobes 120 contact nearly all of the vessel wall 300'. The lobes 120 contact the vessel wall 300' except for the area near the strips 200. The lobes 120 contact nearly the entire circumference.

The pressure in the balloon 100 can be low, less than 0.5 atm, less than 1 atm, less than 2 atm. The pressure in the balloon 100 can push the strips 200 to the desired orientation. The pressure can rotate the strips 200 to the perpendicular orientation. The fluid fills areas of less resistances. The fluid fills the lobes 120. The lobes 120 act on the strips 200, thereby rotating the strips 200 to the perpendicular orientation.

While not to be limited by a theory, the portion of the lobe 130 can be fully expanded against the sides of the strip 200. The portion 130 can expand from a location between the surface of the strip 200 and the inner member of the balloon catheter 150 to a location beside the inner facing surfaces of neighboring strips 200. The portion 130 can expand to be against the strip 200. The portion 130 can apply a force or torque on the strip 200 to orient the strip 200 perpendicularly. Two adjacent lobes 120 can apply a force to the strip 200. The two adjacent lobes 120 can apply a pressure to orient the strip 200 perpendicularly. During this phase of the expansion, the pressure of the fluid can be under 2 atm. The pressure can be sufficient to rotate the strip 200. The strip 200 rotates from the transverse orientation shown in FIG. 74A to the perpendicular orientation in FIG. 74C. The balloon 100 can include one or more intermediate orientations as the strip 200 rotates.

In some embodiments the strip 200 side walls are sloped, with the base wider than the top. FIG. 15 schematically illustrates an example of the sloped side walls. The strip 200 can include strip-facing surface width $W_B$ which slopes to the radially outwardly facing surface width $W_U$. There can be an angle that is equal to or less than about 90 degrees that defines the slope from the strip-facing surface width $W_B$ to the radially outwardly facing surface width $W_U$. There can be a constant slope angle or a plurality of different angles, such as more than a single slope angle such as a double, triple or more bevel. In some embodiments, there can be a series of steps at different heights where the width transitions to a narrower width toward the unhoned tip. The sloped side walls of the strip 200 can be adjacent to the lobes 120. The lobes 120 apply a pressure to the sloped side walls of the strip 200. The lobes 120 apply a pressure to the sloped side walls to rotate the strips 200 during inflation, as described herein. This slope of the side walls 200, in combination with the expansion of the portion 130 of the lobes 120 adjacent to the strips, allows for more effective control of the perpendicular orientation of the strips 200. The lobes 120 apply a pressure to the sloped side walls to maintain the perpendicular orientation during inflation, as described herein. The lobes 120 can apply pressure to the sides of the sloped surface of the strip 200. The lobes can also apply pressure to the sides of the unhoned tip. The lobes 120 can bulge out around the profile the strip 200. The lobes 120 can bulge out above the unhoned tip. With the lobes 120 bulging out in the regions above the strip, the base of the strip is more effectively positioned into the optimized perpendicular orientation. The sloped side walls can be considered another element that enable the strip 200 to be perpendicular. The lobes 120 can expand in and around the tip of the strip to help maintain the perpendicular orientation. In some embodiments, the two side walls of a single strip 200 can have the same slope. The side walls can experience the same loads from adjacent lobes 120. The lobes 120 can reach an equilibrium based on the sloped side walls 100. As the lobes 120 extend up the sloped side walls, the lobes 120 steady the strip in a perpendicular orientation.

The pressure can be sufficient to slightly expand the vessel wall from 300 to 300'. The vessel wall 300' can allow the strips 200 to have the perpendicular orientation. The strips 200 may be positioned inward from the vessel wall 300'. In some methods, the unhoned tip of the strip 200 does not contact the vessel wall 300'. In some methods, there is no serration effect or minimal serration effect in the position of the strips 200 shown in FIG. 74C. In this position, the unhoned tip may not touch the vessel wall 300'. The rigidness of the strips 200 along with the hardness of the disease can limit or prevent penetration into the vessel wall 300'. The vessel wall 300 can allow for slight expansion under low pressure from 300 to 300'. The vessel wall 300' can be tightly bound. The vessel wall 300' can be calcified or diseased, thereby limiting the penetration depth of the strip 200. The balloon 100 is able to slightly expand the diseased vessel outward under low pressure. The vessel wall expands to 300'. The lobes 120 of the balloon 100 push against the vessel wall to expand the vessel wall 300'. The lobes 120 of the balloon 100 continue to align the strips 200 between the lobes 120. The lobes 120 of the balloon 100 continue to align the strips 200 perpendicularly. The lobes 120 of the balloon continue to align the strips 200 radially outward from the inner member of the balloon catheter 150.

The strips 200 can be attached to an outer surface of the balloon 100. The strips 200 can have one or more layers overlapping the strips 200. The strips 200 can be bonded to the surface of the balloon 100. The strips 200 are not contained in a rigid structure. The strips 200 are free to rotate as the balloon 100 expands. The strips 200 are delivered in a flattened, rotated state. The strips 200 undergo rotation as the balloon 100 expands. The strips 200 undergo rotation as the balloon 100 deflates. The strips 200 can be considered self-righting. The strips 200 can be considered self-laying down. The strips 200 rotate to the proper orientation during use. The strips 200 rotate to the proper orientation during deflation. The lobes 120 provide repeatable and predicable orientation of the strips 200.

Figure 74D:
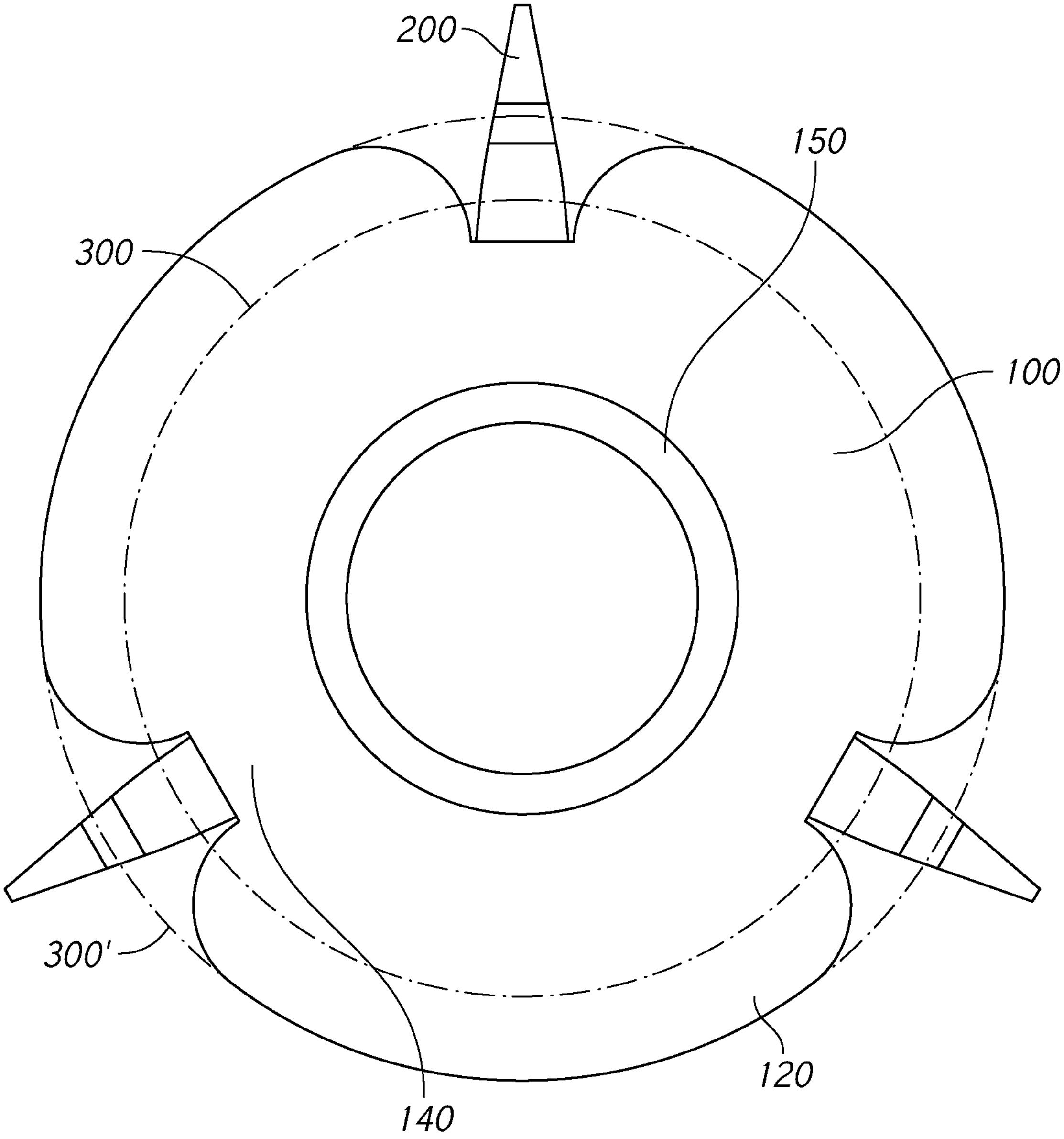

FIG. 74D illustrates the continued expansion event with pressure of the balloon at atmospheres of between 2 and 4. During this phase of the expansion, the pressure exerts a greater force at the base of the strips 200 while still aiding the strips 200 to maintain their perpendicular orientation. Note the second ring 300' is a circle illustrating a penetration into tissue with a 3 mm inner diameter. The balloon in this phase can be producing serrated lines through the intimal tissue and into the medial plane. At this phase, the physician can hold the balloon 100 for 60 or more seconds to allow the serrated lines to seat and initiate the serration effect as described herein.

With the serrated elements on the strips 200 being pushed into the vessel, a series of lines of weakness is formed along the serrated lines. The serrated lines have spaced between the microperforations. The serrated lines are not continuous. The serrated lines barely disrupt the diseased vessel wall. The lobes 120 exert a pressure on the vessel wall 300'. The lobes 120 are in contact with a significant majority of the circumference of the vessel. The lobes 120 push on the vessel wall 300'. As the lobes 120 expand the vessel 300', the lobes 120 generate a tensile force under the regions where the serrated elements have penetrated the tissue. This stretching of the vessel enables the vessel lumen to expand. A linear dissection line is produced as the expansion of the diseased vessel increases. The lumen gain is with minimal arterial injury. The weakened tissue more easily gives to the pressure of the balloon 100 and the lobes 120 and yields. The balloon 100 is more easily able to push the diseased vessel outward, the serrated elements 200 form serrations which slowly combine into a linear dissected line pulling away from the serrated elements 200 and gently expanding the arterial diameter. The lobes 120 are pushing the vessel, thereby creating a tensile force. Under the stretching of the vessel due to the lobes 120, the permanent linear dissection line can be created. Under the stretching of the vessel due to the lobes 120, there can be permanent lumen gain. Under the stretching of the vessel due to the lobes 120, the low pressure force can prevent or reduce arterial injury. The lobes 120 can stretch the vessel to cause the vessel to open and the permanent linear dissection line to be created. The tearing along the microperforations can be significantly caused by the lobes 120. The lobes 120 can exert a tensile force to facilitate the tearing.

The balloon continues to fill under increased pressure. The pressure inside the lobes 120 rises. While the lobes 120 were around 2 atm or less in the previous phase, the pressure increases. The pressure can increase gradually from 2 atm to up to 4 atm, for instance up to 2 atm, at least 2 atm, 2.5 atm, up to 2.5 atm, at least 2.5 atm, not more than 2.5 atm, 3 atm, up to 3 atm, at least 3 atm, not more than 3 atm, 3.5 atm, up to 3.5 atm, at least 3.5 atm, not more than 3.5 atm, 4 atm, up to 4 atm, at least 4 atm, not more than 4 atm, or any range of two of the foregoing values. The lobes 120 can be fully expanded against the surface of the vessel wall 300'. The vessel wall can be diseased, thereby resisting further expansion of the vessel wall 300'. The vessel wall can be diseased, thereby allowing minimal expansion from the lobes 120 of the vessel wall 300' of less than 0.5 mm, less than 1.0 mm, less than 1.5 mm, less than 2.0 mm of any range of two or more of the foregoing values. The balloon 100 can cause minimal dissection. The balloon 100 can expand the vessel wall 300' very slightly. The serrated lines, acting under the tensile force of the lobes 120, cause a bigger growth in the vessel wall diameter. The permanent linear dissection line which occurs later in the procedure allow for increased lumen gain. The balloon expansion under low pressure at this stage does little to expand the vessel wall, since the permanent linear dissection line have not been formed.

The fluid can fill the balloon area with least resistance. There is a portion of the balloon under the strip 200. This portion 140 can be inflated after the lobes 120, in most methods. The lobes 120 present less resistance to filling, in most situations. There is a balance between which area exerts a greater resistance to flow. In most instances, the portion 140 presents less of resistance than further expansion of the vessel wall 300'. The portion 140 can be inflated under increased pressure from the fluid. The increased pressure overcome the inertial force or rigidity of the strip 200 to initiate the node of penetration into the intimal tissues of the vessel wall. The pressure of the fluid of the balloon 100 exerts a greater force. The pressure exerts a force on the base of the strips 200. The pressure exerts a force after the strips 200 are in their perpendicular orientation.

The strip 200 gradually pushes outward. The strips penetrate the intimal tissue. The strip 200 expands radially outward relative to the inner member of the balloon catheter 150. The strips penetrate the internal elastic lamina. The strips 200 are disposed between the lobes 120. The lobes 120 facilitate the perpendicular orientation. The strips 200 maintain their orientation relative to the lobes 120 during expansion. The lobes 120 guide the strips 200 during expansion. The strip 200 moves radially outward. The strip 200 moves radially outward from the inner member of the balloon catheter 150. The portion 140 of the balloon 100 under the base of the strip 200 continues to expand.

The vessel wall 300' does not expand, in most methods, during this phase. The vessel wall 300' may not expandable at these low pressures, for instance under 4 atm. The low pressure may not be sufficient to cause further expansion of the diameter of the vessel wall 300'. On balance, the area of least resistance can be filling the portion 140 at the base of the strip 200.

While not to be bound by a theory, the area 140 under the strip 200 is able to expand due to many considerations. The area 140 is small relative to the lobes 120 that have already been filled. The geometry of the area 140 of the balloon 100 under the base can facilitate movement of the strip 200. The strip can have a thin base. Referring back to FIG. 15, the base width Wb can be many factors smaller than the base length Lb. The area 140 of the balloon corresponds to the surface area of the base.

While not to be bound by a theory, the area 140 can act to generate a force to move the strip when pressure is increased. The area 140 can be thin and long compared with the lobes 120. The pressure in the area 140 under the strip 200 can cause movement outward as the pressure rises. The increase pressure of the fluid must go somewhere and the area of least resistance is the area 140 of the balloon 100 under the base of the strip 200. There are many factors that contribute to the outward movement of the strips 120. The lobes 120 are filled and act along the sloped sides to maintain the perpendicular direction. The forces of the balloon 100 can provide directional guidance for the outward movement of the strips 200. There is a pressure change from the mechanics of the vessel wall 300'. The reason for the change in pressure distribution is due to the fact that the elevated elements of the strip 200 have induced nodes of separations in the intima. These nodes of separation allow the unhoned tip of the strip to have a place to go. There is low pressure from the vessel wall pushing back on the strip 200. This low pressure from the vessel wall 300' in combination with the pressure from the lobes 120 of the balloon 100 can allow the strips 200 to move radially outward, further into the vessel wall. The strips 200 can rapidly accelerate toward the medial layer when the initial resistance from the vessel wall is overcome by node formation. The low pressure of the balloon 100, such as pressures under 4 atm, is sufficient to drive the serration element of the strip 200 into the vessel wall after node formation. The interaction between the strip 200 and the vessel wall 300' is dynamic, changing over time under sustained pressure. The design and method of the balloon encourages the unhoned tip to penetrate under the increased pressure on the vessel wall by the lobe 120. The elevated strips extend into the tissue at low pressure. The balloon 100 can create a strain under the strip 200 to encourage outward movement.

The strip 200 can be pliable, yet durable and rigid. While not to be bound by a theory, the fluid pressure must overcome the rigidity of the strip 200 to push the strip radially outward into diseased tissue. The pressure must overcome the inertia of the static strip 200 to penetrate the disease. In most methods, the pressure can be 4 atm or less. The strip 200 can be designed to move radially outward at this low pressure.

The vessel wall 300' is illustrated. The vessel wall 300' can have any diameter. The vessel wall 300' can have a greater cross-sectional dimension than the initial vessel wall 300. The vessel wall 300' can be slightly expanded under the low pressure. The pressure can be less than 4 atm. This low pressure can be insufficient to cause significant dilation of the vessel wall 300'. In some methods, the vessel wall 300 can be expanded 0.25 mm, 0.50 mm, 0.75 mm, 1 mm, or any range of two of the foregoing values. In some methods, the vessel wall 300 can be expanded 10%, 20%, 30%, 40%, 50%, or any range of two of the foregoing values. The vessel wall 300 can be slightly expanded to 300' due to the low pressure of the fluid, wherein the pressure is 4 atm or less. The strips 200 can penetrate the intima. The strips 200 can penetrate the internal elastic lamina. The strips 200 can penetrate into the medial tissue.

The strip 200 radially expands to the vessel wall 300'. The tip of the strip 200 can be unhoned. The top view unhoned surface is slightly blunt. The unhoned surface has a width. The width of the unhoned surface is less than the width of the base but can be directly correlated with the slope or slopes of the strip 200. The unhoned surface can be any geometry. In some embodiments, the top or the radially outward facing surface can be rectangular, square, oval, rounded, polygonal, or any other shape having a non-zero width. In some embodiments, an unhoned tip can have a width, for example, that is about 20 nm, 50 nm, 100 nm, 500 nm, 1 μm, 2 μm, 5 μm, 7 μm, 10 μm, 15 μm, 20 μm, 25 μm, and 30 μm, 40 μm, 50 μm, 60 μm, 70 μm, 80 μm, 90 μm, 100 μm, between 5 μm and 30 μm, greater than 30 μm, between 30 μm and 100 μm, or any range of two of the foregoing values, measured at the radially outward facing edge or surface. The unhoned, radially outward facing surface does not include a sharp honed point or edge as described herein. The unhoned, radially outward facing surface has a width that is larger than that of a honed edge. The strip 200 can have a radially outward facing surface that is completely unhoned along its length. The strip 200 can have any feature described herein.

The unhoned surface of the strip 200 contacts the vessel wall 300'. While not to be bound by a theory, the unhoned surface of the strip 200 does not function as a blade. The unhoned surface of the strip 200 is not a honed cutting surface. The unhoned surface of the strip 200 is not sharpened. With honed edges such as blades, the edge applies high pressure with minimal force applied to push the material part. The honed edge cuts through the material from the extremely narrow edge. The effectiveness of the honed edge relates to the sharpness or geometry of the edge. The honed edge separates molecules, such as molecules of a vessel wall. The molecules slip past each other at the honed edge. The narrower in width the edge for honed edges, e.g., the closest it comes to atomic-scale sharpness, the easier the edge cuts through material.

The unhoned radially outward facing surfaces of wedge dissectors can be advantageously slightly blunt. The strip 200 can create serrations, indentations, and/or microperforations in the vessel wall 300'. These serrations, indentations, and/or microperforations in the vessel wall 300' can be desirable rather than making cuts through the luminal wall, such as with a honed surface. While not to be bound by a theory, the serrations, indentations, and/or microperforations in the vessel wall 300' can occur under the influence of many forces. The unhoned radially outward facing surface of the strip 200 can be against the vessel wall 300'. The fluid pressure of the balloon can apply a force to firmly contact the strip 200 with the vessel wall 300'. In some instances, the width of the unhoned surface is too great to penetrate the vessel wall 300' under the influence of the fluid pressure. The pressure can be 4 atm or less. In some instances, the unhoned surface is unable to cut into the vessel wall 300' under pressure at area 140 alone.

The serrations, indentations, and/or microperforations can occur due to, at least in part, the force exert by the lobes 120. While not to be bound by a theory, the lobes 120 exert a force on the vessel wall 300' causing the vessel wall 300' to pull away from the strip 200. In some instances, the vessel wall 300' does not pull apart at the unhoned tip. Rather, the vessel wall 300' pulls apart along the height of the unhoned surface. The mechanics of the expansion of the balloon 100 facilitate the serration by the unhoned surface. The mechanics of the expansion of the balloon 100 allow serrations to form at low pressure, wherein the unhoned surface was unable to penetrate due to pressure on the strip 200 alone.

As described herein, the strip 200 comprises a plurality of wedge dissectors spaced apart along a surface of each strip. The strip 200 does not comprise a longitudinally continuous penetration surface. Rather, the strip comprises discontinuities or spaces between the microperforators. The vessel wall 300' can pull away from the strip 200 only at or near the microperforators. The vessel wall 300' can remain intact at or the discontinuities or spaces between the microperforators. The strip 200 and the balloon thereby create serrations, indentations, and/or microperforations. The serrations, indentations, and/or microperforations can be discontinuous. The serrations, indentations, and/or microperforations pattern can mirror the pattern of the microperforators of the strips 200. Due to crack propagation, the serrations, indentations, and/or microperforations can be slightly larger than the width and length of each microperforator. The vessel wall 300' pulls way from plurality of microperforators of the strip 200 thereby creating serrations, indentations, and/or microperforations. The serrations, indentations, and/or microperforations can be longitudinally oriented. The serrations, indentations, and/or microperforations can be discrete. The serrations, indentations, and/or microperforations can be discontinuous.

The mechanics of creating serrations, indentations, and/or microperforations is a highly complex process. The geometry of the strip 200 can impact the geometry of the resulting serrations, indentations, and/or microperforations. The pressure exerted by the balloon 100 at the lobes 120 can impact the geometry of the resulting serrations, indentations, and/or microperforations. The pressure exerted by the balloon 100 at the area 140 under the base of the strips 200 can impact the geometry of the resulting serrations, indentations, and/or microperforations. The surface of the vessel wall 300' can impact the geometry of the resulting serrations, indentations, and/or microperforations. While not to be bound by a theory, the serrations, indentations, and/or microperforations can be created by the vessel wall 300' separating at an atomic level along the height of the microperforator under the influence of pressure by the balloon 100 both on the vessel wall 300' and on the strip 200.

The strip 200 expands radially outward as serrations, indentations, and/or microperforations form in the vessel wall 300'. As the vessel wall 300' opens, there is less pressure preventing the outward expansion of the strip 200. The balloon 100 does not have to disturb the entire lesion. Rather, the balloon disturbs a very small area near the microperforators to create serrations, indentations, and/or microperforations in the lesion. The strip 200 penetrates into serrations, indentations, and/or microperforations formed in the lesion beyond the vessel wall 300'. The strip 200 penetrates into serrations, indentations, and/or microperforations as the serrations, indentations, and/or microperforations are formed. As the vessel wall 300' opens into serrations, indentations, and/or microperforations due to the mechanics of the balloon 100 and the strip 200, the area 140 of the balloon 100 under the strip has less resistance to expansion. The serrations, indentations, and/or microperforations expand deeper into the vessel wall 300' under the influence of the pressure of the balloon 100. The pressure of the balloon 100 can be 4 atm or less.

The vessel wall 300' is illustrated in relation to the strip 200. The strip 200 can penetrate a distance beyond the vessel wall 300' illustrated in the dashed circle. In some methods, the strips 200 can extend 0.25 mm, 0.50 mm, 0.75 mm, 1 mm, or any range of two of the foregoing values. In some methods, the strips 200 can be extend a percentage of the diameter 300' of the vessel wall such as 10%, 20%, 30%, 40%, 50%, or any range of two of the foregoing values.

The balloon 100 and the strips 200 can produce a serrated line. The lines can be discontinuous, at least initially. The lines can be discrete perforations into the lesion and/or vessel wall, at least initially. The lines can mirror the spacing and separation of the microperforators on the strip 200, at least initially.

The serrated lines can be through the intimal tissue. The serrated lines can be into the medial plane. While not to be bound by a theory, the serrations, indentations, and/or microperforations do not occur instantaneously. For a honed surface, the edge instantly cuts the surface. For the complex interactions between the unhoned surface of the strip 200 and the pressure of the balloon 100, the penetration may not be instantaneous. The pressure of the balloon 100 may cause a tearing along the surface height of the wedge dissector, in some methods. The pressure of the balloon 100 causes slow outward movement of the strip 200 due to the pressure at the portion 140 under the strip 200. The serrations, indentations, and/or microperforations slowly creep through the intimal tissue. The serrations, indentations, and/or microperforations slowly creep through into the medial plane. In some methods, the creation of serrations, indentations, and/or microperforations takes a period of time. This period of time can be 20 seconds, at least 20 seconds, greater than 20 seconds, 30 seconds, at least 30 seconds, greater than 30 seconds, 40 seconds, at least 40 seconds, greater than 40 seconds, 50 seconds, at least 50 seconds, greater than 50 seconds, 60 seconds, at least 60 seconds, greater than 60 seconds, or any range of two of the foregoing values. The period of time can be sufficient to allow the strip 200 to seat within the medial layer. The period of time can be sufficient to allow the serrations, indentations, and/or microperforations to extend to medial layer.

While not to be bound by a theory, the serrations, indentations, and/or microperforations can be described as initially being discrete and then merging. However, due to mechanics of the diseased vessel wall, this may not occur in two stepwise phases. Rather, two or more serrations, indentations, and/or microperforations may merge into a line at any time. The serrations, indentations, and/or microperforations may merge at the intimal layer. The serrations, indentations, and/or microperforations may merge at the medial layer. The serrations, indentations, and/or microperforations merge under the dynamics of crack propagation. Crack propagation is a highly complex process based on the balances of energies. The crack will propagate between discrete serrations, indentations, and/or microperforations when the energy overcomes the resistance of the lesion or tissue. The line will form between discrete serrations, indentations, and/or microperforations if the energy released by the growth of the crack is greater than the energy required to create the crack. The propagation can occur under the dynamic loading of the balloon 100. The propagation can occur under the influence of pressure. The propagation can occur under the influence of time. The mechanics of the expansion of the balloon 100 facilitate subsequent crack propagation.

The balloon can be maintained at low pressure, such as 4 atm or less. The serrations, indentations, and/or microperforations can be formed. The strip 200 can be seated within the serrations, indentations, and/or microperforations. The strip 200 can reach an equilibrium. The strips 200 cannot expand further under the pressure of the balloon 100. The strip 200 can be held at this low pressure for a period of time. The propagation can be time dependent. The strip 200 can be held to allow a line of weakness or crack to be formed along the serrated line.

The strips 200 can be longitudinally oriented along the surface of the balloon 100. The strips 200 can be radially spaced along the surface of the balloon 100. The strips 200 can be equidistant. The strips 200 can be circumferentially spaced such that serrated lines are sufficiently separated. The spacing between serrated lines can prevent or reduce circumferential crack propagation. The spacing between adjacent serrations, indentations, and/or microperforations in a longitudinal direction is less than the spacing between adjacent serrations, indentations, and/or microperforations in a circumferential direction. The spacing between adjacent serrations, indentations, and/or microperforations in a circumferential direction can be a multiple, such as 2× greater, 5× greater, 10× greater, 15× greater, 20× greater, or any range of two of the foregoing values, of the spacing in a longitudinal direction.

The shape of the microperforators on the strip 200 can facilitate crack propagation. The unhoned surface can be rectangular. The unhoned surface can have a greater length than width. The microperforators can have discrete spaces therebetween along the strip 200. The serrations, indentations, and/or microperforations can mirror this shape of the strip 200. The serrations, indentations, and/or microperforations can have a longer length than width. The serrations, indentations, and/or microperforations can have discrete spaces therebetween. While not to be bound by a theory, the serrations, indentations, and/or microperforations may more easily propagate in the longer direction, for instance along the length rather than along the width of the serrations, indentations, and/or microperforations.

The orientation of the strips 200 relative the balloon 100 can facilitate longitudinal crack propagation. The orientation of the strips 200 relative the balloon 100 can reduce or prevent circumferential crack propagation. The orientation of the strips 200 relative the balloon 100 can allow for repeatable and predictable crack formations. The orientation of the strips 200 relative the balloon 100 can produce lines of cracks along length of the balloon 100. The shape of the microperforators on the strip 200 can dictate the direction of crack propagation. The shape of the serrations, indentations, and/or microperforations can dictate the direction of crack propagation.

While not to be bound by a theory, the serrations, indentations, and/or microperforations weaken the tissue. The weakened tissue eventually gives to the pressure of the balloon 100. The weakened tissue gives under the influence of time. The weakened tissue allows the crack to propagate along the serrations, indentations, and/or microperforations. The serrations, indentations, and/or microperforations slowly combine into a linear dissected line. The serrations, indentations, and/or microperforations are initially formed by the strip 200. The strip 200 does not act as a blade to form the linear dissected line. Rather, the linear dissected line is formed only through crack propagation along the series of serrations, indentations, and/or microperforations, in some embodiments. The crack propagates longitudinally. The balloon 100 can create one longitudinal crack, corresponding to one strip 200. The balloon 100 can create two longitudinal cracks, corresponding to two strips 200. The balloon 100 can create three longitudinal cracks, corresponding to three strips 200. The longitudinal cracks allow the vessel diameter to be expanded outward. As the crack propagates, the balloon 100 may be able to more easily push the vessel wall outward.

Figure 74E:
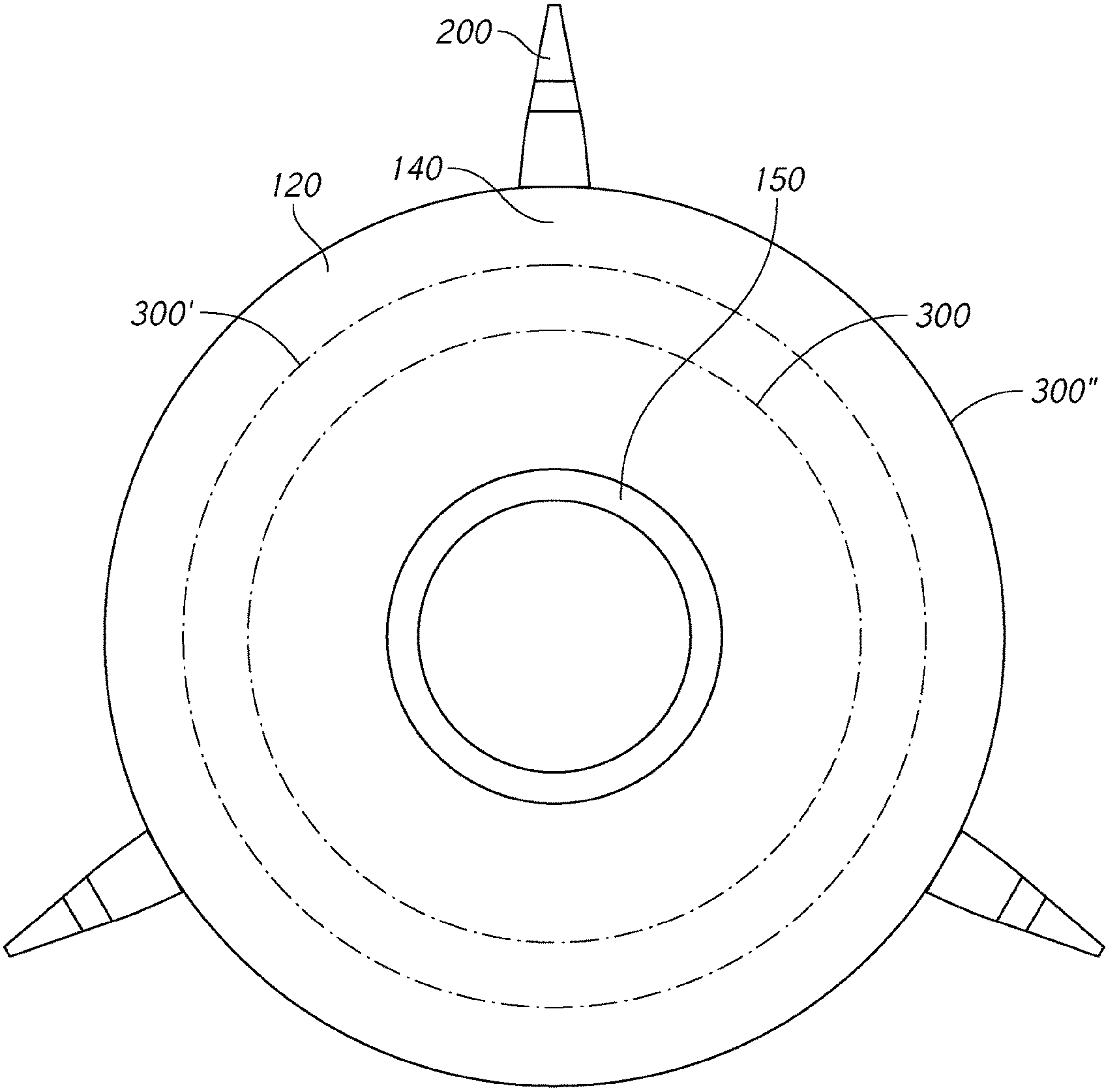

FIG. 74E illustrates the final resting balloon in the fully expanded diameter typically at atmospheres of 4 or more. During this phase of the expansion, the pressure exerts a greater force at the base of the strips 200 while still aiding the strips to maintain their perpendicular orientation. Note the second ring is a circle illustrating a penetration into tissue with a 3 mm inner diameter. The balloon 100 in this phase is producing serrated lines through the intimal tissue and into the medial plane. At this phase, the physician can hold the balloon 100 for 60 seconds to allow the serrated lines to seat and initiate the serration effect as described herein. With the serrated elements 200 being pushed into the vessel, a series of lines of weakness is formed along the serrated lines. The weakened tissue more easily gives to the pressure of the balloon and yields. The balloon 100 is more easily able to push the diseased vessel outward, the serrated elements 200 form serrations which slowly combine into a linear dissected line pulling away from the serrated elements and gently expanding the arterial diameter.

The balloon continues to fill. The pressure inside the lobes 120 rises. While the lobes were around 4 atm or less in the previous phase, the pressure increases. The pressure can increase gradually from 4 atm, for instance up to 4 atm, at least 4 atm, 4.5 atm, up to 4.5 atm, at least 4.5 atm, not more than 4.5 atm, 5 atm, up to 5 atm, at least 5 atm, not more than 5 atm, 5.5 atm, up to 5.5 atm, at least 5.5 atm, not more than 5.5 atm, 6 atm, up to 6 atm, at least 6 atm, not more than 6 atm, 7 atm, up to 7 atm, at least 7 atm, not more than 7 atm, 8 atm, up to 8 atm, at least 8 atm, not more than 8 atm, 9 atm, up to 9 atm, at least 9 atm, not more than 9 atm, 10 atm, up to 10 atm, at least 10 atm, not more than 10 atm, 11 atm, up to 11 atm, at least 11 atm, not more than 11 atm, 12 atm, up to 12 atm, at least 12 atm, not more than 12 atm, between 4 atm and 6 atm, or any range of two of the foregoing values.

The lobes 120 can be fully expanded against the surface of the vessel wall. The vessel wall can expand from 300' in FIG. 74D to 300" in FIG. 74E. The one or more linear dissected lines can be formed in the vessel wall 300". The one or more linear dissected lines can allow further expansion of the vessel wall from 300' to 300". In some methods, the vessel wall 300' can be expanded 0.25 mm, 0.50 mm, 0.75 mm, 1 mm, or any range of two of the foregoing values to reach the vessel wall 300". In some methods, the vessel wall 300' can be expanded 10%, 20%, 30%, 40%, 50%, or any range of two of the foregoing values to reach the vessel wall 300". The vessel wall 300' can be slightly expanded due to the higher pressure of the fluid, wherein the pressure can be greater than 4 atm.

The pressure of the fluid exerts a force on the area 140 under the base of the strips 200. The pressure aids in maintaining the perpendicular orientation of the strips 200. The surface tension of the lobes can aid in maintaining the perpendicular orientation of the strips 200. The pressure allows the strips 200 to further expand outward from the from the inner member of the balloon catheter 150. This further expansion of the strips 200 can facilitate crack propagation. The expansion of the balloon 100 and the crack propagation are synergistic. As the balloon 100 expands, the linear dissected line lengthens by connecting more serrations, indentations, and/or microperforations. As the serrations, indentations, and/or microperforations connect to form a linear dissected line, the balloon 100 can further expand. The linear dissected line can be formed through the intimal tissue and into the medial plane.

The linear dissected line slowly creeps through the intimal tissue. The linear dissected line slowly creeps through into the medial plane. In some methods, the creation of the linear dissected line takes a period of time. This period of time can be 20 seconds, at least 20 seconds, greater than 20 seconds, 30 seconds, at least 30 seconds, greater than 30 seconds, 40 seconds, at least 40 seconds, greater than 40 seconds, 50 seconds, at least 50 seconds, greater than 50 seconds, 60 seconds, at least 60 seconds, greater than 60 seconds, or any range of two of the foregoing values. The period of time can be sufficient to allow the expanded strips 200 to seat within the tissue layers. The period of time can be sufficient to allow the linear dissected line to extend to medial layer. The period of time can be sufficient to allow the serrated lines to seat and initiate the serration effect as described herein.

While not to be bound by a theory, the serrated line weakens the tissue. The weakened tissue gives to the pressure of the balloon 100. The weakened tissue gives under the influence of time. The weakened tissue allows the crack to propagate along the serrated line deeper until the medial layer is reached. The serrations, indentations, and/or microperforations slowly combine into a linear dissected line, and the serrated line slowly deepen through the layers of the tissue. The serrations, indentations, and/or microperforations are initially formed by the strip 200. The linear dissected line is formed by means of crack propagation along the series of serrations, indentations, and/or microperforations which deepen over time and as the balloon 100 exerts more pressure. As the crack propagates, the balloon 100 may be able to more easily push the vessel wall outward thereby deepening the serrated line. The crack propagates longitudinally between the serrations, indentations, and/or microperforations.

While not to be bound by a theory, the crack deepens as the balloon 100 expands. The crack deepens as the pressure of the balloon 100 is increased. The crack deepens as the strip 200 fully seats within the serrations, indentations, and/or microperforations. The crack deepens as the strip 200 wedges more tissue apart along the height of the microperferator. The crack deepens as the balloon 100 exerts a greater pressure of the vessel wall 300" thereby pulling the vessel wall away from the strip 200. While not to be bound by a theory, the crack propagation is spaced from the unhoned tip. The tip itself doesn't not further deepen the crack. Rather, the tissue tears along the length of the microperforator to deep the crack. The crack is deeper than the height of the microperforator.

The balloon 100 can facilitate vascular remodeling as described herein. The vessel wall can be expanded to 300". In FIG. 74B, the vessel wall 300 was contracted due to the diseased state. For instance, extensive stenosis may have constricted the vessel thereby preventing flow. Even with the serrations, indentations, and/or microperforations formed, the vessel wall 300' can still be constricted. The vessel wall 300" can be expanded due to the serrated line formed by the joining of adjacent serrations, indentations, and/or microperforations under crack propagation. The serrated line is predictably formed by the balloon 100. The balloon 100 repeatedly forms the same pattern of serrations, indentations, and/or microperforations based on the shape of the strips 200. The balloon 100 repeatedly forms the same pattern of one or more serrated line based on the shape of the strips 200. The balloon 100 repeatedly forms longitudinal serrated lines.

The strips 200 only disturb a small portion of the circumference of the vessel wall. Compared to the circumference of the vessel wall, the strips 200 have a small width. The width of the strip 200 can be a percentage of the of the circumference of the vessel wall, such as 1%, 2%, 3%, 4%, 5%, 6%, 7%, 8%, 9%, 10%, 15%, less than 5%, less than 10%, or any range of two of the foregoing values.

The width of the lobe 120 can be a large percentage of the of the circumference of the vessel wall, such as 110%, 111%, 112%, 113%, 114%, 115%, 116%, 117%, 118%, 119%, 120%, less than 120%, less than 115%, more than 110% or any range of two of the foregoing values. With the strips 200 being pushed into the vessel, a series of deep and long crack are formed. The crack extends to the medial layer. The crack is relatively thin corresponding generally to the width of the strip 200. The crack is relatively long corresponding generally to the length of the strip 200. The crack is relatively deep, extending deeper than the height of the strip 200. The crack extend beyond the unhoned surface. The serrations, indentations, and/or microperforations are formed and slowly combined into the linear dissected line over a time period of about 60 seconds, 65 seconds, 70 seconds, 75 seconds, 80 seconds, 85 seconds, 90 seconds, 95 seconds, 100 seconds, 115 seconds, 110 seconds, 115 seconds, 120 seconds, 125 seconds, 130 seconds, 135 seconds, 140 seconds, 145 seconds, 150 seconds, 155 seconds, 160 seconds, 165 seconds, 170 seconds, 175 seconds, 180 seconds, more than 60 seconds, more than 120 seconds, less than 180 seconds, or any range of two of the foregoing values.

The serrations, indentations, and/or microperforations pull away from the strip 100 overtime and under increased pressure by the balloon, thus forming a linear dissected line. The linear dissected line allows for the low pressure expansion of the vessel wall 300". The balloon 100 can be deflated. The balloon 100 can be removed from the vessel. The vessel wall 300" remains expanded. The linear dissected line allows for positive vessel remodeling. The linear dissected line allows for substantial lumen gain. The linear dissected line allows for reduction in recoil. As described herein, the vessel experiences far less recoil than expected. As described herein, the vessel is remodeled back to the pre-diseased state, thereby increasing flow.

In some methods, one or more steps can be reversed. The balloon 100 inflation and deflation can be bi-directional. The balloon 100 can go from the inflate state to the deflated state. The balloon 100 can go from the deflated state to the inflated state. The strip rotation from perpendicular to transverse can be bi-directional. The strip 200 can go from the perpendicular orientation to the transverse orientation. The strip 200 can go from the transverse orientation to the perpendicular orientation. By inflating and deflating the balloon 100, the strip 200 rotates in both direction.

FIG. 74E illustrates the final resting balloon 100 with the fully expanded diameter. The strips 200 are maintained in their perpendicular orientation. The balloon 100 produced serrated lines through the intimal tissue and into the medial plane. The physician held the balloon 100 for a period of time, including 5 seconds, 10 seconds, 20 seconds, 30 seconds, 40 seconds, 50 seconds, 60 seconds, 120 seconds or any range of two or more of the foregoing values to allow the serrated lines to seat and initiate the serration effect. The balloon 100 can push the diseased vessel outward. The serrations slowly combine into the linear dissected line and pull away from the serrated elements. The balloon 100 gently expands the arterial diameter.

The balloon 100 can be inflated typically at atmospheres of 4 or more. The pressure inside the lobes 120 reaches a maximum pressure. The maximum pressure can be 4 atm, 4.5 atm, 5 atm, 5.5 atm, 6 atm, 7 atm, 8 atm, 9 atm, 10 atm, 11 atm, 12 atm, between 4 atm and 6 atm, between 4 atm and 8 atm, or any range of two or more of the foregoing values. The lobes 120 can be expanded against the surface of the vessel wall 300", thereby urging the wall outward. The vessel wall 300" is expanded. The dissected lines facilitate lumen gain and vascular remodeling, as described herein. The expansion of the balloon 100 and the crack propagation function together to allow for vessel expansion.

The balloon 100 can begin to deflate. The balloon 100 can deflate from the maximum pressure. The pressure can gradually decrease over a period of time, including 5 seconds, 10 seconds, 20 seconds, 30 seconds, 40 seconds, 50 seconds, 60 seconds, or any range of two or more of the foregoing values. The decreased pressure can be 4 atm or less. The balloon 100 can deflate in a similar manner as shown in FIG. 74D. The vessel wall can remain at 300" during deflation. The vessel wall 300" can permanently retain the expanded diameter. The vessel wall may experience very slight recoil, which is significantly less than traditionally angioplasty. The recoil effect is dampened due to the permeant linear dissected lines created by the balloon 100. The linear dissected lines create segments of the vessel wall 300". The segments are separated by the lines to the medial layers. These segments are less likely to recoil into the smaller diameter 300' or 300.

The decreased pressure within the balloon 100 exerts a lesser force at the base of the strips 200. Even at lower pressures, the strips 200 can maintain their perpendicular orientation. The pressure can decrease to between 2 atm and 4 atm. The serrated elements on the strips 200 retract from the permeant linear dissected lines. The serrated elements on the strips 200 retract radially inward. The retraction can occur faster than the expansion. The expansion can be slowed to allow the serrated lines to seat and initiate the serration effect. The retraction can be quicker since the permanent linear dissected lines are created. The serrated elements on the strips 200 easily retract from the expanded vessel wall 300".

The balloon 100 continues to deflate under decreasing pressure. The pressure inside the lobes 120 falls. The lobes 120 can decrease to about 2 atm. The pressure can decrease gradually from 4 atm to 2 atm, such as deceasing to 2 atm, 2.5 atm, 3 atm, 3.5 atm, 4 atm, or any range of two or more of the foregoing values. The lobes 120 can deflate from their position against the surface of the vessel wall 300". In some methods, the lobes 120 and the portion 140 under the strips 200 deflate about equally. In some methods, the lobes 120 deflate slightly before the portion 140 under the strips 200. In some methods, the portion 140 under the strips 200 deflates slightly before the lobes 120. The strips 200 can maintain their perpendicular orientation during a portion of the deflation. The lobes 120 can be positioned on either side of the strip 200. The lobes 120 can exert a pressure to maintain the perpendicular orientation of the strip 200.

The strip 200 gradually moves inward as the balloon 100 deflates. The strip 200 contract radially relative to the inner member of the balloon catheter 150. The strips 200 retract out from the permeant linear dissected lines. The strips 200 retract out from the internal elastic lamina. The strips 200 are disposed between the lobes 120 during retraction. The strips 200 maintain their orientation relative to the lobes 120 during retraction. The lobes 120 guide the strips 200 during retraction. The strip 200 moves radially inward. The strip 200 moves radially inward toward the inner member of the balloon catheter 150. The portion 140 of the balloon 100 under the base of the strip 200 continues to deflate as the pressure decreases. The vessel wall 300" maintains the expanded state while the balloon 100 deflates. The expansion of the vessel wall 300" can be due to the permeant linear dissected lines. The permeant linear dissected lines reconstruct the vessel to increase flow. The balloon 100 is not needed to support the vessel wall 300" in the expanded state after the permeant linear dissected lines are formed. Further, the permanent linear dissected lines can reduce the need for lumen support such as stents.

The strip 200 can retract into the space between the lobes 120. The balloon can deflate in a similar manner as shown in FIG. 74C. The vessel wall can remain at 300" during deflation. The vessel wall 300" can permanently retain the expanded diameter. In some methods, the vessel wall 300" does not recoil as the balloon 100 deflates. The strip 200 maintain a perpendicular orientation during deflation. The portion 140 of the balloon 100 under the base of the strip 200 is small relative to the lobes 120. The geometry of the area 140 of the balloon 100 under the base can facilitate retraction. The narrow strips 200 can easily fit between the lobes 120 during deflation. The strips 200 can displace fluid toward the lobes 120 during deflation. The strips 200 can retract inward faster than the lobes 120 can deflate. The strip 200 can be designed to move radially inward at the low pressure. In most methods, the pressure can be 4 atm or less when the strips 200 fall below the circumference of the lobes 120. The fluid can fill less than a majority of the balloon 100. The lobes 120 can begin to pull away from the vessel wall 300". The lobes 120 can be deflated such that only a small portion of the circumference contacts the vessel wall 300". The pressure can continue to fall. The pressure can be below 2 atm. The strips 200 can remain in the perpendicular orientation at low pressure.

The pressure in the balloon 100 can continue to fall, less than 0.5 atm, less than 1 atm, less than 2 atm. The low pressure in the balloon 100 can facilitate the folding the strips 200 to the desired orientation. The decreasing pressure can rotate the strips 200 from the perpendicular orientation. The pressure in the lobes 120 continues to decrease. The lobes 120 act on the strips 200 during deflation. The deflation of the lobes 120 can cause rotation of the strips 200 from the perpendicular orientation.

The portion of the lobe 130 against the sides of the strip 200 can deflate. The portion 130 can apply a force or torque on the strip 200 to orient the strip 200 transversely during deflation. Two adjacent lobes 120 can apply a force to the strip 200. The two adjacent lobes 120 can apply a pressure to orient the strip 200 transversely. During this phase of the deflation, the pressure of the fluid can be under 2 atm. The loss of pressure can be sufficient to rotate the strip 200. The strip 200 rotates from the perpendicular orientation shown in FIG. 74C to the transverse orientation in FIG. 74B. The balloon 100 can include one or more intermediate orientations as the strip 200 rotates. This slope of the side walls, in combination with the deflation of the balloon 100, allows for effective control of the orientation of the strips 200. With the lobes 120 deflating in the regions near the strip 200, the strip 200 is effectively positioned into the optimized transverse orientation. The vessel wall 300" can remain expanded during this further deflation of the balloon 100. The balloon 100 and the strips 200 can be out of contact with the vessel wall 300". The strips 200 can fold due in part on the dynamics of deflation of the balloon 100 including the shape of the strips 200 and the lobes 120. The strip 200 can assume a flattened, rotated state when the balloon 100 is deflated. The strip 200 undergoes rotation as the balloon 100 deflates. The strip 200 can be considered self-orienting. The strip 200 rotates to the proper orientation during deflation. The lobes 120 provide repeatable and predicable orientation of the strips 200 during deflation The strip 200 rotates to the transverse orientation as shown in FIG. 74A. The strip 200 returns to a tangential orientation. The strip 200 can be positioned under the wing 110 of the balloon material. As the lobes 120 deflate, the lobes 120 can partially cover the strips 200. The balloon 100 can deflate within the expanded vessel wall 300". This series of illustrations in reverse can show subsequent deflation. The strips 200 rotate during deflation of the balloon 100. The strips 200 return to their delivery or tangential orientation. The strips 200 can be at least partially or fully covered by the balloon 100 after deflation. The strips 200 lie down after deflation. The deflation of the balloon can cause the strips 200 to turn from the perpendicular orientation to the tangential orientation. The strips 200 can rotate within the expanded vessel wall 300".

The balloon 100 can be folded to a low profile. The balloon 100 can include one or more pleats. The number of pleats can correspond to the number of strips 200. The pleats can be designed to at least partially cover the strip 200 when the balloon is deflated. The strip 200 can be disposed between the pleat and a surface of the balloon when the balloon is deflated. The pleat can form the wing 110. The wing 110 can be a portion of the balloon 100 that overlies a portion of the strip 200 when the balloon is deflated. The strips 200 can be at least partially covered by the balloon 100 once the balloon is deflated. The strips 200 can be at least partially covered by the balloon 100 for removal from the vessel. The strips 200 can be at least partially covered by the balloon 100 for movement to another location in the vessel. The balloon 100, in particular the wing 110, can serve as a buffer between the vessel lumen and the strips 200 during any movement within the vessel or retrieval. The balloon 100 can cover the tip of the strip 200. The tip of the strip 200 can be covered to protect the vessel wall during movement or retrieval. The strip 200 can be in a tangential orientation during movement or retrieval. The tangential orientation allows the strips 200 to have a low profile retrieval configuration.

The balloon 100 can be placed at another location within the same vessel. The balloon 100 can be moved in the deflated state. The balloon 100 can be subsequently inflated to create permanent linear dissected lines. The balloon 100 can be redeployed within the same vessel without retrieval. The balloon 100 can be moved longitudinally within the same vessel. The balloon 100 can be rotated within the same vessel. The balloon 100 can create permanent linear dissected lines at two or more locations along the vessel. The balloon 100 can be subsequently deflated and inflated along two or more locations.

In some methods, the permanent linear dissected lines from at a first location and the permanent linear dissected lines from a second location can merge. For instance, the balloon 100 can be shifted longitudinally within a vessel about equal to the length of the strips 200. The balloon 100 can be moved longitudinally but not rotated. The permanent linear dissected lines from the first location can align with permanent linear dissected lines of the second location. The balloon 100 can create permanent linear dissected lines longer than the length of the strip 200 by subsequent deployments. The balloon 100 can be subsequently deflated and inflated to create permanent linear dissected lines of the desired length.

The balloon 100 can be placed at another location within the another vessel. The balloon 100 can be moved to an adjacent vessel. The balloon 100 can be moved to a paired vessel. The balloon 100 can be moved in the deflated state. The balloon 100 can be subsequently inflated to create permanent linear dissected lines. The balloon 100 can reconstruct two or more vessels before retrieval. The balloon 100 can quickly create permanent linear dissected lines at two or more locations.

The balloon 100 can be retrieved from the patient's vasculature. The balloon 100 can be moved through vasculature. The balloon 100 can be moved in the deflated state. The balloon 100 can have a low profile configuration similar to the delivery configuration. The strips 200 can be at least partially covered during retrieval.

FIG. 75 is a semi-log plot of Plain Old Balloon Angioplasty (POBA) and serrated balloon 100 data of flow rate ratio of post/pre-treatment versus pre-treatment radius. This figure illustrates the flow rate ratio of post-treatment and pre-treatment versus the pre-treatment radius. The y-axis is flow rate ratio of post-treatment flow rate to pre-treatment flow rate. The x-axis is the pre-treatment radius in millimeters. The cases were less than 99% pre-treatment stenosis. For very small pre-treatment radius, the flow rate ratio is larger. POBA data is illustrated in blue. The serrated balloon 100 data is illustrated in orange. The POBA had a sample size of 20. The serrated balloon had a sample size of 9. The best fit line is shown for the POBA and the serrated balloon. The graph is a semi-log plot. The serrated balloon produces a higher volume flow rate over POBA. The serrated balloon produces a higher volume flow rate ratio of post-treatment and pre-treatment across all tested pre-treatment radius.

The serrated balloon 100 can have numerous advantages. The serrated balloon 100 can lead to consistently higher flow rates for all vessel sizes. The serrated balloon 100 can lead to increased flow rates. The serrated balloon 100 can increase flow rates after creating the linear dissected line compared with POBA. While not bound by a theory, POBA relies on simple expansion of the vessel wall. POBA increases pressure to force the vessel wall outward. The POBA does not remodel the vessel wall. Rather, the POBA applies a high pressure force that physically pushes the diseased wall outward. With POBA, the vessel recoils when the balloon is removed. This is shown by the resulting flow rate ratio. While POBA increases the flow rate through the vessel, the serrated balloon 100 consistently produces a greater flow rate ratio. The orange best fit line is always above the blue best fit line. For any give pre-treatment radius, the serrated balloon 100 produces a greater flow rate ratio. The greater flow rate ratio can be greater that POBA by a factor of 2, 3, 4, 5, 6, 7, 8, 9, 10 or any range of the foregoing values. For small pre-treatment radius, such as under 0.15 mm, the serrated balloon 100 can increase flow rate ratio up to a factor of 10 compared with POBA.

The serrated balloon 100 can also lead to more predictable results. The flow rate ratio for the serrated balloon 100 for all of the data points is close to the best fit line. The flow rate ratio for POBA has much more variation in the data points. This variation in data points for POBA may be caused by dissections that increase the diameter unexpectedly. POBA are more prone to dissection than serrated balloons 200. POBA creates unpredictable fractures due to high pressure. This variation in data points for POBA may be caused by varying degrees of recoil depending on the state of the vessel. POBA is a simple expansion and contraction. POBA is more prone to recoil that serrated balloons. This variation in data points for POBA may be caused by the temporary nature of POBA. POBA only supports the expanded state of the vessel while the balloon is inflated. POBA does not remodel the vessel in a predictable and permanent way.

The serrated balloon 100 has much less variation in the data points. This low variance for the serrated balloon 100 may be caused by the predictable and repeatable creation of linear dissected lines. The dissected lines can have a narrow width compared to the length. The dissected lines can have a narrow width compared with the circumference of the vessel. The dissected lines can have a narrow width thereby disturbing less of the surface of the vessel wall. The serrated balloon 100 creates predictable dissected lines under lower pressure than POBA. This low variance for the serrated balloon 100 may be caused by less recoil. The vessel is less likely to return to a small diameter or cross-section. The dissected lines provide room for the vessel wall to expand without disturbing the integrity of the diseased portion or plaque. The dissected lines provide flexibility for the vessel to expand under the fluid flow. This low variance for the serrated balloon 100 may be caused by the permanent nature of linear serration line created by the serrated balloon 100. The serrated balloon 100 permanently changes by vessel wall by the addition of one or more permanent and predictable dissected lines. The serrated balloon 100 remodels the vessel in a permanent and predictable manner. The remodeling can lead to less variation in the data points for the serrated balloon 100.

For pre-treatment radius between 0.05 mm and 0.15 mm, the serrated balloon 100 can increase the flow rate ratio post-treatment versus pre-treatment between 1000 and 10000. For pre-treatment radius between 0.15 mm and 0.25 mm, the serrated balloon 100 can increase the flow rate ratio post-treatment versus pre-treatment between 100 and 1000. For pre-treatment radius between 0.25 mm and 0.35 mm, the serrated balloon 100 can increase the flow rate ratio post-treatment versus pre-treatment between 100 and 1000. For pre-treatment radius between 0.35 mm and 0.45 mm, the serrated balloon 100 can increase the flow rate ratio post-treatment versus pre-treatment between 10 and 1000. The serrated balloon 100 produces a higher flow rate ratio compared to POBA. The serrated balloon 100 improves the flow rate post-treatment substantially better than POBA.

FIG. 76 is graph comparing post-treatment percentage stenosis of plain balloon versus serrated balloon where the data set incorporated pre-treatment stenosis of either 99% or 100% occluded. This figure illustrates the percentage of stenosis post-treatment versus pre-treatment of renal vascular disease (RVD) for cases with 99% or 100% pre-treatment stenosis. The Plain Old Balloon Angioplasty (POBA) is illustrated in blue. The serrated balloon 100 is illustrated in orange. The best fit line is shown for the POBA and the serrated balloon. This figure illustrates a comparison of post-treatment percentage of stenosis of five POBA and eight serrated balloons, illustrated by the data points. The y-axis is lumen gain. The x-axis is the arterial dimension. The lumen gain is the percentage of stenosis post-treatment versus pre-treatment. For the serrated balloon, the lumen gain is consistently around 20% for all arterial dimensions tested. For POBA, the lumen gain varies with the arterial dimension. The pre-treatment stenosis were either 99% or 100% occluded. It can be interpreted from this data that serration angioplasty has a tendency to offer stable and more repeatable lumen gain independent of the arterial dimension which is not observed in this data with plain angioplasty.

The serrated balloon 100 can have numerous advantages. The serrated balloon 100 can have a consistent percent of stenosis post-treatment. The percent of stenosis post-treatment for the serrated balloon 100 can be approximately 20%. The percent of stenosis post-treatment for the serrated balloon 100 can range from 10% to 30%. Most samples were between 19% and 23%. The percent of stenosis post-treatment for POBA can range from 20% to 50%.

The serrated balloon 100 can have a consistent percent of stenosis for all pre-treatment RVD. The variation for the serrated balloon 100 can be less than 20%. The variation for the serrated balloon 100 can range from about 15% to about 29%. With POBA, the results varied greatly across pre-treatment RVD. The variation for POBA can be greater than 20% The variation for POBA can range from about 20% to 48%. These results were consistent for cases with 99% pre-treatment stenosis. These results were consistent for cases with 100% pre-treatment stenosis.

The serrated balloon 100 can have consistent lumen gain. For all arterial dimensions, the lumen gain was remarkably consistent. The best fit line for serrated balloon 100 is flat. The serrated balloon produced consistent lumen gain. POBA had inconsistent lumen gain. For all arterial dimensions tested, the lumen gain varied greatly. The best fit line for POBA increases lumen gain with arterial dimension. The lumen gain is greater for larger arteries. The lumen gain varied from 20% to 50%.

The serrated balloon 100 produces stable results across all arterial dimensions tested. The serration angioplasty has a tendency to offer more repeatable lumen gain compared to POBA. The serration angioplasty has a tendency to offer more repeatable lumen gain independent of the arterial dimension. For POBA, lumen gain appeared to be dependent on the arterial dimension.

For pre-treatment RVD between 1.5 mm and 2 mm, the serrated balloon 100 can have a percentage stenosis post-treatment of between 10% and 20%. For pre-treatment RVD between 2 mm and 2.5 mm, the serrated balloon 100 can have a percentage stenosis post-treatment between 10% and 30%. For pre-treatment RVD between 2.5 mm and 3.0 mm, the serrated balloon 100 can have a percentage stenosis post-treatment between 20% and 30%. For pre-treatment RVD between 3.0 mm and 3.5 mm, the serrated balloon 100 can have a percentage stenosis post-treatment of between 20% and 30%. For pre-treatment RVD between 3.5 mm and 4.0 mm, the serrated balloon 100 can have a percentage stenosis post-treatment of between 20% and 30%. The serrated balloon 100 produces a consistent percentage stenosis post-treatment compared to POBA.

FIG. 77A-77B is a set of images taken from within the artery pre and post treatment with a serrated balloon technology 100 showing positive remodeling of the artery containing serrated marks throughout the vessel wall.

FIG. 77A illustrates angiographic and IntraVascular Ultra Sound (IVUS) imaging of the posterior tibial artery. The pre-intervention images showed diffuse circumferential superficial calcification (top angioplasty image, A-D). The post-intervention images show the artery after serration angioplasty. The post-intervention images shown slits, indicated with yellow arrows (bottom angioplasty image, A'-D'). The slits in the superficial calcium enable enlargement of the lumen without any dissection. The imaging is shown along the left side for pre-intervention and post intervention. The imaging illustrates the locations of A, B, C, and D in the pre-intervention image. The imaging illustrates the locations of A', B', C', and D' in the post-intervention image. This figure illustrates angiographic and IVUS images of the diseased lesion pre serration angioplasty and post serration angioplasty. On the image set to the left, pre intervention is shown on the right pane and post intervention on the left. Corresponding image sets to both pre and post are on the upper and lower panels (respectively) to the right. This figure illustrates the serration effect in the lower panel series of cross-sectional images collected by IVUS. This figure also illustrates how the serration effect improved lumen gain and blood flow by the flat view of the arterial flow of the left images.

FIG. 77B illustrates angiographic and optical coherence tomography (OCT). This figure includes both angiographic and optical coherence tomography (OCT) images of diseased lesion pre and post serration angioplasty. The pre-intervention shows blocked blood flow along a vessel. The post-intervention images show the artery after serration angioplasty. The post-intervention images shown slits, indicated with white arrows. On the image set to the left, pre intervention is shown on the right pane and post intervention on the left. Corresponding image sets to both pre and post serration angioplasty are on the upper and lower panels (respectively) to the right. This figure illustrates the serration effect in the lower panel series of cross-sectional images collected by OCT. This figure also illustrates how the serration effect improved lumen gain and blood flow by the flat view of the arterial flow of the left images.

Vessel remodeling can include alterations in the structure of the vessel. The serrated balloon 100 can alter the structure of the vessel wall by creating linear serration lines. The serrated balloon 100 can change the vessel size at the site of the disease, such as an lesion. The serrated balloon 100 can increase the cross-sectional dimension or diameter of the vessel. The vessel can positively remodeled by expanding the vessel. The remodeled vessel allows for greater flow therethrough. The serrated balloon 100 can remodel the vessel such that the vessel maintains the lumen size. The serrated balloon 100 can facilitate the expanded vessel despite the accumulated lesions.

The serrated balloon 100 can create linear cracks which are the key structural alternation in the vessel. The serrated balloon 100 can create a crack past the intima layer. The serrated balloon 100 can create a linear crack to the medial layer. The serrated balloon 100 can create changes to the internal elastic lamina. The serrated balloon 100 can create changes to the intima. The serrated balloon 100 can create changes to the media.

The serrated balloon 100 can reverse the progression of cardiovascular conditions. Stenosis can be caused by artherosclerosis whereby the vessel is narrowed due to deposits. These deposits can be fatty deposits such as plaques which harden over time. The serrated balloon 100 can reverse this blockage. The serrated balloon 100 can enlarge the vessel without major disruption the deposits. The serrated balloon 100 separates the vessel wall into segments. The adjacent segments of the vessel wall are separated by cracks that extend to the medial layer. While not bound by a theory, the cracks can allow the segments to more easily expand under pressure. The cracks can allow the segments to allow blood flow to dramatically improve. The cracks can prevent the segments from recoiling to a small diameter.

The angioplasty images of FIGS. 77A and 77B (panels on the left) illustrate pre-intervention and post-intervention with the serrated balloon 100. The locations that will be serrated are shown in the left panel before intervention. These same locations are shown in the right panel after intervention. The serrated balloon 100 remodels the vessel. The serrated balloon 100 can create a crack between locations A'-D' along the length of the vessel. The crack can be continuous between locations A'-D'. The crack can be longitudinally extending along a portion of the length of the vessel. The lumen gain is visible by the darkened artery. The blood flow is restored. The serrated balloon 100 improves lumen gain. The serrated balloon 100 expands the vessel. The serrated balloon 100 increases the blood flow. The flat view of the arterial flow the angioplasty images of FIGS. 77A and 77B illustrate this improvement.

The IVUS images of FIG. 77A (panels on the right) illustrate pre-intervention and post-intervention with the serrated balloon 100. The locations that will be serrated are shown in the top panel before intervention. These same locations are shown in the bottom panel after intervention. The arrow points to the crack formed by the serrated balloon 100. The linear dissected lines extend through cross-sectional locations A'-D'. The linear dissected lines extend through the intima to the medial layer. The linear dissected lines appear as slits into the vessel wall. The linear dissected lines can extend through plaque or other deposits. The linear dissected lines can extend through hardened or calcified sections. The hardened or calcified sections are shown in white along the intima. The hardened or calcified sections remain largely intact with the serration balloon technology. The hardened or calcified sections are only disturbed at the narrow cracks.

The serrated balloon 100 remodels the vessel. The serrated balloon 100 can allow the lumen to expand. The lumen gain is visible by the comparison between the cross-section at each location. For instance, at a first location (designated A for pre-intervention and A' for post-intervention), the lumen can increase in cross-sectional dimension. The lumen can also be reshaped in some methods. The lumen can change from an oval shape to a more rounded shape. The lumen can change back to a pre-diseased shape. The lumen can change back to a pre-diseased diameter or cross-section.

The OCT images of FIG. 77B (panels on the right) illustrate pre-intervention and post-intervention with the serrated balloon 100. The locations that will be serrated are shown in the top panel before intervention. These same locations are shown in the bottom panel after intervention. The arrow points to the crack formed by the serrated balloon 100. The linear dissected lines extend through the intima to the medial layer. The linear dissected lines appear as slits or channels into the vessel wall. As most clearly shown in this figure, the linear dissected lines can form v-shaped channels. The linear dissected lines can extend through plaque or other deposits.

The serrated balloon 100 dramatically remodels the vessel. The serrated balloon 100 can allow the lumen to expand. The lumen gain is visible by the comparison between the cross-section at each location. For instance, at a second location (shown as the rightmost location), the lumen can increase in cross-sectional dimension. This lumen gain can be dramatic, such as increasing the ratio of flow post-intervention compared with pre-intervention by 100%, 1000%, 10,000%, 100,000%, or any range of two of the foregoing values. The lumen can also be reshaped in some methods. The lumen can be expanded to accommodate the flow of blood normally accommodated by the vessel. The lumen can be expanded by the fluid flow itself after serration technology, in some methods. The blood flow is restored through the lumen of the vessel.

The lumen can maintain this expanded shape after the removal of the serrated balloon 100. The serrated balloon 100 is an interventional technology. The serrated balloon 100 does not remain in the body of the patient after expansion, in most methods. The serrated balloon 100 is removed. With POBA, the vessel recoils when the POBA is removed. The vessel recoils to a smaller diameter when the vessel is not supported by the pressure of POBA. The hardened plaque can function to snap the vessel back toward the pre-interventional diameter. With the serrated balloon 100, the recoil of the vessel is dramatically less. The vessel does not recoil as much since the vessel is permanently changed by linear serration lines. The vessel does not recoil because the plaque is separated into segments. The plaque is interrupted by the linear serration lines thereby decreasing the ability of the plaque to snap back.

FIGS. 78A-78B show a comparison of the lumen gain for plain balloon technology (POBA) and serration balloon 100 technology. FIG. 78A illustrates serration versus POBA for final residual stenosis. The blue bar represents pre-stenosis percentage. The green bar represents post-stenosis percentage. The serrated balloon had a sample size of 17. The serrated balloon had an average pre-stenosis percentage of 86.2. The serrated balloon had an average post-stenosis percentage of 17.2. The POBA had a sample size of 25. The POBA had an average pre-stenosis percentage of 81.4. The POBA had an average post-stenosis percentage of 33.7. There was a 49% improvement of the final stenosis with the serrated balloon 100 compared with POBA. This figure illustrates a comparison of the lumen gain between the effects of plain balloon (POBA) and the serration balloon. Both artery sets start at nearly the same amount of pre-treatment stenosis with serration angioplasty improving final stenosis by 49% over plain balloon alone. Lower final stenosis is directly correlated with an increase in lumen diameter.

The serrated balloon 100 has numerous advantages. The serrated balloon 100 can have a dramatically lower final residual stenosis. The serrated balloon 100 and POBA were utilized with vessels having a high pre-intervention stenosis percentage. For the samples with the serrated balloon 100, the average pre-intervention stenosis percentage was 86.2%. For the samples with POBA, the average pre-intervention stenosis percentage was 81.4%. The serrated balloon 100 had remarkable lumen gain. The serrated balloon 100 had an average post-intervention stenosis percentage of 17.2%. POBA had an average post-intervention stenosis percentage of 33.7%. POBA had a much smaller lumen gain. The serrated balloon 100 had a much greater lumen gain.

The serrated balloon 100 had an improved final stenosis compared with POBA. The final residual stenosis was improved by 49%. The final residual stenosis can be improved over POBA by 10%, at least 10%, 20%, at least 20%, 30%, at least 30%, 40%, at least 40%, 50%, at least 50%, 60%, at least 60%, or any range of two of the foregoing values.

FIG. 78B illustrates a comparison for serration technology between severe calcification and lesser calcification, e.g., none, mild, or moderate. The vessels were treated with the serrated balloon 100 for serration angioplasty. The y-axis illustrates lumen gain. The severe calcification had a sample size of 7. The sample with no, mild, or moderate calcification had a sample size of 18. The mean lumen gain for the severe calcification was 3.45 mm. The mean lumen gain for the lesser calcification was 3.33. This figure illustrates a comparison of the lumen gain between vessels with severely calcified lesions and vessels with no/mild/moderate calcified lesions. Both disease morphologies show nearly the same amount of lumen gain. Independent of the level of calcification, serration angioplasty offers effective lumen gain and positive remodeling of the diseased lesion. FIGS. 76, 78A, and 78B illustrate ability for serration angioplasty to generate a larger lumen.

The serrated balloon 100 produces stable results across all calcifications tested. The serration angioplasty has a tendency to offer more repeatable lumen gain for severely calcified lesions and none/mild/moderate calcified lesions. While not to be limited by a theory, the serrated balloon 100 creates cracks to the medial layers regardless of the diseased state of the vessel wall. The serrated balloon 100 acts to segment the vessel wall between the cracks regardless of the diseased state of the vessel wall. These segments can be easier to expand regardless of the diseased state of the vessel wall. The serration angioplasty has a tendency to offer more repeatable lumen gain independent of the calcifications. For POBA, lumen gain may be dependent on the calcifications. The calcifications may cause recoil, thus diminishing any lumen gain experienced while the POBA exerted pressure.

FIG. 79 is a graph comparing the translation of force originating at the hub of the catheter to the tip of the catheter. The serrated balloon 100 can translate greater forces across the balloon body to the tip than other technologies with metal on the outside of the balloon. The comparison is between serration angioplasty (Serrantor®) rail angioplasty (Angiosculpt®) and constrained angioplasty (Chocolate®). The serration angioplasty is illustrated in blue diamonds. The rail angioplasty is illustrated in orange squares. The constrained angioplasty is shown in gray triangles. The best fit lines are shown. The y-axis is output in grams. The x-axis is the sample number. This figure illustrates a comparison of different technologies translating force from the catheter hub along the catheter body across the balloon to the tip of the catheter. The translation of the column strength from the catheter to tip can be quickly lost across the balloon when the balloon lacks effective longitudinal support structures to aid in the transfer of force across the balloon. By pleating and folding, the balloon some of the column strength is increased across the balloon. For serration angioplasty, the linear integrated strips across the serration balloon offers unique advantage and support for the translation of the force across the balloon from the hub to the tip.

The serrated balloon 100 can have numerous advantages. The strip 200 can increase the column strength of the balloon 100. The strip 200 can be longitudinally placed. The strip 200 can allow force to be transmitted from the hub of the catheter to the tip of the catheter. The strip 200 can strengthen the balloon 100 in a longitudinal direction.

The strip 200 can facilitate placement of the balloon 100. The strip 200 can stiffen the balloon along the length. The strip 200 can allow the balloon to be pushed without buckling. The strip 200 can be flexible in a direction perpendicular to the longitudinal axis of the strip. The strip 200 can allow the balloon 100 to flex right and left as the balloon 100 navigates the vasculature.

The strip 200 can improve column strength in the delivery configuration shown in FIG. 74A. The strip 200 can be transversely oriented. The strip 200 can function as a support strut. The strip 200 can have column strength in the folded and pleated configuration. The strip 200 can have column strength when transversely oriented. The strip 200 can have column strength when in the insertion or delivery configuration. The strip 200 can have column strength when folded under the wings 110 of the balloon 100.

The strip 200 can improve column strength any configuration shown in FIG. 74B-74E. The strip 200 can be less transversely oriented. The strip 200 can be perpendicularly oriented. The strip 200 can have column strength in the expanded configuration. The strip 200 can have column strength when perpendicularly oriented. The strip 200 can have column strength when penetrating the vessel wall. The strip 200 can have column strength when seated in the serrations.

FIG. 80 shows the low incidence of dissections with the serration angioplasty using the serration balloon catheter at different clinical sites. In this figure, there was a low incidence of dissection rate for serration angioplasty across a pool of different physician sites. Site one had a sample size of four. Site two had a sample size of eight. Site three had a sample size of seventeen. Site five had a sample size of eleven. Site six had a sample size of six. Site seven had a sample size of seven. There was a total of 53 samples. In the majority of samples, there was no dissection. Sites two, three, five, and seven had a small percentage of A type dissections. Sites one, two, six, and seven had a small percentage of B type dissections. Site 2 had a small percentage of D type dissection and a small percentage of unknown dissections. Site 2 had a D type dissection when the balloon diameter was greater than twice the reference vessel diameter.

The serrated balloon 100 can have numerous advantages. The serrated balloon 100 can greatly reduce the likelihood of dissection. The serrated balloon 100 can allow the diseased lumen to be expanded and stretched using low pressure. The serrated balloon 100 can create the serrations, indentations, and/or microperforation at low pressures. The serrated balloon 100 can create the serrations, indentations, and/or microperforation at pressures between 2 atm and 4 atm. The serrated balloon 100 can facilitate crack propagation at low pressure. The serrated balloon 100 can facilitate crack propagation at pressures greater than 4 atm. The serrated balloon 100 can facilitate crack propagation at pressures lower than POBA. The serrated balloon 100 can create linear serration lines without creating numerous and substantial dissections and elevated flaps. For the majority of interventions at each site, there were no dissections.

The serrated balloon 100 can enable the plaque to be dilated more evenly and smoothly. The serrated balloon 100 creates segments of the vessel wall which may or may not include plaque. The serrated balloon 100 creates segments that can easily dilated or pushed outward. The serrated balloon 100 creates segments that can be expanded independently. The serrated balloon 100 creates segments that can be expanded with less force. The serrated balloon 100 creates segments that can be expanded under fluid flow, in some methods. The serrated balloon 100 creates segments can be dilated with lower pressure. The serrated balloon 100 advantageously avoids forming random cracks. The serrated balloon 100 creates linear serration lines which are predictable. The serrated balloon 100 creates linear serration lines which are repeatable.

The serrated balloon 100 advantageously increases arterial diameter while minimizing vessel injury. The serrated balloon 100 advantageously involves an innovative approach to the use of angioplasty's mechanism of action. The serrated balloon 100 advantageously increases volumetric flow. The serrated balloon 100 advantageously minimizes the degree of dissections and other forms of vessel injury. The serrated balloon 100 advantageously reduces the need for stents. The serrated balloon 100 advantageously combines angioplasty with longitudinally oriented serrations along the intima of the artery. The serrated balloon 100 advantageously alters the mechanism of action of angioplasty alone.

The serrated balloon 100 advantageously combines features of angioplasty and serration. The serrated balloon 100 advantageously requires minimal atmospheric pressure to achieve improvements in blood flow. The serrated balloon 100 can include a set of strips 200 which are integrated into the angioplasty balloon 100. The serrated balloon 100 advantageously produces a series of serrated lines along the intima when the balloon 100 is inflated. The strips 200 can penetrate the media. The serrated balloon 100 advantageously creates serrated lines. The serrated balloon 100 advantageously promotes the angioplasty energy to follow these lines of weakness which are oriented along the arterial axis. As the lumen expands, the intima and medial tissues separate more gently and predictably. As the lumen expands, the intima and medial tissues separate enabling more effective blood flow past the repaired stenotic lesion. The crack can extend past the intimal. The crack can extend into the intimal layers. The crack can penetrate the internal elastic lamina. The crack can extend into the medial layers.

The volume flow rate can be highly dependent of the cross section of the artery. For peripheral arteries, restoring lumen diameter to its unconstrained diameter increases the flow rate. The serrated balloon 100 advantageously generates a larger lumen in a consistent and predictable manner. The serrated balloon 100 advantageously produces a higher volume flow rate over other forms of angioplasty. The ability for serration angioplasty to achieve higher volume flow rate can be described in relation to vessel remodeling. The serrated balloon 100 advantageously treats a diseased vessel such that the vessel behavior, including one or more of compliance, flow dynamics, and internal diameter, are improved. The serrated balloon 100 advantageously allows the internal elastic lamina to be serrated. The serrated balloon 100 advantageously allows the internal elastic lamina to relax under the balloon pressure. The serrated balloon 100 advantageously allows the treated diseased region to become less turbulent or less rough. The serrated balloon 100 advantageously allows the treated diseased region to have fewer interruptions or perturbations in the flow stream. The serrated balloon 100 advantageously reduces wall friction. The serrated balloon 100 advantageously reduces flow resistance. The serrated balloon 100 advantageously allows serration angioplasty to be used as either a standalone treatment. The serrated balloon 100 advantageously allows serration angioplasty to be used as a conjunctive therapy. The serrated balloon 100 advantageously results in an arterial outline and flow dynamics with minimal to no appearance of vessel or disease discontinuity or disruption to the flow. The serrated balloon 100 advantageously allows positive vessel remodeling.

The serrated balloon 100 advantageously improves volumetric flow rates. The serrated balloon 100 advantageously improves residual stenosis versus pre-treatment RVD (pre-treatment). The serrated balloon 100 advantageously consistently outperformed POBA. The serrated balloon 100 advantageously achieves at least a two time greater average flow rate ratio over POBA for stenotic lesions. The serrated balloon 100 advantageously achieves at least 50% less residual stenosis for stenotic lesions. Other advantages are disclosed herein.

The serrated balloon 100 can incorporate any technologies of angioplasty balloons catheters. The serrated balloon 100 can treat patients with peripheral artery disease. The serrated balloon 100 can replace current treatments. The serrated balloon 100 can be built on familiar balloon catheter technology. The serrated balloon 100 can be used in conjunction with current treatments. The serrated balloon 100 can make subsequent angioplasty treatments more effective. The serrated balloon 100 can make drug coated balloon treatments more effective. The serrated balloon 100 can advantageously spare soft tissue. The serrated balloon 100 can treat severely calcified lesions.

In some configurations, the serrated balloon 100 advantageously incorporates sound wave technology. The serrated balloon 100 can utilize sound waves to break up plaque or other lesions in blocked vessels. The serrated balloon 100 can utilize lithrotripsy. The serrated balloon 100 can utilize sounds waves to break up deposits. The serrated balloon 100 can include an additional energy source in combination with serrations on the outer surface of the balloon. The energy source and the serrations can be synergistic. The energy source and the serrations can safely modify lesions including deep or highly calcified regions. The energy source and the serrations can reliably dilate vessels, even vessels containing highly calcified regions. The energy source can produce ultra-sonic vibrations or ultrasound. The energy source can include a miniature array of emitters. The energy source can include lithotripsy emitters. The energy source can create a localized effect at the treatment site. The energy source can reduce cardiovascular calcium deposits. The energy source can discharge energy. The energy source can vaporize the fluid within the balloon 100. The energy source can create a bubble that expands and contracts. The energy source can generate sonic pressure waves. The energy source can create waves that produce a localized effect at the treatment site. The energy source creates a wave that travels through soft vascular tissue. The energy source can selectively crack deposits. The energy source can crack calcium deposits at the intimal layer. The energy source can crack calcium deposits at the medial layer. The energy source can crack calcium deposits within the vessel wall. The balloon 100 can create serrations before use of the energy source. The balloon 100 can create serrations after use of the energy source. The balloon 100 can be used to dilate the lesion. The balloon 100 can be used to dilate at low pressure. The balloon 100 can be used to dilate the vessel for lumen gain. While not bound by a theory, the energy source can crack deposits which have a different density than soft tissue.

The balloon 100 can emit energy from a transducer within the balloon body. The sound energy or other energy can be transmitted through the liquid medium used to fill the balloon 100. The sound energy or other energy can be transmitted through the balloon wall. The strips 200 can allow energy to be transmitted. The energy wave can pass undisturbed through the balloon 100 with the strips 200. The strips 200 can include a modified shape to allow the energy to be transmitted. The strips 200 can include a modified material to allow the energy to be transmitted. In some embodiments, the material of the strips 200 can have a similar density to soft tissue. The strips 200 can be modified to enable effective transmission of an acoustic wave. The energy source may produce an acoustic pulse wave. The energy source may produce a high-powered sound wave. The energy source may produce sonic pressure waves. The energy source can allow fewer strips 200 to be utilized on the balloon 100 while producing similar clinical results. In some embodiments, one or more strips 200 are utilized.

The energy source and the strips can be synergistic. The energy source can allow greater spacing between microperferators. The energy source can allow the microperferators to be shallower or shorter in height. The energy source can allow the serrations to penetrate through less material. The energy source can reduce the layer of deposits thereby decreasing the height to the medial layer. The balloon 100 can allow the combination of pressure dilation and serrations, with the optional inclusion of energy delivery. The energy delivery can be available for all clinical events, but only utilized for highly calcified lesions in some embodiments. The energy delivery can be available for all clinical events and utilized for all calcified lesions, in some embodiment. The serrations can reduce the number of emitters. The serrations can reduce the number of transducers. The serrations can reduce the complexity of energy delivery. The energy source would not need to reduce all of the deposits, in some methods. The energy source would only need to reduce the deposits, in some methods. The energy source could deliver less energy to the treatment site.

The combination of the strips 200 and the energy source can reduce the thickness of deposits. The energy source could deliver less energy when serration is used. The serration could require less penetration when an energy source is used. The energy source could reduce the thickness of the calcium to a lesser degree than to the medial layer. The serrations could penetrate less thickness due to the sonic pressure disruption of the calcium layer.

Various other modifications, adaptations, and alternative designs are of course possible in light of the above teachings. Therefore, it should be understood at this time that within the scope of the appended claims the invention may be practiced otherwise than as specifically described herein. It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "creating microperforations in an arterial plaque" includes "instructing the creating of microperforations in an arterial plaque." The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. An intravascular device comprising:

a catheter comprising a balloon and a plurality of strips disposed on an outer surface of the balloon, each strip of the plurality of strips including a plurality of wedge dissectors spaced apart along a surface of each strip, wherein each of the plurality of wedge dissectors comprises a blunt top surface; and a plurality of pumps connected to the balloon and acting on a liquid medium used to fill the balloon, wherein a pump of the plurality of pumps is configured to produce hydraulic waves for calcium fracturing, wherein the plurality of wedge dissectors is configured to cause cleavage planes allowing plaque to separate only along longitudinal lines, wherein a longitudinal crack is configured to propagate faster with the production of the hydraulic waves, and wherein the combined plurality of wedge dissectors and the hydraulic waves break the plaque into smaller particles allowing more effective vessel expansion.

2. The intravascular device of claim 1, wherein the hydraulic waves are configured to be transmitted through the liquid medium used to fill the balloon.

3. The intravascular device of claim 1, wherein the hydraulic waves are configured to be transmitted through a wall of the balloon.

4. The intravascular device of claim 1, wherein the hydraulic waves are configured to be transmitted through the plurality of strips.

5. The intravascular device of claim 1, wherein the plurality of pumps is configured to compress the plaque.

6. The intravascular device of claim 1, wherein the plurality of wedge dissectors comprise a shape to enable the effective transduction of the hydraulic waves into tissue.

7. The intravascular device of claim 1, wherein the energy delivery is more effective in combination with nucleation sites provided by the plurality of wedge dissectors.

8. The intravascular device of claim 1, wherein the longitudinal crack is configured to propagate in a more controlled manner with the production of the hydraulic waves.

9. The intravascular device of claim 1, wherein the plurality of pumps is configured to produce effective lumen gain.

10. The intravascular device of claim 1 wherein the plurality of pumps is configured to crack medial plaque.

11. The intravascular device of claim 1, wherein the plurality of pumps is configured to crack intimal plaque.

12. The intravascular device of claim 1, wherein the plurality of pumps is configured for lesion preparation.

13. The intravascular device of claim 1, wherein the hydraulic waves are configured to be transmitted through metal.

14. The intravascular device of claim 1, wherein the plurality of pumps is separate from the catheter.

15. The intravascular device of claim 1, wherein the plurality of pumps is integrated with the catheter.

16. The intravascular device of claim 1, wherein the plurality of wedge dissectors increases tissue transduction of energy.

17. The intravascular device of claim 1, wherein the plurality of wedge dissectors concentrates energy delivery.

18. The intravascular device of claim 1, wherein the plurality of wedge dissectors penetrates plaque easier with the production of the hydraulic waves.

19. The intravascular device of claim 1, wherein the longitudinal crack propagates easier with the production of the hydraulic waves.

20. The intravascular device of claim 1, wherein the longitudinal crack is configured to propagate in a more controlled manner with the production of the hydraulic waves.

* * * * *